US006908935B2

(12) United States Patent
Kelly et al.

(10) Patent No.: US 6,908,935 B2
(45) Date of Patent: Jun. 21, 2005

(54) CALCIUM RECEPTOR MODULATING AGENTS

(75) Inventors: Michael G. Kelly, South San Francisco, CA (US); Shimin Xu, Moorpark, CA (US); Ning Xi, Thousand Oaks, CA (US); Philip Miller, Headington (GB); John F. Kincaid, San Diego, CA (US); Chiara Ghiron, Wootton (GB); Thomas Coulter, Wantage (GB)

(73) Assignee: Amgen Inc., Thousand Oaks, CA (US)

( * ) Notice: Subject to any disclaimer, the term of this patent is extended or adjusted under 35 U.S.C. 154(b) by 39 days.

(21) Appl. No.: 10/444,946

(22) Filed: May 22, 2003

(65) Prior Publication Data

US 2004/0082625 A1 Apr. 29, 2004

Related U.S. Application Data

(60) Provisional application No. 60/441,065, filed on Jan. 17, 2003, and provisional application No. 60/383,050, filed on May 23, 2002.

(51) Int. Cl.[7] .................. A61K 31/4439; C07D 401/12

(52) U.S. Cl. .................................. 514/340; 546/276.4

(58) Field of Search ........................ 546/276.4; 514/340

(56) References Cited

U.S. PATENT DOCUMENTS

| | | | |
|---|---|---|---|
| 5,981,599 | A | 11/1999 | Moe et al. |
| 6,011,068 | A | 1/2000 | Nemeth et al. |
| 6,031,003 | A | 2/2000 | Nemeth et al. |
| 6,103,737 | A | 8/2000 | Cocuzza et al. |
| 6,172,091 | B1 | 1/2001 | Cohen et al. |
| 6,225,316 | B1 | 5/2001 | Bos et al. |
| 6,335,338 | B1 | 1/2002 | Bhatnagar et al. |
| 6,403,832 | B1 | 6/2002 | Oikawa et al. |
| 6,407,111 | B1 | 6/2002 | Bos et al. |
| 6,436,152 | B1 | 8/2002 | Chassot et al. |
| 2002/0143212 | A1 | 10/2002 | Oikawa et al. |

FOREIGN PATENT DOCUMENTS

| | | |
|---|---|---|
| EP | 039051 | 4/1981 |
| EP | 0 933 354 | 8/1999 |
| WO | WO 93/04373 | 3/1993 |
| WO | WO 94/18959 | 9/1994 |
| WO | WO 95/11221 | 4/1995 |
| WO | WO 96/05818 | 2/1996 |
| WO | WO 96/09818 | 4/1996 |
| WO | WO 96/12697 | 5/1996 |
| WO | WO 96/31475 | 10/1996 |
| WO | WO 97/05252 | 2/1997 |
| WO | WO 97/37967 | 10/1997 |
| WO | WO 98/01417 | 1/1998 |
| WO | WO 98/37061 | 8/1998 |
| WO | WO 98/45255 | 10/1998 |
| WO | WO 99/01439 | 1/1999 |
| WO | WO 99/48888 | 9/1999 |
| WO | WO 00/21910 | 4/2000 |
| WO | WO 01/34562 | 5/2001 |
| WO | WO 01/90069 | 11/2001 |
| WO | WO 01/96307 | 12/2001 |
| WO | WO 01/96312 | 12/2001 |
| WO | WO 01/96365 | 12/2001 |
| WO | WO 03/020723 | 3/2003 |

OTHER PUBLICATIONS

U.S. Appl. No. 10/444,945, filed May 22, 2003, Kelly et al.

Nemeth et al. (1998), "Calcimimetics with potent and selective activity on the parathyroid calcium receptor," *Proc. Natl. Acad. Sci. USA* 95:4040–4045.

Berge et al., "Pharmaceutical Salts," *J. Pharm. Sci.* 66(1):1–19 (1977).

Brown et al., "Neomycin Mimics the Effects of High Extracellular Calcium Concentrations on Parathyroid Function in Dispersed Bovine Parathyroid Cells," *Endocrinology* 128(6):3047–3054 (1991).

Bungaard et al., "A Novel Solution–Stable, Water–Soluble Prodrug Type for Drugs Containing a Hydroxyl or an NH–Acidic Group," *J. Med. Chem.* 32(12):25032507 (1989).

Chen et al., "The Diltiazem Analog TA–3090 Mimics the Actions of High Extracellular $Ca^{2+}$ on Parathyroid Function in Dispersed Bovine Parathyroid Cells," *J. Bone Miner. Res.* 5(6):581–587 (1990).

Dauban et al., "$N^1$–Arylsulfonyl–$N^2$–(1–aryl)ethyl–3–phenylpropane–1, 2–diamines as Novel Calcimimetics Acting on the Calcium Sensing Receptor," *Bioorg. Med. Chem. Let.* 10(17):2001–2004 (2000).

Garrett et al., "Calcitonin–Secreting Cells of the Thyroid Express an Extracellular Calcium Receptor Gene," *Endocrinology* 136(11):5202–5211, 1995.

(Continued)

*Primary Examiner*—Taofiq Solola

(74) *Attorney, Agent, or Firm*—Mary Susan Howard; Ron K. Levy; Stuart L. Watt

(57) ABSTRACT

The compounds of the invention are represented by the following general structure

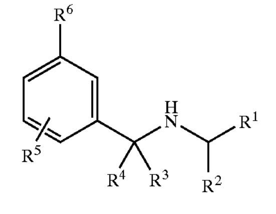

or a pharmaceutically acceptable salt thereof, and compositions containing them, wherein the variables are defined herein, and their use to reduce or inhibit PTH secretion, including methods for reducing or inhibiting PTH secretion and methods for treatment or prophylaxis of diseases associated with bone disorders, such as osteoporosis, or associated with excessive secretion of PTH, such as hyperparathyroidism. The subject invention also relates to processes for making such compounds as well as to intermediates useful in such processes.

57 Claims, No Drawings

OTHER PUBLICATIONS

*J. Bone Miner. Res.* 9(Supple. 1):S282 (1994).

*J. Bone Miner. Res.* 9(Supple. 1):S409 (1994).

Kabalka et al., "The Reduction of Azides With Borohydride Supported on an Ion Exchange Resin," *Synthetic Commun.* 20(2):293–299 (1990).

Keseru et al., "Total Synthesis of Plagiochins C, and D, Macrocyclic Bis(bibenzyl) Constituents of *Plagiochila Acantophylla,*" *Tetrahedron* 48(5):913–922 (1992).

Liedholm "Simple Synthetic Route to 4–Aminobenzaldehydes From anilines," *J. Chem. Soc., Perkin Trans.* 1:2234–2237 (1992).

Nemeth, "Regulation of Cytosolic Calcium by Extracellular Divalent Cations in C–cells and Parathyroid Cells," *Cell Calcium* 11:323–327 (1990).

Sande et al., "Borohydride Reducing Agent Derived From Anion Exchange Resin: Selective Reduction of α, β–unsaturated Carbonyl Compounds," *Tetrahedron Lett.* 25(32):3501–3504 (1984).

Svensson and Tunek, "The Design and Bioactivation of Presystemically Stable Prodrugs," *Drug Metabolism Reviews* 19(2):165–194 (1988).

Zaidi, "Intracellular Calcium in the Control of Osteoclast Function," *Biochem. Biophys. Res. Commun.* 167(2):807–812 (1990).

Zaidi, "Calcium Receptors' on Eukaryotic Cells with Special Reference to the Osteoclast," *Bioscience Reports* 10(6):493–507 (1990).

CALCIUM RECEPTOR MODULATING AGENTS

This application claims the benefit of U.S. Provisional Application No. 60/441,065, filed Jan. 17, 2003, and U.S. Provisional Application No. 60/383,050, filed May 23, 2002, which are hereby incorporated by reference.

BACKGROUND OF THE INVENTION

Extracellular calcium ion concentration is involved in a variety of biological processes, such as blood clotting, nerve and muscle excitability and bone formation (Cell Calcium 11:319, 1990). Calcium ion receptors, which are present on the membranes of various cells in the body, such as parathyroid and kidney cells (Nature 366:574, 1993; J. Bone Miner. Res. 9, Supple. 1, s282, 1994; J. Bone Miner. Res. 9, Supple. 1, s409, 1994; Endocrinology 136:5202, 1995), are important to the regulation of the extracellular calcium ion concentration. For example, concentration of extracellular calcium ion regulates the bone resorption by osteoclasts (Bioscience Reports 10:493, 1990), secretion of parathyroid hormone (PTH) from parathyroid cells and secretion of calcitonin from C-cells (Cell Calcium 11:323, 1990). Parathyroid hormone (PTH) is an important factor in regulating extracellular calcium ion concentration. Secretion of PTH increases extracellular calcium ion concentration by acting on various cells, such as bone and kidney cells, and the extracellular calcium ion concentration reciprocally inhibits the secretion of PTH by acting on parathyroid cells.

Several classes of calcimimetic compounds have been disclosed for regulating extracellular calcium ion concentration, particularly for reducing or inhibiting secretion of PTH. For example, U.S. Pat. Nos. 6,011,068 and 5,981,599 disclose arylalkylamines that are calcium receptor active molecules. EP 933354; WO 0021910, WO 96/12697; WO 95/11221; WO 94/18959; WO 93/04373; *Endocrinology* 128:3047, 1991; *Biochem. Biophys. Res. Commun.* 167:807, 1990; *J. Bone Miner. Res.* 5:581, 1990; and Nemeth et al., "Calcium-binding Proteins in Health and Disease," Academix Press, Inc., pp. 33–35 (1987) disclose various agents that interact with calcium receptors.

Dauban et al., Bioorg. Med. Chem. Let. 10:2001–4, 2000, disclose various N1-arylsulfonyl-N2-(1-aryl)ethyl-3-phenylpropane-1,2-diamine compounds as calcimimetics acting on the calcium sensing receptor.

Oikawa et al., in U.S. Pat. No. 6,403,832, and publication No. US2002/143212, describes aryl amine compounds useful as chiral intermediates in the synthesis of optically active propionic acid derivatives. Chassot et al., U.S. Pat. No. 6,436,152, describes arylalkylamine compounds useful as hair dye precursor compounds.

Bös et al., U.S. Pat. No. 6,407,111, describes phenyl substituted pyridine and benzene derivates that are antagonistic to the NK-1 receptor.

SUMMARY OF THE INVENTION

The present invention relates to selected calcimimetic compounds and pharmaceutically acceptable salts thereof. The invention compounds advantageously reduce or inhibit PTH secretion. Therefore, this invention also encompasses pharmaceutical compositions, methods for reducing or inhibiting PTH secretion and methods for treatment or prophylaxis of diseases associated with bone disorders, such as osteoporosis, or associated with excessive secretion of PTH, such as hyperparathyroidism. The subject invention also relates to processes for making such compounds as well as to intermediates useful in such processes.

The compounds of the invention are represented by the following general structure:

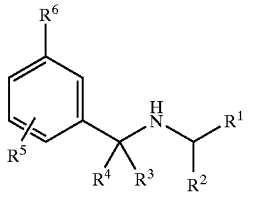

or a pharmaceutically acceptable salt thereof, wherein the variables are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

The invention provides compounds of Formula (I):

(I)

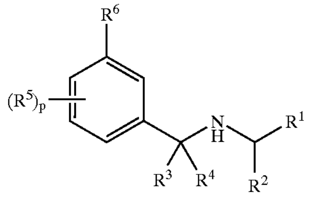

or a pharmaceutically acceptable salt thereof, wherein:

$R^1$ is aryl, substituted aryl, heterocyclyl, substituted heterocyclyl, cycloalkyl, or substituted cycloalkyl;

$R^2$ is alkyl or haloalkyl;

$R^3$ is H, alkyl, or haloalkyl;

$R^4$ is H, alkyl, or haloalkyl;

each $R^5$ present is independently selected from the group consisting of alkyl, substituted alkyl, alkoxy, substituted alkoxy, halogen, —C(=O)OH, —CN, $—NR^dS(=O)_mR^d$, $—NR^dC(=O)NR^dR^d$, $—NR^dS(=O)_mNR^dR^d$, or $—NR^dC(=O)R^d$;

$R^6$ is aryl, substituted aryl, heterocyclyl, substituted heterocyclyl, cycloalkyl, or substituted cycloalkyl;

each $R^a$ is, independently, H, alkyl or haloalkyl;

each $R^b$ is, independently, aryl, aralkyl, heterocyclyl, or heterocyclylalkyl, each of which may be unsubstituted or substituted by up to 3 substituents selected from the group consisting of alkyl, halogen, haloalkyl, alkoxy, cyano, and nitro;

each $R^c$ is, independently, alkyl, haloalkyl, phenyl or benzyl, each of which may be substituted or unsubstituted;

each $R^d$ is, independently, H, alkyl, aryl, aralkyl, heterocyclyl, or heterocyclylalkyl wherein the alkyl, aryl, aralkyl, heterocyclyl, and heterocyclylalkyl are substituted by 0, 1, 2, 3 or 4 substituents selected from alkyl, halogen, haloalkyl, alkoxy, cyano, nitro, $R^b$, $—C(=O)R^c$, $OR^b$, $—NR^aR^a$, $—NR^aR^b$, $—C(=O)OR^c$, $C(=O)NR^aR^a$, $—OC(=O)R^c$, $—NR^aC(=O)R^c$, $—NR^aS(=O)_nR^c$ and $—S(=O)_nNR^aR^a$;

m is 1 or 2;

n is 0, 1 or 2; and p is 0, 1, 2, 3, or 4;

provided that if $R^2$ is methyl, p is 0, and $R^6$ is unsubstituted phenyl, then $R^1$ is not 2,4-dihalophenyl, 2,4-dimethylphenyl, 2,4-diethylphenyl, 2,4,6-trihalophenyl, or 2,3,4-trihalophenyl.

Another aspect of the invention relates to compounds having the general structure II:

(II)

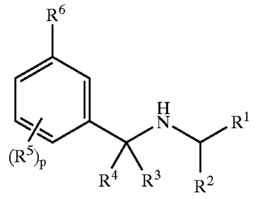

or a pharmaceutically acceptable salt thereof, wherein:

$R^1$ is phenyl, benzyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl or heterocycle are substituted by 0, 1, 2 or 3 substituents selected from $C_{1-6}$alkyl, halogen, $C_{1-4}$haloalkyl, —$OC_{1-6}$alkyl, cyano and nitro;

$R^2$ is $C_{1-8}$alkyl or $C_{1-4}$haloalkyl;

$R^3$ is H, $C_{1-4}$haloalkyl or $C_{1-8}$alkyl;

$R^4$ is H, $C_{1-4}$haloalkyl or $C_{1-8}$alkyl;

$R^5$ is, independently, in each instance, H, $C_{1-8}$alkyl, $C_{1-4}$haloalkyl, halogen, cyano, —$NR^aR^d$, —$NS(=O)_2R^c$, —$NR^aC(=O)NR^aR^d$, —$NR^dC(=O)R^d$ or —$OC_{1-6}$alkyl substituted by 0, 1, 2 or 3 substituents selected from halogen, —$OC_{1-6}$alkyl, —$NR^aR^d$, —$NS(=O)_2R^c$, —$NR^aC(=O)NR^aR^d$, —$NR^dC(=O)R^d$ or cyano;

$R^6$ is phenyl, benzyl, naphthyl, a saturated or unsaturated 5- or 6-membered ring heterocycle containing 1, 2 or 3 atoms selected from N, O and S, with no more than 2 of the atoms selected from O and S, or a saturated or unsaturated 8-, 9-, 10- or 11-membered heterobicycle containing 1, 2, 3, 4 or 5 atoms selected from N, O and S, with no more than 2 of the atoms selected from O and S, wherein the phenyl, benzyl, naphthyl, heterocycle and heterobicycle are substituted by 0, 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^aC(=O)C_{1-6}$alkyl, —$S(=O)_nC_{1-6}$alkyl, cyano and nitro;

$R^a$ is, independently, at each instance, H, $C_{1-4}$haloalkyl or $C_{1-6}$alkyl;

$R^b$ is, independently, aryl, aralkyl, heterocyclyl, or heterocyclylalkyl, each of which may be unsubstituted or substituted by up to 3 substituents selected from the group consisting of alkyl, halogen, haloalkyl, alkoxy, cyano, and nitro;

$R^c$ is, independently, at each instance, $C_{1-6}$alkyl, $C_{1-4}$haloalkyl, phenyl or benzyl;

$R^d$ is, independently, at each instance, H, $C_{1-6}$alkyl, phenyl, benzyl or a saturated or unsaturated 5- or 6-membered ring heterocycle containing 1, 2 or 3 atoms selected from N, O and S, with no more than 2 of the atoms selected from O and S, wherein the $C_{1-6}$alkyl, phenyl, benzyl, naphthyl and heterocycle are substituted by 0, 1, 2, 3 or 4 substituents selected from $C_{1-6}$alkyl, halogen, $C_{1-4}$haloalkyl, —$OC_{1-6}$alkyl, cyano and nitro, $R^b$, —$C(=O)R^c$, —$OR^b$, —$NR^aR^a$, —$NR^aR^b$, —$C(=O)OR^c$, —$C(=O)NR^aR^a$, —$OC(=O)R^c$, —$NR^aC(=O)R^c$, —$NR^aS(=O)_mR^c$ and —$S(=O)_mNR^aR^a$;

m is 1 or 2;

n is 0, 1 or 2; and p is 0, 1, 2, 3 or 4.

In one embodiment, in conjunction with any one of the above and below embodiments, $R^1$ is phenyl substituted by 0, 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ is benzyl substituted by 0, 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ is naphthyl substituted by 0, 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ a saturated or unsaturated 5- or 6-membered ring heterocycle containing 1, 2 or 3 atoms selected from N, O and S, with no more than 2 of the atoms selected from O and S, wherein the heterocycle is substituted by 0, 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^6$ is phenyl, wherein the phenyl is substituted by 0, 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^aC(=O)C_{1-6}$alkyl, —$S(=O)_nC_{1-6}$alkyl, cyano and nitro.

In another embodiment, in conjunction with any one of the above and below embodiments, $R^6$ is benzyl, wherein the benzyl is substituted by 0, 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^aC(=O)C_{1-6}$alkyl, —$S(=O)_nC_{1-6}$alkyl, cyano and nitro.

In another embodiment, in conjunction with any one of the above and below embodiments, $R^6$ is naphthyl, wherein the naphthyl is substituted by 0, 1, 2 or 3 substituents selected from $C_{1-6}$alkyl, halogen, $C_{1-4}$haloalkyl, —$OC_{1-6}$ alkyl, —$OC_{1-4}$haloalkyl, —$NR^aR^a$, —$NR^aC(=O)C_{1-6}$ alkyl, —$S(=O)_nC_{1-6}$alkyl, cyano and nitro.

In another embodiment, in conjunction with any one of the above and below embodiments, $R^6$ is a saturated or unsaturated 5- or 6-membered ring heterocycle containing 1, 2 or 3 atoms selected from N, O and S, with no more than 2 of the atoms selected from O and S, wherein the heterocycle is substituted by 0, 1, 2 or 3 substituents selected from $C_{1-6}$alkyl, halogen, $C_{1-4}$haloalkyl, —$OC_{1-6}$alkyl, —$OC_{1-4}$ haloalkyl, —$NR^aR^a$, —$NR^aC(=O)C_{1-6}$alkyl, —$S(=O)_n$ $C_{1-6}$alkyl, cyano and nitro.

In another embodiment, in conjunction with any one of the above and below embodiments, $R^6$ is a saturated or unsaturated 8-, 9-, 10- or 11-membered heterobicycle containing 1, 2, 3, 4 or 5 atoms selected from N, O and S, with no more than 2 of the atoms selected from O and S, wherein the heterobicycle is substituted by 0, 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^aC(=O)C_{1-6}$alkyl, —$S(=O)_nC_{1-6}$alkyl, cyano and nitro.

In another embodiment, in conjunction with any one of the above and below embodiments, $R^1$ is phenyl, naphthyl or ($OC_{1-4}$alkyl)phenyl.

In another embodiment, in conjunction with any one of the above and below embodiments, $R^1$ is phenyl substituted by 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ is benzyl substituted by 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ is naphthyl substituted by 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ a saturated or unsaturated 5- or 6-membered ring heterocycle containing 1, 2 or 3 atoms selected from N, O and S, with no more than 2 of the atoms selected from O and S, wherein the heterocycle is substituted by 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, one of $R^3$ or $R^4$ is $C_{1-4}$haloalkyl or $C_{1-8}$alkyl.

In another embodiment, in conjunction with any one of the above and below embodiments, $R^5$ is $C_{1-8}$alkyl, $C_{1-4}$haloalkyl, halogen or —$OC_{1-6}$alkyl.

In another embodiment, in conjunction with any one of the above and below embodiments, $R^6$ is phenyl, wherein the phenyl is substituted by 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^aC(=O)C_{1-6}$alkyl, —$S(=O)_nC_{1-6}$alkyl, cyano and nitro.

In another embodiment, in conjunction with any one of the above and below embodiments, $R^6$ is benzyl, wherein the benzyl is substituted by 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^aC(=O)C_{1-6}$alkyl, —$S(=O)_nC_{1-6}$alkyl, cyano and nitro.

In another embodiment, in conjunction with any one of the above and below embodiments, $R^6$ is naphthyl, wherein the naphthyl is substituted by 0, 1, 2 or 3 substituents selected from $C_{1-6}$alkyl, halogen, $C_{1-4}$haloalkyl, —$OC_{1-6}$ alkyl, —$OC_{1-4}$haloalkyl, —$NR^aR^a$, —$NR^aC(=O)C_{1-6}$ alkyl, —$S(=O)_nC_{1-6}$alkyl, cyano and nitro.

In another embodiment, in conjunction with any one of the above and below embodiments, $R^6$ is a saturated or unsaturated 5- or 6-membered ring heterocycle containing 1, 2 or 3 atoms selected from N, O and S, with no more than 2 of the atoms selected from O and S, wherein the heterocycle is substituted by 1, 2 or 3 substituents selected from $C_{1-6}$alkyl, halogen, $C_{1-4}$haloalkyl, —$OC_{1-6}$alkyl, —$OC_{1-4}$ haloalkyl, —$NR^aR^a$, —$NR^aC(=O)C_{1-6}$alkyl, —$S(=O)_n$ $C_{1-6}$alkyl, cyano and nitro.

In another embodiment, in conjunction with any one of the above and below embodiments, $R^6$ is a saturated or unsaturated 8-, 9-, 10- or 11-membered heterobicycle containing 1, 2, 3, 4 or 5 atoms selected from N, O and S, with no more than 2 of the atoms selected from O and S, wherein the heterobicycle is substituted by 1, 2 or 3 substituents selected from $C_{1-6}$alkyl, halogen, $C_{1-4}$haloalkyl, —$OC_{1-6}$ alkyl, —$OC_{1-4}$haloalkyl, —$NR^aR^a$, —$NR^aC(=O)C_{1-6}$ alkyl, —$S(=O)_nC_{1-6}$alkyl, cyano and nitro.

Another aspect of the invention involves a pharmaceutical composition comprising a pharmaceutically acceptable amount of a compound according to any one of the above embodiments and a pharmaceutically acceptable diluent or carrier.

Another aspect of the inventions involve the use of a compound according to any one of the above embodiments as a medicament.

Another aspect of the invention involves the use of a compound according to any one of the above embodiments in the manufacture of a medicament for the treatment of diseases associated with bone disorders or associated with excessive secretion of PTH.

Another aspect of the invention involves the use of a compound according to any one of the above embodiments in the manufacture of a medicament for the treatment of osteoporosis or hyperparathyroidism.

Another aspect of the invention involves a method of using a compound according to any one of the above embodiments for the treatment of diseases associated with bone disorders or associated with excessive secretion of PTH.

Another aspect of the invention involves a method of using a compound according to any one of the above embodiments for the treatment of osteoporosis or hyperparathyroidism.

Another aspect of the invention involves a process for making a compound according to claim 1 wherein $R^3$ and $R^4$ are both hydrogen comprising the steps of:

placing a compound having the structure

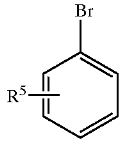

in the presence of acid followed by treatment with a hydride and methanol to form

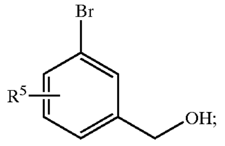

reacting the resulting alcohol with $R^6$—$B(OH)_2$ to form

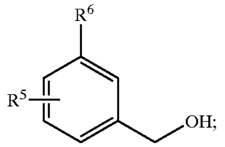

oxidizing the alcohol to form

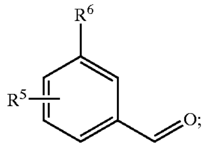

and reacting the aldehyde with an amine having the structure

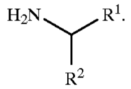

Unless otherwise specified, the following definitions apply to terms found in the specification and claims:

"Alkyl" and the prefix "alk-" refer to alkyl groups or substituents wherein the carbon atoms are in a branched, cyclical or linear relationship or any combination of the three. The alkyl groups described in this section contain from 1 to 10 carbon atoms unless otherwise specified and may also contain a double or triple bond. "$C_{V-W}$alkyl" means an alkyl group comprising from V to W carbon atoms. Examples of $C_{1-6}$alkyl include, but are not limited to the following:

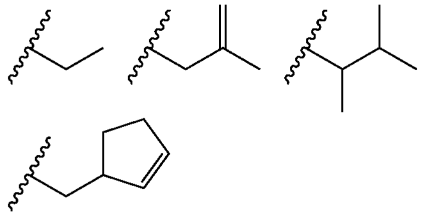

"Aryl" means a carbocyclic aromatic ring or ring system. Examples of aryl groups include phenyl, naphthyl, indenyl, fluorenyl, biphenyl, anthracenyl, 9-(9-phenylfluorenyl), phenanthrenyl, and the like.

"Halogen" means a halogen atom selected from F, Cl, Br and I.

"Haloalkyl", "haloalk-" and "$C_{V-W}$haloalkyl" mean an alkyl group, as described above, wherein any number—at least one—of the hydrogen atoms attached to the alkyl group or chain are replaced by F, Cl, Br or I.

"Heterocycle" means a ring or ring system comprising at least one carbon atom and at least one other atom selected from N, O and S. Heterocyclic groups can be saturated, unsaturated or aromatic. Aromatic heterocyclic groups are also referred to as "heteroaryl" rings or ring systems. Examples of heterocycles that may be found in the claims include, but are not limited to, the following:

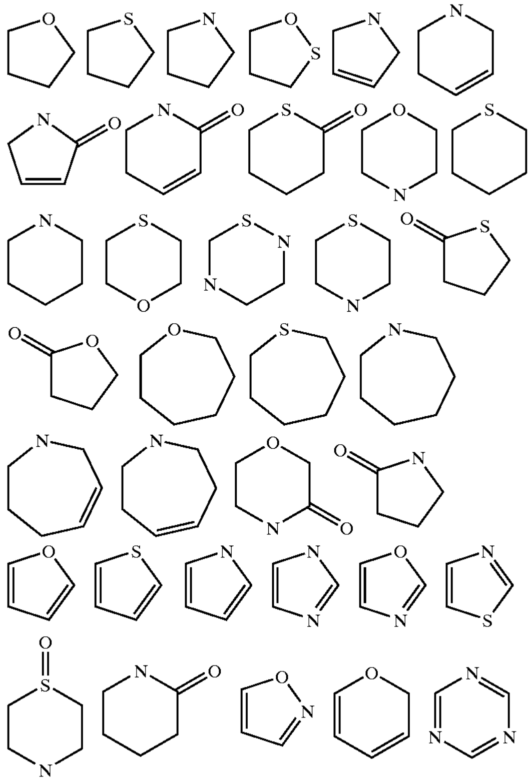

-continued

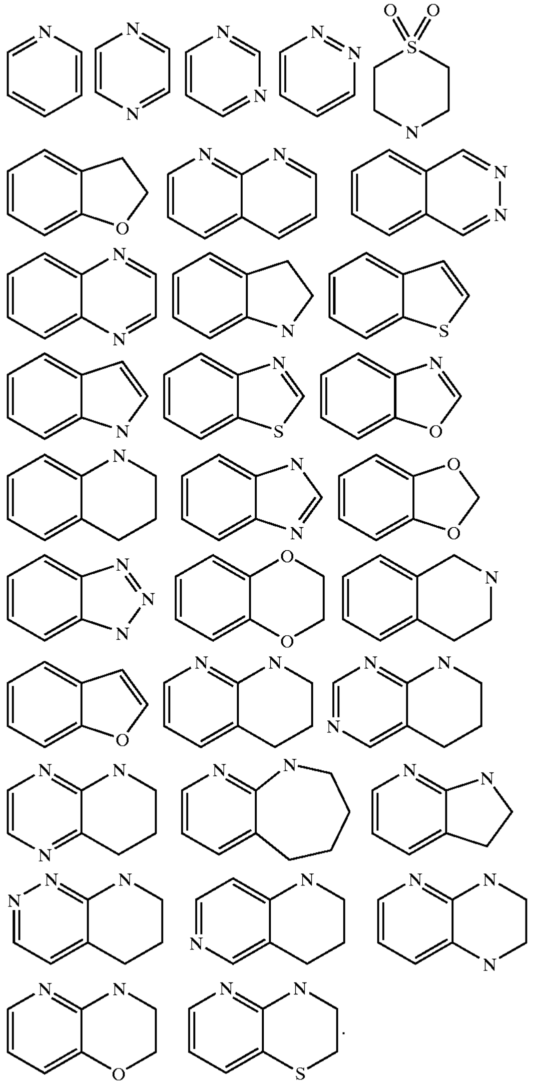

Unless otherwise specified, the term "substituted" means that a group is substituted by one or more substituents independently selected from the group consisting of hydroxy, alkyl, alkoxy, alkylthio, halogen, haloalkyl, haloalkoxy, alkylcarbonyl, haloalkylcarbonyl, arylcarbonyl, heterocyclylcarbonyl, aryl, aralkyl, heterocyclyl, heterocyclylalkyl, —CN, —C(=O)OH, alkoxycarbonyl, alkanoyloxy, alkanoylthio, nitro, —$N(R^a)_2$, —$N(R^a)(R^b)$, $NR^dS(=O)_2R^d$, —$NR^dC(=O)NR^dR^d$, —$NR^dS(=O)_2$ $NR^dR^d$, or —$NR^dC(=O)R^d$ and, in the case of heterocyclyl cycloalkyl groups, oxo.

Preferred compounds include:

(1R)-N-((6-fluoro-4'-(methyloxy)-1,1'-biphenyl-3-yl)methyl)-1-(4(methyloxy)phenyl)ethanamine;

(1R)-N-((4-(methyloxy)-3-(6-(methyloxy)-3-pyridinyl)phenyl)methyl)-1-(1-naphthalenyl)ethanamine;

(1R)-N-((3',6-bis(methyloxy)-1,1'-biphenyl-3-yl)methyl)-1-(3-(methyloxy)phenyl)ethanamine;

(1R)-N-((3',6-bis(methyloxy)-1,1'-biphenyl-3-yl)methyl)-1-(1naphthalenyl)ethanamine;

(1R)-N-((4-(methyloxy)-3-(6-(trifluoromethyl)-3-pyridinyl)phenyl)methyl)-1-phenylethanamine;

(1R)-1-(3-(methyloxy)phenyl)-N-((4-(methyloxy)-3-(6-(trifluoromethyl)-3-pyridinyl)phenyl)methyl)ethanamine;

(1R)-N-((3-(1-methyl-1H-indol-6-yl)-4-(methyloxy)phenyl)methyl)-1-(1-naphthalenyl)ethanamine;

(1R)-N-((3-(1-methyl-1H-indol-6-yl)-4-(methyloxy)phenyl)methyl)-1-phenylethanamine;

(1R)-N-((4-(methyloxy)-3-(6-((2,2,2-trifluoroethyl)oxy)-3-pyridinyl)phenyl)methyl)-1-phenylethanamine;

(1R)-1-(3-(methyloxy)phenyl)-N-((4-(methyloxy)-3-(6-((2,2,2-trifluoroethyl)oxy)-3-pyridinyl)phenyl)methyl)ethanamine;

(1R)-N-((3-(1-methyl-1H-benzimidazol-2-yl)-4-(methyloxy)phenyl)methyl)-1-(1-naphthalenyl)ethanamine;

(1R)-N-((3-(6-(ethyloxy)-3-pyridinyl)-4-(methyloxy)phenyl)methyl)-1-phenylethanamine;

(1R)-N-((3-(6-(ethyloxy)-3-pyridinyl)-4-(methyloxy)phenyl)methyl)-1-(1-naphthalenyl)ethanamine;

(1R)-N-((4-(methyloxy)-3-(1H-pyrrol-1-yl)phenyl)methyl)-1-(1-naphthalenyl)ethanamine;

(1R)-N-((4-(methyloxy)-3-(1-methyl-1H-pyrrolo[2,3-b]pyridin-5-yl)phenyl)methyl)-1-(3-(methyloxy)phenyl)ethanamine;

(1R)-N-((3-(1-methyl-1H-indazol-5-yl)-4-(methyloxy)phenyl)methyl)-1(1-naphthalenyl)ethanamine;

(1R)-N-((3-(1-methyl-1H-indazol-5-yl)-4-(methyloxy)phenyl)methyl)-1-phenylethanamine;

(1R)-1-(3-(methyloxy)phenyl)-N-((6-(methyloxy)-4'-(trifluoromethyl)-1,1'-biphenyl-3-yl)methyl)ethanamine;

(1R)-N-((4-(methyloxy)-3-(1H-pyrrol-1-yl)phenyl)methyl)-1-phenylethanamine;

(1R)-N-((4-(methyloxy)-3-(4-(methyloxy)-2-pyridinyl)phenyl)methyl)-1-phenylethanamine;

ethyl 4-(2-(methyloxy)-5-((((1R)-1-(1naphthalenyl)ethyl)amino)methyl)phenyl)-3,6-dihydro-1(2H)-pyridinecarboxylate;

(1R)-N-((6-(methyloxy)-3'-(trifluoromethyl)-1,1'-biphenyl-3-yl)methyl)-1-phenylethanamine;

(1R)-N-((3-(3-furanyl)-4-(methyloxy)phenyl)methyl)-1-(1-naphthalenyl)ethanamine;

(1R)-N-((3-(2,2-difluoro-1,3-benzodioxol-5-yl)-4-(methyloxy)phenyl)methyl)-1-(1-naphthalenyl)ethanamine;

(1R)-N-((3-(2,2-difluoro-1,3-benzodioxol-5-yl)-4-(methyloxy)phenyl)methyl)-1-phenylethanamine;

(1R)-N-((3-(2,2-difluoro-1,3-benzodioxol-5-yl)-4-(methyloxy)phenyl)methyl)-1-(3-(methyloxy)phenyl)ethanamine;

(1R)-N-((3-(3-furanyl)-4-(methyloxy)phenyl)methyl)-1-(3-(methyloxy)phenyl)ethanamine;

(1R)-N-((6-chloro-4'-((trifluoromethyl)oxy)-1,1'-biphenyl-3-yl)methyl)-1-phenylethanamine;

(1R)-N-((6-chloro-4'-((trifluoromethyl)oxy)-1,1'-biphenyl-3-yl)methyl)-1-(3-(methyloxy)phenyl)ethanamine;

(1R)-N-((4-(methyloxy)-3-(6-quinolinyl)phenyl)methyl)-1-(1-naphthalenyl)ethanamine;

(1R)-N-((4-(methyloxy)-3-(6-quinolinyl)phenyl)methyl)-1-phenylethanamine;

(1R)-N-((3-(2,1,3-benzoxadiazol-5-yl)-4-(methyloxy)phenyl)methyl)-1-(1-naphthalenyl)ethanamine;

(1R)-N-((4-(methyloxy)-3-(1-(2,2,2-trifluoroethyl)-1H-indol-5-yl)phenyl)methyl)-1-(1-naphthalenyl)ethanamine;

(1R)-N-((4-chloro-3-(6-((2,2,2-trifluoroethyl)oxy)-3-pyridinyl)phenyl)methyl)-1-(1-naphthalenyl)ethanamine;

(1R)-N-((3-(2,1,3-benzoxadiazol-5-yl)-4-(methyloxy)phenyl)methyl)-1-(3-(methyloxy)phenyl)ethanamine;

(1R)-N-((3-(2,1,3-benzoxadiazol-5-yl)-4-(methyloxy)phenyl)methyl)-1-phenylethanamine;

(1R)-N-((3-(2,3-dihydro-1-benzofuran-5-yl)-4-(methyloxy)phenyl)methyl)-1-phenylethanamine;

(1R)-N-((3-(2,3-dihydro-1-benzofuran-5-yl)-4-(methyloxy)phenyl)methyl)-1-(3-(methyloxy)phenyl)ethanamine;

(1R)-N-((3-(2,3-dihydro-1-benzofuran-5-yl)-4-(methyloxy)phenyl)methyl)-1-(1-naphthalenyl)ethanamine;

(1R)-N-((4'-fluoro-6-(methyloxy)-1,1'-biphenyl-3-yl)methyl)-1-(3-fluorophenyl)ethanamine;

(1R)-N-((4',6-bis(trifluoromethyl)-1,1'-biphenyl-3-yl)methyl)-1-(3-(methyloxy)phenyl)ethanamine;

(1R)-N-((3-(2,1,3-benzothiadiazol-5-yl)-4-(methyloxy)phenyl)methyl)-1-phenylethanamine;

(1R)-N-((3-(2,1,3-benzothiadiazol-5-yl)-4-(methyloxy)phenyl)methyl)-1-(3-(methyloxy)phenyl)ethanamine;

(1R)-N-((3-(1-benzothien-3-yl)-4-(methyloxy)phenyl)methyl)-1-phenylethanamine;

1-(3-fluorophenyl)-N-((6-(methyloxy)-4'-(trifluoromethyl)-1,1'-biphenyl-3-yl)methyl)ethanamine;

1-(3-bromophenyl)-N-((6-(methyloxy)-4'-(trifluoromethyl)-1,1'-biphenyl-3-yl)methyl)ethanamine;

1-(3,5-difluorophenyl)-N-((6-(methyloxy)-4'-(trifluoromethyl)-1,1'-biphenyl-3-yl)methyl)ethanamine;

(1R)-N-((3-(1,3-benzothiazol-2-yl)-4-(methyloxy)phenyl)methyl)-1-(3-(methyloxy)phenyl)ethanamine;

(1R)-N-((6-chloro-4'-((trifluoromethyl)oxy)-1,1'-biphenyl-3-yl)methyl)-1-(1-naphthalenyl)ethanamine;

(1R)-N-((4'-chloro-6-(methyloxy)-1,1'-biphenyl-3-yl)methyl)-1-phenylethanamine;

(1R)-N-((4-(methyloxy)-3-(6-quinoxalinyl)phenyl)methyl)-1-(1-naphthalenyl)ethanamine;

(1R)-N-((6-(methyloxy)-3'-((trifluoromethyl)oxy)-1,1'-biphenyl-3-yl)methyl)-1-phenylethanamine;

(1R)-N-((6-iodo-4'-(trifluoromethyl)-1,1'-biphenyl-3-yl)methyl)-1-(1-naphthalenyl)ethanamine;

(1R)-N-((6-iodo-4'-(trifluoromethyl)-1,1'-biphenyl-3-yl)methyl)-1-(3-(methyloxy)phenyl)ethanamine;

(1R)-N-((4'-chloro-6-(methyloxy)-1,1'-biphenyl-3-yl)methyl)-1-(1-naphthalenyl)ethanamine;

(1R)-N-((3-(2-methyl-1,3-oxazol-4-yl)-4-(methyloxy)phenyl)methyl)-1-phenylethanamine;

(1R)-N-((3-(2-methyl-1,3-oxazol-4-yl)-4-(methyloxy)phenyl)methyl)-1-(1-naphthalenyl)ethanamine;

ethyl 2'-(methyloxy)-5'-((((1R)-1-phenylethyl)amino)methyl)-1,1'-biphenyl-4-carboxylate;

ethyl 2'-(methyloxy)-5'-((((1R)-1-(1-naphthalenyl)ethyl)amino)methyl)-1,1'-biphenyl-4-carboxylate;

4-(2-(methyloxy)-5-((((1R)-1-phenylethyl)amino)methyl)phenyl)-1,3-thiazol-2-amine;

(1R)-N-((3-(1-(cyclopropylmethyl)-1H-indol-5-yl)-4-(methyloxy)phenyl)methyl)-1-phenylethanamine;

(1R)-N-((6-(methyloxy)-4'-(trifluoromethyl)-1,1'-biphenyl-3-yl)methyl)-1-phenylethanamine;

(1R)-N-((3-(1-(cyclopropylmethyl)-1H-indol-5-yl)-4-(methyloxy)phenyl)methyl)-1-(1-naphthalenyl)ethanamine;

(1R)-N-((4-(methyloxy)-3-(2-((tetrahydro-2-furanylmethyl)oxy)-3-pyridinyl)phenyl)methyl)-1-phenylethanamine;

(1R)-N-((3-(2-fluoro-3-pyridinyl)-4-(methyloxy)phenyl)methyl)-1-phenylethanamine;

N,N-dimethyl-5-(2-(methyloxy)-5-((((1R)-1-phenylethyl)amino)methyl)phenyl)-2-pyridinamine;

(1R)-N-((4-(methyloxy)-3-(1-methyl-2-(trifluoromethyl)-1H-benzimidazol-5-yl)phenyl)methyl)-1-(1-naphthalenyl)ethanamine;

(1R)-N-((4-(methyloxy)-3-(1-methyl-2-(trifluoromethyl)-1H-benzimidazol-5-yl)phenyl)methyl)-1-phenylethanamine;

(1R)-N-((4-(methyloxy)-3-(2-thienyl)phenyl)methyl)-1-phenylethanamine;

(1R)-N-((4-(methyloxy)-3-(2-thienyl)phenyl)methyl)-1-(1-naphthalenyl)ethanamine;

(1R)-1-(3-(methyloxy)phenyl)-N-((4-(methyloxy)-3-(2-thienyl)phenyl)methyl)ethanamine;

(1R)-N-((4-(methyloxy)-3-(6-methyl-3-pyridinyl)phenyl)methyl)-1-(1naphthalenyl)ethanamine;

(1R)-N-((4-(methyloxy)-3-(2-pyridinyl)phenyl)methyl)-1-(1-naphthalenyl)ethanamine;

(1R)-N-((3-(1,3-benzoxazol-5-yl)-4-(methyloxy)phenyl)methyl)-1-(1-naphthalenyl)ethanamine (1R)-N-((3-(2-methyl-1,3-benzoxazol-5-yl)-4-(methyloxy)phenyl)methyl)-1-phenylethanamine;

2'-(methyloxy)-5'-((((1R)-1-phenylethyl)amino)methyl)-1,1'-biphenyl-3-carbonitrile;

(1R)-N-((6-(methyloxy)-4'-((trifluoromethyl)oxy)-1,1'-biphenyl-3-yl)methyl)-1-(1-naphthalenyl)ethanamine;

(1R)-1-(3-fluorophenyl)-N-((6-(methyloxy)-4'-(trifluoromethyl)-1,1'-biphenyl-3-yl)methyl)ethanamine;

(1R)-N-((6-(ethyloxy)-4'-(methyloxy)-1,1'-biphenyl-3-yl)methyl)-1-phenylethanamine;

(1R)-N-((4-(methyloxy)-3-(3-pyridinyl)phenyl)methyl)-1-(1-naphthalenyl)ethanamine;

(1R)-N-((4-(methyloxy)-3-(6-(trifluoromethyl)-3-pyridinyl)phenyl)methyl)-1-(1-naphthalenyl)ethanamine;

(1R)-N-((4-(methyloxy)-3-(6-((2,2,2-trifluoroethyl)oxy)-3-pyridinyl)phenyl)methyl)-1-(1-naphthalenyl)ethanamine;

(1R)-1-(3-chlorophenyl)-N-((6-(methyloxy)-4'-(trifluoromethyl)-1,1'-biphenyl-3-yl)methyl)ethanamine;

(1R)-1-(3-(methyloxy)phenyl)-N-((4-(methyloxy)-3-(3-pyridinyl)phenyl)methyl)ethanamine;

2'-(methyloxy)-5'-((((1R)-1-(1-naphthalenyl)ethyl)amino)methyl)-1,1'-biphenyl-3-carbonitrile;

(1R)-N-((2'-fluoro-1,1'-biphenyl-3-yl)methyl)-1-(4-methylphenyl)ethanamine;

(1R)-N-((6-(methyloxy)-1,1'-biphenyl-3-yl)methyl)-1-(4-methylphenyl)ethanamine;

(1R)-N-((4-(methyloxy)-3-(6-(methyloxy)-3-pyridazinyl)phenyl)methyl)-1-(3-(methyloxy)phenyl)ethanamine;

(1R)-N-((4-(methyloxy)-3-(2-pyrazinyl)phenyl)methyl)-1-(1-naphthalenyl)ethanamine;

(1R)-N-((4-(methyloxy)-3-(6-((tetrahydro-2-furanylmethyl)oxy)-3-pyridinyl)phenyl)methyl)-1-phenylethanamine;

(1R)-N-((4-(methyloxy)-3-(2-(4-morpholinyl)-3-pyridinyl)phenyl)methyl)-1-phenylethanamine;

(1R)-N-((3-(1-methyl-1H-imidazol-4-yl)-4-(methyloxy)phenyl)methyl)-1(1-naphthalenyl)ethanamine;

(1R)-N-((4-(methyloxy)-3-(1-pyrrolidinyl)phenyl)methyl)-1-phenylethanamine;

ethyl 2'-(methyloxy)-5'-((((1R)-1-(3-(methyloxy)phenyl)ethyl)amino)methyl)-1,1'-biphenyl-4-carboxylate;

N-((6-(methyloxy)-4'-(trifluoromethyl)-1,1'-biphenyl-3-yl)methyl)-1-(3-methylphenyl)ethanamine;

(1R)-N-((6-fluoro-4'-(trifluoromethyl)-1,1'-biphenyl-3-yl)methyl)-1phenylethanamine;

N,N-dimethyl-2'-(methyloxy)-5'-((((1R)-1-(3-(methyloxy)phenyl)ethyl)amino)methyl)-1,1'-biphenyl-4-carboxamide;

N,N-dimethyl-2'-(methyloxy)-5'-((((1R)-1-(1-naphthalenyl)ethyl)amino)methyl)-1,1'-biphenyl-4-carboxamide;

N,N-dimethyl-2'-(methyloxy)-5'-((((1R)-1-phenylethyl)amino)methyl)-1,1'-biphenyl-4-carboxamide;

(1R)-N-((6-iodo-4'-(trifluoromethyl)-1,1'-biphenyl-3-yl)methyl)-1-phenylethanamine;

(1R)-N-((6-(methyloxy)-3'-((trifluoromethyl)oxy)-1,1'-biphenyl-3-yl)methyl)-1-(1-naphthalenyl)ethanamine;

(1R)-1-(3-(methyloxy)phenyl)-N-((6-(methyloxy)-3'-((trifluoromethyl)oxy)-1,1'-biphenyl-3-yl)methyl)ethanamine;

(1R)-N-((4'-chloro-6-(methyloxy)-1,1'-biphenyl-3-yl)methyl)-1-(3(methyloxy)phenyl)ethanamine;

(1R)-1-(3-(methyloxy)phenyl)-N-((4-(methyloxy)-3-(2-((2,2,2-trifluoroethyl)oxy)-5-pyrimidinyl)phenyl)methyl)ethanamine;

(1R)-N-((4-(methyloxy)-3-(6-quinoxalinyl)phenyl)methyl)-1-phenylethanamine;

(1R)-N-((3-(1,3-benzothiazol-2-yl)-4-(methyloxy)phenyl)methyl)-1-phenylethanamine;

(1R)-N-((6-((2-(methyloxy)ethyl)oxy)-4'-(trifluoromethyl)-1,1'-biphenyl-3-yl)methyl)-1-(3-(methyloxy)phenyl)ethanamine;

(1R)-N-((4-(methyloxy)-3-(2-naphthalenyl)phenyl)methyl)-1-(3-(methyloxy)phenyl)ethanamine;

(1R)-N-((4-(methyloxy)-3-(2-naphthalenyl)phenyl)methyl)-1-(1-naphthalenyl)ethanamine;

(1R)-N-((4-(methyloxy)-3-(2-naphthalenyl)phenyl)methyl)-1-phenylethanamine;

(1R)-N-((6-chloro-4'-(trifluoromethyl)-1,1'-biphenyl-3-yl)methyl)-1-phenylethanamine;

(1R)-N-((4-(methyloxy)-3-(1-(2,2,2-trifluoroethyl)-1H-indol-5-yl)phenyl)methyl)-1-phenylethanamine;

(1R)-N-((6-((2-(methyloxy)ethyl)oxy)-4'-(trifluoromethyl)-1,1'-biphenyl-3-yl)methyl)-1-(1-naphthalenyl)ethanamine;

(1R)-N-((6-((2-(methyloxy)ethyl)oxy)-4'-(trifluoromethyl)-1,1'-biphenyl-3-yl)methyl)-1-phenylethanamine;

(1R)-1-(3-(methyloxy)phenyl)-N-((4-(methyloxy)-3-(6-quinolinyl)phenyl)methyl)ethanamine;

2'-(methyloxy)-5'-((((1R)-1-(1-naphthalenyl)ethyl)amino)methyl)-1,1'-biphenyl-3-carboxamide;

(1R)-1-(1-naphthalenyl)-N-((3-(6-(trifluoromethyl)-3-pyridinyl)phenyl)methyl)ethanamine;

(1R)-N-((3-(3-furanyl)-4-(methyloxy)phenyl)methyl)-1-phenylethanamine;

(1R)-N-((6-(methyloxy)-3'-(trifluoromethyl)-1,1'-biphenyl-3-yl)methyl)-1-(1-naphthalenyl)ethanamine;

(1R)-N-((4-(methyloxy)-3-(2-methyl-1,3-thiazol-4-yl)phenyl)methyl)-1-(3-(methyloxy)phenyl)ethanamine;

(1R)-N-((4-((difluoromethyl)oxy)-3-(3-pyridinyl)phenyl)methyl)-1-(1-naphthalenyl)ethanamine;

(1R)-N-((3-(2-methyl-2H-indazol-5-yl)-4-(methyloxy)phenyl)methyl)1-(1-naphthalenyl)ethanamine;

(1R)-N-((4-(methyloxy)-3-(5-(trifluoromethyl)-1,3,4-oxadiazol-2-yl)phenyl)methyl)-1-(1-naphthalenyl)ethanamine;

(1R)-N-((4-chloro-3-(3-pyridinyl)phenyl)methyl)-1-(3-(methyloxy)phenyl)ethanamine;

(1R)-N-((3-(2-ethyl-2H-1,2,3-benzotriazol-5-yl)-4-(methyloxy)phenyl)methyl)-1-phenylethanamine; and (1R)-N-((4',6-difluoro-1,1'-biphenyl-3-yl)methyl)-1-(3-(methyloxy)phenyl)ethanamine Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt. The (R) isomer is generally preferred.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hyroxy-ethanesulfonate, lactate, maleate, mandelate, methansulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. Other examples include salts with alkali metals or alkaline earth metals, such as sodium, potassium, calcium or magnesium or with organic bases. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$–$C_4$)alkyloxy)ethyl; for example, methoxyethyl, ethoxyethyl, propoxyethyl, iso-propoxyethyl, etc.; 2-oxo-1, 3-dioxolen-4-ylmethyl groups, such as 5-methyl-2-oxo-1,3, dioxolen-4-ylmethyl, etc.; $C_1$–$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as solvates and/or hydrates of the parent compounds or their pharmaceutically acceptable salts. All of such forms likewise are to be construed as falling within the scope of the invention.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, orthomethylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis (dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

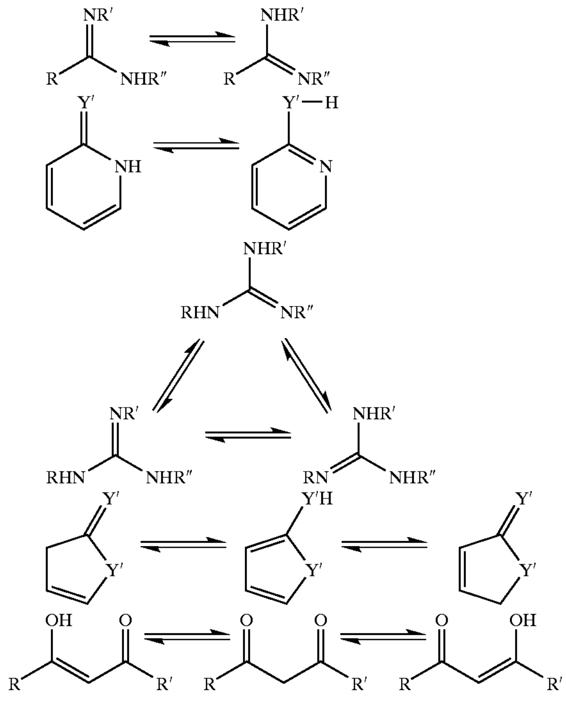

and though one form is named, described, displayed and/or claimed herein, all the tautomeric forms are intended to be inherently included in such name, description, display and/or claim.

A "derivative" of a compound of the invention includes salts, isomers, enantiomers, prodrugs, and metabolites of the compound.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek, *Drug Metabolism Reviews* 165 q (1988) and Bundgaard, *Design of Prodrugs*, Elsevier (1985). One method of preparing a prodrug of a compound is by masking one or more potentially reactive groups on the compound, such as carboxylates, hydroxy groups, and amines. Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard, *J. Med. Chem.* 2503 (1989)). Also, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little, Apr. 11, 1981) discloses Mannich-base hydroxamic acid prodrugs, their preparation and use.

Experimental

General:

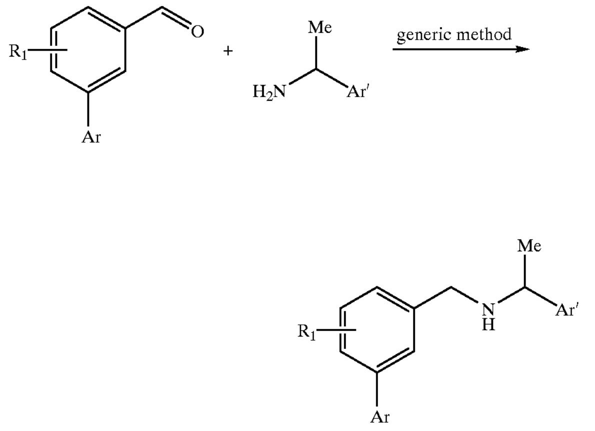

Method A: the aldehyde (1.6 mmol) is dissolved in methanol (5 mL) and the amine (1.9 mmol) is added. The reaction is shaken for 24 hours or until imine formation is complete (as monitored by LCMS), then solid supported borohydride is added (prepared according to Kabalka, G. W.; Wadgaonkar, P. P.; Chatla, N.; *Synth. Commun.*; (1990), 20 (2), 293–299) (ca 2.5 mmol/g; 3.1 mmol) and the mixture is shaken for 24 hours or until reduction is complete (as monitored by LCMS). Dichloromethane (ca 3 mL) is then added followed by Wang-aldehyde resin (4-benzyloxybenzaldehyde, polymer-bound; ca 1.25 mmol/g; 0.6 mmol) and the mixture is shaken for further 24 hours. The resins are filtered off and the solvents are evaporated under reduced pressure, to afford an oil which is purified by column chromatography (usually Hexane/AcOEt 7/3 or DCM/MeOH 95/5). The free-base oil is then treated with 1.5–2.5 1N HCl in diethyl ether and the solvents are evaporated under reduced pressure to afford the mono or bis-HCl salt.

Method B: the aldehyde (1.6 mmol) is dissolved in methanol (5 mL) and the amine (1.9 mmol) is added. The reaction is heated to reflux for 10 minutes then left to cool overnight until imine formation is complete (as monitored by LCMS). Solid supported cyanoborohydride is added (prepared according to Sande, A. R.; Jagadale, M. H.; Mane, R. B.; Salunkhe, M. M.; *Tetrahedron Lett.* (1984), 25 (32), 3501–4) (ca 2.5 mmol/g; 3.1 mmol) and the mixture is heated at 50 C for 15 hours or until reduction is complete (as monitored by LCMS). Dichloromethane (ca 3 mL) is then added followed by Wang-aldehyde resin (4-benzyloxybenzaldehyde, polymer-bound; ca 1.25 mmol/g; 0.6 mmol) and the mixture is shaken for further 24 hours. The resins are filtered off and the solvents are evaporated under reduced pressure, to afford an oil which is purified by column chromatography (usually Hexane/AcOEt 7/3 or DCM/MeOH 95/5). The free-base oil is then treated with 1.5–2.5 1N HCl in diethyl ether and the solvents are evaporated under reduced pressure to afford the mono or bis-HCl salt.

Method C: The aldehyde is (1.6 mmol) is dissolved in 1,2-dichloroethane (12 mL) and the amine (1.9 mmol) is added, followed by acetic acid (0.09 mL, 1.6 mmol) and finally sodium triacetoxyborohydride (500 mg, 2.4 mmol). The mixture is stirred overnight or until complete by TLC; upon reaction completion, the mixture is diluted with ethyl acetate, washed with saturated $NaHCO_3$ then with saturated brine, and finally dried over sodium sulphate. The solvents are evaporated under reduced pressure, to afford an oil which is purified by column chromatography on silica gel (usually Hexane/AcOEt 7/3 or DCM/MeOH 95/5). The free-base oil is then treated with 1.5–2.5 equivalents 1N HCl in diethyl ether and the solvents are evaporated under reduced pressure to afford the mono or bis-HCl salt.

Method D: Compounds wherein both $R^3$ and $R^4$ are other than hydrogen can be prepared by combining an appropriately substituted phenylacetic acid with a strong base such as lithium diisopropylamide or the like at a temperature between −78 and 20° C. to yield a red dianion. The dianion is then reacted with an alkylating agent of formula $R^3$-Z, wherein Z is a halide, a sulfonate, or other suitable leaving group to provide an $R^3$ substituted compound. Treatment of the compound thus obtained with a strong base such as lithium diisopropylamide or the like at a temperature between −78 and 20° C. yields a second red dianion, which is reacted with an alkylating agent of formula $R^4$-Z, wherein Z is a halide, a sulfonate, or other suitable leaving group to yield the $R^3$, $R^4$ disubstituted compound. Treatment of the resultant carboxylic acid with diphenylphosphoryl azide in a refluxing solvent (for example toluene, benzene, chlorobenzene, 1,4-dioxane or the like), followed by aqueous workup yields the $R^3$ substituted $R^4$amine. Reductive coupling of the amine with an aldehyde or ketone according to Method C affords the final product.

Method E: Compounds wherein only one of $R^3$ and $R^4$ is hydrogen can be prepared by reacting the α-monosubstituted carboxylic acid obtained by reacting an appropriately substituted phenylacetic acid with a strong base such as lithium diisopropylamide and then with an alkylating agent of formula $R^3$-Z as described above with diphenylphosphoryl azide in a refluxing solvent such as, for example, toluene, benzene, chlorobenzene, 1,4-dioxane, etc. followed by an aqueous workup to yield a mono-α-substituted amine. This amine can then be reacted with an aldehyde or ketone according to Method C to obtain the final product.

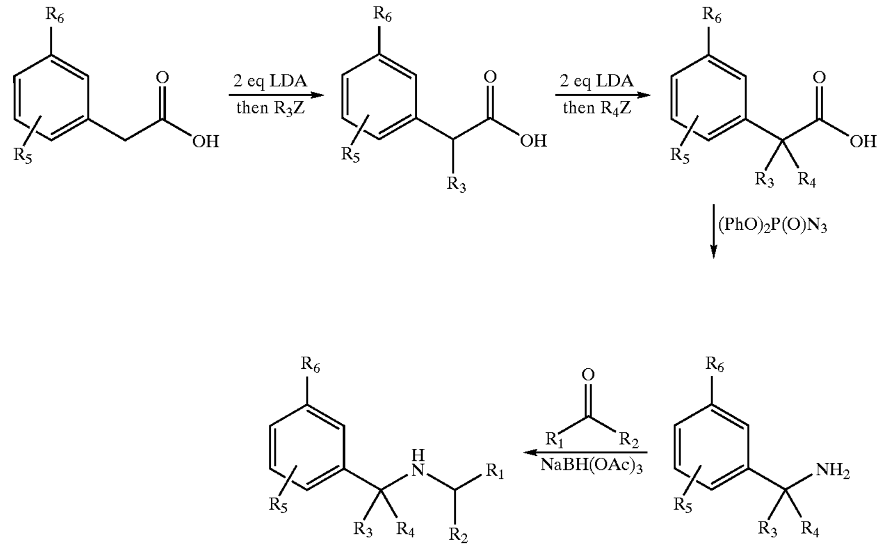

The following examples are representative of the invention, but are not to be construed as limiting the claimed invention in any way. The structure of the prepared compounds is verified by mass spectral data; $C^{13}$ NMR data is also provided for some compounds. For some compounds, ions having mass greater than M+H are reported. These ions generally represent dimers or trimers of the synthesized compound, and in some instances represent trifluoroacetate adducts generated from the mobile phase of the LC/MS. The trifluoroacetate adducts will have a weight of M+115.

EXAMPLE 1

(R)-N-(1-phenylethyl)-N-((4-acetamido-3-(4-methoxyphenyl)phenylmethyl)amine

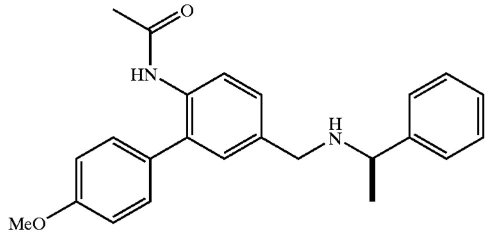

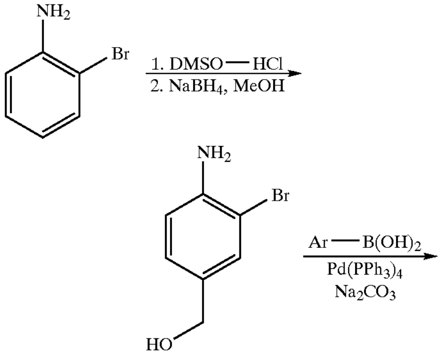

-continued

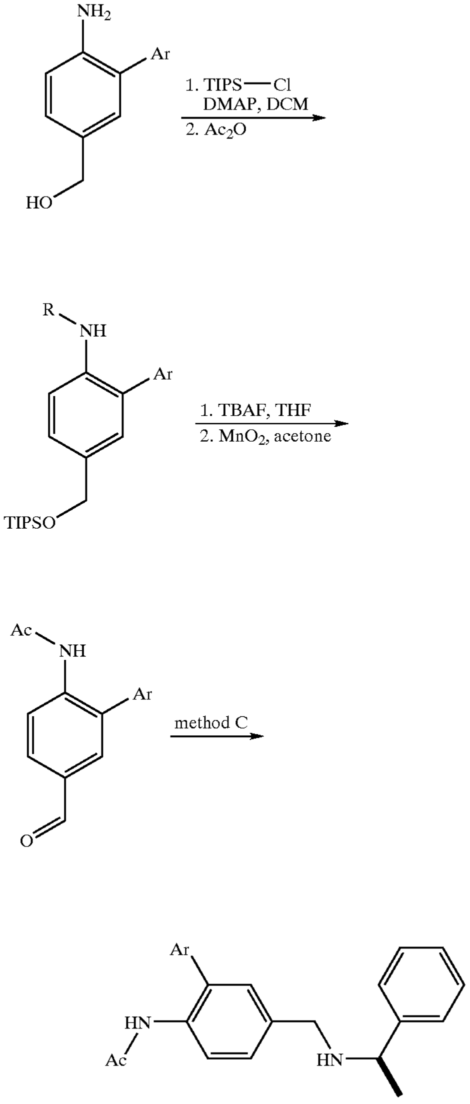

Step 1) 2-bromo-4-hydroxymethylaniline:

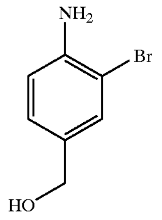

To a solution of 4-amino-3-bromobenzaldehyde (2.6 g, 13 mmol) (prepared as in *J. Chem. Soc., Perkin Trans.* 1 (1992), 2235) in methanol (130 mL) solid supported borohydride 6.2 g, 15.5 mmol) was added. The reaction was stirred for 1.5 hours at room temperature, then the resin filtered off and rinsed with little methanol. The filtrate was concentrated in vacuo to give 2.58 g of a brown oil.

$C_7H_8BrNO$ Mass (calculated) [202.05]; (found) [$M^+$]=202 (bromine); Lc Rt=0.63, 89%.

Step 2) 4-Hydroxymethyl-2-(4'-methoxyphenyl)aniline:

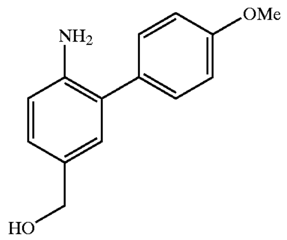

To a degassed solution of crude 2-bromo-4-hydroxymethylaniline (3.2 g, 15.8 mmol), 4-methoxybenzeneboronic acid (2.89 g, 19 mmol) and potassium carbonate (4.77 g, 34.8 mmol) in toluene/ethanol 2/1 (45 mL) a catalytic amount of $Pd(PPh_3)_4$ (0.2 g, 1 mmol %) was added and the mixture was heated at 90 C for 5 hours. The residue was extracted into ethyl acetate and washed with water and then saturated brine and dried over sodium sulphate. The solvent was removed under reduced pressure to afford 5 g of crude product. $C_{14}H_{15}BNO_2$ Mass (calculated) [229.28]; (found) [$M+H^+$]=230 Lc Rt=0.88, 89%. NMR (400 MHz, CDC13): 3.75 (3H, s, MeO); 4.5 (2H, s, $CH_2O$); 6.65 (1H, d, J=8.5 Hz, aryl-H); 6.9 (2H, d, J=8.5 Hz, aryl-H); 7–7.1 (2H, m, aryl-H); 7.25 (2H, d, J=8.5 Hz, aryl-H).

Step 3) 4-Tri-isopropoxymethyl-2-(4'-methoxyphenyl) aniline:

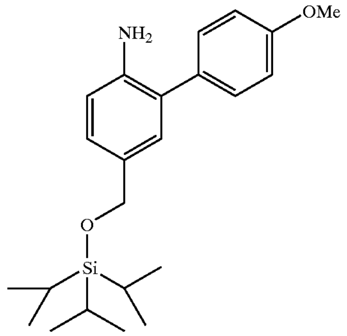

To a solution of the crude alcohol from Step2 and 4-dimethylaminopyridine (2.12 g, 17.4 mmol) in dichloromethane (45 mL) tri-isopropylsilyl chloride (3.05 g, 15.8 mmol) was added. The reaction was stirred at room temperature for 16 hours and then diluted with dichloromethane and washed with water. The organic phase was dried over sodium sulphate and the solvent removed in vacuo. The crude was purified by column (silica, 5%-10 AcOEt in hexane to 10% methanol in AcOEt) to give 4.70 g of title compound.

$C_{23}H_{35}NO_2Si$ Mass (calculated) [385.63]; (found) [$M+H^+$]=386 Lc Rt=1.77.

Step 4) 4-Tri-isopropoxymethyl-2-(4'-methoxyphenyl) acetanilide:

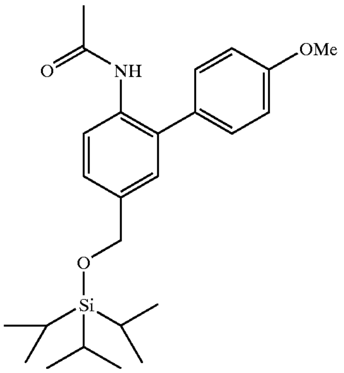

To a solution of 4-tri-isopropoxymethyl-2-(4'-methoxyphenyl)aniline (1.57 g, 4.07 mmol) and 4-pyridine (0.35 mg, 4.48 mmol) in dichloromethane (9 mL), acetic anhydride (0.4 mL, 4.27 mmol) was added and the reaction stirred at room temperature for 72 hours. The reaction mixture was then diluted with dichloromethane and washed with saturated ammonium chloride and water, then dried over sodium sulphate to afford 1.87 g of a solid.

$C_{25}H_{37}NO_3Si$ Mass (calculated) [427.66]; (found) [M+H+]=428; Lc Rt=2.10.

Step 5) 4-Hydroxymethyl-2-(4'-methoxyphenyl)acetanilide:

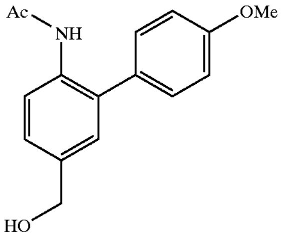

Tetra-butylammonium fluoride (4.48 mL of a 1M solution in THF) was added to a solution of 4-tri-isopropoxymethyl-2-(4'-methoxyphenyl)acetanilide (1.87 g, 4.07 mmol) in THF (12 mL) and stirred for 2 hours. The reaction was diluted with ethyl acetate and washed with saturated ammonium chloride then water and finally dried over sodium sulphate. The solvent was evaporated to afford 1.66 g of a yellow oil.

$C_{16}H_{17}NO_3$ Mass (calculated) [271.32]; (found) [$M+H^+$]=272; Lc Rt=0.95.

Step 6) 4-Acetamido-3-(4'-methoxyphenyl)benzaldehyde:

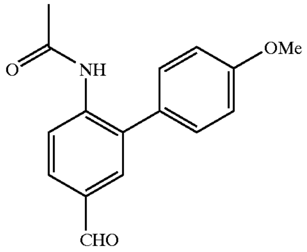

Manganese dioxide (1.77 g, 20.3 mmol) was added portionwise to a stirred solution of the crude alcohol (1.66 g) from step 5 in acetone (12 mL). The reaction was stirred at room temperature for 20 hours, then refluxed for a further 8 hours. The reaction mixture was then filtered on paper and the solvent removed under reduced pressure. The crude was purified on silica (hexane/AcOEt 3/1) to give 0.6 g of title product.

$C_{16}H_{15}NO_3$ Mass (calculated) [269.30]; (found) [$M+H^+$]=270; Lc Rt=1.21. NMR (400 MHz, $CDCl_3$): 2.6 (3H, s, $CH_3CO$); 3.86 (3H, s, MeO); 6.96 (2H, d, J=8.5 Hz, aryl-H); 7.3 (2H, d, J=8.5 Hz, aryl-H); 7.44 (1H, bs, NH); 7.72 ((1H, d, J=2 Hz, aryl-H); 7.84 (1H, dd, J=2 and 8.5 Hz, aryl-H); 8.6 (1H, bd, J=8.5 Hz, aryl-H); 9.5 (1H, s, CHO).

Step 7) (R)-N-(1-Phenylethyl)-N-((4-acetamido-3-(4-methoxyphenyl)phenylmethyl)amine:

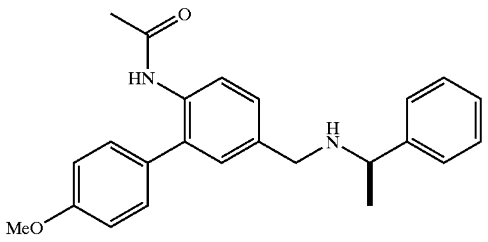

The title compound was prepared from N-[4-formyl-2-(4-methoxyphenyl)phenyl]acetamide and (R)-α-methylbenzylamine according to general procedure C.

$C_{24}H_{26}N_2O_2$ Mass (calculated): [374]; (found): [$M+H^+$]=375. NMR (400 MHz, $CDCl_3$): 1.3 (3H, d, J=6 Hz, $NCHCH_3$); 1.95 (3H, s, $CH_3CO$); 3.5 and 3.55 (2H, dd, J=12 Hz, $CH_2N$); 3.7 (1H, q, J=6 Hz, NC<u>H</u>Me); 3.75 (3H, s, MeO); 6.9 (2H, d, J=8 Hz, aryl-H); 7–7.1 (2H, m, aryl-H); 7.1–7.35 (7H, m, aryl-H); 8.1 (1H, d, J=8 Hz, aryl-H).

EXAMPLE 2

(R)-N-(1-(3-Methoxyphenyl)ethyl)-N-((4-acetamido-3-(4-methoxyphenyl)phenylmethyl)amine

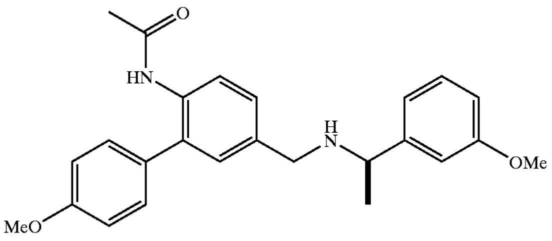

The title compound was prepared from N-[4-formyl-2-(4-methoxyphenyl)phenyl]acetamide and (R)-3-methoxy-α-methylbenzylamine according to general procedure C.

$C_{25}H_{28}N_2O_3$ Mass (calculated): [404]; (found): [$M+H^+$]=254, 405. NMR (400 MHz, $CDCl_3$): 1.3 (3H, d, J=6 Hz, $NCHCH_3$); 1.95 (3H, s, $CH_3CO$); 3.5 and 3.55 (2H, dd, J=12 Hz, $CH_2N$); 3.7–3.75 (4H, m, MeO and NCHMe); 3.75 (3H, s, MeO); 6.7 (1H, dd, J=1 and 8 Hz, aryl-H); 6.75–6.8 (2H, m, aryl-H); 6.9 (2H, d, J=8 Hz, aryl-H); 7–7.1 (2H, m, aryl-H); 7.1–7.35 (3H, m, aryl-H); 8.1 (1H, d, J=8 Hz, aryl-H).

EXAMPLE 3

(R)-N-(1-(1-Naphthyl)ethyl)-N-((4-acetamido-3-(4-methoxyphenyl)-phenylmethyl)amine

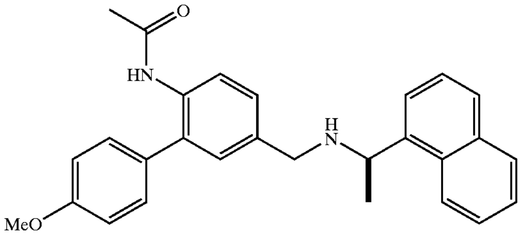

The title compound was prepared from N-[4-formyl-2-(4-methoxyphenyl)-phenyl]acetamide and (R)-1-(1-naphthyl)ethylamine according to general procedure C.

$C_{28}H_{28}N_2O_2$ Mass (calculated): [424]; (found): [$M+H^+$]=425, 254. NMR (400 MHz, $CDCl_3$): 1.45 (3H, d, J=6 Hz, $NCHCH_3$); 1.95 (3H, s, $CH_3CO$); 3.6 and 3.65 (2H, dd, J=12 Hz, $CH_2N$); 3.8 (3H, s, MeO); 4.65 (1H, q, J=6 Hz, NCHMe); 6.9 (2H, d, J=8 Hz, aryl-H); 7.0–7.05 (2H, m, aryl-H); 7.1–7.15 (2H, m, aryl-H); 7.35–7.5 (3H, m, aryl-H); 7.7 (2H, d, J=8 Hz, aryl-H); 7.75–7.85 (1H, m, aryl-H); 8–8.05 (1H, m, aryl-H); 8.1 (1H, d, J=8 Hz, aryl-H).

EXAMPLE 4

(R)-N-(1-Phenylethyl)-N-((4-methoxy-3-(1-methylbenzimidazol-5-yl)phenylmethyl)amine

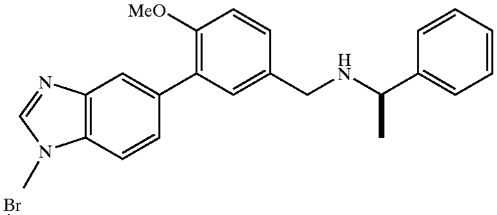

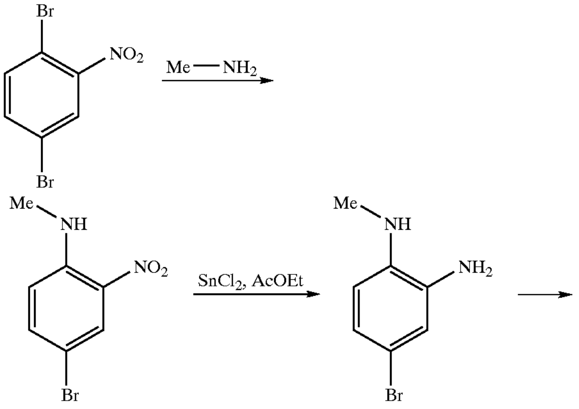

-continued

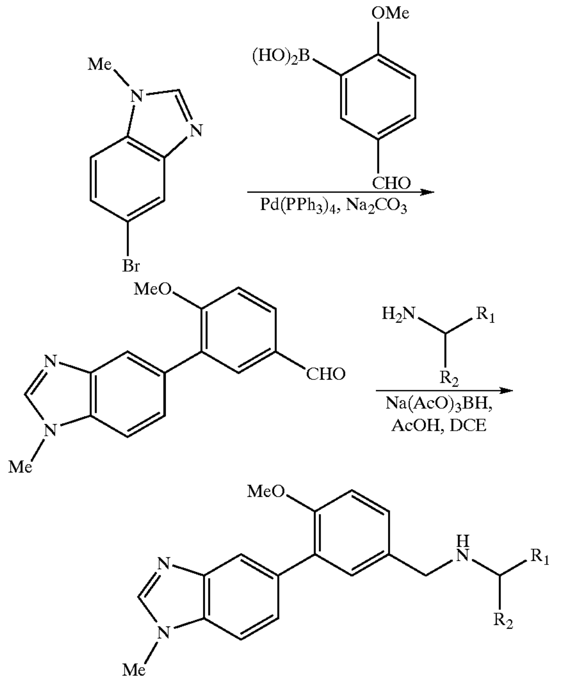

Step 1) N-Methyl-4-bromo-2-nitroaniline/(4-Bromo-2-nitrophenyl)methylamine

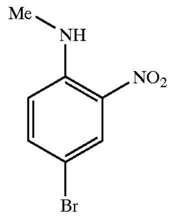

2,5-Dibromobenzene (5 g, 17.8 mmol) was added to a solution of methylamine (13.8 mL of a 40% aq. solution) and the mixture was stirred for 16 hours, then 8 mL of THF were added and the reaction was stirred for 2 hours at room temperature and then for further 2 hours at 50° C. The reaction mixture was then cooled and extracted twice into ethyl acetate. The solvent was removed under reduced pressure and the crude was chromatographed (silica, AcOEt 2–10% in hexane) to afford 2 g of orange crystals.

NMR (400 MHz, $CDCl_3$): 2.95 (3H, d, J=5 Hz, NCH3); 3.92 (3H, s, MeN); 6.7 (d, J=8.5 Hz, aryl-H); 7.45 (1H, dd, J=2 and 8.5 Hz, aryl-H); 7.9 (1H, bs, NH); 8.2 (1H, d, J=2 Hz, aryl-H).

Step 2) 2-N-Methylamino-5-bromoaniline/(2-Amino-4-bromophenyl)methylamine

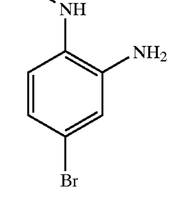

A solution of the nitroaniline from Step 1 (1.56 g, 6.75 mmol) and tin(II) chloride (7.62 g, 33.7 mmol) in ethyl acetate (40 mL) was refluxed under nitrogen for 3 hours. The mixture was then poured onto ice, neutralized with saturated $NaHCO_3$ and extracted into ethyl acetate. The organic layer was washed with brine and dried over sodium sulphate to afford 1.5 g of crude red oil which was used without further purification.

$C_7H_9BrO_2$Mass (calculated): [201.07]; (found): [M+]=201 (bromine). NMR (400 MHz, MeOH-$d_4$): 3.88 (3H, s, MeO); 2.8 (3H, s, MeN); 6.7 (1H, d, J=8.5 Hz, aryl-H); 6.85 (1H, dd, J=2 and 8.5 Hz, aryl-H); 6.9 (1H, d, J=2 Hz, aryl-H).

Step 3) 5-Bromo-1-methylbenzimidazole:

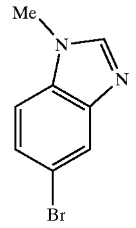

A solution of 2-N-methylamino-5-bromoaniline (1 g, 4.97 mmol) in triethyl orthoformate (30 mL) was refluxed for 5 hours. The solvent was removed under reduced pressure to afford 1 g of the title bromobenzimidazole.

$C_8H_7BrN_2$ Mass (calculated): [211.06]; (found): [M+]=211 (bromine). NMR (400 MHz, MeOH-$d_4$): 3.88 (3H, s, MeO); 2.8 (3H, s, MeN); 6.7 (1H, d, J=8.5 Hz, aryl-H); 6.85 (1H, dd, J=2 and 8.5 Hz, aryl-H); 6.9 (1H, d, J=2 Hz, aryl-H).

Step 4) 4-Methoxy-3-(1'-methylbenzimidazol-5'-yl)benzenecarboxaldehyde/4-Methoxy-3-(1-methylbenzimidazol-5-yl)benzaldehyde:

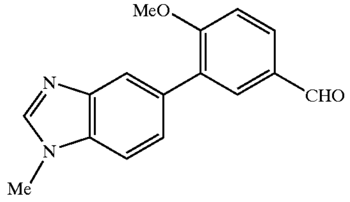

To a degassed solution of 5-bromo-1-methylbenzimidazole (0.56 g, 2.63 mmol), 5-formyl-2-methoxybenzeneboronic acid (0.57 g, 3.2 mmol) and potassium carbonate (0.91 g, 6.6 mmol) in toluene/ethanol 2/1 (30 mL) a catalytic amount of $Pd(PPh_3)_4$ (0.03 g, 1 mmol %) was added and the solution was degassed for further 5 minutes. The mixture was refluxed for 5 hours. The residue was extracted into ethyl acetate and washed with water and then saturated brine and dried over sodium sulphate. The solvent was removed under reduced pressure and the crude was purified by column (silica, EtOAc to 5% MeOH in AcOEt) to afford 0.6 g of product.

$C_8H_7BrN_2$ Mass (calculated): [266.30]; (found): [$M^+$]=267. NMR (400 MHz, $CDCl_3$): 3.88 (3H, s, MeO); 3.92 (3H, s, MeN); 7.12 (1H, d, J=8.5 Hz, aryl-H); 7.4–7.5 (2H, m, aryl-H); 7.8–7.95 (3H, m, aryl-H); 7.98 (1H, s, imidazole N═CHN); 9.95 (1H, s, CHO).

Step 5) (R)-N-(1-Phenylethyl)-N-((4-methoxy-3-(1-methylbenzimidazol-5-yl)phenylmethyl)amine

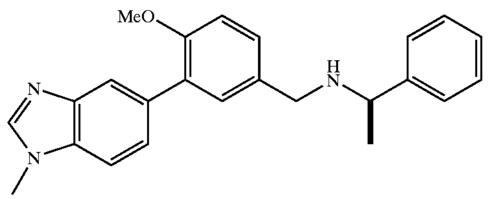

The title compound was prepared from 4-methoxy-3-(1-methylbenzimidazol-5-yl)benzaldehyde and (R)-α-methylbenzylamine according to general procedure C.

$C_{24}H_{25}N_3O$ Mass (calculated): [371]; (found): $[M+H^+]$= 251, 372, 268. NMR (400 MHz, $CDCl_3$): 1.3 (3H, d, J=6 Hz, $NCHCH_3$); 3.55 and 3.6 (2H, dd, J=12 Hz, $CH_2N$); 3.7 (3H, s, NMe); 3.75–3.85 (4H, m and s, NCHMe and MeO); 6.9 (2H, d, J=8 Hz, aryl-H); 7.25–7.3 (3H, m, aryl-H); 7.3–7.4 (5H, m, aryl-H); 7.45 (1H, dd, J=1 and 8 Hz, aryl-H); 7.8 (1H, aryl H); 7.9 (1H, m, aryl-H).

EXAMPLE 5

(R)-N-(1-(3-Methoxyphenyl)ethyl)-N-((4-methoxy-3-(1-methylbenzimidazol-5-yl)phenylmethyl)amine

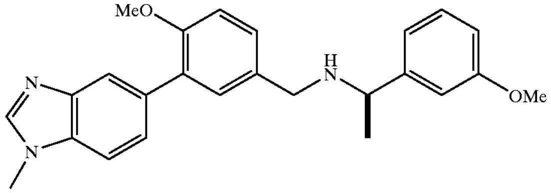

The title compound was prepared from 4-methoxy-3-(1-methylbenzimidazol-5-yl)benzaldehyde and (R)-3-methoxy-α-methylbenzylamine according to general procedure C.

$C_{25}H_{27}N_3O_2$ Mass (calculated): [401]; (found): $[M+H^+]$= 402, 251, 268. NMR (400 MHz, $CDCl_3$): 1.3 (3H, d, J=6 Hz, $NCHCH_3$); 3.55 and 3.6 (2H, dd, J=12 Hz, $CH_2N$); 3.7–3.9 (10H, m and 2s, NCHMe, NMe and MeO); 6.7 (1H, dd, J=1 and 8 Hz, aryl-H); 6.85–6.95 (3H, m, aryl-H); 7.15–7.3 (3H, m, aryl-H); 7.35 (1H, m, aryl-H); 7.45 (1H, m, aryl-H); 7.8–7.95 (2H, m, aryl-H).

EXAMPLE 6

(R)-N-(1-(1-Naphthyl)ethyl)-N-((4-methoxy-3-(1-methylbenzimidazol-5-yl)phenylmethyl)amine

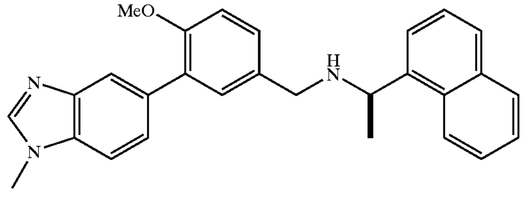

The title compound was prepared from 4-methoxy-3-(1-methylbenzimidazol-5-yl)benzaldehyde and (R)-1-(1-naphthyl)ethylamine according to general procedure C.

$C_{28}H_{27}N_3O$ Mass (calculated): [371]; (found): $[M+H^+]$= 155, 422, 268, 251. NMR (400 MHz, $CDCl_3$): 1.6 (3H, d, J=6 Hz, $NCHCH_3$); 3.6–3.7 (4H, m, $CH_2N$ and Nme); 3.7–3.8 (4H, m, $CH_2N$ and MeO); 4.8 (1H, q, J=6 Hz, $NCHCH_3$); 6.8 (1H, d, J=8 Hz, aryl-H); 7.15 (1H, d, J=1 Hz, aryl-H); 7.2–7.3 (1H, m, aryl-H); 7.3–7.35 (2H, m, aryl-H); 7.35–7.5 (2H, m, aryl-H); 7.5 (1H, t, J=7 Hz, aryl-H); 7.7 (1H, d, J=8 Hz, aryl-H); 7.8–7.95 (5H, m, aryl-H).

EXAMPLE 7

(R)-N-(1-(4-Methylphenyl)ethyl)-N-((4-methoxy-3-(4'-methoxyphenyl)-phenylmethyl)amine

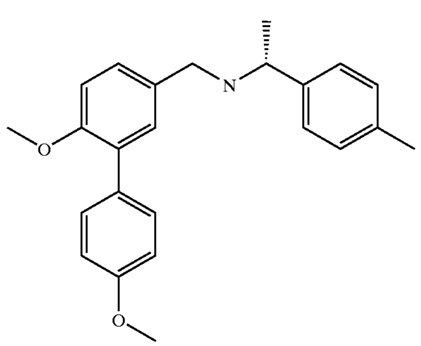

Step 1) 4-Methoxy-3-(4-methoxyphenyl)benzaldehyde

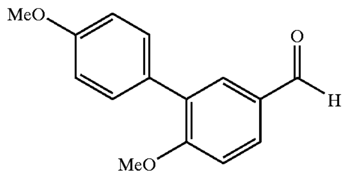

3-Bromo-4-methoxybenzaldehyde (1.92 g, 9 mmol, Aldrich) and 4-methoxyphenylboronic acid (1.52 g, 10 mmol, Aldrich) were dissolved in ethylene glycol dimethyl ether (15 mL, Aldrich). To the solution was added lithium chloride (0.72 g, 30 mmol, Aldrich) and aqueous 2 M sodium carbonate solution (15 mL, 30 mmol). After the mixture was bubbled with nitrogen for 10 min at room temperature, tetrakis(triphenylphosphine)palladium(0) (1.15 g, 1.0 mmol, Aldrich) was added to the mixture. The mixture was stirred under nitrogen at 80 C for overnight then the reaction was cooled at room temperature and diluted in ethyl acetate (50 mL). The solid portion was filtered out through Celite pad. The organic phase was separated and washed by water (30 mL) and brine (30 mL). The resulting organic layer was dried over anhydrous magnesium sulfate and concentrated via vacuo. The title compound was purified by column chromatography (silica gel, hexane/ethyl acetate 5/1) to give the title compound as white solid in 88% yield (2.12 g, 8.8 mmol).

$C_{15}H_{14}O_3$ MS (ESI, pos. ion) m/z: 243.1 (M+1); MS (ESI, neg. ion) m/z: 241.0 (M−1).

Step 2) (R)-N-(1-(4-Methylphenyl)ethyl)-N-((4-methoxy-3-(4'-methoxyphenyl)-phenylmethyl)amine

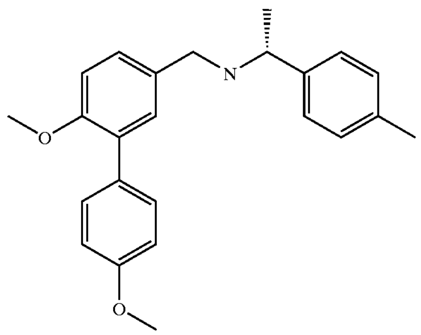

The title compound was prepared from 4-methoxy-3-(4-methoxyphenyl)-benzaldehyde and (R)-4-methyl-α-methylbenzylamine according to general procedure A.

$C_{24}H_{27}NO_2$ Mass (calculated): [361]; (found): [M+H$^+$]=262; NMR (400 MHz, MeOH-$d_4$): 1.55 (3H, d, J=7 Hz, $NCHCH_3$); 2.5 (3H, s, aryl-CH3) 3.65 and 3.75 (2H, dd, J=12 Hz, $CH_2N$); 3.9 (3H, s, MeO); 3.9 (1H, m, NCHMe); 3.95 (3H, s, MeO); 7.05–7.15 (3H, m, aryl-H); 7.3–7.45 (6H, m, aryl-H); 7.62 (2H, d, J=7 Hz, aryl-H).

EXAMPLE 8

(R)-N-(1-Phenylethyl)-N-((4-methoxy-3-(4'-methoxyphenyl)phenylmethyl)amine

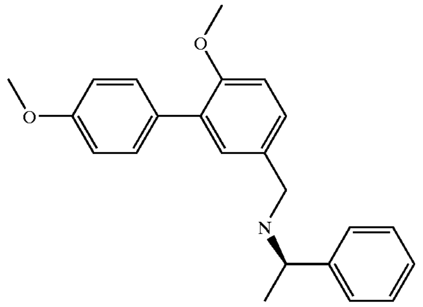

The title compound was prepared from 4-methoxy-3-(4-methoxyphenyl)-benzaldehyde and (R)-α-methylbenzylamine according to general procedure A.

$C_{23}H_{25}NO_2$ Mass (calculated): [347]; (found): [M+H$^+$]=348. NMR (400 MHz, MeOH-$d_4$): 1.55 (3H, d, J=7 Hz, $NCHCH_3$); 2.5 (3H, s, aryl-CH3) 3.65 and 3.75 (2H, dd, J=12 Hz, $CH_2N$); 3.9 (3H, s, MeO); 3.9 (1H, m, NCHMe); 3.95 (3H, s, MeO); 7.05–7.15 (3H, m, aryl-H); 7.3–7.45 (6H, m, aryl-H); 7.62 (2H, d, J=7 Hz, aryl-H).

EXAMPLE 9

(R)-N-(1-(1-Naphthyl)ethyl)-N-((4-methoxy-3-(4'-methoxyphenyl)-phenylmethyl)amine

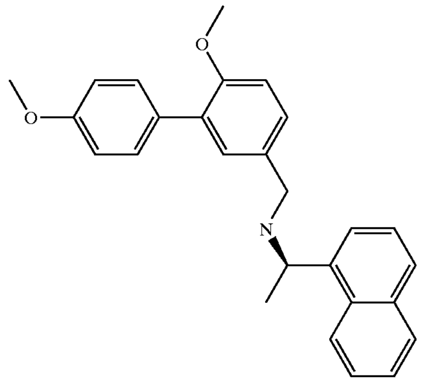

The title compound was prepared from 4-methoxy-3-(4-methoxyphenyl)-benzaldehyde and (R)-1-(1-naphthyl) ethylamine according to general procedure A.

$C_{27}H_{27}NO_2$ Mass (calculated): [397]; (found): [M+H$^+$]=398. NMR (400 MHz, MeOH-$d_4$): 1.65 (3H, d, J=7 Hz, $NCHCH_3$); 3.8 and 3.85 (2H, dd, J=15 Hz, $CH_2N$); 3.9 (3H, s, MeO); 4 (3H, s, MeO); 3.9 (1H, m, NCHMe); 4.85 (1H, q, J=7 Hz, NCHMe); 7.05 (2H, d, J=7 Hz, aryl-H); 7.15 (1H, d, J=7 Hzaryl-H); 7.25 (1H, d, J=1 Hz, aryl-H); 7.35 (1H, dd, J=1 and 7 Hz, aryl-H); 7.5 (2H, d, J=7 Hz, aryl-H); 7.55–7.7 (2H, m, naphthyl-H); 7.7 (1H, t, J=7 Hz, naphthyl-H); 7.9 (1H, d, J=7 Hz, naphthyl-H); 7.95 (1H, d, J=7 Hz, naphthyl-H); 8.05 (1H, d, J=7 Hz, naphthyl-H); 8.15 (1H, d, J=7 Hz, naphthyl-H).

EXAMPLE 10

(R)-N-(1-Phenylethyl)-N-((4-methoxy-3-(pyrid-3-yl) phenylmethyl)amine

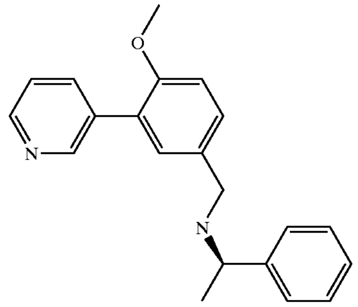

The title compound was prepared from 4-methoxy-3-(3-pyridyl)benzaldehyde and (R)-α-methylbenzylamine according to general procedure A.

$C_{21}H_{22}N_2O$ Mass (calculated): [318]; (found): [M+H$^+$]=319, 198. NMR (400 MHz, MeOH-$d_4$): 1.75 (3H, d, J=7 Hz, $NCHCH_3$); 3.92 (3H, s, MeO); 3.55 and 4.2 (2H, dd, J=10 Hz, $CH_2N$); 4.5 (1H, q, J=4.5 Hz; NCHMe); 3.95 (3H, s, MeO); 7.3 (1H, d, J=7 Hz, aryl-H); 7.45–7.65 (7H, m, aryl-H); 8.05 (1H, bt, pyridyl-H); 7.75 (1H, d, J=7 Hz, pyridyl-H); 8.8 (1H, bs, pyridyl-H); 9.05 (1H, bs, pyridyl-H).

EXAMPLE 11

(R)-N-(1-((3-Methoxyphenyl)ethyl)-N-((4-methoxy-3-(4'-fluorophenyl)-phenylmethyl)amine

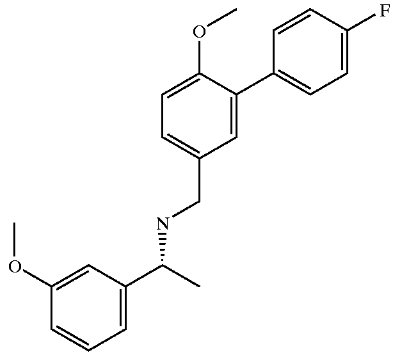

The title compound was prepared from 3-(4-fluorophenyl)-4-methoxybenzaldehyde and (R)-3-methoxy-α-methylbenzylamine according to general procedure C.

$C_{23}H_{24}FNO_2$ Mass (calculated): [365]; (found): $[M+H^+]$= 366, 215 base peak NMR (400 MHz, $CDCl_3$): 1.4 (3H, d, J=7 Hz, $NCHCH_3$); 3.65 and 3.75 (2H, dd, J=12 Hz, $CH_2N$); 3.82 (3H, s, MeO); 3.85 (3H, s, MeO); 3.8–3.9 (1H, m, NCHMe); 6.85 (1H, dd, J=7 and 2 Hz, aryl-H); 6.9–7.0 (3H, m, aryl-H); 7.1–7.2 (2H, m, aryl-H); 7.2–7.35 (3H, m, aryl-H); 7.5–7.55 (2H, m, aryl-H).

EXAMPLE 12

(R)-N-(1-Phenylethyl)-N-((4-methoxy-3-(4'-fluorophenyl)phenylmethyl)amine

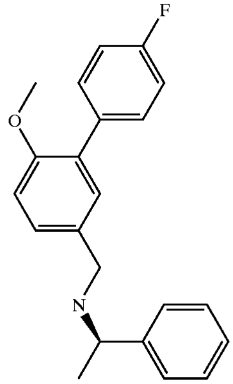

The title compound was prepared from 3-(4-fluorophenyl)-4-methoxybenzaldehyde and (R)-α-methylbenzylamine according to general procedure C.

$C_{22}H_{22}FNO$ Mass (calculated): [335]; (found): $[M+H^+]$= 336, 215 base peak NMR (400 MHz, $CDCl_3$): 1.35 (3H, d, J=7 Hz, $NCHCH_3$); 3.5 and 3.6 (2H, dd, J=11 Hz, J=7 Hz; $CH_2N$); 3.7 (3H, s, MeO); 4.82 (1H, q, J=7 Hz; NCHMe); 6.85 (1H, d, J=7, aryl-H); 7.0 (2H, t, J=7 Hz; aryl-H); 7.15 (1H, d, J=2 Hz, aryl-H); 7.15–7.25 (2H, m, aryl-H); 7.25–7.35 (4H, m, aryl-H); 7.5 (2H, dd, J=7 and 6 Hz, aryl-H).

EXAMPLE 13

R)-N-(1-Phenylethyl)-N-((4-methoxy-3-(2'-methylpyrid-5'-yl)phenylmethyl)-amine

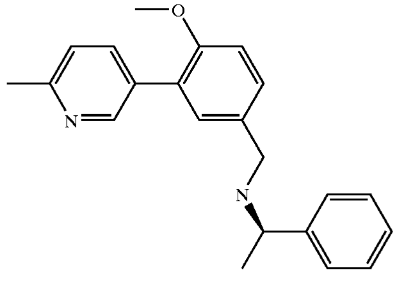

Step 1) 4-Methoxy-3-(1-methylpyrid-5-yl) benzenecarboxaldehyde:

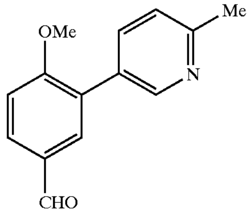

To a degassed solution of 5-bromo-2-methylpyridine (2.75 g, 15 mmol) and potassium carbonate (4.5 g, 33 mmol) in toluene (70 mL) a catalytic amount of $Pd(PPh_3)_4$ (0.17 g, 0.15 mmol) was added and the solution was degassed for further 5 minutes. A degassed solution of 5-formyl-2-methoxybenzeneboronic acid (prepared according to Keseru, G. M. et al. *Tetrahedron* (48), 2, 913–922 (1992)) (2.7 g, 15 mmol) in ethanol (30 mL) was then added and the mixture was refluxed for 15 hours. The residue was extracted into ethyl acetate and washed with saturated sodium bicarbonate solution and dried over sodium sulphate. The solvent was removed under reduced pressure and the crude was purified by column chromatography (silica, THF/DCM 2/1) to afford 2 g of pale yellow solid.

$C_{14}H_{13}NO_2$ Mass (calculated) [227]; (found) $[M+H^+]$= 228; Lc Rt=1.0, 92%. NMR (400 MHz, MeOH-d4): 2.65 (3H, s, Me-pyridine); 4.05 (3H, s, MeO); 7.35 (1H, d, J=10 Hz, pyridyl-H); 7.45 (1H, 2, J=7 Hz, aryl-H); 7.95 (1H, m, pyridyl-H); 8 (1H, d, J=2 Hz ; aryl-H); 8.1 (1H, dd, J=2 and 7 Hz, aryl-H); 8.65 (1H, d, J=2 Hz, —H); 10 (1H, s, CHO).

Step 2) (R)-N-(1-Phenylethyl)-N-((4-methoxy-3-(2'-methylpyrid-5'-yl)-phenylmethyl)-amine

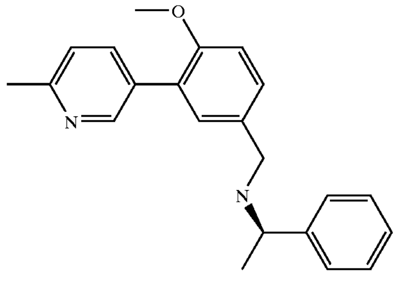

The title compound was prepared from 4-methoxy-3-(1-methylpyrid-5-yl)-benzenecarboxaldehyde and (R)-α-methylbenzylamine according to general procedure C.

$C_{22}H_{24}N_2O$ Mass (calculated): [332]; (found): $[M+H^+]$= 333 NMR (400 MHz, $CDCl_3$): 1.4 (3H, d, J=6.5 Hz, $NCHCH_3$); 2.65 (3H, s, pyridyl-CH3); 3.61 and 3.67 (2H, dd, J=13 Hz, $CH_2N$); 3.82 (3H, s, MeO); 3.86 (1H, q, J=6.5 Hz, $CH_3CH$); 6.45 (1H, d, J=8.5 Hz); 7.2–7.35 (4H, m, aryl-H); 7.35–7.4 (4H, m, aryl-H); 7.77 (dd, 1H, J=2.2 and 8.1 Hz, aryl-H); 8.66 (1H, d, J=1.8 Hz, aryl-H).

EXAMPLE 14

(R)-N-(1-Phenylethyl)-N-((4-methoxy-3-(2'-methoxypyrid-5'-yl)phenylmethyl)-amine

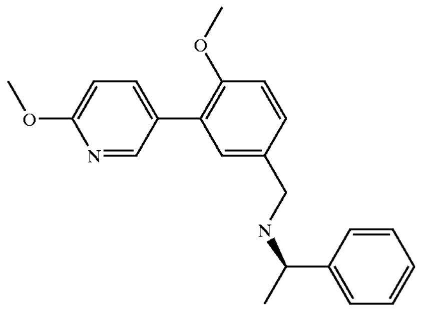

The title compound was prepared from 4-methoxy-3-(6-methoxy(3-pyridyl))-benzaldehyde and (R)-α-methylbenzylamine according to general procedure C.

$C_{22}H_{24}N_2O_2$ Mass (calculated): [348]; (found): $[M+H^+]$= 349, 228; NMR (400 MHz, $CDCl_3$): 1.32 (3H, d, J=6.8 Hz, $NCHCH_3$); 3.5 and 3.57 (2H, dd, J=13 Hz, $CH_2N$); 3.72 (3H, s, $OCH_3$); 3.78 (1H, q, J=6.8 Hz, $CHCH_3$); 6.7 (1H, dd, J=0.6 and 8.6 Hz, aryl-H); 6.8 (1H, d, J=8.4 Hz, aryl-H); 7.10–6.35 (7H, m, aryl-H); 7.7 (1H, dd, J=2.5 and 8.6 Hz, aryl-H); 8.2 (1H, dd, J=1.8 and 8.2 Hz, aryl-H).

EXAMPLE 15

(R)-N-(1-(1-Naphthyl)ethyl)-N-((4-methoxy-3-(6'-methoxypyridazin-3'-yl))phenylmethyl)amine

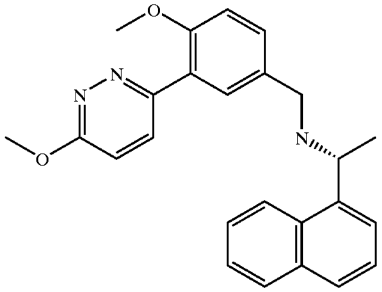

The title compound was prepared from 4-methoxy-3-(6-methoxypyridazin-3-yl)benzaldehyde and (R)-1-(1-naphthyl)ethylamine according to general procedure A.

$C_{25}H_{25}N_3O_2$ Mass (calculated): [399]; (found): $[M+H^+]$= 400, $[2M+H^+]$=799.

EXAMPLE 16

(R)-N-(1-(Phenylethyl)-N-((4-methoxy-3-(3,4-methylendioxyphenyl)-phenylmethyl)amine

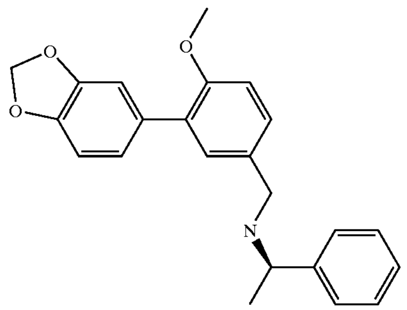

The title compound was prepared from 3-(2H-benzo[d]1,3-dioxolan-5-yl)-4-methoxybenzaldehyde and (R)-α-methylbenzylamine according to general procedure B.

$C_{23}H_{23}NO_3$ Mass (calculated): [361]; (found): $[M+H^+]$= 362, 241 NMR (400 MHz, $CDCl_3$): 1.29 (3H, d, J=6.8 Hz, $CHCH_3$); 3.50 and 3.54 (2H, dd, J=13 Hz, $CH_2N$); 3.72 (3H, s, $CH_3O$); 3.75 (1H, q, J=6.8 Hz, $CHCH_3$); 5.90 (2H, s, $OCH_2O$); 6.78 (1H, d, J=7.7 Hz, aryl-H); 6.83 (1H, d, J=7.7 Hz, aryl-H); 6.9 (1H, dd, J=1.7 and 7.7 Hz, aryl-H); 6.97 (1H, d, J=1.7 Hz, aryl-H); 7.10–7.15 (2H, m, aryl-H); 7.15–7.22 (1H, m, aryl-H); 7.24–7.31 (4H, m, aryl-H).

EXAMPLE 17

(R)-N-(1-(3-Methoxyphenyl)ethyl)-N-((4-methoxy-3-(4'-methoxyphenyl)phenylmethyl)amine

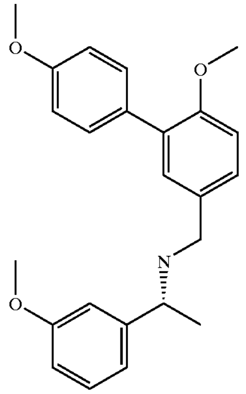

The title compound was prepared from 4-methoxy-3-(4-methoxyphenyl)-benzaldehyde and (R)-3-methoxy-α-methylbenzylamine according to general procedure A.

$C_{24}H_{27}NO_3$ Mass (calculated): [377]; (found): $[M+H^+]$= 378, $[M+MeCN+H^+]$=419.

EXAMPLE 18

(R)-N-(1-(3-Methoxyphenyl)ethyl)-N-((4-methoxy-3-(4,5-methylendioxyphenyl)phenylmethyl)amine

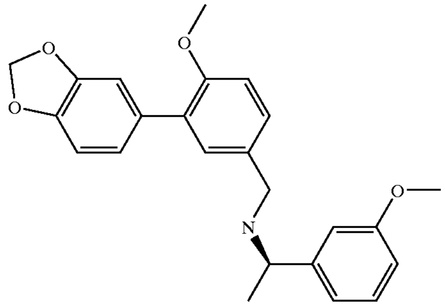

The title compound was prepared from 3-(2H-benzo[d]1,3-dioxolan-5-yl)-4-methoxybenzaldehyde and (R)-3-methoxy-α-methylbenzylamine according to general procedure B.

$C_{24}H_{25}NO_4$ Mass (calculated): [391]; (found): [M+H$^+$]=392. NMR (400 MHz, $CDCl_3$): 1.35 (3H, d, J=6.8 Hz, $NCHCH_3$); 3.4–3.8 (9H, m, $OCH_3$, $OCH_3$, $CHCH_3$, $CH_2N$); 5.9 (2H, s, $OCH_2O$); 6.7–7 (8H, m, aryl-H); 7.1–7.2 (2H, m, aryl-H),

EXAMPLE 19

R)-N-(1-Phenylethyl)-N-(4-methoxy-3-phenyl)phenylmethyl)amine

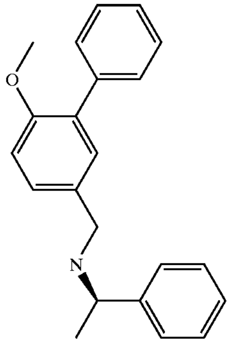

The title compound was prepared from 4-methoxy-3-phenylbenzaldehyde and (R)-α-methylbenzylamine according to general procedure A.

$C_{22}H_{23}NO$ Mass (calculated): [317]; (found): [M+H$^+$]=318, 197 (base peak).

EXAMPLE 20

(R)-N-(1-Phenylethyl)-N-((4-trifluoromethoxy-3-(pyrid-3-yl)phenylmethyl)amine

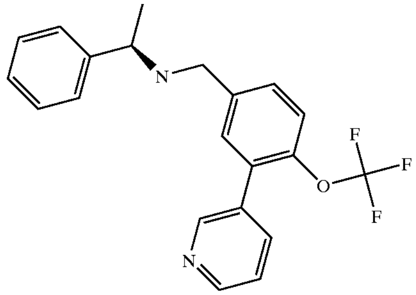

Step 1) 4-Trifluoromethoxy-3-(pyrid-3-yl)benzaldehyde

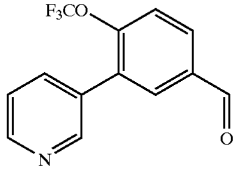

A solution of 3-chloro-4-trifluoromethoxybenzaldehyde (3 g, 13.3 mmol) and 3-pyridylboronic acid (1.97 g, 16.0 mmol) in dioxane (70 mL) and 2M $K_2CO_3$ (20 mL) is degassed with nitrogen prior to addition of $Pd(PPh_3)_4$ (1.5 g, 1.33 mmol). The mixture was stirred at 100° C. under nitrogen for 40 hours, then cooled and filtered on celite/silica and the filtrate concentrated under reduced pressure. The crude was purified by column chromatography (2/1 heptane/ethyl acetate) to give 1.51 g of title compound.

$C_{13}H_8F_3NO_2$ Mass (calculated): [267]; (found) [M+H$^+$]=268 NMR (400 MHz, $CDCl_3$: 7.3–7.35 (1H, m, aryl-H); 7.4–7.45 (1H, m, aryl-H); 7.7–7.75 (1H, m, aryl-H); 7.9–8 (2H, n, aryl-H); 8.65 (1H, bs, aryl-H); 8.7 (1H, bs, aryl-H).

Step 2) (R)-N-(1-Phenylethyl)-N-((4-trifluoromethoxy-3-(pyrid-3-yl)phenylmethyl)amine The title compound was prepared from 4-trifluoromethoxy-3-(pyrid-3-yl)benzenecarboxaldehyde and (R)-α-methylbenzylamine according to general procedure C.

$C_{21}H_{19}F_3N_2O$ Mass (calculated): [372]; (found): [M+H$^+$]=373 NMR (400 MHz, CDCl3): 1.3 (3H, d, J=6 Hz, $NCHCH_3$); 3.6 (2H, s, $CH_2N$); 3.8 (1H, q, J=6 Hz; NCHMe); 7.20–7.40 (9H, m, aryl-H); 7.7 (1H, dt, J=1 and 8 Hz, aryl-H); 8.55 (1H, d, J=3 Hz, aryl-H); 8.65 (1H, bs, aryl-H).

EXAMPLE 21

(R)-N-(1-(3-Methoxyphenyl)ethyl)-N-((4-trifluoromethoxy-3-(pyrid-3-yl)phenylmethyl)amine

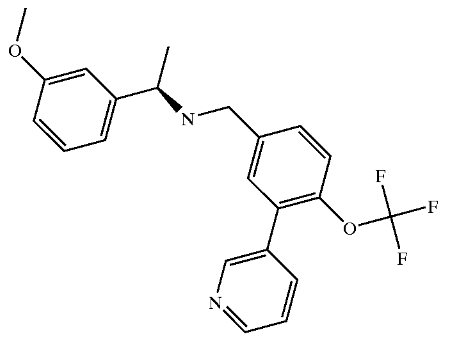

The title compound was prepared from 4-trifluoromethoxy-3-(pyrid-3-yl)benzenecarboxaldehyde and (R)-3-methoxy-α-methylbenzylamine according to general procedure C.

$C_{22}H_{21}F_3N_2O_2$ Mass (calculated): [402]; (found): $[M+H^+]$=403 NMR (400 MHz, CDCl3): 1.3 (3H, d, J=6 Hz, $NCHCH_3$); 3.6 (2H, m, $CH_2N$); 3.7–3.8 (4H, m, NCHMe and $CH_3O$); 6.7 (1H, dd, J=1 and 8 Hz, aryl-H); 6.8–6.9 (2H, m, aryl-H); 7.20–7.40 (5H, m, aryl-H); 7.7 (1H, dt, J=1 and 8 Hz, aryl-H); 8.55 (1H, d, J=3 Hz, aryl-H); 8.65 (1H, bs, aryl-H).

EXAMPLE 22

(R)-N-(1-(1-Naphthyl)ethyl)-N-((4-trifluoromethoxy-3-(pyrid-3-yl)phenylmethyl)amine

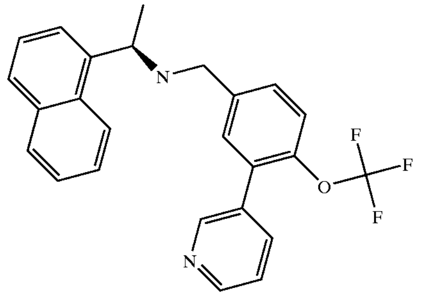

The title compound was prepared from 4-trifluoromethoxy-3-(pyrid-3-yl)benzenecarboxaldehyde and (R)-1-(1-naphthyl)ethylamine according to general procedure C.

$C_{25}H_{21}F_3N_2O$ Mass (calculated): [422]; (found): $[M+H^+]$=423 NMR (400 MHz, CDCl3): 1.45 (3H, d, J=6 Hz, $NCHCH_3$); 3.65 and 3.75 (2H, dd, J=12 Hz$CH_2N$); 4.65 (1H, q, J=6 Hz; NCHMe); 7.30–7.40 (4H, m, aryl-H); 7.40–7.5 (3H, m, aryl-H); 7.6–7.7 (3H, m, aryl-H); 7.8–7.85 (1H, m, aryl-H); 8.05–8.1 (1H, m, aryl-H); 8.55 (1H, d, J=3 Hz, aryl-H); 8.65 (1H, bs, aryl-H).

EXAMPLE 23

(R)-N-(1-Phenylethyl)-N-((4-methoxy-3-(benzimidazol-2-yl)lmethyl)amine

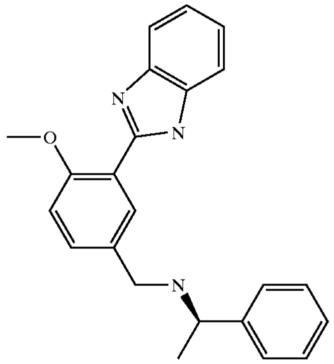

Step 1) 4-Methoxy-3-(benzimidazol-2-yl)benzenecarboxaldehyde $Pd(Ph_3)_4$ (72 mg, 0.062 mmol) was added to a degassed solution of 2-chlorobenzimidazole (0.95 g, 6.25 mmol) in 1,2-dimethoxyethane (25 mL), followed by 2M $Na_2CO_3$ (15 mL) and 5-formyl-2-methoxybenzeneboronic acid (1.35 g, 7.5 mmol). The mixture was stirred at 115 C for 16 hours then more catalyst was added (2% mol) and reaction stirred for further 4 hours. The mixture was cooled and extracted with ethyl acetate. The organic layer was concentrated under reduced pressure and the residue purified by column chromatography (1/1 hexane/ethyl acetate) to afford 0.285 g of title compound. $C_{15}H_{12}N_2O_2$ Mass (calculated): [252]; (found) $[M+H^+]$=253 NMR (400 MHz, $CDCl_3$: 4.1 (3H, s, $CH_3O$); 7.2 (1H, d, J=8 Hz, aryl-H); 7.3–7.35 (2H, m, aryl-H); 7.5 (1H, m, aryl-H); 7.8 (1H, m, aryl-H); 8 (1H, dd, J=2 and 8 Hz, aryl-H); 9 (1H, d, J=1 Hz, aryl-H); 10 (1H, s, CHO); 10.4 (1H, bd, NH).

Step 2) (R)-N-(1-Phenylethyl)-N-((4-methoxy-3-(benzimidazol-2-yl)lmethyl)amine

The title compound was prepared from 4-methoxy-3-(benzimidazol-2yl)-benzenecarboxaldehyde and (R)-α-methylbenzylamine according to general procedure C.

$C_{23}H_{23}N_3O$ Mass (calculated): [357]; (found): $[M+H^+]$=358, 715 NMR (400 MHz, CDCl3): 1.3 (3H, d, J=6 Hz, $NCHCH_3$); 3.55 and 3.65 (2H, dd, J=12 Hz, $CH_2N$); 3.75 (1H, q, J=6 Hz; NCHMe); 4.0 (3H, s, $CH_3O$); 6.95 (1H, d, J=8 Hz, aryl-H); 7.15–7.25 (3H, m, aryl-H); 7.25–7.35 (5H, m, aryl-H); 7.45 (1H, bd, aryl-H); 7.75 (1H, bd, aryl-H); 8.3 (1H, d, J=1 Hz, aryl-H).

EXAMPLE 24

(R)-N-(1-(1-Naphthyl)ethyl)-N-((4-methoxy-3-(benzimidazol-2-yl)lmethyl)amine

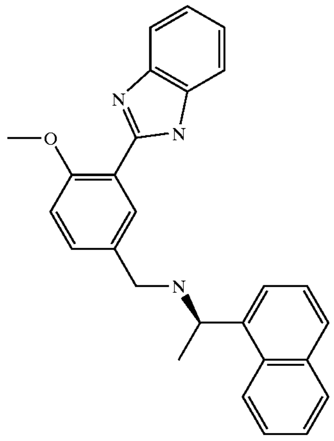

The title compound was prepared from 4-methoxy-3-(benzimidazol-2-yl)benzenecarboxaldehyde and (R)-1-(1-naphthyl)ethylamine according to general procedure C.

$C_{27}H_{25}N_3O$ Mass (calculated): [407]; (found): [M+H$^+$]=408 NMR (400 MHz, CDCl3): 1.5 (3H, d, J=6 Hz, $NCHCH_3$); 3.75 and 3.8 (2H, dd, J=12 Hz, $CH_2N$); 4.1 (3H, s, $CH_3O$); 4.75 (1H, q, J=6 Hz; NCHMe); 7.0 (1H, d, J=8 Hz, aryl-H); 7.25–7.3 (2H, m, aryl-H); 7.45–7.55 (4H, m, aryl-H); 7.75–7.9 (4H, m, aryl-H); 8.2 (1H, d, J=8 Hz, aryl-H); 8.55 (1H, d, J=1 Hz, aryl-H).

EXAMPLE 25

(R)-N-(1-Phenylethyl)-N-((4-methoxy-3-(1,4-benzodioxan-5-yl)lmethyl)amine

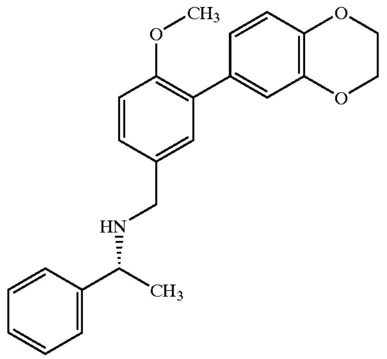

Step 1) 4-methoxy-3-(1,4-benzodioxan-5-yl)benzenecarboxaldehyde

A solution of 5-formyl-2-methoxybenzeneboronic acid (1 g, 5.6 mmol), 3,4-ethylenedioxybromobenzole (1 g, 4.65 mmol) and $K_2CO_3$ (1.6 g, 11.6 mmol) in ethanol (20 mL) and toluene (40 mL) was degassed prior to addition of $Pd(Ph_3)_4$ (54 mg, 0.046 mmol). The mixture was refluxed for 24 hours then cooled and filtered through diatomaceous earth. The filtrate was concentrated in vacuo, extracted with ethyl acetate, washed with water and the organic layer dried over sodium sulphate. The crude was purified by column chromatography (heptane/ethyl acetate 7/3) to give 1 g of title compound. $C_{16}H_{14}O_4$ Mass (calculated): [270]; (found): [M+H$^+$]=271, 312

NMR (400 MHz, CDCl3): 3.95 (3H, s, $CH_3O$); 4.3 (4H, s, $OCH_2CH_2O$); 6.9–7.15 (4H, m, aryl-H); 7.9–7.95 (2H, m, aryl-H); 10 (1H, s, CHO).

Step 2) (R)-N-(1-Phenylethyl)-N-((4-methoxy-3-(1,4-benzodioxan-5-yl)lmethyl)amine The title compound was prepared from 4-methoxy-3-(1,4-benzodioxan-5-yl)benzenecarboxaldehyde and (R)-α-methylbenzylamine according to general procedure C.

$C_{24}H_{25}NO_3$ Mass (calculated): [375]; (found): [M+H$^+$]=376, 255 NMR (400 MHz, CDCl3): 1.3 (3H, d, J=6 Hz, $NCHCH_3$); 3.55 and 3.65 (2H, dd, J=12 Hz, $CH_2N$); 3.7 (3H, s, $CH_3O$); 3.75 (1H, q, J=6 Hz; NCHMe); 4.2 (4H, s, $OCH_2CH_2O$); 6.8 (2H, m, aryl-H); 6.95 (1H, dd, J=1 and 8 Hz, aryl-H); 7.05 (1H, d, J=1 Hz, aryl-H); 7.15–7.3 (3H, m, aryl-H); 7.35–7.45 (4H, m, aryl-H).

EXAMPLE 26

(R)-N-(1-(3-Methoxyphenyl)ethyl)-N-((4-methoxy-3-(1,4-benzodioxan-5-yl)lmethyl)amine

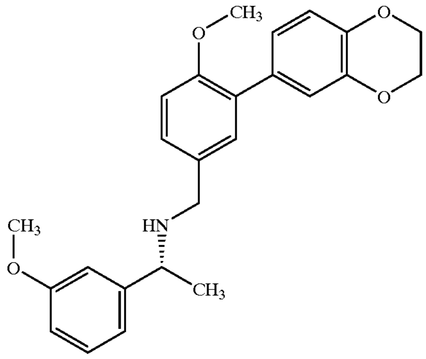

The title compound was prepared from 4-methoxy-3-(1,4-benzodioxan-5-yl)benzenecarboxaldehyde and (R)-3-methoxy-α-methylbenzylamine according to general procedure C.

$C_{25}H_{27}NO_4$ Mass (calculated): [405]; (found): [M+H$^+$]=406, 255 NMR (400 MHz, CDCl3): 1.3 (3H, d, J=6 Hz, $NCHCH_3$); 3.55 and 3.65 (2H, dd, J=12 Hz, $CH_2N$); 3.75 (3H, s, $CH_3O$); 3.77 (3H, s, $CH_3O$); 3.75 (1H, m; NCHMe); 4.2 (4H, s, $OCH_2CH_2O$); 6.7 (1H, dd, J=1 and 8 Hz, aryl-H); 6.8–6.9 (4H, m, aryl-H); 7.0 (1H, dd, dd, J=1 and 8 Hz, aryl-H); 7.1 (1H, d, J=1 Hz, aryl-H); 7.25–7.3 (3H, m, aryl-H).

EXAMPLE 27

(R)-N-(1-(1-Naphthyl)ethyl)-N-((4-methoxy-3-(1,4-benzodioxan-5-yl)-methyl)amine

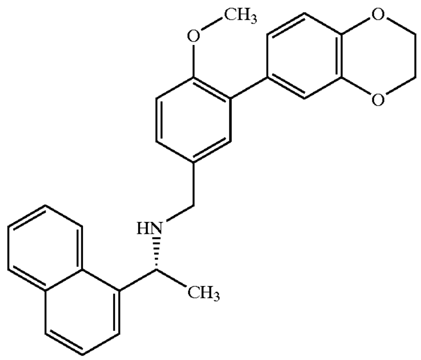

The title compound was prepared from 4-methoxy-3-(1,4-benzodioxan-5-yl)benzenecarboxaldehyde and (R)-1-(1-naphthyl)ethylamine according to general procedure C.

$C_{28}H_{28}NO_3$ Mass (calculated): [425]; (found): $[M+H^+]$=426, 255. NMR (400 MHz, CDCl3): 1.45 (3H, d, J=6 Hz, $NCHCH_3$); 3.55 and 3.65 (2H, dd, J=12 Hz, $CH_2N$); 3.7 (3H, s, $CH_3O$); 4.2 (4H, s, $OCH_2CH_2O$); 4.65 (1H, q, J=6 H; NCHMe); 6.8 (2H, m, aryl-H); 6.9 (1H, dd, J=1 and 8 Hz, aryl-H); 7.0 (1H, d, J=1 Hz, aryl-H); 7.1–7.15 (2H, m, aryl-H); 7.35–7.45 (3H, m, aryl-H); 7.7 (2H, d, J=8 Hz, aryl-H); 7.8 (1H, m, aryl-H); 8.0 (1H, m, aryl-H).

EXAMPLE 28

(R)-N-(1-Phenylethyl)-N-((4-methoxy-3-(2-methylbenzoxazol-5-yl)methyl)amine

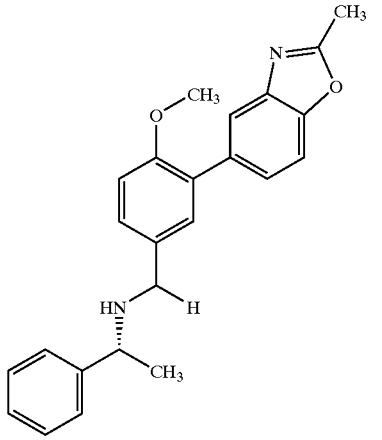

Step 1) 2-Amino-4-bromophenol:

A solution of 4-bromo-2-nitrophenol (2 g, 9.17 mmol) and tin (II) chloride (10.35 g, 45.9 mmol) in ethanol (20 mL) was heated at 70° C. for 2 hours, then cooled, poured onto ice, neutralized with $NaHCO_3$. The aqueous phase was then extracted with ethyl acetate, dried over sodium sulphate and the solvent removed in vacuo to afford 1.61 g of the title compound. $C_6H_6BrNO$ Mass (calculated): [188]; (found): $[M+H^+]$=188, 190 (Br) NMR (400 MHz, dmso-$d_6$): 4.8 (2H, bs, $NH_2$); 6.5 (1H, dd, J=2 and 8 Hz, aryl-H); 6.6 (1H, d, J=8 Hz, aryl-H); 6.75 (1H, d, J=2 Hz, aryl-H); 9.3 (1H, bs, OH).

Step 2) 2-methyl-5-bromobenzoxazole:

A solution of 2-amino-4-bromophenol (1 g, 5.32 mmol) in trimethyl orthoacetate (20 mL) was refluxed for 1.5 hours. The reaction was then cooled and the solvent removed under reduced pressure to give 1.1 g of title compound.

$C_8H_6BrNO$ Mass (calculated): [212]; (found): $[M+H^+]$=212, 214 (Br). NMR (400 MHz, dmso-$d_6$): 2.55 (3H, s, $CH_3$); 7.3 (1H, d, J=8 Hz, aryl-H); 7.35 (1H, dd, J=1 and 8 Hz, aryl-H); 7.75 (1H, d, J=2 Hz, aryl-H).

Step 3) 4-methoxy-3-(2-methylbenzoxazol-5-yl) benzenecarboxaldehyde

A solution of 5-formyl-2-methoxybenzeneboronic acid (1 g, 5.6 mmol), 2-methyl-5-bromobenzoxazole (1 g, 4.72 mmol) and $K_2CO_3$ (1.63 g, 11.8 mmol) in ethanol (20 mL) and toluene (40 mL) was degassed prior to addition of $Pd(Ph_3)_4$ (55 mg, 0.047 mmol). The mixture was refluxed for 20 hours then cooled and filtered through diatomaceous earth. The filtrate was concentrated in vacuo, extracted with ethyl acetate, washed with water and the organic layer dried over sodium sulphate. The crude was purified by column chromatography (heptane/ethyl acetate 7/3 to 6/4) to give 1.13 g of title compound.

$C_{16}H_{13}NO_4$ Mass (calculated): [267]; (found): $[M+H^+]$: 268. NMR (400 MHz, CDCl3): 2.6 (3H, s, $CH_3$); 3.85 (3H, s, $CH_3O$); 7.05 (1H, d, J=8 Hz, aryl-H); 7.35 (1H, d, J=8 Hz, aryl-H); 7.45 (1H, d, J=8 Hz, aryl-H); 7.75 (1H, s, aryl-H); 7.8–7.85 (2H, m, aryl-H); 9.9 (1H, s, CHO).

Step 4) (R)-N-(1-Phenylethyl)-N-((4-methoxy-3-(2-methylbenzoxazol-5-yl)methyl)amine:

The title compound was prepared from 4-methoxy-3-(benzimidazol-2-yl)benzenecarboxaldehyde and (R)-α-methylbenzylamine according to general procedure C.

$C_{24}H_{24}N_2O_2$ Mass (calculated): [372]; (found): $[M+H^+]$=373. NMR (400 MHz, CDCl3): 1.3 (3H, d, J=6 Hz, $NCHCH_3$); 2.6 (3H, s, $CH_3$); 3.55 and 3.6 (2H, dd, J=12 Hz, $CH_2N$); 3.7 (3H, s, $CH_3O$); 3.75 (1H, q, J=6 Hz; NCHMe); 6.8 (1H, d, J=8 Hz, aryl-H); 7.2–7.3 (3H, m, aryl-H); 7.3–7.35 (4H, m, aryl-H); 7.4 (1H, dd, J=1 and 8 Hz, aryl-H); 7.45 (1H, d, J=8 Hz, aryl-H); 7.7 (1H, d, J=1 Hz, aryl-H).

EXAMPLE 29

(R)-N-(1-(3-Methoxyphenyl)ethyl)-N-((4-methoxy-3-(2-methylbenzoxazol-5-yl)methyl)amine

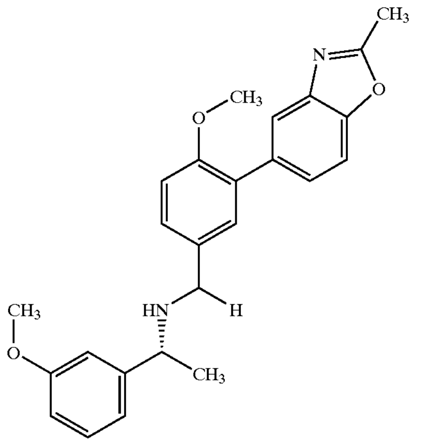

The title compound was prepared from 4-methoxy-3-(2-methylbenzoxazol-5-yl)benzenecarboxyaldehyde and (R)-3-methoxy-α-methylbenzylamine according to general procedure C.

$C_{25}H_{26}N_2O_3$ Mass (calculated): [402]; (found): $[M+H^+]$= 403. NMR (400 MHz, CDCl3): 1.3 (3H, bd, J=6 Hz, $NCHCH_3$); 2.6 (3H, s, $CH_3$); 3.55 and 3.6 (2H, dd, J=12 Hz, $CH_2N$); 3.7 (3H, s, $CH_3O$); 3.72 (3H, s, $CH_3O$); 3.75 (1H, q, J=6 Hz; NCHMe); 6.75 (1H, dd, J=1 and 8 Hz, aryl-H); 6.8–6.9 (3H, m, aryl-H); 7.2–7.3 (3H, m, aryl-H); 7.4 (1H, dd, J=1 and 8 Hz, aryl-H); 7.45 (1H, d, J=8 Hz, aryl-H); 7.7 (1H, d, J=1 Hz, aryl-H).

EXAMPLE 30

(R)-N-(1-(1-Naphthylethyl)-N-((4-methoxy-3-(2-methylbenzoxazol-5-yl)methyl)amine

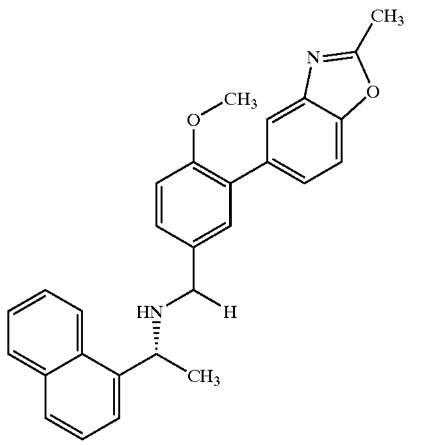

The title compound was prepared from 4-methoxy-3-(2-methylbenzoxazol-5-yl)benzenecarboxyaldehyde and (R)-1-(1-naphthyl)ethylamine according to general procedure C.

$C_{28}H_{26}N_2O_2$ Mass (calculated): [422]; (found): $[M+H^+]$= 423. NMR (400 MHz, CDCl3): 1.45 (3H, d, J=6 Hz, $NCHCH_3$); 2.6 (3H, s, $CH_3$); 3.6 and 3.65 (2H, dd, J=12 Hz, $CH_2N$); 3.7 (3H, s, $CH_3O$); 4.6 (1H, q, J=6 Hz; NCHMe); 6.8 (1H, d, J=8 Hz, aryl-H); 7.2–7.3 (3H, m, aryl-H); 7.35 (1H, dd, J=1 and 8 Hz, aryl-H); 7.4–7.5 (3H, m, aryl-H); 7.7–7.75 (3H, m, aryl-H); 7.8–7.85 (1H, m, aryl-H); 8.05–8.1 (1H, m, aryl-H).

EXAMPLE 31

(R)-N-(1-Phenylethyl)-N-((4-methoxy-3-(benzoxazol-5-yl)methyl)amine

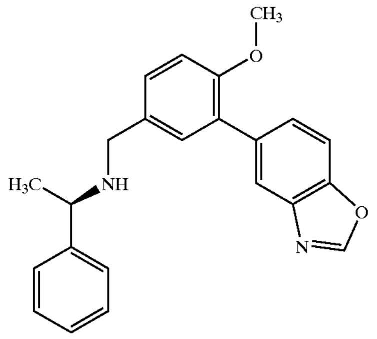

Step 1) 5-Bromobenzoxazole:

A solution of 2-amino-4-bromophenol (2 g, 10.6 mmol) in triethylorthoformate (40 mL) was refluxed for 1.5 hours. The reaction was then cooled and the solvent removed under reduced pressure to give a crude which was purified by washing through a plug of silica eluting with hexane/ethyl acetate 3/2 to afford 1.1 g of title compound. $C_7H_4BrNO$ Mass (calculated): [198]; (found): $[M+H^+]$=198, 200 (Br) NMR (400 MHz, $CDCl_3$): 7.25–7.3 (2H, m, aryl-H); 7.8 (1H, d, J=1, aryl-H); 8.0 (1H, s, aryl-H).

Step 2) 4-Methoxy-3-(benzoxazol-5-yl) benzenecarboxyaldehyde:

A solution of 5-formyl-2-methoxybenzeneboronic acid (1 g, 5.6 mmol), 2-methyl-5-bromobenzoxazole (1 g, 4.72 mmol) and $K_2CO_3$ (1.63 g, 11.8 mmol) in ethanol (20 mL) and toluene (40 mL) was degassed prior to addition of $Pd(Ph_3)_4$ (55 mg, 0.047 mmol). The mixture was refluxed for 20 hours then cooled and filtered through diatomaceous earth. The filtrate was concentrated in vacuo, extracted with ethyl acetate, washed with water and the organic layer dried over sodium sulphate. The crude was purified by column chromatography (heptane/ethyl acetate 7/3 to 6/4) to give 1.13 g of title compound.

$C_{15}H_{11}NO_3$ Mass (calculated): [253]; (found): $[M+H^+]$: 254, 295. NMR (400 MHz, CDCl3): 2.6 (3H, s, $CH_3$); 3.95 (3H, s, $CH_3O$); 7.15 (1H, d, J=8 Hz, aryl-H); 7.55 (1H, d, J=8 Hz, aryl-H); 7.65 (1H, d, J=8 Hz, aryl-H); 7.85–7.95 (2H, aryl-H); 8 (1H, s, aryl-H); 8.15 (1H, s, aryl-H); 10.0 (1H, s, CHO).

Step 3) (R)-N-(1-Phenylethyl)-N-((4-methoxy-3-(benzoxazol-5-yl)methyl)amine:

The title compound was prepared from 4-methoxy-3-(benzoxazol-5-yl)benzenecarboxyaldehyde and (R)-α-methylbenzylamine according to general procedure C.

$C_{23}H_{22}N_2O_2$ Mass (calculated): [358]; (found): $[M+H^+]$= 359, 831. NMR (400 MHz, CDCl3): 1.3 (3H, d, J=6 Hz, $NCHCH_3$); 2.6 (3H, s, $CH_3$); 3.5 and 3.55 (2H, dd, J=12 Hz, $CH_2N$); 3.7 (3H, s, $CH_3O$); 3.75 (1H, q, J=6 Hz; NCHMe); 6.85 (1H, d, J=8 Hz, aryl-H); 7.1–7.2 (3H, m, aryl-H); 7.2–7.3 (4H, m, aryl-H); 7.45 (1H, dd, J=1 and 8 Hz, aryl-H); 7.5 (1H, d, J=8 Hz, aryl-H); 7.8 (1H, d, J=1 Hz, aryl-H); 8 (1H, s, aryl-H).

EXAMPLE 32

(R)-N-(1-(1-(3-Methoxyphenyl)ethyl)-N-((4-methoxy-3-(benzoxazol-5-yl)methyl)amine

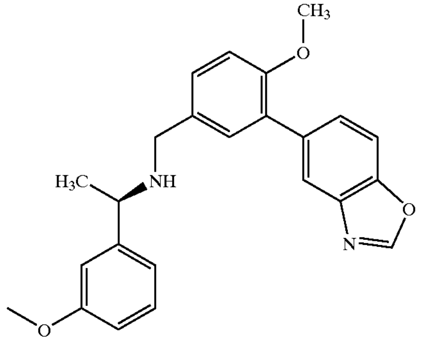

The title compound was prepared from 4-methoxy-3-(benzoxazol-5-yl)benzene-carboxyaldehyde and (R)-3-methoxy-α-methylbenzylamine according to general procedure C.

$C_{24}H_{24}N_2O_3$ Mass (calculated): [388]; (found): $[M+H^+]$= 389, 891. NMR (400 MHz, CDCl3): 1.3 (3H, d, J=6 Hz, $NCHCH_3$); 2.6 (3H, s, $CH_3$); 3.5 and 3.55 (2H, dd, J=12 Hz, $CH_2N$); 3.7–3.8 (4H, m, $CH_3O$ and NCHMe); 6.7 (1H, dd, J=2 and 8 Hz, aryl-H); 6.8–6.9 (3H, m, aryl-H); 7.15–7.25 (3H, m, aryl-H); 7.45 (1H, dd, J=1 and 8 Hz, aryl-H); 7.5 (1H, d, J=8 Hz, aryl-H); 7.85 (1H, d, J=1 Hz, aryl-H); 8 (1H, s, aryl-H).

EXAMPLE 33

(R)-N-1-(1-Naphthyl)ethyl)-N-((4-methoxy-3-(benzoxazol-5-yl)methyl)amine

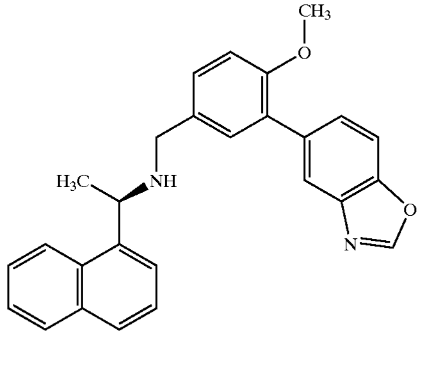

The title compound was prepared from 4-methoxy-3-(benzoxazol-5-yl)benzenecarboxyaldehyde and (R)-1-(1-naphthyl)ethylamine according to general procedure C.

$C_{27}H_{24}N_2O_2$ Mass (calculated): [408]; (found): [M+H$^+$]=409, 931. NMR (400 MHz, CDC13): 1.45 (3H, d, J=6 Hz, $NCHCH_3$); 3.6 and 3.65 (2H, dd, J=12 Hz, $CH_2N$); 3.7 (3H, s, $CH_3O$); 4.65 (1H, q, J=6 Hz; NCHMe); 6.85 (1H, d, J=8 Hz, aryl-H); 7.2–7.3 (2H, m, aryl-H); 7.4–7.5 (4H, m, aryl-H); 7.5 (1H, d, J=6 Hz, aryl-H); 7.7–7.75 (2H, m, aryl-H); 7.75–7.8 (1H, m, aryl-H); 7.85 (1H, d, J=1 Hz, aryl-H); 8 (1H, s, aryl-H); 8.05–8.1 (1H, m, aryl-H).

EXAMPLE 34

(R)-N-(1-Phenylethyl)-N-((4-chloro-3-(4'-methoxyphenyl)phenylmethyl)amine

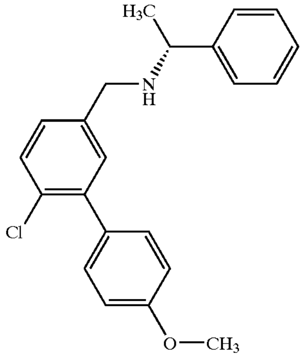

Step 1) 3-Bromo-4-chlorobenzyl alcohol:

A solution of 3-bromo-4-chlorobenzoic acid (3.53 g, 15 mmol) was dissolved in anhydrous THF (20 mL) and cooled to 0 C prior to addition of borane (1M soln in THF, 20 mL, 20 mmol). The solution was then heated at 65 C for 12 hours then cooled to 0 C and methanol was added dropwise to quench excess borane. The solvent was evaporated under reduced pressure, the residue was redissolved in ethyl acetate and washed with saturated $NH_4Cl$ then brine, dried over sodium sulphate. The solvent was removed in vacuo to afford 3.23 g of title compound.

$C_7H_6BrClO$ Mass (calculated): [221], MH$^+$ not found. NMR (400 MHz, $CDCl_3$): 4.6 (2H, S, $CH_2OH$); 7.15 (1H, dd, J=1 and 8 Hz, aryl-H); 7.35 (1H, d, J=8 Hz, aryl-H); 7.55 (1H, d, J=1 Hz, aryl-H).

Step 2) 3-Bromo-4-chlorobenzaldehyde:

A solution of 3-bromo-4-chlorobenzyl alcohol (3.24 g, 14.6 mmol) in acetone (100 mL) was treated with $MnO_2$ (16.2 g, 73 mmol) and the mixture stirred for 3 days then filtered over diatomaceous earth. The filtrate was concentrated under reduced pressure to afford 2.0 g of title compound.

$C_7H_4BrClO$ Mass (calculated): [219]; MH$^+$ not found. NMR (400 MHz, $CDCl_3$): 7.55 (1H, d, J=8 Hz, aryl-H); 7.7 (1H, dd, J=1 and 8 Hz, aryl-H); ; 8.05 (1H, d, J=1 Hz, aryl-H); 9.85 (1H, s, CHO).

Step 3) 4-chloro-3-(4-methoxyphenyl) benzenecarboxaldehyde:

To a degassed solution of 4-methoxybenzeneboronic acid (1.51 g, 10 mmol), 3-bromo-4-chlorobenzaldehyde (2 g, 9.13 mmol), and potassium carbonate (3.13 g, 22.8 mmol) in toluene/ethanol 2/1, (60 mL), $Pd(PPh_3)_4$ (130 mg, 1 mol %) is added and the mixture is degassed for further 5 minutes. The mixture is then refluxed for 2 days. The mixture was partitioned between ethyl acetate and water and extracted. The organic solvent was dried over sodium sulphate, removed under reduced pressure, and the residue purified by column chromatography (heptane/ethyl acetate 19/1 to afford 1.41 g of product.

$C_{14}H_{11}ClO_2$ Mass (calculated): [246]; MH$^+$ not found. NMR (400 MHz, $CDCl_3$): 3.8 (3H, s, MeO); 6.9 (2H, d, J=8 Hz, aryl-H); 7.35 (2H, d, J=8 Hz, aryl-H); 7.55 (1H, d, J=8 Hz, aryl-H); 7.7 (1H, dd, J=2 and 8 Hz, aryl-H); 7.75 (1H, d, J=2 Hz, aryl-H); 9.9 (1H, s, CHO).

Step 4) (R)-N-(1-Phenylethyl)-N-((4-chloro-3-(4'-methoxyphenyl)phenylmethyl)amine:

The title compound was prepared from 4-chloro-3-(4-methoxyphenyl)-benzenecarboxaldehyde and (R)-α-methylbenzylamine according to general procedure C.

$C_{22}H_{22}ClNO$ Mass (calculated): [351]; (found): [M+H$^+$]=352, 354 (Cl). NMR (400 MHz, $CDCl_3$): 1.15 (3H, d, J=6 Hz, $NCHCH_3$); 3.4 and 3.45 (2H, dd, J=12 Hz, $CH_2N$); 3.55 (1H, m, NCHMe); 3.6 (3H, s, MeO); 6.8 (2H, d, J=8 Hz, aryl-H); 7 (1H, dd, J=1 and 8 Hz, aryl-H); 7.05–7.1 (2H, m, aryl-H); 7.15–7.25 (7H, m, aryl-H).

EXAMPLE 35

(R)-N-(1-(3-Methoxyphenyl)ethyl)-N-((4-chloro-3-(4'-methoxyphenyl)-phenylmethyl)amine

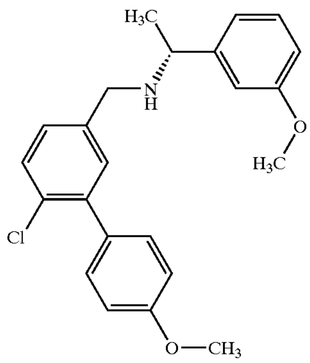

The title compound was prepared from 4-chloro-3-(4-methoxyphenyl)benzene-carboxaldehyde and (R)-3-methoxy-α-methylbenzylamine according to general procedure C.

$C_{23}H_{23}ClNO_2$ Mass (calculated): [381]; (found): [M+H$^+$]=382, 384 (Cl). NMR (400 MHz, $CDCl_3$): 1.3 (3H, d, J=6 Hz, $NCHCH_3$); 3.55 and 3.6 (2H, dd, J=12 Hz, $CH_2N$); 3.7–3.75 (4H, m, NCHMe and MeO); 3.8 (3H, s, MeO); 6.75 (1H, dd, J=2 and 8 Hz, aryl-H); 7.85 (1H, d, J=1 Hz, aryl-H); 7.9 (2H, d, J=8 Hz, aryl-H); 7.15 (1H, dd, J=1 and 8 Hz, aryl-H); 7.15–7.25 (2H, m, aryl-H); 7.3–7.4 (3H, m, aryl-H).

EXAMPLE 36

(R)-N-(1-(1-Naphthyl)ethyl)-N-((4-chloro-3-(4'-methoxyphenyl)phenylmethyl)amine

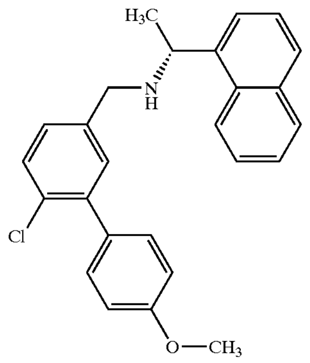

The title compound was prepared from 4-chloro-3-(4-methoxyphenyl)benzene-carboxaldehyde and (R)-1-(1-naphthyl)ethylamine according to general procedure C.

$C_{26}H_{24}ClNO$ Mass (calculated): [401]; (found): [M+H$^+$]=402, 404 (Cl). NMR (400 MHz, $CDCl_3$): 1.45 (3H, d, J=6 Hz, $NCHCH_3$); 3.6 and 3.65 (2H, dd, J=12 Hz, $CH_2N$); 3.75 (3H, s, MeO); 4.6 (1H, m, NCHMe); 6.85 (2H, d, J=8 Hz, aryl-H); 7.1 (1H, dd, J=1 and 8 Hz, aryl-H); 7.2 (1H, d, J=1 Hz, aryl-H); 7.3–7.35 (3H, m, aryl-H); 7.4–7.45 (3H, m, aryl-H); 7.65–7.7 (2H, m, aryl-H); 7.8–7.85 (1H, m, aryl-H); 8.05–8.1 (1H, m, aryl-H).

EXAMPLE 37

(R)-N-(1-Phenylethyl)-N-((4-propargyloxy-3-(4'-methoxyphenyl)phenylmethyl)amine

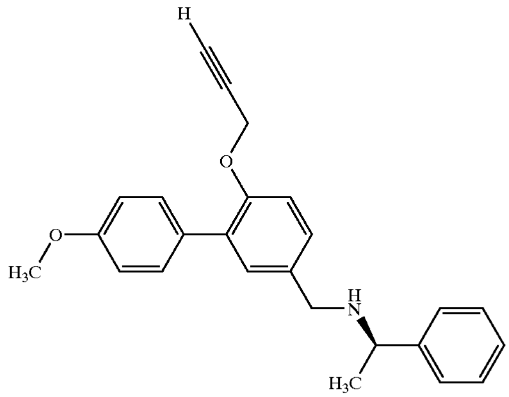

Step 1) Benzyl 4-benzyloxy-3-bromobenzoate:

A 500 mL round bottom flask was charged with DMF (250 mL), 3-bromo-4-hydroxybenzoic acid (8.68 g, 40 mmol), potassium carbonate (22.06 g, 160 mmol) potassium iodide (50 mg) and benzyl bromide (9.26 mL, 78 mmol). The mixture was heated at 75 C for 3 days, then cooled, the solvent removed under reduced pressure and the residue redissolved in ethyl acetated and washed with aqueous potassium carbonate, then brine. The organic layer was dried over sodium sulphate then removed under reduced pressure to give an off-white solid which was purified by column chromatography (eluting with DCM/hexane 1/1) to give 12.1 g of title compound).

$C_{21}H_{17}BrO_3$ Mass (calculated): [397]; found 397, 399 (Br). NMR (400 MHz, $CDCl_3$): 5.15 (2H, s, $OCH_2Ph$); 5.25 (2H, s, $OCH_2Ph$); 6.85 (1H, d, J=8 Hz, aryl-H); 7.3–7.5 (10H, m, aryl-H); 7.9 (1H, dd, J=1 and 8 Hz, aryl-H); 8.2 (1H, d, J=1 Hz, aryl-H).

Step 2) Benzyl 4-benzyloxy-3-(4-methoxyphenyl)benzoate:

To a degassed solution of 4-methoxybenzeneboronic acid (5.0 g, 32.9 mmol), benzyl 4-benzyloxy-3-bromobenzoate (12.1 g, 30.5 mmol), and potassium carbonate (10.4 g, 76.2 mmol) in toluene/ethanol 2/1, (140 mL), $Pd(PPh_3)_4$ (400 mg, 1 mol %) was added and the mixture is degassed for further 5 minutes. The mixture is then refluxed for 12 hours. The mixture was partitioned between ethyl acetate and water and extracted. The organic solvent was dried over sodium sulphate, removed under reduced pressure, and the residue purified by column chromatography (9/1 DCM/hexane) to afford 0.73 g of pure title compound, 9.74 g of a 4:6 mixture of title compound and the corresponding ethyl ester, and 0.71 g of the ethyl ester derivative.

$C_{28}H_{24}O_4$ NMR (400 MHz, $CDCl_3$): $C_{28}H_{24}O_4$ Ethyl ester: NMR (400 MHz, $CDCl_3$): 1.3 (3H, t, J=6 Hz, $OCH_2CH_3$); 3.75 (3H, s, $CH_3O$); 4.3 (2H, q, J=6 Hz, $OCH_2CH_3$); 5.1 (2H, s, OCH2Ph); 6.95 (2H, m, aryl-H); 7.2–7.3 (2H, m, aryl-H); 7.45 (2H, m, aryl-H); 7.85 (1H, dd, J=1 and 8 Hz, aryl-H). Benzyl ester: NMR (400 MHz, $CDCl_3$): 3.75 (3H, s, $CH_3O$); 4.65 (2H, s, $OCH_2Ph$); 5.1 (2H, s, OCH2Ph); 7 (2H, m, aryl-H); 7.2–7.3 (2H, m, aryl-H); 7.45 (2H, m, aryl-H); 8.05 (1H, dd, J=1 and 8 Hz, aryl-H).

Step 3) Ethyl 4-hydroxy-3-(4-methoxyphenyl)benzoate and 4-hydroxy-3-(4-methoxyphenyl)benzoic Acid:

A mixture of benzyl and ethyl 4-benzyloxy-3-(4-methoxyphenyl)benzoates (9.74 g, ca, 22.9 mmol) was hydrogenated in THF/ethanol (100 mL) under atmospheric pressure for 60 hours, then the catalyst removed by filtration and the solvent evaporated in vacuo to afford 6.62 g of a mixture of the title compounds.

$C_{12}H_{16}O_4$ Mass (calculated): [244]; found: 245. NMR (400 MHz, $CDCl_3$): 3.8 (3H, s, $CH_3O$); 5.8 (1H, bs, OH); 6.95 (3H, m, aryl-H); 7.35 (2H, d, J=8 Hz, aryl-H); 7.9–8 (2H, m, aryl-H). $C_{16}H_{16}O_4$ Mass (calculated): [272]; found: 273. NMR (400 MHz, $CDCl_3$): 1.3 (3H, t, J=6 Hz, $CH_3CH_2O$); 3.8 (3H, s, $CH_3O$); 4.3 (2H, q, J=6 Hz, $CH_3CH_2O$); 5.75 (1H, s, OH); 6.9–7 (3H, m, aryl-H); 7.35 (2H, d, J=8 Hz, aryl-H); 7.9–7.95 (2H, m, aryl-H).

Step 4) 4-hydroxy-3-(4-methoxyphenyl)benzyl Alcohol:

A solution of Ethyl 4-hydroxy-3-(4-methoxyphenyl) benzoate and 4-hydroxy-3-(4-methoxyphenyl)benzoic acid (5.3 g, 19.47 mmol) in anhydrous THF (100 mL) was cooled to 0° C. and treated with $LiAlH_4$ (2.95 g, 77.8 mmol); the mixture was then heated at 65 C for one hour then cooled and aqueous NaOH (5%, 19.4 mL) was added drop wise. The resulting precipitate was filtered off and the filtrate concentrated under reduced pressure to afford 5.54 g of crude product.

$C_{14}H_{14}O_3$ Mass (calculated): [230]; found: 213 [MH$^+$—OH]. NMR (400 MHz, $CDCl_3$): 3.8 (3H, s, $CH_3O$); 4.55 (2H, s, $CH_2$); 6.9 (1H, d, J=8 Hz, aryl-H); 6.9–7 (2H, m, aryl-H); 7.25–7.35 (2H, m, aryl-H); 7.4–7.45 (2H, m, aryl-H).

Step 5) 4-Hydroxy-3-(4-methoxyphenyl)benzaldehyde:

A solution of 4-hydroxy-3-(4-methoxyphenyl)benzyl alcohol (5.54 g, 24 mmol) in acetone (250 mL) was treated with $MnO_2$ and the mixture stirred for 3 days. The solid was filtered on diatomaceous earth and the filtrate was concentrated under reduced pressure to afford 5.96 g of title compound as a pale green oil, impure with manganese salts.

$C_{14}H_{12}O_3$ Mass (calculated): [228]; found: 229.

Step 6) 4-Propargyloxy-3-(4-methoxyphenyl)benzaldehyde:

A solution of 4-hydroxy-3-(4-methoxyphenyl) benzaldehyde (1.14 g, 5 mmol) in DMF (10 mL) was treated with potassium carbonate (2.48 g, 18 mmol), potassium iodide (10 mg) and propargyl bromide (0.67 mL, 6 mmol). The mixture was heated at 80 C for 3 days, then cooled and the solvent removed under reduced pressure. The residue was redissolved in ethyl acetate and washed water then brine. The organic layer was dried over sodium sulphate then the solvent removed under reduced pressure and the residue purified by column chromatography (3/1 hexane/ethyl acetate) to afford 0.078 g of title compound.

$C_{17}H_{14}O_3$ Mass (calculated): [266]; found: 267. NMR (400 MHz, $CDCl_3$): 2.45 (1H, t, J=1 Hz, C#CH); 3.75 (3H, s, $CH_3O$); 4.7 (2H, d, J=1 Hz, C#$CCH_2O$); 6.85 (2H, d, J=8 Hz, aryl-H); 7.15 (1H, d, J=8 Hz, aryl-H); 7.4 (2H, d, J=8 Hz, aryl-H); 7.75–7.85 (2H, m, aryl-H).

Step 7) (R)-N-(1-Phenylethyl)-N-((4-propargyloxy-3-(4'-methoxyphenyl)phenylmethyl)amine:

The title compound was prepared from 4-propargyloxy-3-(4-methoxyphenyl)-benzaldehyde and (R)-α-methylbenzylamine according to general procedure C.

$C_{25}H_{25}NO_2$ Mass (calculated): [371]; (found): $[M+H^+]$=372. NMR (400 MHz, $CDCl_3$): 1.3 (3H, d, J=6 Hz, $NCHCH_3$); 2.3 (1H, t, J=1 Hz, C#CH); 3.5 and 3.55 (2H, dd, J=12 Hz, $CH_2N$); 3.75–3.8 (4H, m, NCHMe and MeO); 4.55 (2H, d, J=1 Hz, C#$CCH_2O$); 6.85 (2H, d, J=8 Hz, aryl-H); 7 (1H, d, J=8 Hz, aryl-H); 7.1–7.2 (3H, m, aryl-H); 7.25–7.35 (4H, m, aryl-H); 7.4 (2H, d, J=8 Hz, aryl-H).

EXAMPLE 38

(R)-N-(1-Phenylethyl)-N-((4-ethoxy-3-(4'-methoxyphenyl)phenylmethyl)amine

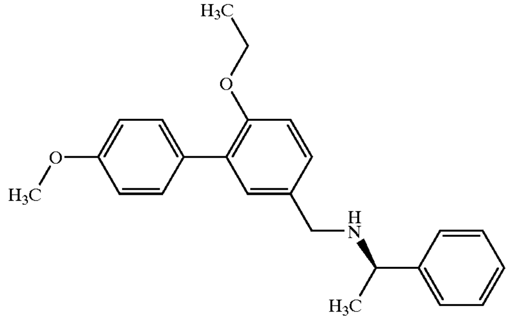

Step 1) 4-Ethoxy-3-(4-methoxyphenyl)benzaldehyde:

A solution of 4-hydroxy-3-(4-methoxyphenyl) benzaldehyde (0.5 g, 2.19 mmol) in DMF (5 mL) was treated with potassium carbonate (0.9 g, 6.57 mmol), potassium iodide (10 mg) and ethyl iodide (0.21 mL, 02.63 mmol). The mixture was heated at 80° C. for 3 days, then cooled and the solvent removed under reduced pressure. The residue was redissolved in ethyl acetate and washed water then brine. The organic layer was dried over sodium sulphate then the solvent removed under reduced pressure and the residue purified by column chromatography (3/1 hexane/ethyl acetate) to afford 0.043 g of title compound.

$C_{16}H_{16}O_3$ Mass (calculated): [256]; found: 257. NMR (400 MHz, $CDCl_3$): 1.3 (3H, t, J=6 Hz, $CH_3CH_2O$); 3.75 (3H, s, $CH_3O$); 4.1 (2H, q, J=6 Hz, $CH_3CH_2O$); 6.85 (2H, d, J=8 Hz, aryl-H); 6.95 (1H, d, J=8 Hz, aryl-H); 7.4 (2H, d, J=8 Hz, aryl-H); 7.7 (1H, dd, J=1 and 8 Hz, aryl-H); 7.75 (1H, d, J=1 Hz, aryl-H).

Step 2) (R)-N-(1-Phenylethyl)-N-((4-ethoxy-3-(4'-methoxyphenyl)phenylmethyl)amine The title compound was prepared from 4-ethoxy-3-(4-methoxyphenyl)benzaldehyde and (R)-α-methylbenzylamine according to general procedure C.

$C_{24}H_{27}NO_2$ Mass (calculated): [361]; (found): $[M+H^+]$=362. NMR (400 MHz, $CDCl_3$): 1.25 (3H, t, J=6 Hz, $OCH_2CH_3$) 1.3 (3H, d, J=6 Hz, $NCHCH_3$); 3.5 and 3.55 (2H, dd, J=12 Hz, $CH_2N$); 3.75–3.8 (4H, m, NCHMe and MeO); 3.95 (2H, q, J=6 Hz, $OCH_2CH_3$); 6.8 (1H, d, J=8 Hz, aryl-H); 6.85 (2H, d, J=8 Hz, aryl-H); 7.15–7.35 (2H, m, aryl-H); 7.35–7.4 (4H, m, aryl-H); 7.45 (2H, d, J=8 Hz, aryl-H).

EXAMPLE 39

(R)-N-(1-Phenylethyl)-N-((4-methoxy-3-(3,4-dimethoxyphenyl)phenylmethyl)amine

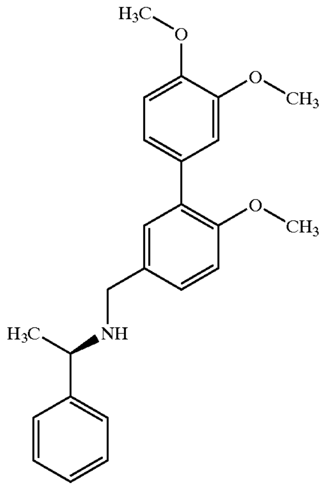

Step 1) 4-Methoxy-3-(3,4-dimethoxyphenyl) benzenecarboxaldehyde:

To a degassed solution of 3,4-dimethoxybenzeneboronic acid (2.18 g, 12 mmol), 3-bromo-4-methoxybenzaldehyde (3.23 g, 15 mmol) and potassium carbonate (5.18 g, 37.5 mmol) in toluene/ethanol 2/1 (72 mL), $Pd(PPh_3)_4$ (173 mg, 1.2 mol %) was added and the mixture was degassed for further 5 minutes. The mixture was then refluxed for 15 hours. The solid was filtered off and the filtrate concentrated under reduced pressure. The residue was dissolved in AcOEt, partitioned between ethyl acetate and water and extracted then washed with brine. The organic solvent was dried over sodium sulphate, removed under reduced pressure, and the residue purified by column chromatography (heptane/ethyl acetate 1/1) to afford 2.95 of title compound.

$C_{16}HI_6O_4$ Mass (calculated): [272]; found: 273. NMR (400 MHz, $CDCl_3$): 3.85–3.87 (9H, 3s, 3 $CH_3O$); 6.9 (1H, d, J=8 Hz, aryl-H); 6.9–7.05 (3H, m, aryl-H); 7.85–7.9 (2H, m, aryl-H); 9.85 (1H, s, CHO).

Step 2) (R)-N-(1-Phenylethyl)-N-((4-methoxy-3-(3,4-dimethoxyphenyl)-phenylmethyl)amine:

The title compound was prepared from 4-methoxy-3-(3,4-dimethoxyphenyl)benzenecarboxaldehyde and (R)-α-methylbenzylamine according to general procedure C.

$C_{24}H_{27}NO_3$ Mass (calculated): [377]; (found): $[M+H^+]$= 378. NMR (400 MHz, $CDCl_3$): 1.3 (3H, t, J=6 Hz, $NCHCH_3$); 3.55 and 3.6 (2H, dd, J=12 Hz, $CH_2N$); 3.7 (3H, s, $CH_3O$); 3.8–4 (7H, m, NCHMe and 2 MeO); 6.8–68.5 (2H, m, aryl-H); 6.95–7.05 (2H, m, aryl-H); 7.1–7.15 (2H, m, aryl-H); 7.25–7.4 (4H, m, aryl-H).

EXAMPLE 40

(R)-N-(1-(3-Methoxyphenyl)ethyl)-N-((4-methoxy-3-(3,4-dimethoxyphenyl)phenylmethyl)amine

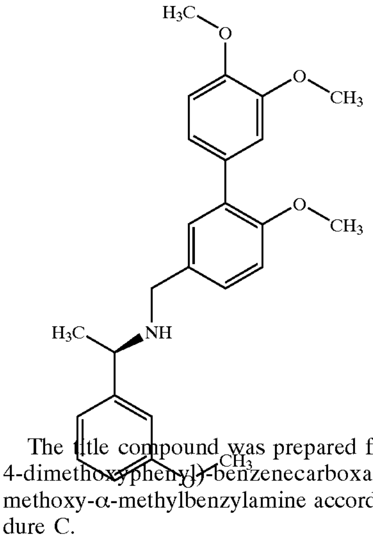

The title compound was prepared from 4-methoxy-3-(3, 4-dimethoxyphenyl)-benzenecarboxaldehyde and (R)-3-methoxy-α-methylbenzylamine according to general procedure C.

$C_{25}H_{29}NO_4$ Mass (calculated): [407]; (found): $[M+H^+]$= 408. NMR (400 MHz, $CDCl_3$): 1.3 (3H, t, J=6 Hz, $NCHCH_3$); 3.55 and 3.6 (2H, dd, J=12 Hz, $CH_2N$); 3.7 and 3.72 (6H, 2 s, 2 $CH_3O$); 3.8–3.9 (4H, m, NCHMe and $CH_3O$); 6.8 (1H, dd, J=2 and 8 Hz, aryl-H); 6.8–6.9 (2H, m, aryl-H); 6.9–7 (2H, m, aryl-H); 7–7.05 (2H, m, aryl-H); 7.15–7.3 (3H, m, aryl-H).

EXAMPLE 41

(R)-N-(1-(1-Naphthyl)ethyl)-N-((4-methoxy-3-(3,4-dimethoxyphenyl)-phenylmethyl)amine

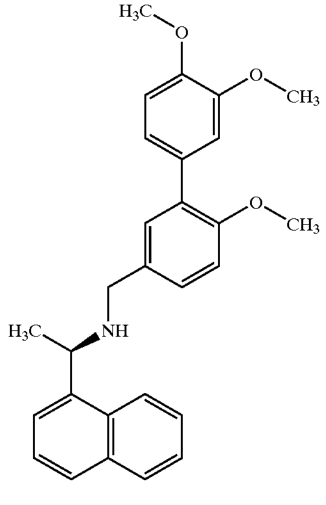

The title compound was prepared from 4-methoxy-3-(3, 4-dimethoxyphenyl)benzenecarboxaldehyde and (R)-1-(1-naphthyl)ethylamine according to general procedure C.

$C_{28}H_{29}NO_3$ Mass (calculated): [427]; (found): $[M+H^+]$= 428, 257, 155. NMR (400 MHz, $CDCl_3$): 1.4 (3H, t, J=6 Hz, $NCHCH_3$); 3.55 and 3.6 (2H, dd, J=12 Hz, $CH_2N$); 3.7 (3H, s, $CH_3O$); 3.8 and 3.82 (6H, 2 s, 2 CH+O); 6.8–6.85 (2H, m, aryl-H); 6.95–7.0 (2H, m, aryl-H); 7.1–7.2 (2H, m, aryl-H); 7.3–7.5 (3H, m, aryl-H); 7.65–7.7 (2H, m, aryl-H); 7.75–7.8 (1H, m, aryl-H); 8.05–8.1 (1H, m, aryl-H).

EXAMPLE 42

(R)-N-(1-Phenylethyl)-N-((4-methoxy-3-(pyrid-2-yl)phenylmethyl)amine

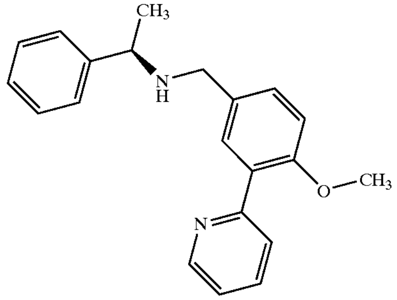

Step 1) 4-Methoxy-3-(pyrid-2-yl)benzenecarboxaldehyde:

A degassed solution of 2-bromopyridine (1.0 g, 6.33 mmol), 3-borono-4-methoxybenzaldehyde (1.37 g, 7.6 mmol) and $[(PPh_3)_2PdCl_2$ (64 mg, 0.09 mmol) in dimethoxyethane (30 mL), methanol (5 mL) and $Na_2CO_3$ (2M, 20 mL) was heated at 75° C. for 16 hours. The mixture was then cooled, diluted with water and extracted with DCM. The organic layer was dried over sodium sulphate and the solvent removed under reduced pressure. The crude was purified by column chromatography (heptane/AcOEt 7/3 to 6/4) to afford 1.31 g of title compound.

$C_{13}H_{11}NO_2$ Mass (calculated): [213]; (found) $[M+H^+]$= 214. NMR (400 MHz, $CDCl_3$): 3.85 (3H, s, MeO); 7.05 (1H, d, J=8 Hz, aryl/pyridyl-H); 7.2 (1H, m, aryl/pyridyl-H); 7.65 (1H, m, aryl/pyridyl-H); 7.75 (1H, m, aryl/pyridyl-H); 7.85 (1H, m, aryl/pyridyl-H); 8.2 (1H, s, aryl/pyridyl-H); 8.65 (1H, s, aryl/pyridyl-H); 9.9 (1H, s, CHO).

Step 2) (R)-N-(1-Phenylethyl)-N-((4-methoxy-3-(pyrid-2-yl)phenylmethyl)amine

The title compound was prepared from 4-methoxy-3-(pyrid-2-yl)-benzenecarboxaldehyde and (R)-α-methylbenzylamine according to general procedure C.

$C_{21}H_{22}N_2O$ Mass (calculated): [318]; (found): $[M+H^+]$= 319, 198. NMR (400 MHz, $CDCl_3$): 1.3 (3H, d, J=6 Hz, $NCHCH_3$); 3.5 and 3.55 (2H, dd, J=12 Hz, $CH_2N$); 3.7 (3H, s, MeO); 3.75 (1H, q, J=7 Hz; NCHMe); 6.8 (1H, d, J=8 Hz, aryl-H); 7.05–7.1 (1H, m, aryl-H); 7.15–7.35 (6H, m, aryl-H); 7.55–7.6 (2H, m, aryl-H); 7.7 (1H, d, J=8 Hz, aryl-H); 8.55–8.6 (1H, m, pyridyl-H).

EXAMPLE 43

(R)-N-(1-(3-Methoxyphenyl)ethyl)-N-((4-methoxy-3-(pyrid-2-yl)phenylmethyl)amine

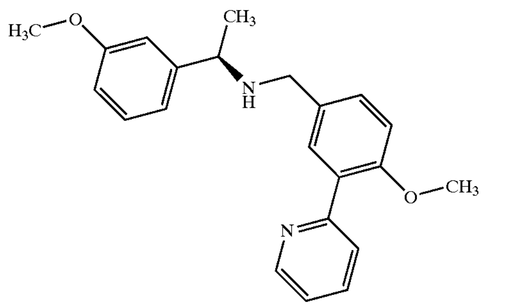

The title compound was prepared from 4-methoxy-3-(pyrid-2-yl)benzenecarboxaldehyde and (R)-3-methoxy-α-methylbenzylamine according to general procedure C.

$C_{22}H_{24}N_2O_2$ Mass (calculated): [348]; (found): $[M+H^+]$=349, 198. NMR (400 MHz, $CDCl_3$): 1.3 (3H, d, J=6 Hz, $NCHCH_3$); 3.55 and 3.6 (2H, dd, J=12 Hz, $CH_2N$); 3.7–3.8 (7H, m, 2 MeO and NCHMe); 6.7 (1H, dd, J=1 and 8 Hz, aryl-H); 6.8–6.9 (3H, m, aryl-H); 7.05–7.3 (3H, m, aryl-H); 7.55–7.65 (2H, m, aryl-H); 7.75 (1H, d, J=8 Hz, aryl-H); 7.7 (1H, d, J=8 Hz, aryl-H); 8.6 (1H, m, pyridyl-H).

EXAMPLE 44

(R)-N-(1-(1-Naphthyl)ethyl)-N-((4-methoxy-3-(pyrid-2-yl)phenylmethyl)amine

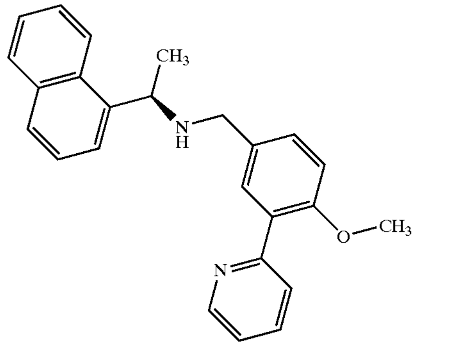

The title compound was prepared from 4-methoxy-3-(pyrid-2-yl)benzenecarboxaldehyde and (R)-1-(1-naphthyl) ethylamine according to general procedure C.

$C_{25}H_{24}N_2O$ Mass (calculated): [368]; (found): $[M+H^+]$=369, 198. NMR (400 MHz, $CDCl_3$): 1.45 (3H, d, J=6 Hz, $NCHCH_3$); 3.6 and 3.65 (2H, dd, J=12 Hz, $CH_2N$); 3.75 (3H, s, MeO); 4.65 (1H, q, J=7 Hz; NCHMe); 6.8 (1H, d, J=8 Hz, aryl-H); 7.05–7.1 (1H, m, aryl-H); 7.15–7.25 (1H, m, aryl-H); 7.3–7.45 (3H, m, aryl-H); 7.5–7.6 (2H, m, aryl-H); 7.6–7.75 (3H, m, aryl-H); 7.75–7.8 (1H, m, aryl-H): 8–8.05 (1H, m, aryl-H); 8.55–8.6 (1H, m, pyridyl-H).

EXAMPLE 45

(R)-N-(1-Phenylethyl)-N-((4-methoxy-3-(pyrid-4-yl) phenylmethyl)amine

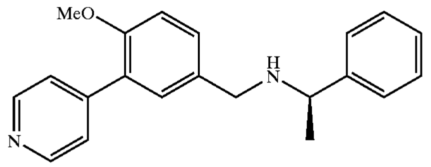

Step 1) 4-Methoxy-3-(pyrid-4-yl)benzenecarboxaldehyde:

A degassed solution of 4-bromopyridine hydrochloride (1.36 g, 7 mmol), 3-borono-4-methoxybenzaldehyde (1.37 g, 7.6 mmol) and $[(PPh_3)_2PdCl_2$ (246 mg, 0.35 mmol) in dimethoxyethane (30 mL), methanol (5 mL) and $Na_2CO_3$ (2M, 20 mL) was heated at 75° C. for 16 hours. The mixture was then cooled, diluted with water and extracted with DCM. The organic layer was dried over sodium sulphate and the solvent removed under reduced pressure. The crude was purified by column chromatography (heptane/AcOEt 3/1) to afford 1.18 g of title compound $C_{13}H_{11}NO_2$ Mass (calculated): [213]; (found) $[M+H^+]$=214. NMR (400 MHz, $CDCl_3$): 3.85 (3H, s, MeO); 7.05 (1H, d, J=8 Hz, aryl-H); 7.4 (2H, d, J=7 Hz, pyridyl-H); 7.8 (1H, d, J=1 Hz, aryl-H); 7.85 (1H, dd, J=1 and 8 Hz); 8.6 (2H, d, J=7 Hz, pyridyl-H).

Step 2) (R)-N-(1-Phenylethyl)-N-((4-methoxy-3-(pyrid-4-yl)phenylmethyl)amine:

The title compound was prepared from 4-methoxy-3-(pyrid-4-yl)benzenecarboxaldehyde and (R)-α-methylbenzylamine according to general procedure C.

$C_{21}H_{22}N_2O$ Mass (calculated): [318]; (found): $[M+H^+]$=319, 215. NMR (400 MHz, $CDCl_3$): 1.3 (3H, d, J=6 Hz, $NCHCH_3$); 3.55 (2H, bq, $CH_2N$); 3.75 (3H, s, MeO); 3.8 (1H, bq, NCHMe); 6.85 (1H, d, J=8 Hz, aryl-H); 7.15–7.25 (3H, m, aryl-H); 7.25–7.3 (4H, m, aryl-H); 7.45 (2H, bs, pyridyl-H); 8.4–8.6 (2H, bs, pyridyl-H).

EXAMPLE 46

(R)-N-(1-(3-Methoxyphenyl)ethyl)-N-((4-methoxy-3-(pyrid-4-yl)phenylmethyl)amine

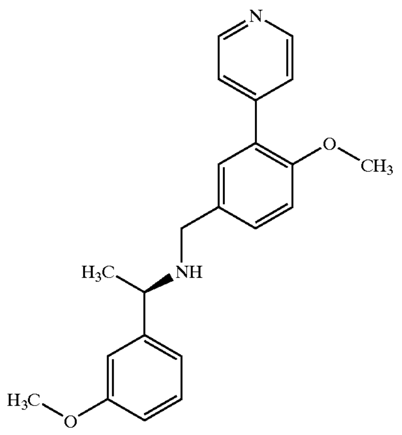

The title compound was prepared from 4-methoxy-3-(pyrid-4-yl)benzenecarboxaldehyde and (R)-3-methoxy-α-methylbenzylamine according to general procedure C.

$C_{22}H_{24}N_2O_2$ Mass (calculated): [348]; (found): $[M+H^+]$=349, 215. NMR (400 MHz, $CDCl_3$): 1.3 (3H, d, J=7 Hz, $NCHCH_3$); 3.55 and 3.6 (2H, dd, J=12 Hz, $CH_2N$); 3.75 (3H, s, MeO); 3.8 (1H, q, J=7 Hz, NCHMe); 6.75 (1H, d, J=8 Hz, aryl-H); 6.85–6.9 (3H, m, aryl-H); 7.15–7.25 (3H, m, aryl-H); 7.4 (2H, bd, pyridyl-H); 8.5 (2H, bs, pyridyl-H).

EXAMPLE 47

(R)-N-(1-(1-Naphthyl)ethyl)-N-((4-methoxy-3-(pyrid-4-yl)phenylmethyl)amine

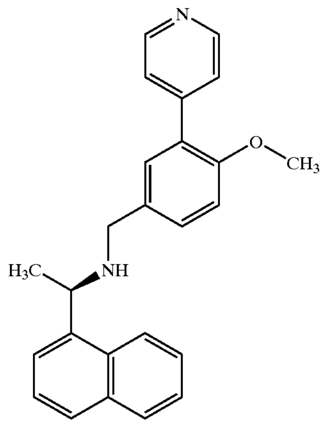

The title compound was prepared from 4-methoxy-3-(pyrid-4-yl)benzenecarboxaldehyde and (R)-1-(1-naphthyl) ethylamine according to general procedure C.

$C_{25}H_{24}N_2O$ Mass (calculated): [368]; (found): $[M+H^+]$= 369, 215. NMR (400 MHz, $CDCl_3$): 1.5 (3H, d, J=6 Hz, $NCHCH_3$); 3.55 and 3.6 (2H, dd, J=12 Hz, $CH_2N$); 3.75 (3H, s, MeO); 4.7 (1H, bq, NCHMe); 6.85 (1H, d, J=8 Hz, aryl-H); 7.15 (1H, d, J=1 Hz, aryl-H); 7.3 (1H, dd, J=1 and 8 Hz, aryl-H); 7.35 (2H, d, J=5 Hz, pyridyl-H); 7.35–7.5 (3H, m, aryl-H); 7.65–7.7 (2H, m, aryl-H); 7.85 (1H, dd, J=1 and 8 Hz, aryl-H); 8 (1H, d, J=8 Hz, aryl-H); 8.5 (2H, bd, pyridyl-H).

EXAMPLE 48

((1R)-1-Phenylethyl){[4-methoxy-3-(1-methylindol-5-yl)phenyl]methyl}amine

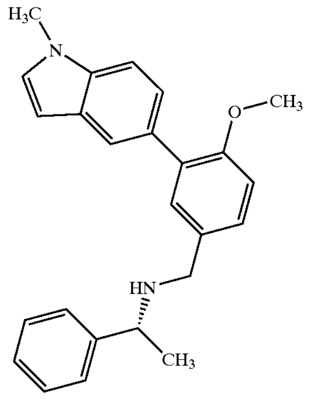

Step 1) 3-(Indol-5-yl)-4-methoxybenzaldehyde:

A solution of 5-formyl-2-methoxybenzeneboronic acid (5 g, 28.5 mmol5-bromoindole (5 g, 25.5 mmol) and $K_2CO_3$ (7.7 g, 56 mmol) in ethanol (25 mL) and toluene (50 mL) was degassed prior to addition of $Pd(Ph_3)_4$ (300 mg, 0.25 mmol). The mixture was refluxed for 16 hours then cooled and concentrated in vacuo, extracted with dichloromethane, washed with water and the organic layer dried over sodium sulphate. The crude was purified by column chromatography (hexane/ethyl acetate 6/4) to give 4.5 g of title compound.

$C_{16}H_{13}NO_2$ Mass (calculated): [251]; (found): $[M+H^+]$= 252. NMR (400 MHz, CDCl3): 3.75 (3H, s, $CH_3O$); 6.45 (1H, m, indole-H); 6.95 (1H, d, J=8 Hz, aryl-H); 7.05–7.15 (1H, m, aryl-H); 7.3 (1H, dd, J=1 and 8 Hz, aryl-H); 7.4 (1H, d, J=8 Hz, aryl-H); 7.65 (1H, s, aryl-H); 7.7 (1H, dd, J=1 and 8 Hz, aryl-H); 7.75 (1H, d, J=1 Hz, aryl-H); 8.1 (1H, bs, NH); 9.8 (1H, s, CHO).

Step 2) 3-(1-Methylindol-5-yl)-4-methoxybenzaldehyde:

A solution of 3-(indol-5-yl)-4-methoxybenzaldehyde (0.50 g, 2.0 mmol) in DMF (10 mL) was cooled to 0° C. and NaH (60% dispersion in mineral oil, 0.14 g, 3.0 mmol) was added. The mixture was stirred at 0° C. for 45 minutes, then methyl iodide (0.34 g, 4.4 mmol) was added and the reaction was stirred for 16 hours at room temperature. The mixture was then poured into water and extracted with ethyl acetate, washed with water and dried over sodium sulphate. The solvent was removed in vacuo and the crude was purified by column chromatography (hexane/ethyl acetate 7/3) to give 0.48 g of title compound.

$C_{17}H_{15}NO_2$ Mass (calculated): [265]; (found): $[M+H^+]$= 266. NMR (400 MHz, CDCl3): 3.85 (3H, s, $CH_3O$); 3.95 (3H, s, $CH_3N$); 6.65 (1H, m, indole-H); 7.10–7.25 (2H, m, aryl-H); 7.4–7.5 (2H, m, aryl-H); 7.8 (1H, s, aryl-H): 7.9 (1H, dd, J=1 and 8 Hz, aryl-H); 8 (1H, d, J=1 Hz, aryl-H); 10 (1H, s, CHO).

Step 3) ((1R)-1-Phenylethyl){[4-methoxy-3-(1-methylindol-5-yl)phenyl]methyl}amine:

The title compound was prepared from 3-(1-methylindol-5-yl)-4-methoxybenzaldehyde and (R)-α-methylbenzylamine according to general procedure C.

$C_{25}H_{26}N_2O$ Mass (calculated): [370]; (found): $[M+H^+]$= 371, 250.

EXAMPLE 49

[(1R)-1-(3-Methoxyphenyl)ethyl]{[4-methoxy-3-(1-methylindol-5-yl)phenyl]methyl}amine

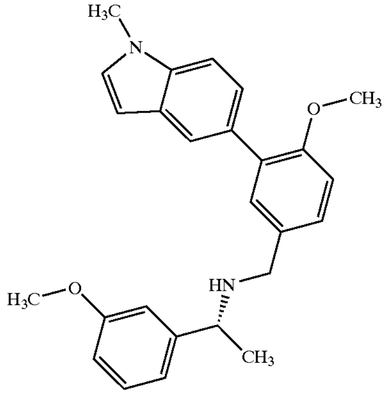

The title compound was prepared from 3-(1-methylindol-5-yl)-4-methoxybenzaldehyde and (R)-3-methoxy-α-methylbenzylamine according to general procedure C.

$C_{26}H_{28}N_2O_2$ Mass (calculated): [400]; (found): $[M+H^+]$= 401. NMR (400 MHz, CDCl3): 1.3 (3H, d, J=6 Hz, $NCHCH_3$); 3.55 and 3.6 (2H, dd, J=12 Hz, $CH_2N$); 3.65–3.8 (10H, m, 3 MeO and NCHMe); 6.4 (1H, d, J=5 Hz, indole-H); 6.7 (1H, dd, J=1 and 8 Hz, aryl-H); 6.8–6.9 (3H, m, aryl-H); 6.95 (1H, d, J=2 Hz, aryl-H); 7.1–7.3 (4H, m, aryl-H); 7.35 (1H, dd, J=1 and 8 Hz, aryl-H 7.65 (1H, d, J=1 Hz, aryl-H).

EXAMPLE 50

((1R)-1-Naphthylethyl){[4-methoxy-3-(1-methylindol-5-yl)phenyl]methyl}amine

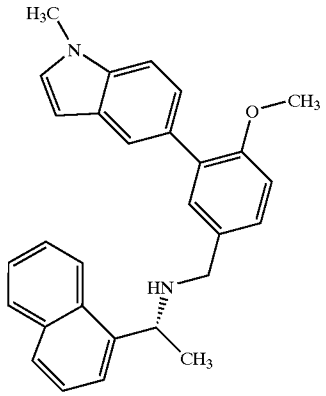

The title compound was prepared from 3-(1-methylindol-5-yl)-4-methoxybenzaldehyde and (R)-1-(1-naphthyl) ethylamine according to general procedure C.

$C_{29}H_{28}N_2O$ Mass (calculated): [420]; (found): $[M+H^+]$= 421. NMR (400 MHz, CDCl3): 1.6 (3H, d, J=6 Hz, $NCHCH_3$); 3.8 and 3.85 (2H, dd, J=12 Hz, $CH_2N$); 3.85 and 3.87 (6H, m, 2 MeO); 4.8 (1H, q, J=6 Hz, NCHMe); 6.6 (1H, d, J=5 Hz, indole-H); 7 (1H, d, J=8 Hz, aryl-H); 7.1 (1H, d, J=1 Hz, aryl-H); 7.3 (1H, dd, J=1 and 8 Hz, aryl-H); 7.35–7.4 (2H, m, aryl-H); 7.5 (1H, dd, J=1 and 8 Hz, aryl-H); 7.5–7.6 (3H, m, aryl-H); 7.8–7.9 (3H, m, aryl-H); 7.95–7.8 (1H, m, aryl-H); 8.2–8.3 (1H, m, aryl-H).

EXAMPLE 51

(R)-N-(1-Phenylethyl)-N-((4-methoxy-3-(3-methoxyphenyl)phenylmethyl)amine

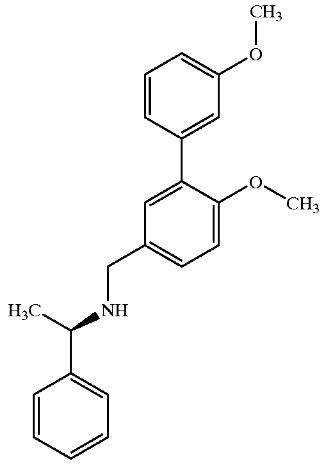

Step 1) 4-Methoxy-3-(3-methoxyphenyl) benzenecarboxaldehyde:

A degassed solution of 3-bromoanisole (1.31 g, 7 mmol), 3-borono-4-methoxybenzaldehyde (1.38 g, 7.4 mmol) and $[(PPh_3)_2PdCl_2$ (246 mg, 0.35 mmol) in dimethoxyethane (35 mL), methanol and $Na_2CO_3$ 2M (20 mL) was heated at 75° C. for 24 hours. The mixture was then cooled, diluted with water and extracted with ethyl acetate. The organic layer was dried over sodium sulphate and the solvent removed under reduced pressure. The crude was purified by column chromatography (heptane/AcOEt 4/1) to afford 1.14 g of title compound.

$C_{15}H_{14}O_3$ Mass (calculated): [242]; (found): $[M+H^+]$= 243; $[M+H^++MeCN]$=284. NMR (400 MHz, $CDCl_3$): 3.85 (3H, s, MeO); 3.95 (3H, s, MeO); 6.9 (1H, dd, J=1 and 8 Hz, aryl-H); 7.05–7.15 (1H, m, aryl-H); 7.35 (1H, t, J=8 Hz, aryl-H); 7.85–7.95 (2H, m, aryl-H); 9.85 (1H, s, CHO).

Step 2) (R)-N-(1-Phenylethyl)-N-((4-methoxy-3-(3-methoxyphenyl) phenylmethyl)amine:

The title compound was prepared from 4-methoxy-3-(3-methoxyphenyl)benzenecarboxaldehyde and (R)-α-methylbenzylamine according to general procedure C.

$C_{23}H_{25}NO_2$ Mass (calculated): [347]; (found): $[M+H^+]$= 348. NMR (400 MHz, $CDCl_3$): 1.3 (3H, d, J=6 Hz, $NCHCH_3$); 3.5 and 3.55 (2H, dd, J=12 Hz, $CH_2N$); 3.7 (3H, s, MeO); 3.75–3.85 (4H, m, NCHMe and MeO); 6.75–6.9 (2H, m, aryl-H); 7–7.1 (2H, m, aryl-H); 7.1–7.2 (3H, m, aryl-H); 7.2–7.3 (5H, m, aryl-H).

EXAMPLE 52

(R)-N-(1-(3-Methoxyphenyl)ethyl)-N-((4-methoxy-3-(3-methoxyphenyl)phenylmethyl)amine

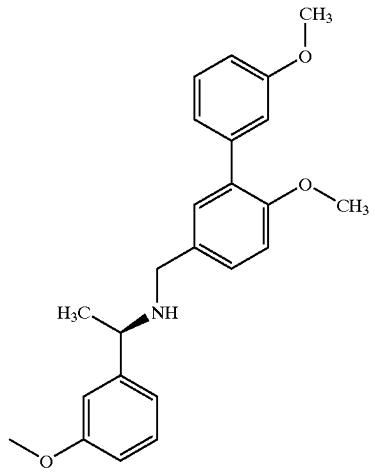

The title compound was prepared from 4-methoxy-3-(3-methoxyphenyl)benzenecarboxaldehyde and (R)-3-methoxy-α-methylbenzylamine according to general procedure C.

$C_{24}H_{27}NO_3$ Mass (calculated): [377]; (found): $[M+H^+]$= 378. NMR (400 MHz, $CDCl_3$): 1.4 (3H, d, J=6 Hz, $NCHCH_3$); 3.6 and 3.65 (2H, dd, J=12 Hz, $CH_2N$); 3.8–3.9 (10H, 3 s and m, NCHMe and 3 MeO); 6.8 (1H, dd, J=1 and 8 Hz, aryl-H); 6.9 (1H, dd, J=1 and 8 Hz, aryl-H); 6.95–7 (3H, m, aryl-H); 7.1–7.2 (2H, m, aryl-H); 7.2–7.4 (4H, m, aryl-H).

EXAMPLE 53

(R)-N-(1-(1-Napthyl)ethyl)-N-((4-methoxy-3-(3-methoxyphenyl)phenylmethyl)amine

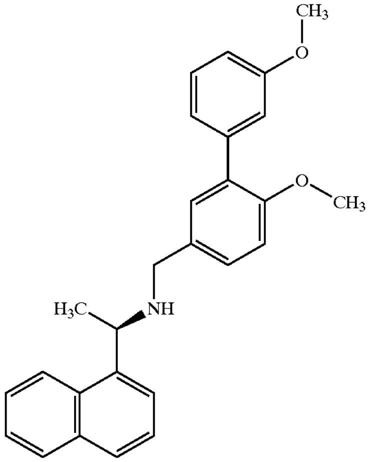

The title compound was prepared from 4-methoxy-3-(3-methoxyphenyl)benzenecarboxaldehyde and (R)-1-(1-naphthyl)ethylamine according to general procedure C.

$C_{27}H_{27}NO_2$ Mass (calculated): [397]; (found): [M+H$^+$]=398. NMR (400 MHz, $CDCl_3$): 1.45 (3H, d, J=6 Hz, $NCHCH_3$); 3.6 and 3.65 (2H, dd, J=12 Hz, $CH_2N$); 3.7 and 3.75 (6H, 2 s, 2 MeO); 4.65 (1H, q, J=6 Hz, NCHBMe); 6.75–6.9 (2H, m, aryl-H); 7–7.1 (2H, m, aryl-H); 7.1–7.25 (3H, m, aryl-H); 7.4–7.45 (3H, m, aryl-H); 7.7 (2H, d, J=8 Hz, aryl-H); 7.75–7.8 (1H, m, aryl-H); 8.05–8.1 (1H, m, aryl-H).

EXAMPLE 54

N-(1-(Quinol-5-yl)ethyl)-N-((4-methoxy-3-(4'-methoxyphenyl)phenylmethyl)amine

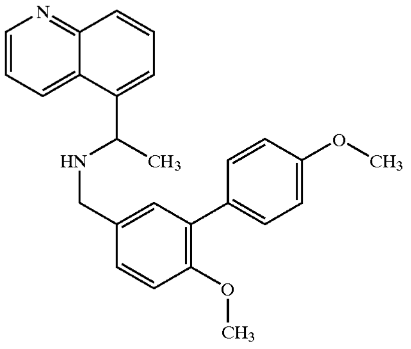

Step 1) 5-Trifluoromethanesulphonyloxyguinoline:

A solution of 5-hydroxyquinoline (0.5 g, 3.4 mmol) in DCM (5 mL) was treated with pyridine (1.08 g, 13.7 mmol) and then trifluoromethanesulphone anhydride (1.1 g, 4.12 mmol). The mixture was stirred overnight then diluted with dichloromethane and washed with water. The organic layer was concentrated under reduced pressure and the excess pyridine azeotropically removed with toluene, to afford 0.47 g of title compound.

Step 2) 5-Acetylquinoline:

A degassed solution of 5-trifluoromethanesulphonyloxyquinoline (0.41 g, 1.47 mmol), butyl vinyl ether (0.38 mL, 2.94 mmol), palladium acetate (10 mg, 0.043 mmol), potassium carbonate (0.24 g, 1.76 mmol), 1,3-bis(diphenylphosphino)propane (40 mg, 0.097 mmol) in DMF (3.67 mL) and water (0.88 mL) was heated in a sealed tube at 100° C. for 16 hours. The reaction mixture was then cooled and treated with 1M HCl and the mixture stirred for 30 minutes, then basified and extracted with dichloromethane. The organic layer was then evaporated under reduced pressure to afford the title compound.

Step 3) 4-Methoxy-3-(4-methoxyphenyl)benzyl alcohol:

A solution of 4-methoxy-3-(4-methoxyphenyl)benzenecarboxaldehyde (1 g, 4.13 mmol) in methanol (12 mL) was treated with polymer-supported borohydride (10.3 mmol) and the mixture shaken for 16 hours. The resin was then filtered and the filtrate concentrated under reduced pressure to afford 0.88 g of title compound.

Step 4) 4-Methoxy-3-(4-methoxyphenyl)benzylazide:

A solution of 4-methoxy-3-(4-methoxyphenyl)benzyl alcohol (0.88 g, 3.59 mmol) and diphenylphosphoryl azide (1.18 g, 4.32 mmol) in anhydrous THF (15 mL) was cooled in an ice-bath prior to addition of 1,8-diazabicyclo[5.4.0]undec-7-ene (0.87 g, 5.76 mmol). The resulting mixture was then stirred at room temperature for 48 hours. More diphenylphosphoryl azide was added (1.4 mol, 0.39 g) and the mixture stirred for further 16 hours. The solvent was then evaporated, the residue taken into dichloromethane and washed with acid. The organic layer was separated and the solvent removed under reduced pressure to afford 0.82 g of title compound.

Step 5) 4-Methoxy-3-(4-methoxyphenyl)benzylamine:

A solution of 4-methoxy-3-(4-methoxyphenyl)benzylazide (0.82 g, 3.07 mmol) in ethanol (50 mL) was hydrogenated under atmospheric pressure for 16 hours. The catalyst was filtered off, the solvent removed under reduced pressure and the crude purified by column chromatography (hexane/ethyl acetate 6/1) to afford 400 mg of title compound.

$C_{15}H_{17}NO2$ Mass (calculated): [243]; found: 227 (MH$^+$—NH2). NMR (400 MHz, $CDCl_3$): 3.65 (3H, s, $CH_3O$); 3.7–3.8 (5H, m, $CH_3O$ and aryl-$CH_2O$); 5.45 (2H, bs, $NH_2$); 6.75–6.95 (3H, m, aryl-H); 7.1–7.25 (2H, m, aryl-H); 7.4 (2H, d, J=8 Hz, aryl-H).

Step 6) N-(1-(Quinol-5-yl)ethyl)-N-((4-methoxy-3-(4'-methoxyphenyl) phenylmethyl)amine:

A solution of 4-methoxy-3-(4-methoxyphenyl)benzylamine (243 mg, 1, mmol) and 5-acetylquinoline (152 mg, 0.89 mmol) in methanol (3 mL) was treated with acetic acid (0.05 mL) and polymer-supported cyanoborohydride (0.9 g, 2.25 mmol). The mixture was stirred at 50 C. for 20 hours, then cooled. The solid was filtered off and the filtrate concentrated in vacuo. The crude was purified by column chromatography (AcOEt/cyHex 7/3 to 100% AcOEt) to afford 91 mg of title compound.

$C_{26}H_{26}N_2O_2$ Mass (calculated): [398]; found: 399, 797. NMR (400 MHz, $CDCl_3$): 1.45 (3H, d, J=6 Hz, $NCHCH_3$); 3.6 and 3.65 (2H, dd, J=12 Hz, $CH_2N$); 3.7 and 3.75 (6H, 2 s, 2 MeO); 4.55 (1H, q, J=6 Hz, $NCHCH_3$); 6.8–6.9 (3H, m, aryl-H); 7.1–7.2 (2H, m, aryl-H); 7.3 (1H, dd, J=4 and 8 Hz, aryl-H); 7.35 (2H, J=8 Hz, aryl-H); 7.75 (1H, t, J=6 Hz, aryl-H); 7.75 (1H, d, J=8 Hz, aryl-H); 7.95 (1H, d, J=8 Hz, aryl-H); 8.55 (1H, d, J=8 Hz, aryl-H); 8.8–8.9 (1H, m, aryl-H).

EXAMPLE 55

(R)-N-(1-(1-Naphthyl)ethyl)-N-((4-(3-N,N-dimethylamino)propoxy-3-(4-methoxyphenyl)phenylmethyl)amine

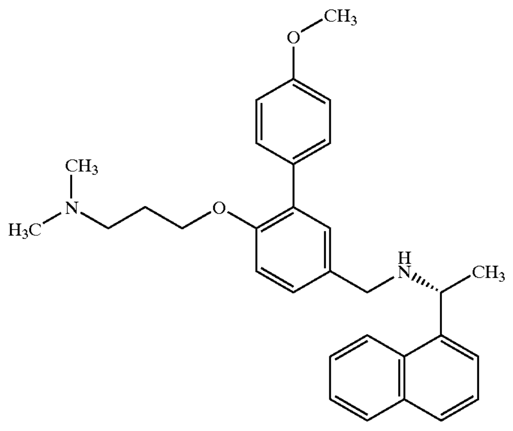

Step 1) 3-Bromo-4-(3-chloropropoxy)benzaldehyde:

A solution of 3-bromo-4-hydroxybenzaldehyde (1.88 g, 9.36 mmol) 1-bromo-3-chloropropane (9.25 mL, 93.6 mmol) and potassium carbonate (3.22 g, 23.4 mmol) in acetonitrile (15 mL)was heated at 80 C. for 2 days. The solid was filtered through a plug of silica eluting with MeCN. The filtrate was evaporated to yield 2.46 g of title compound.

$C_{10}H_{10}BrClO_2$

Step 2) 3-Bromo-4-(3-N,N-dimethylamino)propoxybenzaldehyde:

A suspension of 3-bromo-4-(3-chloropropoxy)benzaldehyde (2.47 g, 8.08 mmol) dimethylamine hydrochloride (6.58 g, 80.8 mmol) and potassium carbonate (11.1 g, 80.8 mmol) in acetonitrile (120 mL) was stirred for 2 days a room temperature, then more $Me_2NH$ HCl 6.58 g, 80.8 mmol) was added together with KI (50 mg). After 4 days the mixture was filtered and the filtrate concentrated under reduced pressure. The residue was dissolved in ethyl acetate and washed with water then brine. The organic layer was dried over $MgSO_4$ then evaporated to give a crude which was purified by column chromatography (DCM/MeOH 9/1) to give 1.24 g of title compound.

$C_{12}H_{16}BrNO_2$

Step 3) 4-(3-N,N-Dimethylamino)propoxy-3-(4-methoxyphenyl)benzaldehyde:

A solution of 4-methoxybenzeneboronic acid (0.79 g, 5.19 mmol), 3-bromo-4-(3-N,N-dimethylamino)propoxybenzaldehyde (1.28 g, 4.33 mmol) and $K_2CO_3$ (1.78 g, 12.9 mmol) in ethanol (12 mL) and toluene (24 mL) was degassed prior to addition of $Pd(Ph_3)_4$ (100 mg, 1 mmol %). The mixture was refluxed for 18 hours then cooled and filtered through diatomaceous earth. The filtrate was concentrated in vacuo, extracted with ethyl acetate, washed with water and the organic layer dried over sodium sulphate. The crude was purified by column chromatography (DCM/MeOH 85/15) to give 0.4 g of title compound.

$C_{19}H_{23}NO_3$

Step 4) (R)-N-(1-(1-Naphthyl)ethyl)-N-((4-(3-N,N-dimethylamino)propoxy-3-(4-methoxyphenyl)phenylmethyl)amine:

The title compound was prepared from 4-(3-N,N-dimethylamino)propoxy-3-(4-methoxyphenyl)benzaldehyde and (R)-1-(1-naphthyl)ethylamine according to general procedure B.

$C_{31}H_{36}N_2O_2$ Mass (calculated): [468]; (found): $[M+H^+]$= 469. NMR (400 MHz, CDC13): 1.45 (3H, d, J=6 Hz, $NCHCH_3$); 1.85–1.95 (2H, m, $OCH_2CH_2CH_2N$); 2.25 (6H, s, $Me_2N$); 2.4–2.5 (2H, m, $OCH_2CH_2CH_2N$);); 3.6 and 3.65 (2H, dd, J=12 Hz, $CH_2N$); 3.7 (3H, s, $CH_3O$); 3.9 (2H, t, J=6 Hz, $OCH_2CH_2CH_2N$); 4.65 (1H, q, J=6 Hz, $NCHCH_3$); 6.8–6.9 (3H, m, aryl-H); 7.1–7.2 (2H, m, aryl-H); 7.3–7.5 (5H, m, aryl-H); 7.7 (2H, d, J=8 Hz, aryl-H); 7.8–7.85 (1H, m, aryl-H); 8.05–8.1 (1H, m, aryl-H).

EXAMPLE 56

(R)-N-(1-Phenylethyl)-N-((4-(cyclopropylmethoxy-3-(4-methoxyphenyl)phenylmethyl)amine

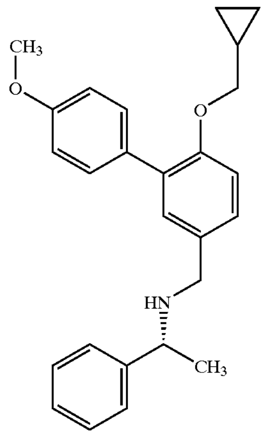

Step 1) 3-bromo-4-cyclopropylmethoxybenzaldehyde:

A suspension of 3-bromo-4-hydroxybenzaldehyde (5.03 g, 25 mmol), bromomethylcyclopropane (28 mmol, 2.72 mL) and potassium carbonate (37.5 mmol, 5.14 g) in DMF (30 mL) was heated at 110 C. for three days. The solid was filtered off and the solvent was removed under reduced pressure, to give an orange residue which was taken into ethyl acetate and washed with water and then saturated brine. The organic phase was dried over $Mg_2SO_4$ and solvent removed to afford 5.56 g of the title material.

$C_{11}H_{11}BrO_2$ Mass (calculated): [255]; (found): 255, 257 and 296, 298 (M+MeCN). NMR (400 MHz, $CDCl_3$): 0.15–0.2 (2H, m, cyclopropyl-$CH_2$); 0.4–0.5 (2H, m, cyclopropyl-$CH_2$); 1–1.15 (1H, m, cyclopropyl-CH); 3.8 (2H, d, J=7 Hz, $OCH_2$); 7.75 (1H, d, J=8 Hz, aryl-H); 7.55 (1H, dd, J=2 and 8 Hz, aryl-H); 7.9 (1H, d, J=2 Hz, aryl-H); 9.6 (1H, s, CHO).

Step 2) 4-Cyclopropylmethoxy-3-(4'-methoxyphenyl)benzenecarboxaldehyde:

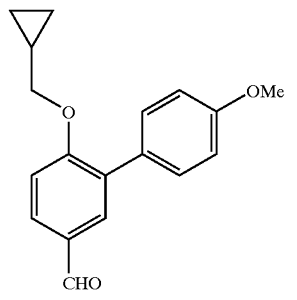

To a degassed solution of 3-bromo-4-cyclopropylmethoxybenzaldehyde (1.53 g, 6 mmol), 4-methoxybenzeneboronic acid (1.22 g, 8 mmol) and potassium carbonate (2.74 g, 20 mmol) in toluene/ethanol 2/1 (40 mL), $Pd(PPh_3)_4$ (100 mg) was added and the mixture was degassed for further 5 minutes. The mixture was then refluxed for 12 hours. The solid is filtered off, and the solvent partitioned between ethyl acetate and water and extracted. The organic solvent was removed under reduced pressure, dried over sodium sulphate and purified by column chromatography on silica (hexane/ethyl acetate 8/2) to afford 1.52 g of product.

$C_{18}H_{18}O_3$ Mass (calculated): [282]; (found): $[M+H^+]$= 283; LC Rt=1.65, 97%. NMR (400 MHz, $CDCl_3$0.15–0.25 (2H, m, cyclopropyl-$CH_2$); 0.45–0.55 (2H, m, cyclopropyl-$CH_2$); 1.05–1.15 (1H, m, cyclopropyl-CH); 3.75 (3H, s, MeO); 3.8 (2H, d, J=7 Hz, aryl$OCH_2$); 6.9 (2H, 2, J=7 Hz, 8.5 Hz, aryl-H); 7.9 (1H, d, J=8.5 Hz, aryl-H); 7.4 (2H, d, J=8.5 Hz, aryl-H); 7.65 (1H, dd, J=2 and 8.5 Hz, aryl-H); 7.75 (1H, d, J=2 Hz, aryl-H); 9.8 (1H, s, CHO).

Step 3) (R)-N-(1-Phenylethyl)-N-((4-(cyclopropylmethoxy-3-(4-methoxyphenyl)phenylmethyl)amine:

The title compound was prepared from 4-cyclopropylmethoxy-3-(4'-methoxyphenyl) benzenecarboxaldehyde and (R)-α-methylbenzylamine according to general procedure A.

$C_{26}H_{29}NO_2$ Mass (calculated): [387]; (found): $[M+H^+]$= 267, 388. NMR (400 MHz, $CDCl_3$): 0.2 (2H, m, cyclopropyl-H); 0.45 (2H, m, cyclopropyl-H); 1.15 (1H, m, cyclopropyl-H); 1.3 (3H, d, J=6 Hz, $NCHCH_3$); 3.5 and 3.55 (2H, dd, J=12 Hz, $CH_2N$); 3.7 (2H, d, J=6 Hz, cyclopropyl$CH_2O$); 3.7–3.8 (4H, m, MeO and NCHMe); 6.8 (1H, d, J=8 Hz, aryl-H); 6.85 (2H, d, J=8 Hz, aryl-H); 7.1 (1H, dd, J=1 and 8 Hz, aryl-H); 7.15–7.25 (2H, m, aryl-H); 7.25–7.35 (4H, m, aryl-H); 7.45 (2H, d, J=8 Hz, aryl-H).

EXAMPLE 57

(R)-N-(1-(3-Methoxyphenyl)ethyl)-N-((4-cyclopropylmethoxy-3-(4'-methoxyphenyl) phenylmethyl)amine

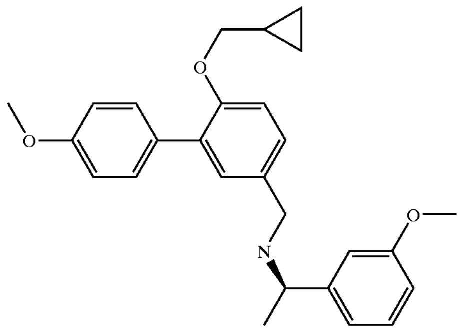

The title compound was prepared from 4-cyclopropylmethoxy-3-(4'-methoxyphenyl) benzenecarboxaldehyde and (R)-3-methoxy-α-methylbenzylamine according to general procedure A.

$C_{27}H_{31}NO_3$ Mass (calculated): [417]; (found): $[M+H^+]$= 267, 418. NMR (400 MHz, $CDCl_3$): 0.2 (2H, m, cyclopropyl-H); 0.45 (2H, m, cyclopropyl-H); 1.1 (1H, m, cyclopropyl-H); 1.3 (3H, d, J=6 Hz, $NCHCH_3$); 3.5 and 3.55 (2H, dd, J=12 Hz, $CH_2N$); 3.65 (2H, d, J=6 Hz, cyclopropyl$CH_2O$); 3.7 (3H, s, $CH_3O$); 3.75–3.85 (4H, m, MeO and NCHMe); 6.75 (1H, dd, J=1 and 8 Hz, aryl-H); 6.8 (1H, d, J=8 Hz, aryl-H); 6.85–6.95 (4H, m, aryl-H); 7.1 (1H, dd, J=1 and 8 Hz, aryl-H); 7.15 (1H, d, J=1 Hz, aryl-H); 7.15–7.25 (1H, m, aryl-H); 7.45 (2H, d, J=8 Hz, aryl-H).

EXAMPLE 58

(R)-N-(1-(1-Naphthyl)ethyl)-N-((4-(cyclopropylmethoxy-3-(4-methoxyphenyl) phenylmethyl)amine

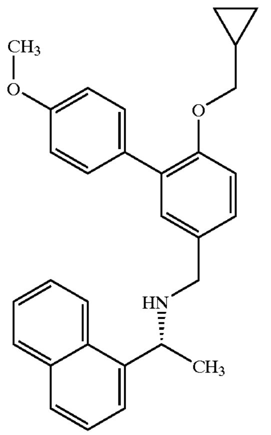

The title compound was prepared from 4-cyclopropylmethoxy-3-(4'-methoxyphenyl) benzenecarboxaldehyde and (R)-1-(1-naphthyl)ethylamine according to general procedure A.

$C_{30}H_{31}NO_2$ Mass (calculated): [437]; (found): $[M+H^+]$= 438, 267, 875. NMR (400 MHz, $CDCl_3$): 0.2 (2H, m, cyclopropyl-H); 0.45 (2H, m, cyclopropyl-H); 1.15 (1H, m, cyclopropyl-H); 1.45 (3H, d, J=6 Hz, $NCHCH_3$); 3.6 (1H, d, J=12 Hz, $CH_2N$); 3.65–3.75 (3H, m, $CH_2N$ and cyclopropyl$CH_2O$); 3.75 (3H, s, MeO); 4.65 (1H, q, J=6 Hz, NCHMe); 6.75–6.9 (3H, m, aryl-H); 7.1–7.2 (2H, m, aryl-H); 7.35–7.5 (5H, m, aryl-H); 7.65–7.5 (2H, m, aryl-H); 7.8–7.9 (1H, m, aryl-H); 8.0–8.1 (1H, m, aryl-H).

EXAMPLE 59

(6,4'-Dimethoxy-biphenyl-3-ylmethyl)-(1-pyridin-3-yl-ethyl)-amine

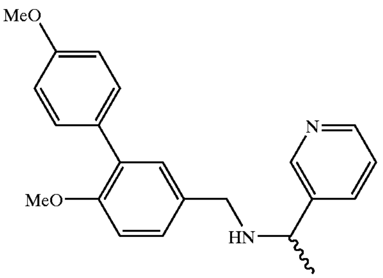

Step 1) 1-Pyridin-3-yl-ethylamine:

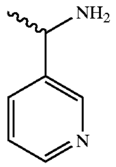

3-Acetylpyridine (2.4 g, 20 mmol, Aldrich) was dissolved in 2M ammonia solution in methyl alcohol (50 mL, 100 mmol, Aldrich) and acetic acid (15 mL, J. T. Baker) was slowly added at 0 C. After stirring for 3 h at room temperature, the sodium cyanoborohydride (5.0 g, 80 mmol, Aldrich) was added to the solution at 0 C. The mixture was stiffed under nitrogen at room temperature for overnight then the reaction was cooled at ice bath and quenched with aqueous 5 N sodium hydroxide (30 mL, 150 mmol, J. T. Baker). The methyl alcohol was removed from the mixture via vacuo. The residue was extracted by diethyl ether (30 mL×4). The combined organic phases were dried over anhydrous magnesium sulfate and concentrated via vacuo to give crude 1-pyridin-3-yl-ethylamine as light yellow oil in 44% yield (1.07 g, 8.8 mmol).

$C_7H_{10}N_2$ MS (ESI, pos. ion) m/z: 123.0 (M+1); MS (ESI, neg. ion) m/z: 121.0 (M−1).

Step 2) (6,4'-Dimethoxy-biphenyl-3-ylmethyl)-(1-pyridin-3-yl-ethyl)-amine:

1-Pyridin-3-yl-ethylamine (245 mg, 2 mmol) and 6,4'-Dimethoxy-biphenyl-3-carbaldehyde (121 mg, 0.5 mmol) were dissolved in dichloroethane (10 mL). After stirring for 6 h at room temperature, the sodium triacetoxyborohydride (212 mg, 1.0 mmol, Aldrich) was added to the solution at 0 C. The mixture was stirred under nitrogen at room temperature for overnight then the reaction was cooled at ice bath and quenched with saturated aqueous sodium bicarbonate (10 mL). The organic phase was separated and the aqueous phase was extracted with dichloroethane (10 mL×3). The combined organic layers were dried over anhydrous magnesium sulfate and concentrated via vacuo. The crude was purified by column chromatography (silica gel, ethyl acetate) to give the title compound as white solid in 50% yield (87 mg, 0.25 mmol).

$C_{22}H_{24}N_2O_2$ MS (ESI, pos. ion) m/z: 349.2 (M+1); MS (ESI, neg. ion) m/z: 347.2 (M−1).

EXAMPLE 60

(6,4'-Dimethoxy-biphenyl-3-ylmethyl)-(1-pyridin-4-yl-ethyl)-amine

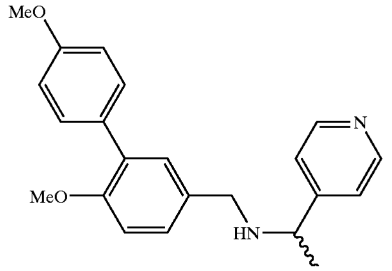

Step 1) 1-Pyridin-4-yl-ethylamine:

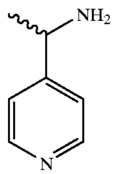

The title compound was prepared by the same procedure for preparing 1-pyridin-3-yl-ethylamine from 4-acetylpyridine (2.4 g, 20 mmol, Aldrich), 2 M ammonia solution in methyl alcohol (50 mL, 100 mmol, Aldrich), acetic acid (15 mL, J. T. Baker) and sodium cyanoborohydride (5.0 g, 80 mmol, Aldrich). The title compound was obtained in form as light yellow oil in 51% yield (1.25 g, 10.2 mmol).

$C_7H_{10}N_2$ MS (ESI, pos. ion) m/z: 123.0 (M+1); MS (ESI, neg. ion) m/z: 121.0 (M−1).

Step 2) (6,4'-Dimethoxy-biphenyl-3-ylmethyl)-(1-pyridin-4-yl-ethyl)-amine:

The title compound was prepared by the same procedure for preparing (6,4'-dimethoxy-biphenyl-3-ylmethyl)-(1-pyridin-3-yl-ethyl)-amine from 1-Pyridin-4-yl-ethylamine (245 mg, 2 mmol), 6,4'-Dimethoxy-biphenyl-3-carbaldehyde (121 mg, 0.5 mmol) and sodium triacetoxyborohydride (212 mg, 1.0 mmol, Aldrich). The title compound was purified by column chromatography (silica gel, ethyl acetate) in form as white solid in 51% yield (89 mg, 0.26 mmol).

$C_{22}H_{24}N_2O_2$ MS (ESI, pos. ion) m/z: 349.2 (M+1); MS (ESI, neg. ion) m/z: 347.2 (M−1).

EXAMPLE 61

(6,4'-Dimethoxy-biphenyl-3-ylmethyl)-(1-quinolin-4-yl-ethyl)-amine

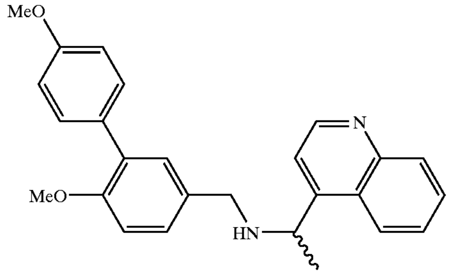

Step 1) 1-Quinolin-4-yl-ethanol:

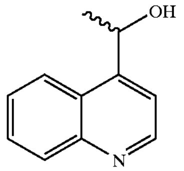

4-Quinolinecarboxaldehyde (1.57 g, 10 mmol, Aldrich) was dissolved in anhydrous THF (30 mL) and cooled to −78° C. The 3 M methyl magnesium iodide solution in diethyl ether (5 mL, 15 mmol, Aldrich) was slowly added to the reaction solution in dry ice bath. The reaction mixture was allowed to stir under nitrogen at room temperature for overnight then the reaction was cooled at ice bath and quenched with saturated aqueous ammonium chloride (30 mL). The organic phase was separated and the aqueous phase was extracted with ethyl acetate (30 mL×2). The combined organic layers were dried over anhydrous magnesium sulfate and concentrated via vacuo to give crude title compound as light yellow syrup in 100% yield (1.73 g, 10 mmol).

$C_{11}H_{11}NO$ MS (ESI, pos. ion) m/z: 174.4 (M+1); MS (ESI, neg. ion) m/z: 172.2 (M−1).

Step 2) 1-Ouinolin-4-yl-ethanone:

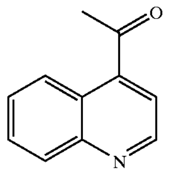

To the mixture of manganese oxide (8.69 g, 100 mmol, Aldrich) in dichloromethane (80 mL) was added 1-quinolin-4-yl-ethanol (1.73 g, 10 mmol). The reaction mixture was refluxed for overnight and then cooled to room, temperature. The solid was filtered out through Celite pad. The organic solution dried over anhydrous magnesium sulfate and concentrated via vacuo to give crude title compound as light yellow solid in 100% yield (1.71 g, 10.0 mmol).

$C_{11}H_9NO$ MS (ESI, pos. ion) m/z: 172.10 (M+1); MS (ESI, neg. ion) m/z: 170.0 (M−1).

Step 3) 1-Quinolin-4-yl-ethylamine:

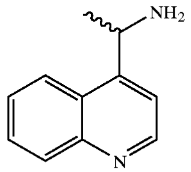

The title compound was prepared by the same procedure for preparing 1-pyridin-3-yl-ethylamine from 1-quinolin-4-yl-ethanone, (1.71 g, 10 mmol, Aldrich), 2 M ammonia solution in methyl alcohol, (40 mL, 80 mmol, Aldrich), acetic acid (10 mL, J. T. Baker) and sodium cyanoborohydride (5.0 g, 80 mmol, Aldrich). The title compound obtained in form as light yellow solid in 100% yield (1.72 g, 10 mmol).

$C_{11}H_{12}N_2$ MS (ESI, pos. ion) m/z: 173.0 (M+1); MS (ESI, neg. ion) m/z: 171.0 (M−1).

Step 4) (6,4'-Dimethoxy-biphenyl-3-ylmethyl)-(1-quinolin-4-yl-ethyl)-amine:

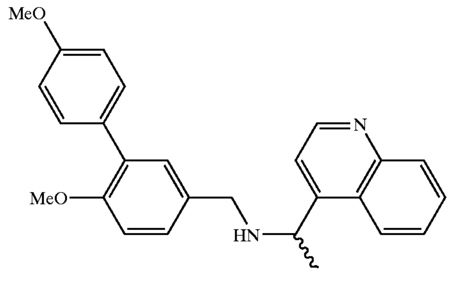

The 1-quinolin-4-yl-ethylamine (510 mg, 3 mmol) and 6,4'-dimethoxy-biphenyl-3-carbaldehyde (242 mg, 1.0 mmol) were stirred with acetic acid (300 mg, J. T. Baker) in methyl alcohol (15 mL0 at room temperature for 4 h. To the reaction solution was added sodium cyanoborohydride (1.0 g, 16 mmol, Aldrich) at 0° C. The mixture was stirred under nitrogen at room temperature for overnight then the reaction was cooled at ice bath and quenched with saturated aqueous sodium bicarbonate (30 mL). The methyl alcohol was removed from the mixture via vacuo. The residue was extracted by ethyl acetate (30 mL×4). The combined organic phases were dried over anhydrous magnesium sulfate and concentrated via vacuo. The title compound was purified by column chromatography (silica gel, ethyl acetate) in form as white solid in 72% yield (287 mg, 0.72 mmol).

$C_{26}H_{26}N_2O_2$ MS (ESI, pos. ion) m/z: 399.2 (M+1); MS (ESI, neg. ion) m/z: 397.2 (M−1).

EXAMPLE 62

(6,4'-Dimethoxy-biphenyl-3-ylmethyl)-(1-quinolin-8-yl-ethyl)-amine

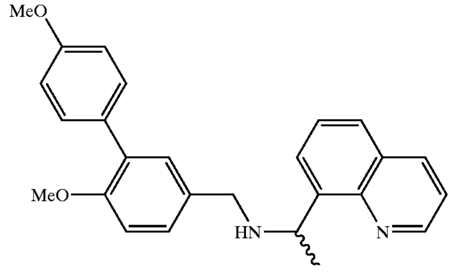

Step 1) Quinoline-8-carboxylic acid methoxy-methyl-amide:

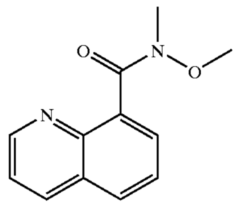

To the solution of 1-isoquinolonecarboxylic acid (1.73 g, 10 mmol, Aldrich) in anhydrous N,N-dimethylformamide (30 mL) were added N,N-diisopropylethylamine (5.29 g, 40 mmol, Aldrich), O-(7-azabenzotriazol-1-yl)-1,1,3,3-tetramethyluronium hexafluorophosphate (7.6 g, 20 mmol, PerSeptive Biosystems GmbH), N,O-dimethylhydroxylamine hydrochloride (1.8 g, 20 mmol, Aldrich) subsequently at room temperature. The reaction solution was allowed to stir for overnight at room temperature. The N,N-Dimethylformamide was removed via vacuo and the resulting residue was diluted in ethyl acetate (50 mL). After being was washed by saturate aqueous sodium bicarbonate (50 mL) and brine (50 mL), the organic portion was dried over anhydrous magnesium sulfate and concentrated. The title compound was purified by column chromatography (silica gel, ethyl acetate) in form as yellow syrup in 94% yield (2.04 g, 9.4 mmol).

$C_{12}H_{12}N_2O_2$ MS (ESI, pos. ion) m/z: 217.1 (M+1); MS (ESI, neg. ion) m/z: 215.0 (M−1).

Step 2) 1-Quinolin-8-yl-ethanone

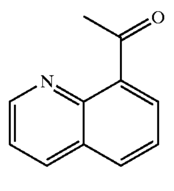

Quinoline-8-carboxylic acid methoxy-methyl-amide (2.16 g, 10 mmol) was dissolved in anhydrous THF (40 mL) and cooled to −78° C. The 3 M methyl magnesium iodide solution in diethyl ether (4.0 mL, 12 mmol, Aldrich) was slowly added to the reaction solution in dry ice bath. The reaction mixture was allowed to stir under nitrogen at room temperature for overnight then the reaction was cooled at ice bath and quenched with saturated aqueous ammonium chloride (40 mL). The organic phase was separated and the aqueous phase was extracted with ethyl acetate (30 mL×2). The combined organic layers were dried over anhydrous magnesium sulfate and concentrated via vacuo to give crude title compound as light yellow solid in 83% yield (1.42 g, 8.3 mmol).

$C_{11}H_9NO$ MS (ESI, pos. ion) m/z: 172.0 (M+1); MS (ESI, neg. ion) m/z: 170.1 (M−1).

Step 3) 1-Ouinolin-8-yl-ethylamine

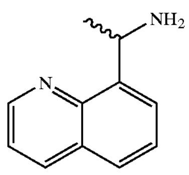

The title compound was prepared by the same procedure for preparing 1-pyridin-3-yl-ethylamine from 1-quinolin-8-yl-ethanone (1.71 g, 10 mmol), 2 M ammonia solution in methyl alcohol, acetic acid (25 mL, 50 mmol, Aldrich) and sodium cyanoborohydride (2.5 g, 40 mmol, Aldrich). The title compound was purified by column chromatography (silica gel, ethyl acetate) in form as light yellow solid in 98% yield (1.68 g, 9.8 mmol). MS (ESI, pos. ion) m/z: 173.2 (M+1); MS (ESI, neg. ion) m/z: 171.0 (M−1).

Step 4) (6,4'-Dimethoxy-biphenyl-3-ylmethyl)-(1-quinolin-8-yl-ethyl)-amine

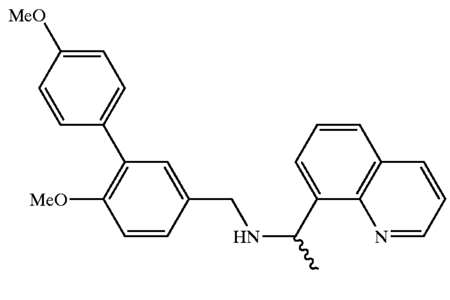

The title compound was prepared by the same procedure for (6,4'-dimethoxy-biphenyl-3-ylmethyl)-(1-quinolin-4-yl-ethyl)-amine from 1-quinolin-8-yl-ethylamine (510 mg, 3.0 mmol), 6,4'-Dimethoxy-biphenyl-3-carbaldehyde (242 mg, 1.0 mmol) and sodium cyanoborohydride (1.0 g, 16 mmol, Aldrich). The title compound was purified by column chromatography (silica gel, ethyl acetate) in form as white solid in 72% yield (287 mg, 0.72 mmol).

$C_{26}H_{26}N_2O_2$ MS (ESI, pos. ion) m/z: 399.2 (M+1); MS (ESI, neg. ion) m/z: 397.2 (M−1).

EXAMPLE 63

(6,4'-Dimethoxy-biphenyl-3-ylmethyl)-[1-(1-methyl-1H-indol-4-yl)-ethyl]-amine

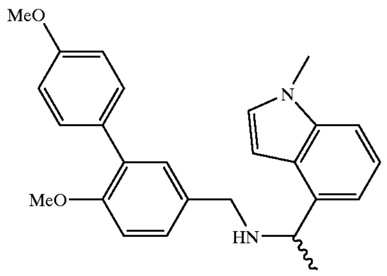

Step 1) 1-Methyl-1H-indole-4-carbonitrile

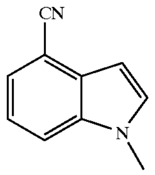

4-Cyanoindole (2.8 g, 20 mmol, Biosynth International) was dissolved in N,N-Dimethylformamide (25 mL). To the solution were added potassium carbonate powder (5.5 g, 40 mmol, 325 mesh, Aldrich) and iodomethane (3.4 g, 24 mmol, Aldrich). The mixture was stirred at room temperature for 48 h then the N,N-Dimethylformamide was removed via vacuo and the residue was diluted in ethyl acetate (100 mL). The organic solution was washed by water (50 mL), brine (50 mL). The resulting organic solution was dried over anhydrous magnesium sulfate and concentrated via vacuo. The title compound was purified by column chromatography (silica gel, hexane/ethyl acetate 3/2) in form as white solid in 97% yield (3.02 g, 19.4 mmol).

$C_{10}H_8N_2$ MS (ESI, pos. ion) m/z: 157.0 (M+1); MS (ESI, neg. ion) m/z: 155.0 (M−1).

Step 2) 1-Methyl-1H-indole-4-carbaldehyde

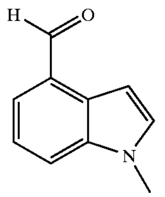

1-Methyl-1H-indole-4-carbonitrile (3.02 g, 19 mmol) was dissolved in anhydrous dichloromethane (30 mL) and the solution was cooled to −78° C. To the reaction solution was slowly added 1.5 M diisobutylaluminum hydride in toluene (12.6 mL, 19 mmol, Aldrich). The reaction mixture was allowed to stir under nitrogen at room temperature for 6 h then it was cooled again in ice bath and quenched with methyl alcohol (4 mL). The resulting solution was poured to 15% aqueous sulfuric acid solution (40 mL) at 0° C. After stirring vigorously for 1 h, the mixture was added aqueous 5 N sodium hydroxide to adjust PH>12. The organic phase was separated and the aqueous phase was extracted with ethyl acetate (40 mL×3). The combined organic layers were dried over anhydrous magnesium sulfate and concentrated via vacuo. The title compound was purified by column chromatography (silica gel, hexane/ethyl acetate 2/3) in form as light yellow oil in 92% yield (2.8 g, 17.6 mmol).

$C_{10}H_9NO$ MS (ESI, pos. ion) m/z: 160.1 (M+1); MS (ESI, neg. ion) m/z: 158.0 (M−1).

Step 3) 1-(1-Methyl-1H-indol-4-yl)-ethanol

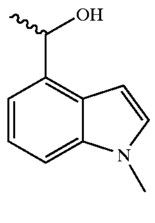

The title compound was prepared by the same procedure for 1-quinolin-4-yl-ethanol from 1-methyl-1H-indole-4-carbaldehyde (2.8 g, 17.6 mmol), 3 M methyl magnesium iodide solution in diethyl ether (10 mL, 30 mmol, Aldrich) and anhydrous tetrahydrofuran (20 mL). The crude title compound obtained in form as yellow oil in 97% yield (3.0 g, 17.1 mmol).

$C_{11}H_{13}NO$ MS (ESI, pos. ion) m/z: 176.0 (M+1); MS (ESI, neg. ion) m/z: 174.0 (M−1).

Step 4) 1-(1-Methyl-1H-indol-4-yl)-ethanone

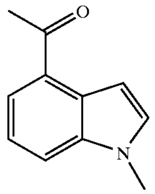

The title compound was prepared by the same procedure for 1-quinolin-4-yl-ethanone from 1-(1-Methyl-1H-indol-4-yl)-ethanol (3.0 g, 17 mmol), manganese oxide (8.69 g, 100 mmol, Aldrich) and dichloromethane (50 mL). The crude title compound was obtained in form as yellow oil in 98% yield (2.9 g, 16.7 mmol).

$C_{11}H_{11}NO$ MS (ESI, pos. ion) m/z: 174.0 (M+1); MS (ESI, neg. ion) m/z: 172.0 (M−1).

Step 5) 1-(1-Methyl-1H-indol-4-yl)-ethylamine

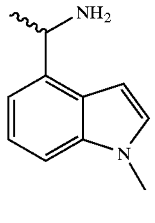

The title compound was prepared by the same procedure for preparing 1-pyridin-3-yl-ethylamine from 1-(1-methyl-1H-indol-4-yl)-ethanone (1.75 g, 10 mmol), 2 M ammonia solution in methyl alcohol (25 mL, 50 mmol, Aldrich), acetic acid (15 mL, J. T. Baker) and sodium cyanoborohydride (2.5 g, 40 mmol, Aldrich). The title compound was purified by column chromatography (silica gel, 2 M ammonia solution in methyl alcohol/ethyl acetate 1/10) in form as light yellow oil in 48% yield (0.83 g, 4.8 mmol).

$C_{11}H_{14}N_2$ MS (ESI, pos. ion) m/z: 175.0 (M+1); MS (ESI, neg. ion) m/z: 173.0 (M−1).

Step 6) (6,4'-Dimethoxy-biphenyl-3-ylmethyl)-[1-(1-methyl-1H-indol-4-yl)-ethyl]-amine

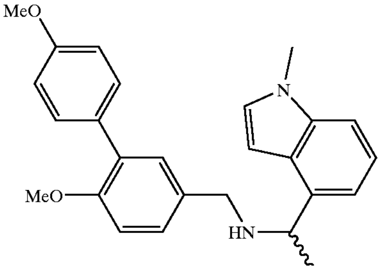

The title compound was prepared by the same procedure for (6,4'-dimethoxy-biphenyl-3-ylmethyl)-(1-quinolin-4-yl-ethyl)-amine from 1-(1-Methyl-1H-indol-4-yl)-ethylamine (522 mg, 3.0 mmol), 6,4'-Dimethoxy-biphenyl-3-carbaldehyde (242 mg, 1.0 mmol) and sodium cyanoborohydride (1.0 g, 16 mmol, Aldrich). The title compound was purified by column chromatography (silica gel, hexane/ethyl acetate 3/2) in form as white solid in 74% yield (296 mg, 0.74 mmol).

$C_{26}H_{28}N_2O_2$ MS (ESI, pos. ion) m/z: 401.6 (M+1); MS (ESI, neg. ion) m/z. 399.2 (M−1).

EXAMPLE 64

(6,4'-Dimethoxy-biphenyl-3-ylmethyl)-[1-(1-methyl-2,3-dihydro-1H-indol-4-yl)-ethyl]-amine

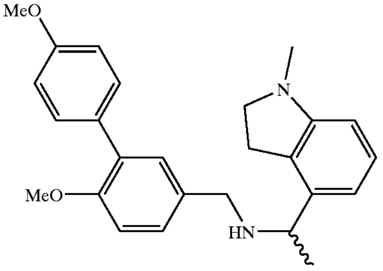

Step 1) 1-(1-Methyl-2,3-dihydro-1H-indol-4-yl)-ethylamine

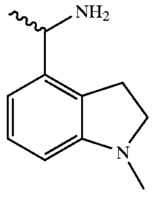

To the solution of 1-(1-Methyl-1H-indol-4-yl)-ethylamine (1.74 g, 10 mmol) with acetic acid (10 mL, J. T. Baker) was added sodium cyanoborohydride (1.0 g, 16 mmol, Aldrich) at 0 C. The reaction mixture was stirred at room temperature for 4 h then quenched with saturate aqueous sodium bicarbonate (40 mL). The aqueous phase was extracted with ethyl acetate (30 mL×4). The combined organic layers were dried over anhydrous magnesium sulfate and concentrated via vacuo. The title crude compound was obtained in form as light yellow oil in 78% yield (1.37, 7.8 mmol).

$C_{11}H_{16}N_2$ MS (ESI, pos. ion) m/z: 177.2 (M+1); MS (ESI, neg. ion) m/z: 175.0 (M−1).

Step 2) (6,4'-Dimethoxy-biphenyl-3-ylmethyl)-[1-(1-methyl-2,3-dihydro-1H-indol-4-yl)-ethyl]-amine The title compound was prepared by the same procedure for (6,4'-dimethoxy-biphenyl-3-ylmethyl)-(1-quinolin-4-yl-ethyl)-amine from 1-(1-Methyl-2,3-dihydro-1H-indol-4-yl)-ethylamine (528 mg, 3.0 mmol), 6,4'-Dimethoxy-biphenyl-3-carbaldehyde (242 mg, 1.0 mmol) and sodium cyanoborohydride (1.0 g, 16 mmol, Aldrich). The title compound was purified by column chromatography (silica gel, ethyl acetate) in form as white solid in 55% yield (221 mg, 5.5 mmol).

$C_{26}H_{30}N_2O_2$ MS (ESI, pos. ion) m/z: 403.3 (M+1); MS (ESI, neg. ion) m/z: 401.4 (M−1).

EXAMPLE 65

((1R)-1-Phenylethyl){[4,5-dimethoxy-3-(4-methoxyphenyl)phenyl]methyl}amine

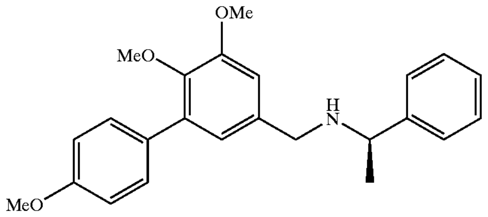

Step 1) ((1R)-1-Phenylethyl)[(3-bromo-4,5-dimethoxyphenyl)methyl]amine

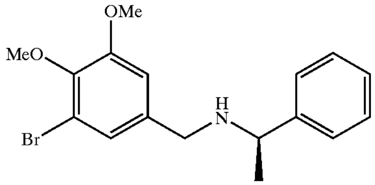

To a solution if 3-bromo-4,5-dimethoxybenzaldehyde (5 g, 0.020 mol, Aldrich), (R)-α-methylbenzylamine (2.6 mL, 0.020 mol) and AcOH (5 mL)in 70 mL of MeOH was stirred at RT for 2 hours. The reaction solution was then cooled to 0 C. and $NaBH_3CN$ (2.51 g, 0.040 mol) was added. The reaction was warmed up to RT in 2 hours and continued to stir for 16 hours. The reaction solution was concentrated in vacuo and the residue was re-dissolved in 150 mL of EtOAc. The organic solution was washed with 50 mL of saturated $NaHCO_3$ aqueous solution, followed by 50 mL of brine. The organic phase was dried over $Na_2SO_4$ and concentrated in vacuo. The crude product was purified by a silica gel column chromatography (50% EtOAc in hexane) to provide white waxy solid (5.1 g).

$C_{17}H_{20}BrNO_2$ MS (ESI, pos. ion) m/z: 350.2 (M+1).

Step 2) ((1R)-1-Phenylethyl){[4,5-dimethoxy-3-(4-methoxyphenyl) phenyl]methyl}amine

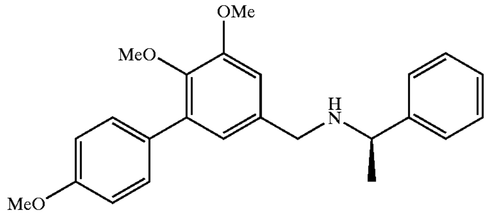

To a mixture of ((1R)-1-phenylethyl)[(3-bromo-4,5-dimethoxyphenyl)methyl]amine (1.1 g, 3.15 mmol), 4-methoxyphenylboronic acid (0.479 g, 3.15 mmol), 2M $Na_2CO_3$ (5 mL). 4 mL of EtOH in 10 mL of toluene was added 83 mg of $PPh_3$ (0.315 mmol) and 0.364 g of Pd $(PPh_3)_4$ (0.315 mmol). The mixture was then heated to 80 C. under $N_2$ for 16 hours. The mixture was cooled to RT and was diluted with 50 mL of EtOAc and 20 mL of sat. $NaHCO_3$ aq. solution. The organic phase was washed with 30 mL of brine, dried over $Na_2SO_4$ and concentrated in vacuo. The light yellow oil was chromatographed (silica gel, 10% to 50% EtOAc in hexane) to provide light yellow oil (0.5 g). The product was treated with 1N HCl in $Et_2O$ to afford the HCl salt, which was re-crystallized in EtOAc to afford light yellow solid (0.5 g).

$C_{24}H_{27}BNO_3$ MS (ESI, pos. ion) m/z: 378.4 (M+1).

EXAMPLE 66

((1R)-1-Phenylethyl)[(4-ethyl-3-(3-pyridyl)phenyl) methyl]amine

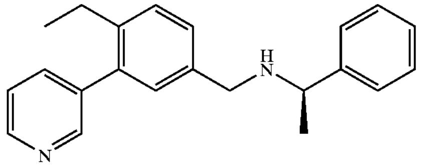

Step 1) 3-Bromo-4-ethylbenzaldehyde

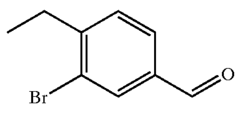

To a solution of 4-ethylbenzaldehyde (10 g, 0.0745 mol, Aldrich) in TFA/98% $H_2SO_4$ (4/1, 125 mL) mixture was added NBS (13.26 g, 0.0745 mol, Aldrich) at RT and continued to stir for 16 hours. The solvent was then removed in vacuo and the residue was dissolved in 200 mL of EtOAc. 1N NaOH solution (about 150 mL) was added to the solution and the organic phase was separated, washed with 100 mL of brine, dried over $Na_2SO_4$ and concentrated in vacuo. The oily residue was chromatographed (silica gel, 50% EtOAc in hexane) to afford orange oil as desired product (11.55 g).

$C_9H_9BrO$ MS (ESI, pos. ion) m/z: 227.0 (M+15).

Step 2) 4-Ethyl-3-(3-pyridyl)benzaldehyde

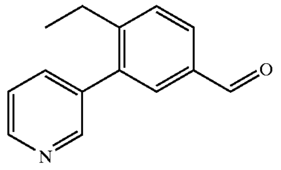

To a mixture of 3-bromo-4-ethylbenzaldehyde (2.45 g, 0.0115 mol), pyridine 3-boronic acid (1.42 g, 0.0115 mol, Matrix Scientific), 2M $Na_2CO_3$ (15 mL) in 30 mL of toluene was added 1.33 g of Pd $(PPh_3)_4$ (1.15 mmol, Aldrich). The mixture was then heated to 80 C. under $N_2$ for 16 hours. The mixture was cooled to RT and was diluted with 100 mL of EtOAc and 40 mL of sat. $NaHCO_3$ aq. solution.

The organic phase was washed with 40 mL of brine, dried over $Na_2SO_4$ and concentrated in vacuo. The crude product was chromatographed (silica gel, 20% EtOAc in hexane) to provide yellow oil (1.2 g).

$C_{14}H_{13}NO$ MS (ESI, pos. ion) m/z: 212.4 (M+1).

Step 3) ((1R)-1-Phenylethyl)[(4-ethyl-3-(3-pyridyl)phenyl) methyl]amine

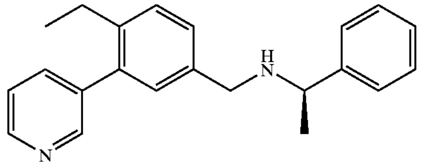

A solution of 4-ethyl-3-(3-pyridyl)benzaldehyde (0.2 g, 0.95 mmol), (R)-α-methylbenzylamine (0.121 mL, 0.95 mmol) and AcOH (1 mL) in 10 mL of MeOH was stirred at RT for 3 hours. The reaction solution was then cooled to 0 C. and $NaBH_3CN$ (0.18 g , 2.85 mmol) was added. The reaction was warmed up to RT continued to stir 3 hours. The reaction solution was concentrated in vacuo and the residue was re-dissolved in 50 mL of EtOAc. The organic solution was washed with 20 mL of saturated $NaHCO_3$ aqueous solution, followed by 20 mL of brine. The organic phase was dried over $Na_2SO_4$ and concentrated in vacuo. The crude product was purified by a silica gel column chromatography (20% of EtOAc in hexane) to provide colorless oil (0.2 g). The product was treated with 1N HCl in $Et_2O$ and the HCl salt was re-crystallized in MeOH/$Et_2O$ (1:10) mixture to provide white solid (0.2 g).

$C_{22}H_{24}N_2$ MS (ESI, pos. ion) m/z: 317.3 (M+1).

EXAMPLE 67

((1R)-1-Naphthylethyl)[(4-ethyl-3-(3-pyridyl) phenyl)methyl]amine

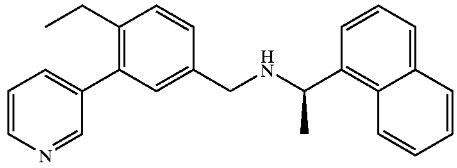

The title compound (0.22 g, white solid as HCl salt) was prepared from 4-ethyl-3-(3-pyridyl)benzaldehyde (0.22 g) and (R)-1-(1-naphthyl)ethylamine (0.17 mL) analogously to Example 66, step 3.

$C_{26}H_{26}N_2$ MS (ESI, pos. ion) m/z: 367.3 (M+1).

EXAMPLE 68

((1R)-1-phenylethyl){[4-ethyl-3-(4-methoxyphenyl) phenyl]methyl}amine

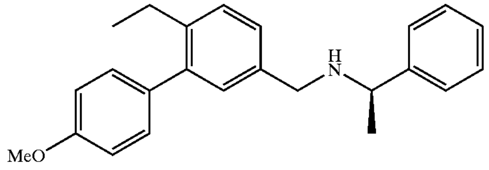

Step 1) 4-Ethyl-3-(4-methoxyphenyl)benzaldehyde

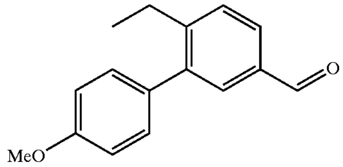

To a mixture of 3-bromo-4-ethylbenzaldehyde (1.5 g, 7.07 mmol), 4-methoxyphenylboronic acid (1.075 g, 7.07 mmol), 2M $Na_2CO_3$ (10 mL) in 20 mL of toluene was added 0.817 g of Pd $(PPh_3)_4$ (0.707 mmol). The mixture was then heated to 80 C. under $N_2$ for 16 hours. The mixture was cooled to RT and was diluted with 100 mL of EtOAc and 50 mL of sat. $NaHCO_3$ aq. solution. The organic phase was washed with 40 mL of brine, dried over $Na_2SO_4$ and concentrated in vacuo. The crude product was chromatographed (silica gel, 10% EtOAc in hexane) to provide light yellow solid (2.1 g).

$C_{16}H_{16}O_2$ MS (ESI, pos. ion) m/z: 241.1 (M+1).

Step 2) ((1R)-1-phenylethyl){[4-ethyl-3-(4-methoxyphenyl) phenyl]methyl}amine

The title compound (0.2 g, white solid as HCl salt) was prepared from 4-ethyl-3-(4-methoxyphenyl)benzaldehyde (0.5 g) and (R)-α-methylbenzylamine (0.265 mL) analogously to Example 66, step 3.

EXAMPLE 69

Methyl 5-(5-{[((1R)-1-phenylethyl)amino]methyl}-2-methoxyphenyl)pyridine-3-carboxylate

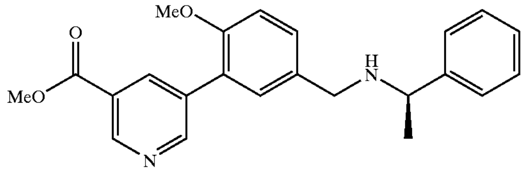

Step 1) Methyl 5-(3-formyl-6-methoxyphenyl)pyridine-3-carboxylate

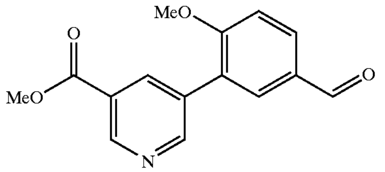

To a mixture of 5-bromonicotinate (2.16 g, 0.01 mol, Avocado Research) and (5-formyl-2-methoxyphenyl) boronic acid (1.79 g, 0.01 mol, Matrix Scientific), 2M $Na_2CO_3$ (10 mL) in 20 mL of toluene was added 1.15 g of Pd $(PPh_3)_4$ (1.0 mmol). The mixture was then heated to 80 C. under $N_2$ for 16 hours. The mixture was cooled to RT and was diluted with 100 mL of EtOAc and 50 mL of sat. $NaHCO_3$ aq. solution. The organic phase was washed with 40 mL of brine, dried over $Na_2SO_4$ and concentrated in vacuo. The crude product was chromatographed (silica gel, 50% EtOAc in hexane) to provide white solid (1.2 g).

$C_{15}H_{13}NO_4$ MS (ESI, pos. ion) m/z: 272.3 (M+1).

Step 2) Methyl 5-(5-{[((1R)-1-phenylethyl)amino]methyl}-2-methoxyphenyl)pyridine-3-carboxylate The title compound (0.4 g, white solid as HCl salt) was prepared from 4-ethyl-3-(4-methoxyphenyl)benzaldehyde (0.5 g) and (R)-α-methylbenzylamine (0.265 mL) analogously to Example 66, step 3.

$C_{23}H_{24}N_2O_3$ MS (ESI, pos. ion) m/z: 377.5 (M+1).

EXAMPLE 70

((1R)-1-Phenylethyl){[4-methoxy-3-(5-methoxy(3-pyridyl))phenyl]methyl}amine

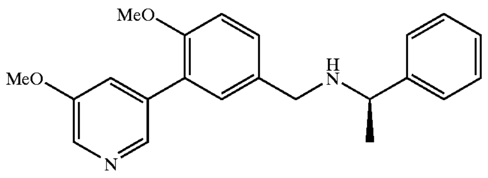

Step 1) 3-Bromo-5-methoxypyridine

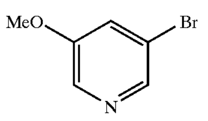

1.45 g of Na (0.063 mol) were added to 100 mL of MeOH and the resulted solution was stirred at RT for 30 minutes. The solution was then concentrated at 65 C. in vacuo for 40 minutes. The white solid obtained was dissolved in 100 mL of DMF. 15 g of 3,5-dibromopyridine (0.063 mol) were added and the reaction was heated to 65 C. for 16 hours. The reaction was cooled to RT and diluted with 200 mL of EtOAc and 100 mL of sat. aq. $NaHCO_3$ solution. The organic phase was separated and was washed with 100 mL of brine, dried over $Na_2SO_4$ and concentrated in vacuo. The crude product was chromatographed (silica gel, 10% EtOAc in hexane) to provide colorless crystals (10 g).

$C_6H_6BrNO$ MS (ESI, pos. ion) m/z: 188.1 (M+1).

Step 2) 4-Methoxy-3-(5-methoxy(3-pyridyl))benzaldehyde

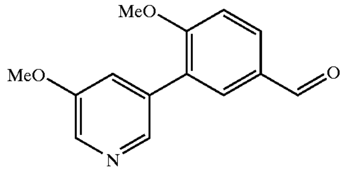

The title compound (2.5 g, white solid) was prepared from 3-Bromo-5-methoxypyridine (2.17 g, 0.0116 mol) and (5-formyl-2-methoxyphenyl)boronic acid (2.5 g, 0.014 mol, Matrix Scientific) analogously to Example 69, step 1.

$C_{14}H_{13}NO_3$ MS (ESI, pos. ion) m/z: 244.4 (M+1).

Step 3) ((1R)-1-Phenylethyl){[4-methoxy-3-(5-methoxy(3-pyridyl)) phenyl]methyl}amine

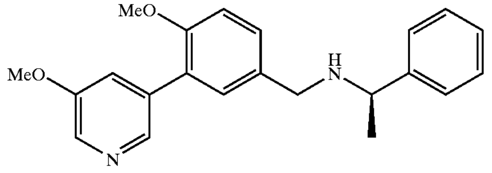

The title compound (0.8 g, white solid as HCl salt) was prepared from 4-methoxy-3-(5-methoxy(3-pyridyl)) benzaldehyde (0.71 g) and (R)-α-methylbenzylamine (0.371 mL) analogously to Example 66, step 3.

$C_{22}H_{24}N_2O_2$ MS (ESI, pos. ion) m/z: 349.4 (M+1).

EXAMPLE 71

((1R)-1-Phenylethyl){[3-(4-methoxyphenyl)-4-methylphenyl]methyl}amine and 4-(5-{[((1R)-1-Phenylethyl)amino]methyl}-2-methylphenyl)phenol Step 1) N-((1R)-1-Phenylethyl)(3-bromo-4-methylphenyl) carboxamide

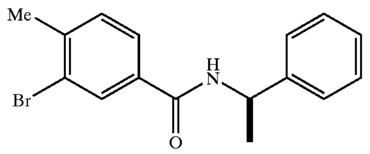

To a solution of 3-bromo-4-methylbenzoic acid (5.0 g, 0.023 mol) in $CH_2CH_2$ (100 mL) was added oxalyl chloride (8.67 g, 0.069 mol). After 10 minutes, 1.0 mL of DMF was added slowly and the mixture was continued to stir at RT for 2 hours. The volatile was removed in vacuo. The residue was re-dissolved in $CH_2CH_2$ (100 mL) and transferred to a 125 mL additional funnel.

To a 500 mL Erlenmeyer flask equipped with a stir bar was added 100 mL of sat. aq. $NaHCO_3$ solution followed by 2.79 g of (R)-α-methylbenzylamine (0.023 mol) in 100 mL of $CH_2CH_2$. 3-Bromo-4-methylbenzoyl chloride in $CH_2Cl_2$ (from above) was added dropwise to the Erlenmeyer flask and the reaction mixture was continued to stir at RT for 16 hours. The organic phase was diluted with 50 mL of $CH_2CH_2$, separated from aqueous phase, dried over $Na_2SO_4$ and concentrated in vacuo. The residue was washed with 50 mL of $Et_2O$ and dried in an oven at 40 C. overnight to afford light yellow solid (7.0 g, 0.022 mol, 96%).

$C_{16}H_{16}BrNO$ MS (ESI, pos. ion) m/z: 316.1 (M+1).

Step 2) N-((1R)-1-Phenylethyl)[3-(4-methoxyphenyl)-4-methylphenyl]carboxamide

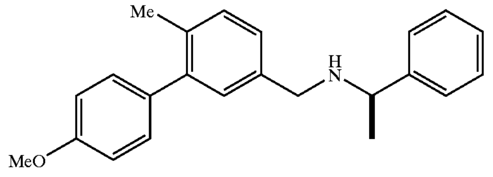

To a mixture of N-((1R)-1-phenylethyl)(3-bromo-4-methylphenyl)carboxamide (1.38 g, 4.32 mmol) and 4-methoxyphenylboronic acid (0.53 g, 4.32 mmol) in 10 mL of 2M $Na_2CO_3$ aq. soln and 20 mL of toluene was bubbled through $N_2$ for 5 min. Catalyst $Pd(PPh_3)_4$ (0.36 g, 0.314 mmol) was then added and the mixture was heated to 80 C. for 19 hours under $N_2$. The reaction mixture was cooled to RT and was diluted with 100 mL of EtOAc and 50 mL of water. The organic layer was separated and washed with 50 mL of brine, and dried over $Na_2SO_4$ and concentrated in vacuo. The residue was purified by silica gel column chromatography ($CHCl_3$ to EtOAc) to provide yellow solid (1.0 g, 2.9 mmol, 92%).

$C_{23}H_{23}NO_2$ MS (ESI, pos. ion) m/z: 346.3 (M+1).

Step 3) ((1R)-1-Phenylethyl){[3-(4-methoxyphenyl)-4-methylphenyl]methyl}amine

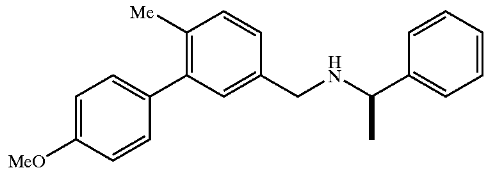

and 4-(5-{[((1R)-1-Phenylethyl)amino]methyl}-2-methylphenyl)phenol

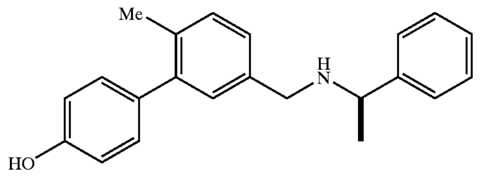

To a solution of N-((1R)-1-phenylethyl)[3-(4-methoxyphenyl)-4-methylphenyl]carboxamide (0.12 g, 0.34 mmol) in 10 mL of toluene was added DIBAL-H (1 mL, 1.5 mmol). The reaction was then heated to 100 C. for 16 hours and cooled to RT. The reaction was quenched with 5 mL of 2N NaOH aq. soln. 100 mL of $CH_2Cl_2$ was used to extract the product. The organic phase was washed with 30 mL of brine, dried over $Na_2SO_3$ and concentrated in vacuo. The desired products were separated by silica gel column chromatography (30% to 60% EtOAc in hexane) provide ((1R)-1-phenylethyl){[3-(4-methoxyphenyl)-4-methylphenyl]methyl}amine and 4-(5-{[((1R)-1-phenylethyl)amino]methyl}-2-methylphenyl)phenol, which were treated with 1N HCl in $Et_2O$ separately to provide the HCl salts as white solids.

((1R)-1-Phenylethyl){[3-(4-methoxyphenyl)-4-methylphenyl]methyl}amine $C_{23}H_{25}NO$ MS (ESI, pos. ion) m/z: 332.3 (M+1).

4-(5-{[((1R)-1-Phenylethyl)amino]methyl}-2-methylphenyl)phenol $C_{22}H_{23}NO$ MS (ESI, pos. ion) m/z: 318.2 (M+1); MS (ESI, neg. ion) m/z: 316.2 (M−1).

EXAMPLE 72

((1R)-1-Phenylpropyl){[4-methoxy-3-(4-methoxyphenyl)phenyl]methyl}amine

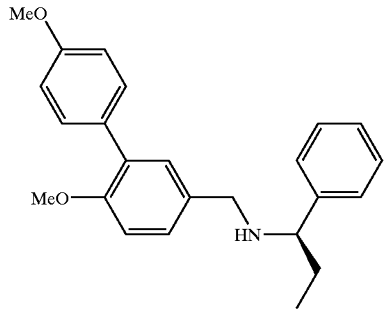

The title compound was prepared by the same procedure for (6,4'-dimethoxybiphenyl-3-ylmethyl)-(1-quinolin-4-yl-ethyl)-amine from (R)-(+)-1-phenyl-propylamine (405 mg, 3.0 mmol, Lancaster Synthesis Ltd.), 6,4'-Dimethoxybiphenyl-3-carbaldehyde (242 mg, 1.0 mmol) and sodium cyanoborohydride (1.0 g, 16 mmol, Aldrich). The title compound was purified by column chromatography (silica gel, hexane/ethyl acetate 2/3) in form as white solid in 52% yield (187 mg, 0.52 mmol).

$C_{24}H_{27}NO_2$ MS (ESI, pos. ion) m/z: 362.4 (M+1); MS (ESI, neg. ion) m/z: 360.3 (M−1).

The final products disclosed in Examples 73 to 109 were prepared according to Method C described earlier.

EXAMPLE 73

(1R)-1-(3-fluorophenyl)-N-((6-(methyloxy)-4'-(trifluoromethyl)-1,1'-biphenyl-3-yl)methyl) ethanamine

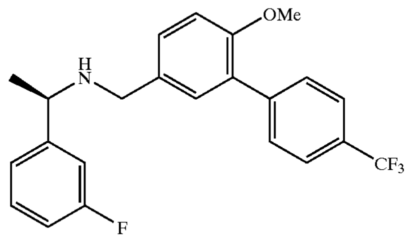

MS(EI) calcd for $C_{23}H_{22}F_4NO$ ($MH^+$) 404.1, Found 404.1, 265.1.

EXAMPLE 74

(1R)-1-(3-((2-(methyloxy)ethyl)oxy)phenyl)-N-((6-(methyloxy)-4'-(trifluoromethyl)-1,1'-biphenyl-3-yl) methyl)ethanamine

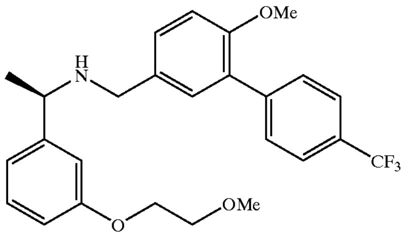

MS(EI) calcd for $C_{26}H_{29}F_3NO_3$ ($MH^+$) 460.2, Found 460.2, 265.1.

EXAMPLE 75

(1R)-1-(3-fluorophenyl)-N-((6-(methyloxy)-4'-(methylsulfonyl)-1,1'-biphenyl-3-yl)methyl) ethanamine

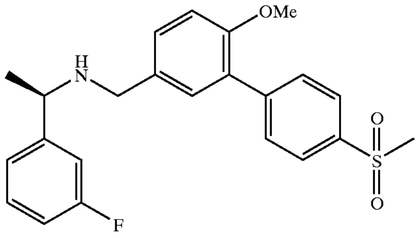

MS (EI) calcd for $C_{23}H_{25}FNO_3S$ ($MH^+$) 414.1, Found 414.2, 275.2.

EXAMPLE 76

(1R)-1-(3-fluorophenyl)-N-((6-(methyloxy)-1,1'-biphenyl-3-yl)methyl)ethanamine

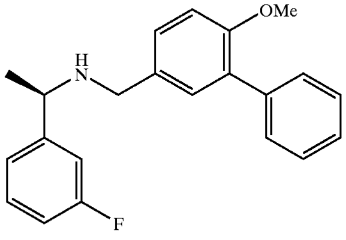

MS(EI) calcd for $C_{22}H_{23}FNO$ ($MH^+$) 336.2, Found 336.2, 197.1.

EXAMPLE 77

(1R)-N-((4-chloro-3-iodophenyl)methyl)-1-(3-fluorophenyl)ethanamine

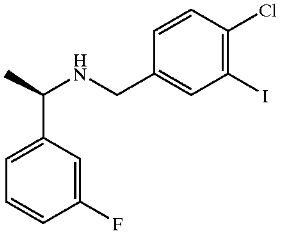

MS(EI) calcd for $C_{15}H_{15}ClFIN$ ($MH^+$) 390.0, Found 390.0, 251.0, 123.1.

EXAMPLE 78

(1R)-N-((4'-fluoro-6-(methyloxy)-1,1'-biphenyl-3-yl) methyl)-1-(3-fluorophenyl)ethanamine

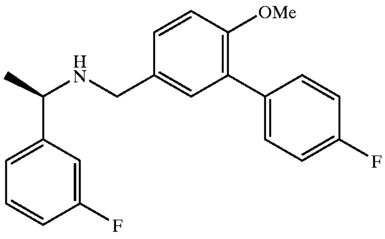

MS(EI) calcd for $C_{22}H_{22}F_2NO$ ($MH^+$) 354.1, Found 354.1, 215.1.

EXAMPLE 79

2,2,2-trifluoro-N-((6-(methyloxy)-4'-(trifluoromethyl)-1,1'-biphenyl-3-yl)methyl)-1-phenylethanamine

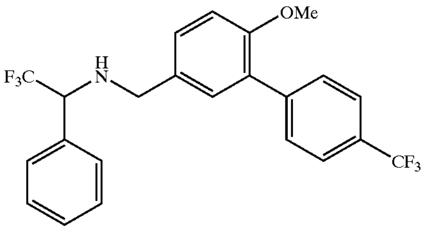

MS(EI) calcd for $C_{23}H_2OF_6NO$ ($MH^+$) 440.0, Found 439.9, 264.7.

EXAMPLE 80

(1R)-1-(3-chlorophenyl)-N-((6-(methyloxy)-4'-(trifluoromethyl)-1,1'-biphenyl-3yl)methyl) ethanamine

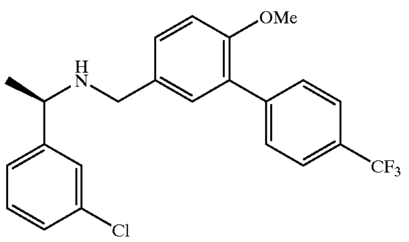

MS(EI) calcd for $C_{23}H_{21}ClF_3NO$ 420.87 (MH+), Found: 420.1; 422.1 265.1

EXAMPLE 81

N-((6-(methyloxy)-4'-(trifluoromethyl)-1,1'-biphenyl-3-yl)methyl)-1-(3-methylphenyl) ethanamine

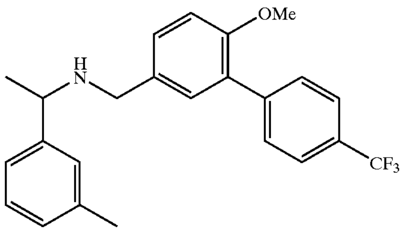

MS(EI) calcd for $C_{24}H_{24}F_3NO$ 400.45 (MH+), Found: 400.1; 265.1

EXAMPLE 82

3-(1-(((6-(methyloxy)-4'-(trifluoromethyl)-1,1'-biphenyl-3-yl)methyl)amino)ethyl)benzonitrile

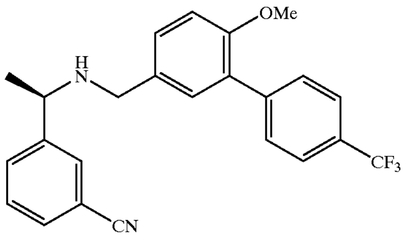

MS(EI) calcd for $C_{24}H_{21}F_3N_2O$ 411.44 (MH+) Found: 411.3; 265.1

EXAMPLE 83

(1R)-N-((6-fluoro-4'-(trifluoromethyl)-1,1'-biphenyl-3-yl)methyl)-1-phenylethanamine

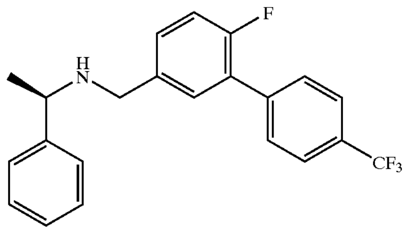

MS(EI) calcd for $C_{22}H_{19}F_4N$ 374.30 (MH+) Found: 374.2;

EXAMPLE 84

1-(3,5-difluorophenyl)-N-((6-(methyloxy)-4'-(trifluoromethyl)-1,1'-biphenyl-3yl)methyl) ethanamine

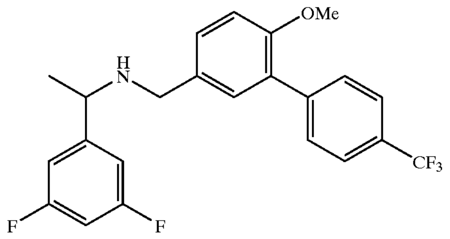

MS(EI) calcd for $C_{23}H_{20}F_5NO$ 422.41 (MH+) Found: 422.2; 265.2

EXAMPLE 85

1-(3-bromophenyl)-N-((6-(methyloxy)-4'-(trifluoromethyl)-1,1'-biphenyl-3-yl)methyl) ethanamine

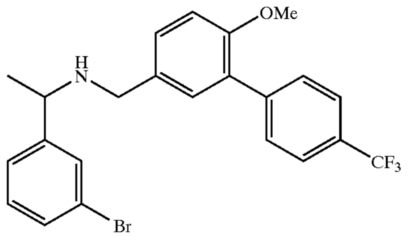

MS(EI) calcd for $C_{23}H_{21}BrF_3NO$ 465.32 (MH+) Found: 466.0; 265.1

EXAMPLE 86

1-(3-fluorophenyl)-N-((6-(methyloxy)-4'-(trifluoromethyl)-1,1'-biphenyl-3-yl)methyl)ethanamine

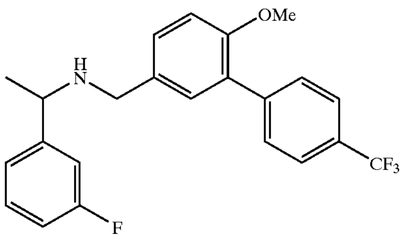

MS(EI) calcd for $C_{23}H_{21}F_4NO$ 404.42 (MH+) Found: 404.2; 265.1

EXAMPLE 87

(1R)-1-(3-chlorophenyl)-N-((6-(methyloxy)-1,1'-biphenyl-3-yl)methyl)ethanamine

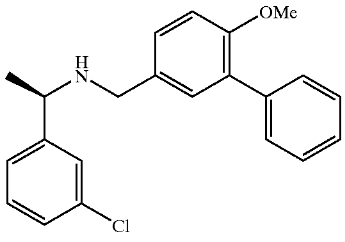

MS(EI) calcd for $C_{22}H_{22}ClNO$ 352.88 (MH+) Found: 353.1; 197.1

EXAMPLE 88

N-1-(3-(dimethylamino)phenyl)ethyl)-N-((6-(methyloxy)-4'-(trifluoromethyl)-1,1'-biphenyl-3-yl)methyl)amine

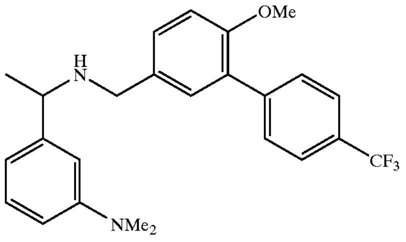

MS(EI) calcd for $C_{25}H_{27}F_3$ $N_2O$ 429.50 (MH+) Found: 429.2; 265.1

EXAMPLE 89

N-((6-(methyloxy)-4'-(trifluoromethyl)-1,1'-biphenyl-3-yl)methyl)-1-(3-((trifluoromethyl)oxy)phenyl)ethanamine

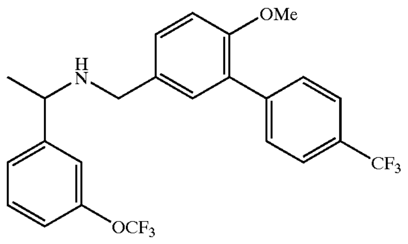

MS(EI) calcd for $C_{24}H_{21}F_6NO_2$ 470.42 (MH+) Found: 470.1; 265.1

EXAMPLE 90

1-(4-fluorophenyl)-N-((6-(methyloxy)-4'-(trifluoromethyl)-1,1'-biphenyl-3-yl)methyl)ethanamine

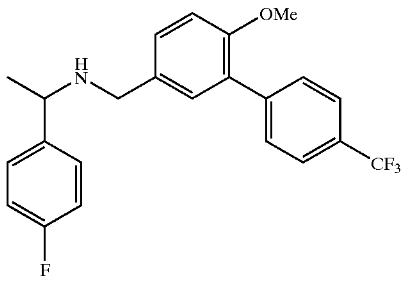

MS(EI) calcd for $C_{23}H_{21}F_4NO$ 404.42 (MH+) Found: 404.2; 265.1

EXAMPLE 91

1-(2,3-dichlorophenyl)-N-((6-(methyloxy)-4'-(trifluoromethyl)-1,1'-biphenyl-3-yl)methyl)ethanamine

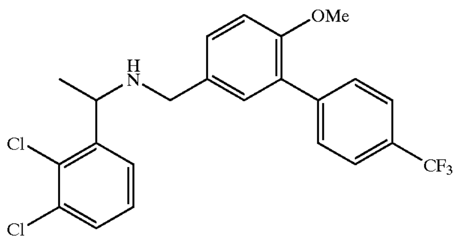

MS(EI) calcd for $C_{23}H_{20}Cl_2F_3NO$ 455.32 (MH+) Found: 454.0; 456.0

EXAMPLE 92

N-((6-(methyloxy)-4'-(trifluoromethyl)-1,1'-biphenyl-3-yl)methyl)-1-(2-(trifluoromethyl)phenyl) ethanamine

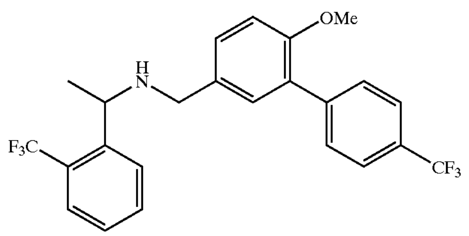

MS(EI) calcd for $C_{24}H_{21}F_6NO$ 454.42 (MH+) Found: 454.2; 265.1

EXAMPLE 93

(1R)-N-((4-(methyloxy)-3-(6-((tetrahydro-2-furanylmethyl)oxy)-3-pyridinyl)phenyl)methyl)-1-phenylethanamine

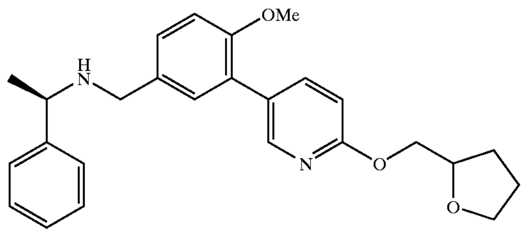

MS (ESI, pos. ion) m/z: Calc'd for $C_{26}H_{30}N_2O_3$: 418.5 g/mol. Found: (M+1) 418.7, 334.9, 297.7

EXAMPLE 94

5-(2-(methyloxy)-5-((((1R)-1-phenylethyl)amino) methyl)phenyl)-2-pyridinamine

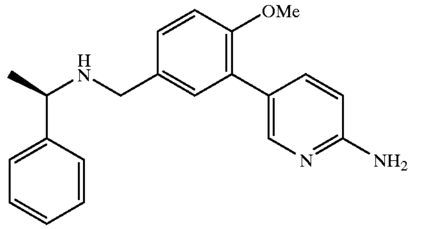

MS (ESI, pos. ion) m/z: Calc'd for $C_{21}H_{23}N_3O$: 333.43 g/mol. Found: (M+1) 334.1, 213.2

EXAMPLE 95

N,N-dimethyl-5-(2-(methyloxy)-5-((((1R)-1-phenylethyl)amino)methyl)phenyl)-2-pyridinamine

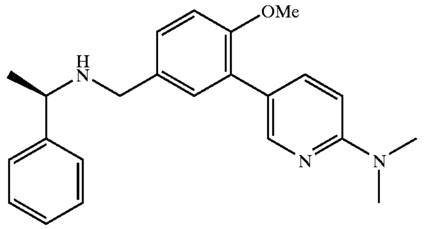

MS (ESI, pos. ion) m/z: Calc'd for $C_{23}H_{27}N_3O$: 361.48 g/mol. Found: (M+1) 362.0, 241.2

EXAMPLE 96

1-(3-((5-(2-(methyloxy)-5-((((1R)-1-phenylethyl) amino)methyl)phenyl)-2-pyridinyl)amino)propyl)-2-pyrrolidinone

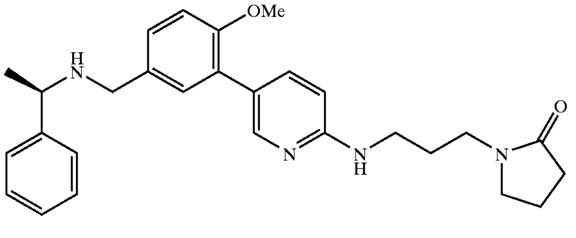

MS (ESI, pos. ion) m/z: Calc'd for $C_{28}H_{34}N_4O_2$: 458.60 g/mol. Found: (M+1) 458.8, 355.0, 337.7, 306.0, 239.1

EXAMPLE 97

(1S)-N-((6-(methyloxy)-4'-(trifluoromethyl)-1,1'-biphenyl-3-yl)methyl)-1-phenylethanamine

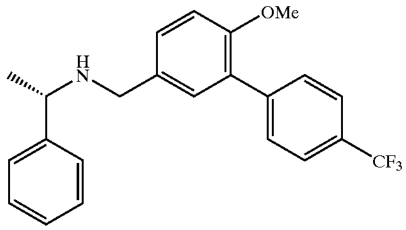

MS (ESI, pos. ion) m/z: Calc'd for $C_{23}H_{22}F_3NO$: 385.43 g/mol. Found: (M+1) 385.9, 264.6, 245.2

EXAMPLE 98

5-(2-(methyloxy)-5-((((1R)-1-phenylethyl)amino) methyl)phenyl)-2(1H)-pyridinone

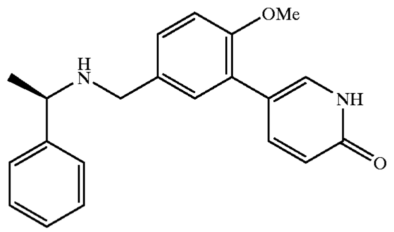

MS (ESI, pos. ion) m/z: Calc'd for $C_{21}H_{22}N_2O_2$: 334.42 g/mol. Found: (M+1) 334.9, 214.2

EXAMPLE 99

(1R)-N-((4-(methyloxy)-3-(6-((2-(methyloxy)ethyl) oxy)-3-pyridinyl)phenyl)methyl)-1-phenylethanamine

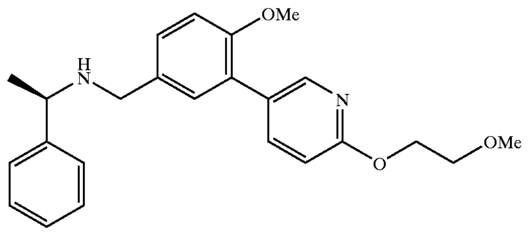

MS (ESI, pos. ion) m/z: Calc'd for $C_{24}H_{28}N_2O_3$: 392.50 g/mol. Found: (M+1) 392.9, 334.9, 271.9, 226.2

EXAMPLE 100

N-methyl-N-(5-(2-(methyloxy)-5-((((1R)-1-phenylethyl)amino)methyl)phenyl)-2-pyridinyl) glycine

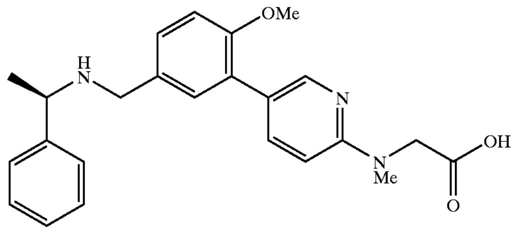

MS (ESI, pos. ion) m/z: Calc'd for $C_{24}H_{27}N_3O_3$: 405.50 g/mol. Found: (M+1) 406.3, 284.9

EXAMPLE 101

N-1-,N-2-dimethyl-N-1-(5-(2-(methyloxy)-5-((((1R)-1-phenylethyl)amino)methyl)phenyl)-2-pyridinyl)-1,2-ethanediamine

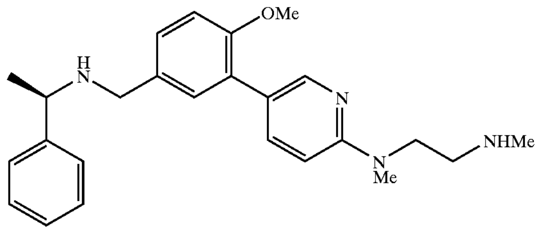

MS (ESI, pos. ion) m/z: Calc'd for $C_{25}H_{32}N_4O$: 404.56 g/mol. Found: (M+1) 404.8, 373.7, 301.0, 284.0, 270.0

EXAMPLE 102

(1R)-N-((3-(6-((2-aminoethyl)oxy)-3-pyridinyl)-4-(methyloxy)phenyl)methyl)-1-phenylethanamine

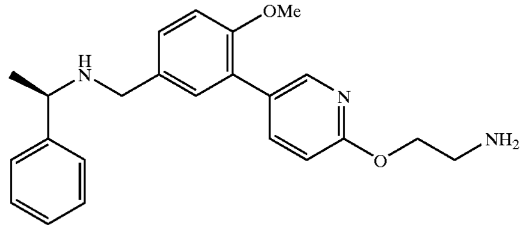

MS (ESI, pos. ion) m/z: Calc'd for $C_{23}H_{27}N_3O_2$: 377.49 g/mol. Found: (M+1) 377.8, 274.1, 256.9

EXAMPLE 103

3-(2-(methyloxy)-5-((((1R)-1-phenylethyl)amino) methyl)phenyl)-N-(3-(4-morpholinyl)propyl)-2-pyridinamine

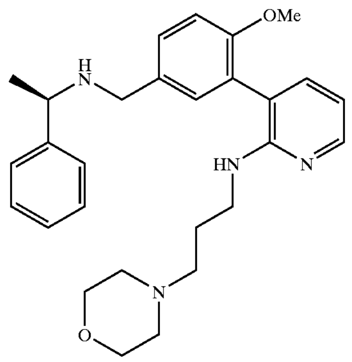

MS (ESI, pos. ion) m/z: Calc'd for $C_{28}H_{36}N_4O_2$: 460.62 g/mol. Found: (M+1) 461.1, 356.8

EXAMPLE 104

3-(2-(methyloxy)-5-((((1R)-1-phenylethyl)amino)methyl)phenyl)-N-(tetrahydro-2-furanylmethyl)-2-pyridinamine

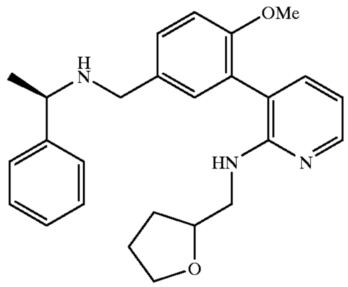

MS (ESI, pos. ion) m/z: Calc'd for $C_{26}H_{31}N_3O_2$: 417.55 g/mol. Found: (M+1) 418.1, 297.1, 265.1

EXAMPLE 105

(1R)-N-((4-(methyloxy)-3-(2-(4-morpholinyl)-3-pyridinyl)phenyl)methyl)-1-phenylethanamine

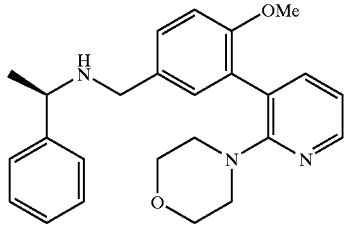

MS (ESI, pos. ion) m/z: Calc'd for $C_{25}H_{29}N_3O_2$: 403.52 g/mol. Found: (M+1) 404.2, 283.0

EXAMPLE 106

(1R)-N-((3-(2-fluoro-3-pyridinyl)-4-(methytoxy)phenyl)methyl)-1-phenylethanamine

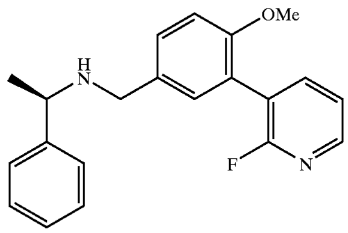

MS (ESI, pos. ion) m/z: Calc'd for $C_{21}H_{21}FN_2O$: 336.41 g/mol. Found: (M+1) 336.9, 233.1, 217.1

EXAMPLE 107

(1R)-N-((4-(methyloxy)-3-(2-((2,2,2-trifluoroethyl)oxy)-3-pyridinyl)phenyl)methyl)-1-phenylethanamine

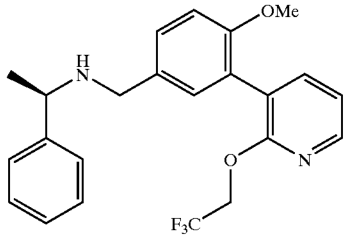

MS (ESI, pos. ion) m/z: Calc'd for $C_{23}H_{23}F_3N_2O_2$: 416.44 g/mol. Found: (M+1) 416.7, 295.8

EXAMPLE 108

(1R)-N-((4-(methyloxy)-3-(2-((tetrahydro-2-furanylmethyl)oxy)-3-pyridinyl)phenyl)methyl)-1-phenylethanamine

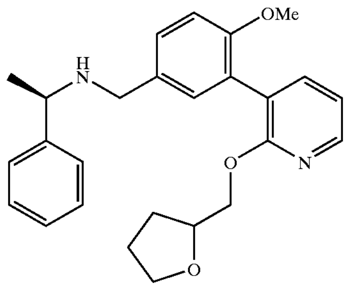

MS (ESI, pos. ion) m/z: Calc'd for $C_{26}H_{30}N_2O_3$: 418.54 g/mol. Found: (M+1) 419.2, 298.1, 216.1

EXAMPLE 109

(1R)-N-(3-(2-chloropyrid-4-yl)-4-methoxyphenyl)methyl-N-1-phenylethylamine

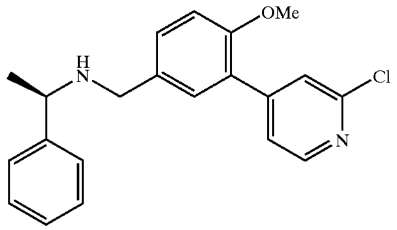

MS (ESI, pos. ion) m/z: Calc'd for $C_{21}H_{21}ClN_2O$: 352.86 g/mol. Found: (M+1) 353.0 (d), 231.9 (d)

EXAMPLE 110

(1R)-N-((6-(methyloxy)-4'-(trifluoromethyl)-1,1'-biphenyl-3-yl)methyl)-1-phenylethanaminePrepared using Method C.

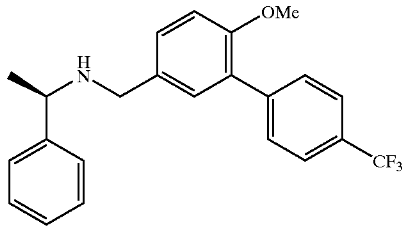

MW 385.427 Mass found: 265, 386.

EXAMPLE 111

(1R)-N-((4-(methyloxy)-3-(6-((2,2,2-trifluoroethyl)oxy)-3-pyridinyl)phenyl)methyl)-1-(1-naphthalenyl)ethanaminePrepared using Method C.

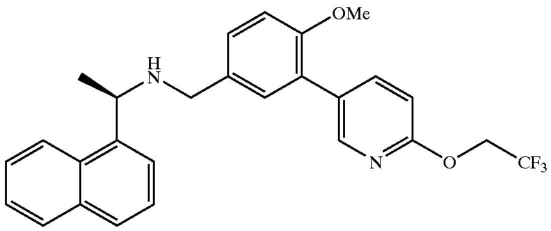

MW 466.5 Mass found: 467, 155.

EXAMPLE 112

(1R)-N-((6-(methyloxy)-4'-((trifluoromethyl)oxy)-1,1'-biphenyl-3-yl)methyl)-1-phenylethanamine Prepared using Method C.

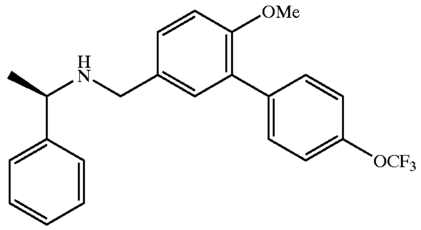

MW 401.426 Mass found: 402, 803, 917.

EXAMPLE 113

(1R)-N-((4-(methyloxy)-3-(6-(trifluoromethyl)-3-pyridinyl)phenyl)methyl)-1-(1-naphthalenyl)ethanamine Prepared using Method C.

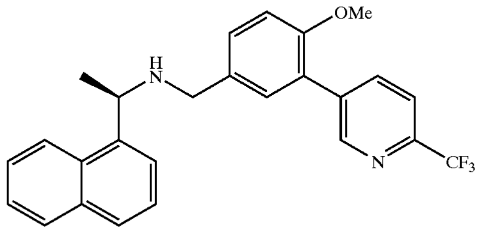

MW 436.475 Mass found: 437, 478.

EXAMPLE 114

(1R)-N-((4-(methyfoxy)-3-(3-pyridinyl)phenyl)methyl)-1-(1-naphthalenyl)ethanamine Prepared using Method A.

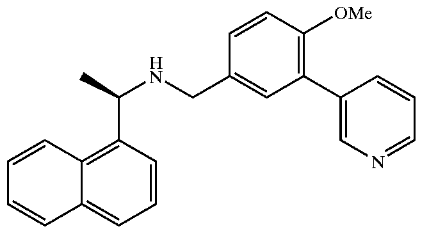

MW 368.478 Mass found: 369, 155.

EXAMPLE 115

(1R)-N-((6-(ethyloxy)-4'-(methyloxy)-1,1'-biphenyl-3-yl)methyl)-1-phenylethanamine Prepared using Method C.

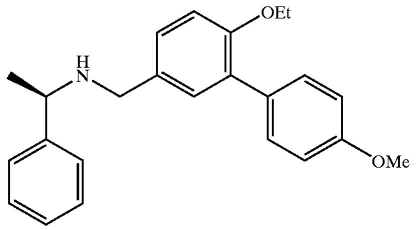

MW 361.482 Mass found: 362.

EXAMPLE 116

(1R)-N-((6-(methyloxy)-4'-((trifluoromethyl)oxy)-1,1'-biphenyl-3-yl)methyl)-1-(1-naphthalenyl)ethanamine Prepared using Method C.

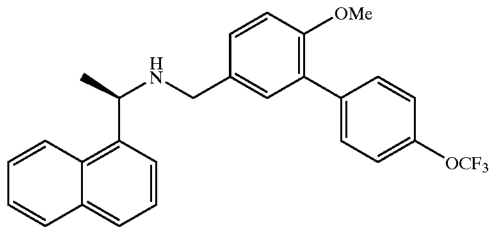

MW 451.486 Mass found: 452, 155.

Examples 117–252 were prepared using Method A:

EXAMPLE 117

(1R)-1-(3-(methyloxy)phenyl)-N-((4-(methyloxy)-3-(3-pyridinyl)phenyl)methyl)ethanamine

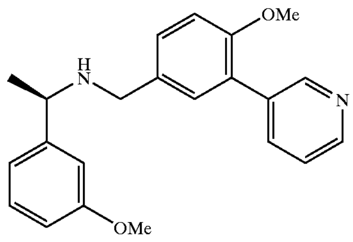

MW 348.444 Mass found: 198, 349.

EXAMPLE 118

(1R)-1-(3-(methyloxy)phenyl)-N-((3-(1,3-thiazol-2-yl)phenyl)methyl)ethanamine

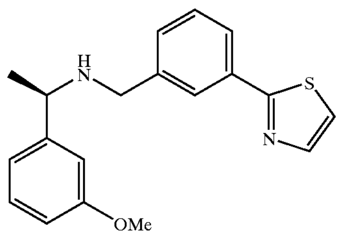

MW 324.446 Mass found: 325, 649.

EXAMPLE 119

(1R)-N-((4-(methyloxy)-3-(3-pyridinyl)phenyl)methyl)-1-(4-methylphenyl)ethanamine

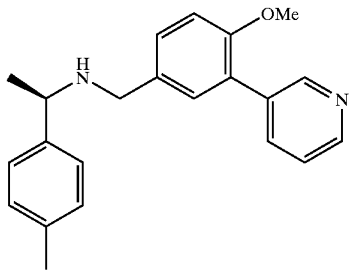

MW 332.445 Mass found: 333, 779.

EXAMPLE 120

(1R)-1-(4-(methyloxy)phenyl)-N-((4-(methyloxy)-3-(3-pyridinyl)phenyl)methyl)ethanamine

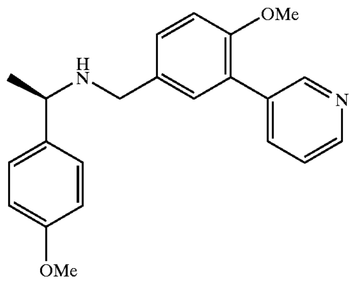

MW 348.444 Mass found: 349.

EXAMPLE 121

(1R)-N-((3-(1,3-benzodioxol-5-yl)phenyl)methyl)-1-phenylethanamine

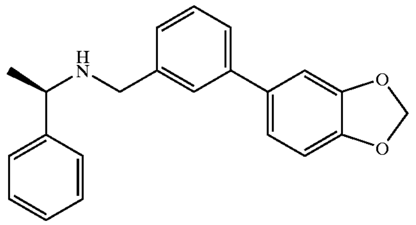

MW 331.413 Mass found: 332, 777.

EXAMPLE 122

(1R)-N-((3-(1,3-benzodioxol-5-yl)phenyl)methyl)-1-(4-methylphenyl)ethanamine

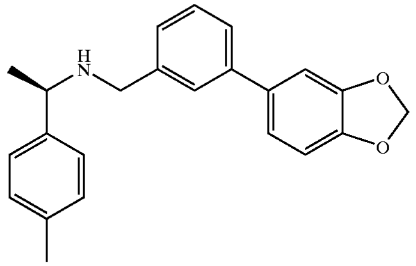

MW 345.44 Mass found: 346.

EXAMPLE 123

(1R)-N-((3-(1,3-benzodioxol-5-yl)phenyl)methyl)-1-(4-(methyloxy)phenyl)ethanamine

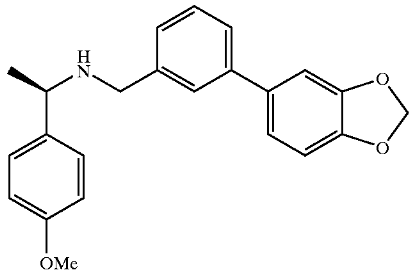

MW 361.439 Mass found: 362.

EXAMPLE 124

(1R)-N-((3-(1,3-benzodioxol-5-yl)phenyl)methyl)-1-(4-(methyloxy)phenyl)ethanamine

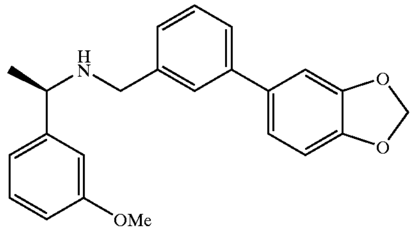

MW 361.439 Mass found: 362.

EXAMPLE 125

2'-(methyloxy)-5'-((((1R)-1-(1-naphthalenyl)ethyl)amino)methyl)-1,1'-biphenyl-3-carbonitrile

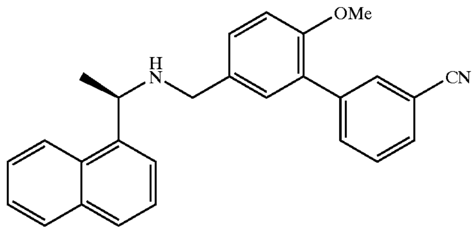

MW 392.5 Mass found: 393.

EXAMPLE 126

2'-(methyloxy)-5'-((((1R)-1-phenylethyl)amino)methyl)-1,1'-biphenyl-3-carbonitrile

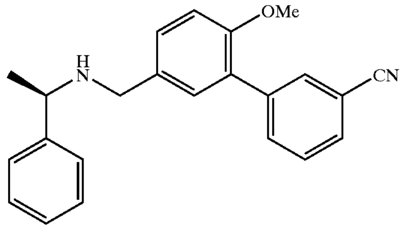

MW 342.44 Mass found: 343, 384.

EXAMPLE 127

2'-(methyloxy)-5'-((((1R)-1-(4-methylphenyl)ethyl)amino)methyl)-1,1'-biphenyl-3-carbonitrile

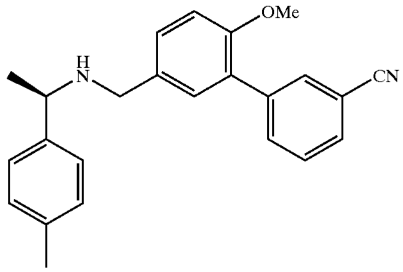

MW 356.467 Mass found: 357, 398.

EXAMPLE 128

2'-(methyloxy)-5'-((((1R)-1-(4-(methyloxy)phenyl)ethyl)amino)methyl)-1,1'-biphenyl-3-carbonitrile

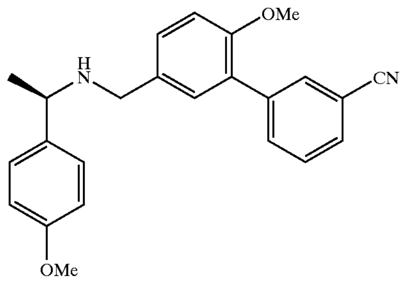

MW 372.466 Mass found: 373, 414.

EXAMPLE 129

2'-(methyloxy)-5'-((((1R)-1-(3-(methyloxy)phenyl)ethyl)amino)methyl)-1,1'-biphenyl-3-carbonitrile

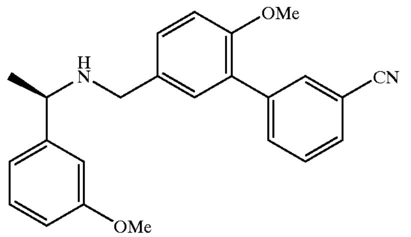

MW 372.466 Mass found: 373, 414.

EXAMPLE 130

(1R)-N-((4-(methyloxy)-3-(2-pyrimidinyl)phenyl)methyl)-1-(1-naphthalenyl)ethanamine

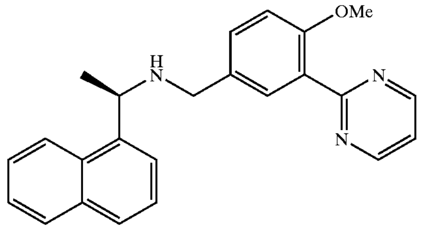

MW 369.466 Mass found: 370, 739.

EXAMPLE 131

(1R)-N-((4-(methyloxy)-3-(2-pyrimidinyl)phenyl)methyl)-1-phenylethanamine

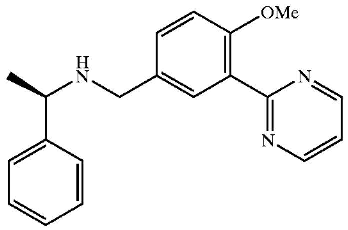

MW 319.406 Mass found: 320.

EXAMPLE 132

(1R)-N-((4-(methyloxy)-3-(2-pyrimidinyl)phenyl)methyl)-1-(4-methylphenyl)ethanamine

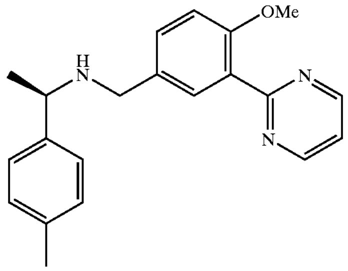

MW 333.433 Mass found: 334, 667.

EXAMPLE 133

(1R)-1-(4-(methyloxy)phenyl)-N-((4-(methyloxy)-3-(2-pyrimidinyl)phenyl)methyl)ethanamine

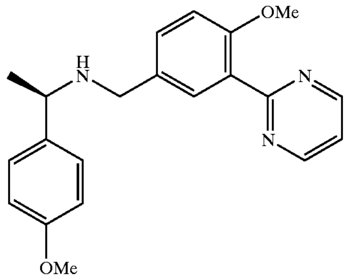

MW 349.432 Mass found: 350, 699.

EXAMPLE 134

(1R)-1-(3-(methyloxy)phenyl)-N-((4-(methyloxy)-3-(2-pyrimidinyl)phenyl)methyl)ethanamine

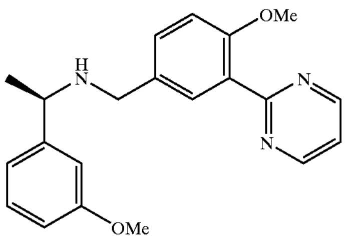

MW 349.432 Mass found: 350, 699.

EXAMPLE 135

(1R)-N-((3'-(methyloxy)-1,1'-biphenyl-3-yl)methyl)-1-phenylethanamine

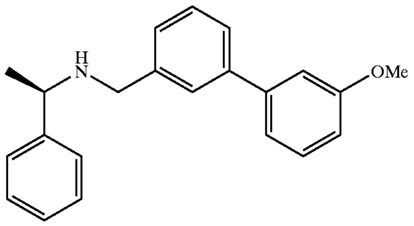

MW 317.43 Mass found: 318, 197, 214.

EXAMPLE 136

(1R)-N-((3'-(methyloxy)-1,1'-biphenyl-3-yl)methyl)-1-(4-methylphenyl)ethanamine

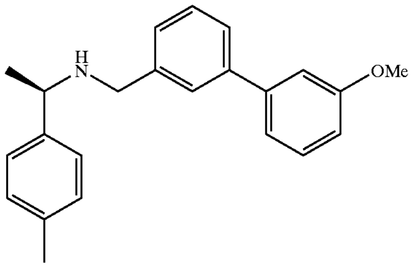

MW 331.457 Mass found: 332, 214.

EXAMPLE 137

(1R)-N-((3'-(methyloxy)-1,1'-biphenyl-3-yl)methyl)-1-(4-(methyloxy)phenyl)ethanamine

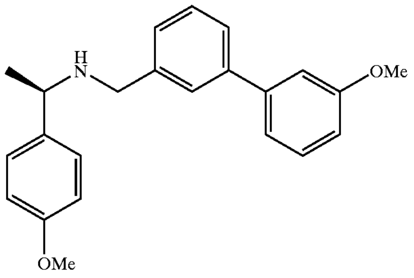

MW 347.456 Mass found: 348, 214.

EXAMPLE 138

(1R)-N-((3'-(methyloxy)-1,1'-biphenyl-3-yl)methyl)-1-(3-(methyloxy)phenyl)ethanamine

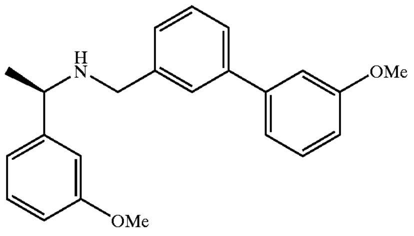

MW 347.456 Mass found: 348, 214, 255.

EXAMPLE 139

(1R)-N-((2'-methyl-1,1'-biphenyl-3-yl)methyl)-1-(4-methylphenyl)ethanamine

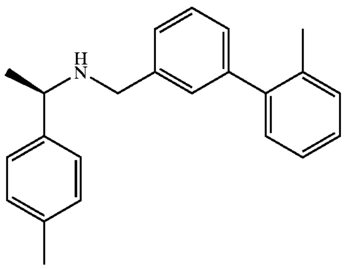

MW 315.457 Mass found: 181, 316, 198.

EXAMPLE 140

(1R)-N-((2'-methyl-1,1'-biphenyl-3-yl)methyl)-1-(4-(methyloxy)phenyl)ethanamine

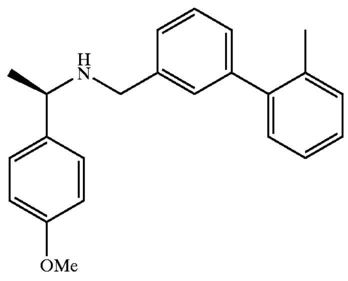

MW 331.457 Mass found: 332, 181, 198.

EXAMPLE 141

(1R)-N-((2'-methyl-1,1'-biphenyl-3-yl)methyl)-1-(3-(methyloxy)phenyl)ethanamine

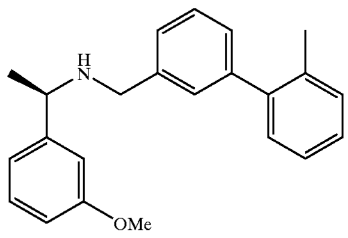

MW 331.457 Mass found: 332, 198, 181.

EXAMPLE 142

(1R)-N-((2'-fluoro-1,1'-biphenyl-3-yl)methyl)-1-phenylethanamine

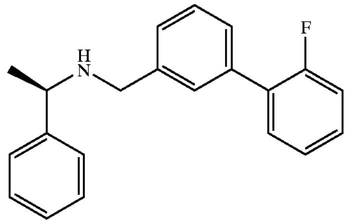

MW 305.394 Mass found: 202, 306, 243.

EXAMPLE 143

(1R)-N-((2'-fluoro-1,1'-biphenyl-3-yl)methyl)-1-(4-methylphenyl)ethanamine

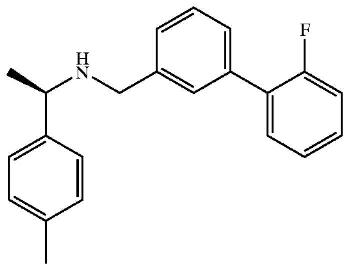

MW 319.421 Mass found: 202, 320, 243.

EXAMPLE 144

(1R)-N-((2'-fluoro-1,1'-biphenyl-3-yl)methyl)-1-(4-(methyloxy)phenyl)ethanamine

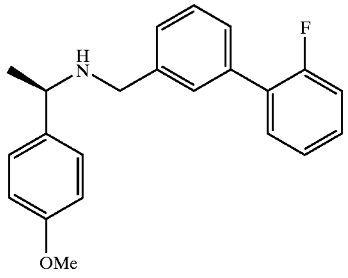

MW 335.42 Mass found: 336, 202, 243.

EXAMPLE 145

(1R)-N-((2'-fluoro-1,1'-biphenyl-3-yl)methyl)-1-(3-(methyloxy)phenyl)ethanamine

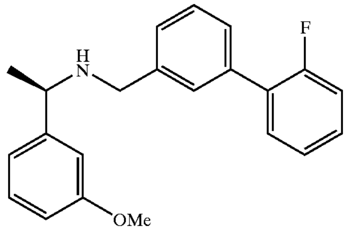

MW 335.42 Mass found: 202, 336, 243.

EXAMPLE 146

5-(2-(methyloxy)-5-((((1R)-1-(3-(methyloxy)phenyl) ethyl)amino)methyl)phenyl)-2-furancarboxylic acid

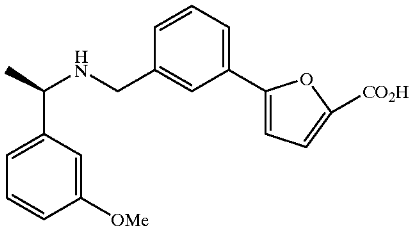

MW 381.426 Mass found: 382, 423.

EXAMPLE 147

5-(2-(methyloxy)-5-((((1R)-1-(4-methylphenyl) ethyl)amino)methyl)phenyl)-2-furancarboxylic acid

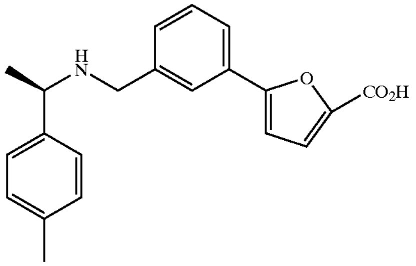

MW 365.427 Mass found: 366, 731.

EXAMPLE 148

5-(2-(methyloxy)-5-((((1R)-1-(4-(methyloxy)phenyl) ethyl)amino)methyl)phenyl)-2-furancarboxylic acid

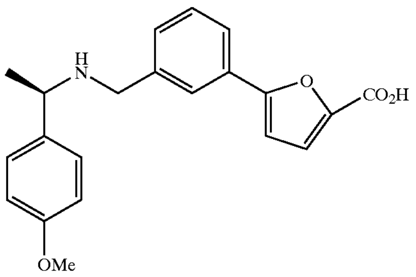

MW 381.426 Mass found: 352, 393.

EXAMPLE 149

4-oxo-4-((5-(3-((((1R)-1-phenylethyl)amino)methyl) phenyl)-2-pyridinyl)amino)butanoic acid

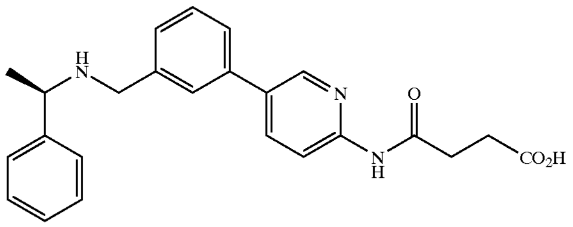

MW 403.479 Mass found: 404, 300.

EXAMPLE 150

4-((5-(3-((((1R)-1-(1-naphthalenyl)ethyl)amino) methyl)phenyl)-2-pyridinyl)amino)-4-oxobutanoic acid

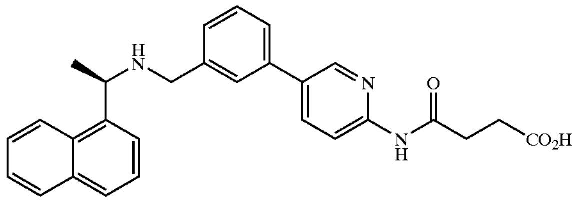

MW 453.539 Mass found: 454, 300.

EXAMPLE 151

4-((5-(3-((((1R)-1-(4-methylphenyl)ethyl)amino) methyl)phenyl)-2pyridinyl)amino)-4-oxobutanoic acid

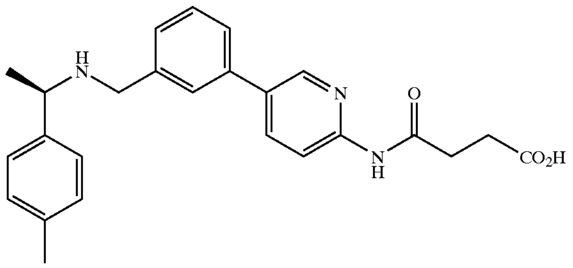

MW 417.506 Mass found: 418, 300.

EXAMPLE 152

4-((5-(3-((((1R)-1-(4-(methyloxy)phenyl)ethyl)amino)methyl)phenyl)-2pyridinyl)amino)-4-oxobutanoic acid

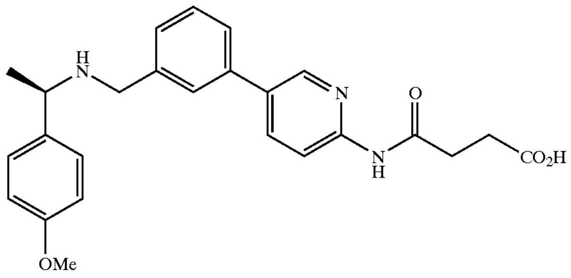

MW 433.505 Mass found: 434, 300.

EXAMPLE 153

(1R)-N-((3-(6-(methyloxy)-3-pyridazinyl)phenyl)methyl)-1-(1-naphthalenyl)ethanamine

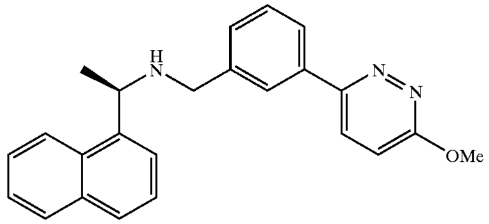

MW 369.466 Mass found: 370, 739.

EXAMPLE 154

(1R)-N-((3-(1H-indol-5-yl)-4-(methyloxy)phenyl)methyl)-1-(4-(methyloxy)phenyl)ethanamine

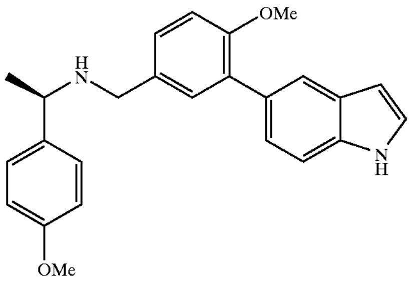

MW 386.492 Mass found: 387, 773.

EXAMPLE 155

(1R)-N-((3-(1H-indol-5-yl)-4-(methyloxy)phenyl)methyl)-1-(3-(methyloxy)phenyl)ethanamine

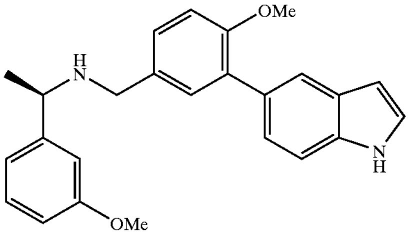

MW 386.492 Mass found: 387, 773.

EXAMPLE 156

(1R)-N-((3-(1H-indol-5-yl)-4-(methyloxy)phenyl)methyl)-1-(2-naphthalenyl)ethanamine

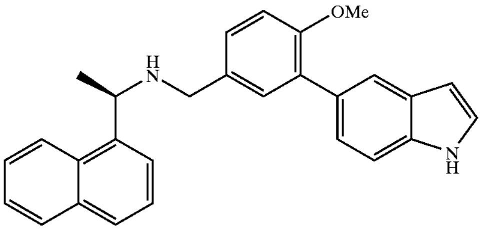

MW 406.526 Mass found: 371, 407, 326.

EXAMPLE 157

(1R)-N-((3-(6-(methyloxy)-3-pyridazinyl)phenyl)methyl)-1-phenylethanamine

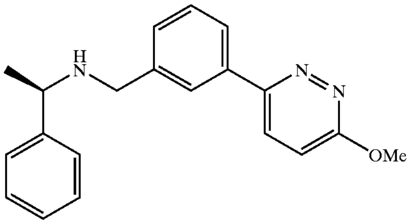

MW 319.406 Mass found: 320, 639.

EXAMPLE 158

(1R)-1-(4-(methyloxy)phenyl)-N-((3-(6-(methyloxy)-3-pyridazinyl)phenyl)methyl) ethanamine

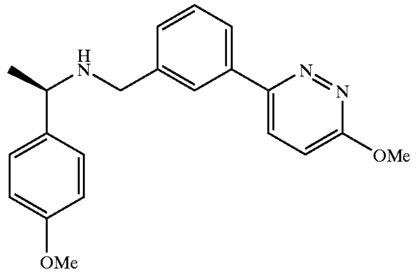

MW 349.432 Mass found: 350, 699.

EXAMPLE 159

(1R)-1-(3-(methyloxy)phenyl)-N-((3-(6-(methyloxy)-3-pyridazinyl)phenyl)methyl) ethanamine

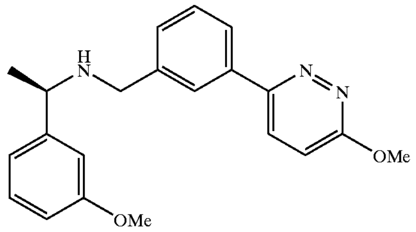

MW 349.432 Mass found: 350, 699.

EXAMPLE 160

(1R)-N-((4'-(methyloxy)-1,1'-biphenyl-3-yl)methyl)-1-(2-naphthalenyl)ethanamine

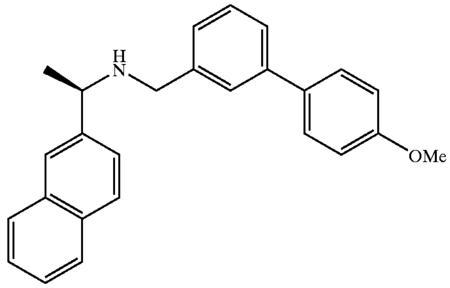

MW 367.49 Mass found: 368.

EXAMPLE 161

(1R)-N-((4'-(methyloxy)-1,1'-biphenyl-3-yl)methyl)-1-(1-naphthalenyl)ethanamine

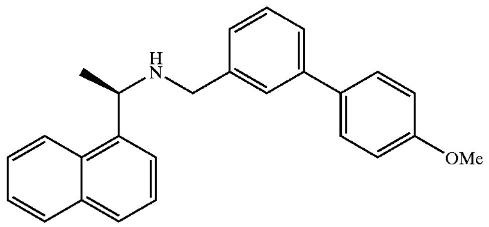

MW 367.49 Mass found: 368, 735.

EXAMPLE 162

(1R)-N-((4'-(methyloxy)-1,1'-biphenyl-3-yl)methyl)-1-(4-(methyloxy)phenyl)ethanamine

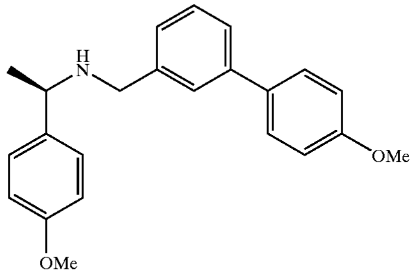

MW 347.456 Mass found: 348, 695.

EXAMPLE 163

(1R)-N-((4'-(methyloxy)-1,1'-biphenyl-3-yl)methyl)-1-(3-(methyloxy)phenyl)ethanamine

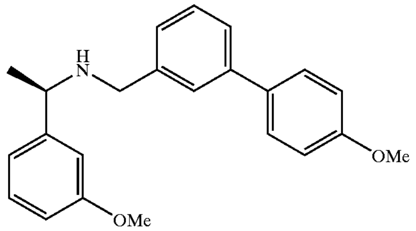

MW 347.456 Mass found: 348, 695.

EXAMPLE 164

(1R)-1-phenyl-N-((3-(2-pyrazinyl)phenyl)methyl)ethanamine

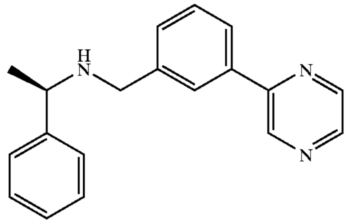

MW 289.38 Mass found: 290, 579, 693.

EXAMPLE 165

(1R)-1-(4-methylphenyl)-N-((3-(2-pyrazinyl)phenyl)methyl)ethanamine

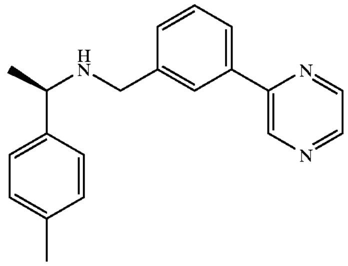

MW 303.407 Mass found: 304, 607, 721.

EXAMPLE 166

(1R)-1-(4-(methyloxy)phenyl)-N-((3-(2-pyrazinyl)phenyl)methyl)ethanamine

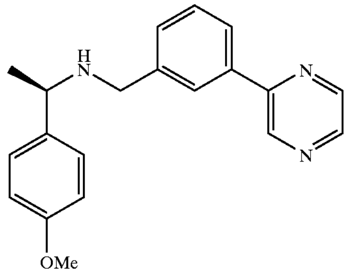

MW 319.406 Mass found: 320, 639, 753.

EXAMPLE 167

(1R)-1-(3-(methyloxy)phenyl)-N-((3-(2-pyrazinyl)phenyl)methyl)ethanamine

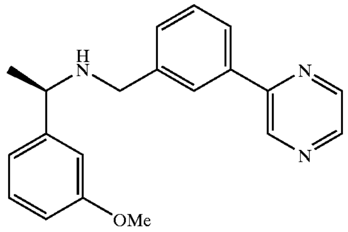

MW 319.406 Mass found: 320, 639, 753.

EXAMPLE 168

(1R)-1-(2-naphthalenyl)-N-((3-(2-pyridinyl)phenyl)methyl)ethanamine

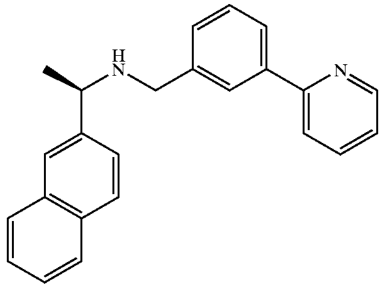

MW 338.452 Mass found: 339, 677.

EXAMPLE 169

(1R)-1-phenyl-N-((3-(2-pyridinyl)phenyl)methyl)ethanamine

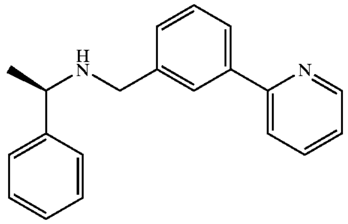

MW 288.392 Mass found: 289, 577.

EXAMPLE 170

(1R)-1-(1-naphthalenyl)-N-((3-(2-pyridinyl)phenyl)methyl)ethanamine

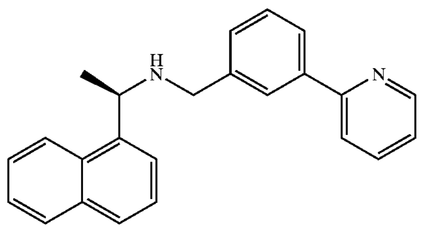

MW 338.452 Mass found: 339, 677.

EXAMPLE 171

(1R)-1-(4-methylphenyl)-N-((3-(2-pyridinyl)phenyl)methyl)ethanamine

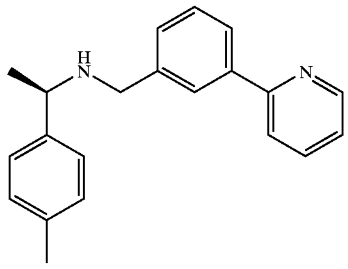

MW 302.419 Mass found: 303, 605.

EXAMPLE 172

(1R)-1-(4-(methyloxy)phenyl)-N-((3-(2-pyridinyl)phenyl)methyl)ethanamine

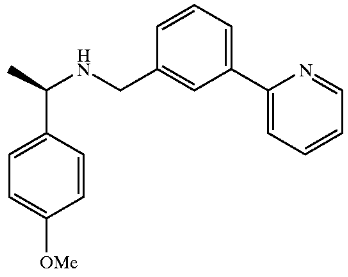

MW 318.418 Mass found: 319, 637.

EXAMPLE 173

(1R)-1-(3-(methyloxy)phenyl)-N-((3-(2-pyridinyl)phenyl)methyl)ethanamine

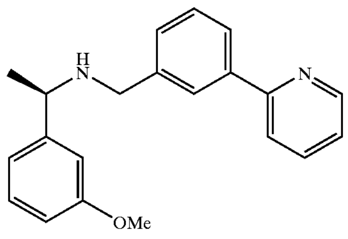

MW 318.418 Mass found: 319, 637.

EXAMPLE 174

(1R)-N-((3-(6-methyl-3-pyridinyl)phenyl)methyl)-1-(2-naphthalenyl)ethanamine

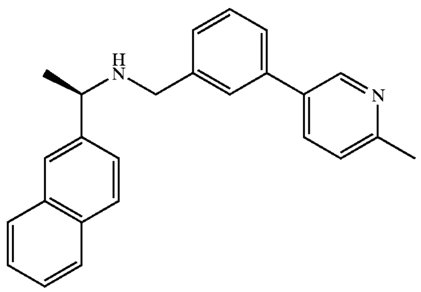

MW 352.479 Mass found: 353, 705.

EXAMPLE 175

(1R)-N-((3-(6-methyl-3-pyridinyl)phenyl)methyl)-1-(1-naphthalenyl)ethanamine

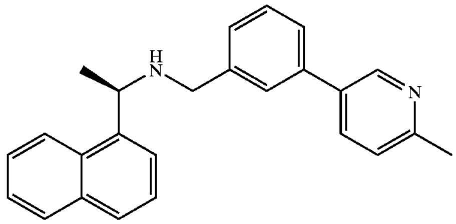

MW 352.479 Mass found: 353, 705.

EXAMPLE 176

(1R)-N-((3-(6-methyl-3-pyridinyl)phenyl)methyl)-1-phenylethanamine

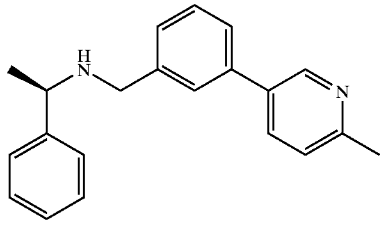

MW 302.419 Mass found: 303, 719.

EXAMPLE 177

(1R)-1-(4-methylphenyl)-N-((3-(6-methyl-3-pyridinyl)phenyl)methyl)ethanamine

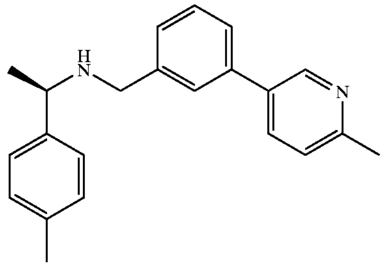

MW 316.446 Mass found: 317, 747.

EXAMPLE 178

(1R)-1-(4-(methyloxy)phenyl)-N-((3-(6-methyl-3-yridinyl)phenyl)methyl)ethanamine

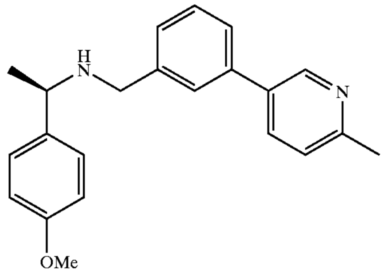

MW 332.445 Mass found: 333, 779, 665.

EXAMPLE 179

(1R)-1-(3-(methyloxy)phenyl)-N-((3-(6-methyl-3-yridinyl)phenyl)methyl)ethanamine

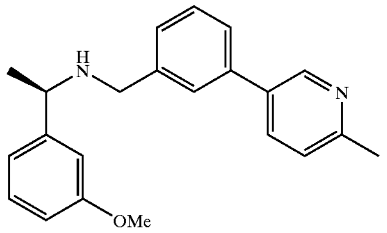

MW 332.445 Mass found: 333, 779, 665.

EXAMPLE 180

(1R)-N-((4-(methyloxy)-3-(3-thienyl)phenyl)methyl)-1-(2-naphthalenyl)ethanamine

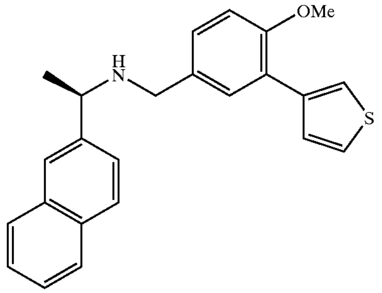

MW 373.518 Mass found: 374, 747.

EXAMPLE 181

(1R)-N-((4-(methyloxy)-3-(3-thienyl)phenyl)methyl)-1-phenylethanamine

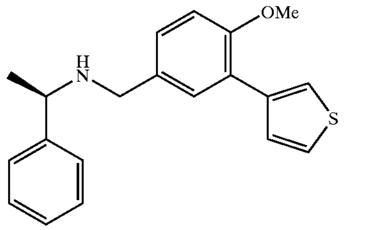

MW 323.458 Mass found: 324, 647, 761.

EXAMPLE 182

(1R)-N-((4-(methyloxy)-3-(3-thienyl)phenyl) methyl)-1-(1-naphthalenyl)ethanamine

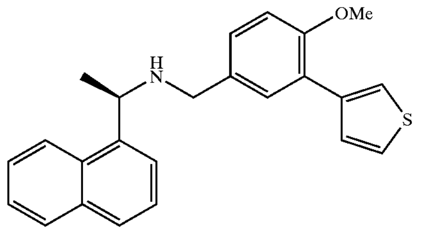

MW 373.518 Mass found: 374, 747.

EXAMPLE 183

(1R)-N-((4-(methyloxy)-3-(3-thienyl)phenyl) methyl)-1-(4-methylphenyl)ethanamine

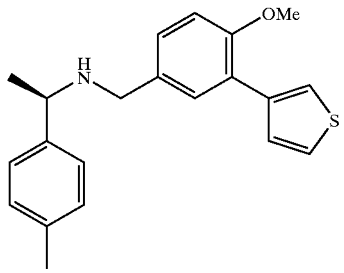

MW 337.485 Mass found: 338, 675.

EXAMPLE 184

(1R)-1-(4-(methyloxy)phenyl)-N-((4-(methyloxy)-3-(3-thienyl)phenyl)methyl)ethanamine

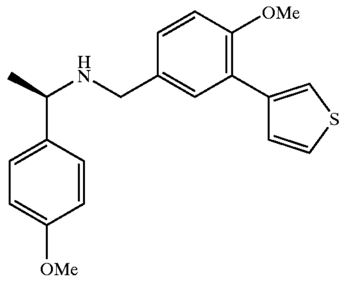

MW 353.484 Mass found: 354, 707.

EXAMPLE 185

(1R)-1-(3-(methyloxy)phenyl)-N-((4-(methyloxy)-3-(3-thienyl)phenyl)methyl)ethanamine

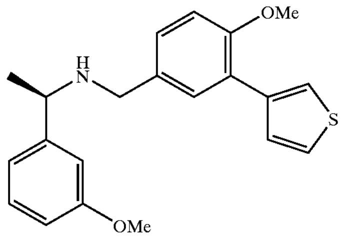

MW 353.484 Mass found: 354, 707.

EXAMPLE 186

(1R)-N-((4-(methyloxy)-3-(5-pyrimidinyl)phenyl) methyl)-1-phenylethanamine

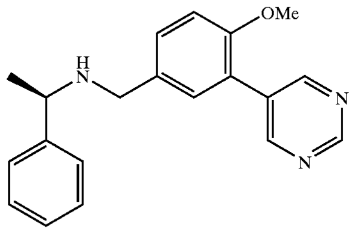

MW 319.406 Mass found: 320, 361, 753.

EXAMPLE 187

(1R)-N-((4-(methyloxy)-3-(5-pyrimidinyl)phenyl) methyl)-1-(4-methylphenyl)ethanamine

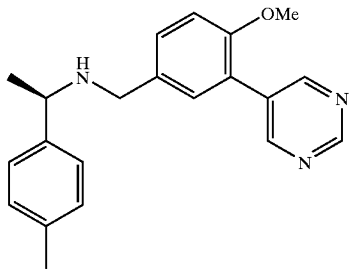

MW 333.433 Mass found: 334, 781.

EXAMPLE 188

(1R)-1-(4-(methyloxy)phenyl)-N-((4-(methyloxy)-3-(5-pyrimidinyl)phenyl)methyl)ethanamine

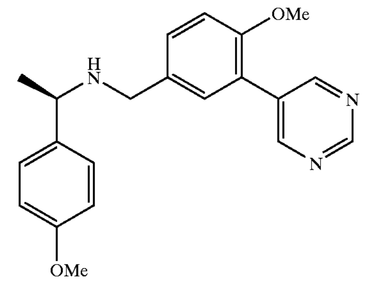

MW 349.432 Mass found: 350, 699.

EXAMPLE 189

(1R)-1-(3-(methyloxy)phenyl)-N-((4-(methyloxy)-3-(5-pyrimidinyl)phenyl)methyl)ethanamine

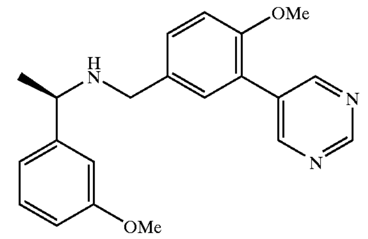

MW 349.432 Mass found: 350, 699.

EXAMPLE 190

N-(3'-((((1R)-1-(2-naphthalenyl)ethyl)amino)methyl)-1,1'-biphenyl-3-yl)acetamide

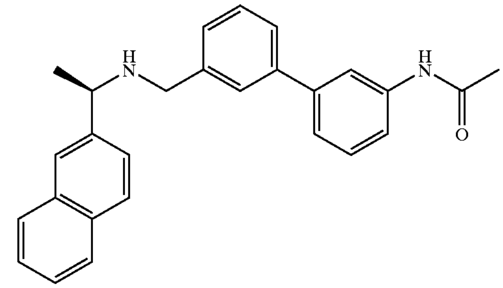

MW 394.515 Mass found: 395, 789.

EXAMPLE 191

(1R)-N-((4'-fluoro-1,1'-biphenyl-3-yl)methyl)-1-phenylethanamine

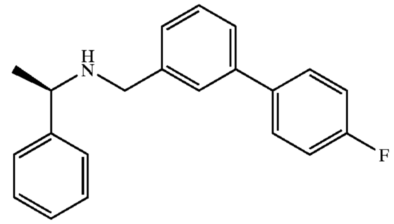

MW 305.394 Mass found: 306, 202, 243.

EXAMPLE 192

N-(3'-((((1R)-1-phenylethyl)amino)methyl)-1,1'-biphenyl-3-yl)acetamide

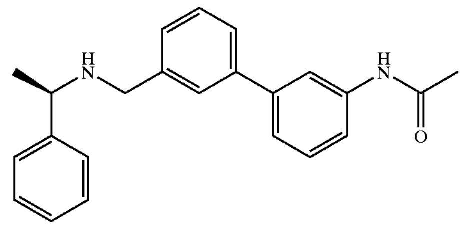

MW 344.456 Mass found: 345, 689.

EXAMPLE 193

N-(3'-((((1R)-1-(1-naphthalenyl)ethyl)amino)methyl)-1,1'-biphenyl-3-yl)acetamide

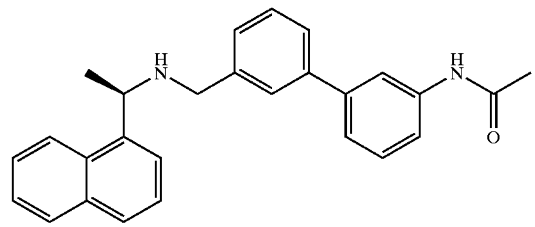

MW 394.515 Mass found: 395, 789.

EXAMPLE 194

N-(3'-((((1R)-1-(4-methylphenyl)ethyl)amino) methyl)-1,1'-biphenyl-3-yl)acetamide

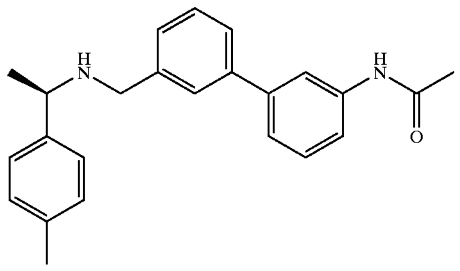

MW 358.482 Mass found: 359, 717.

EXAMPLE 195

N-(3'-((((1R)-1-(4-(methyloxy)phenyl)ethyl)amino) methyl)-1,1'-biphenyl-3-yl)acetamide

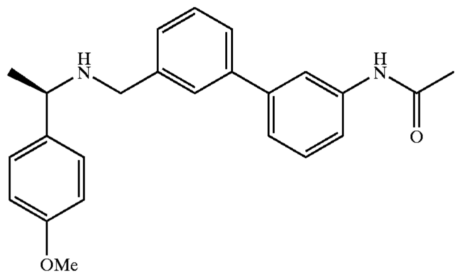

MW 374.481 Mass found: 375, 749.

EXAMPLE 196

N-(3'-((((1R)-1-(3-(methyloxy)phenyl)ethyl)amino) methyl)-1,1'-biphenyl-3-yl)acetamide

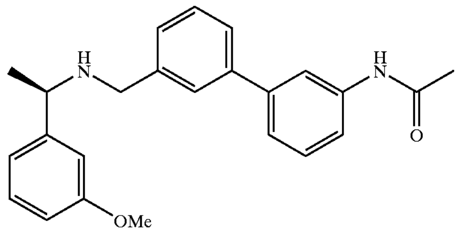

MW 374.481 Mass found: 375, 749, 416.

EXAMPLE 197

(1R)-N-((4'-fluoro-1,1'-biphenyl-3-yl)methyl)-1-(4-methylphenyl)ethanamine

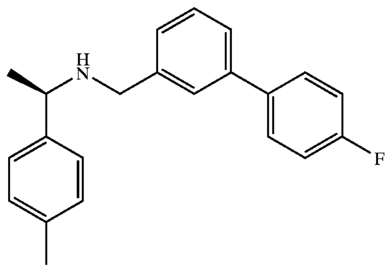

MW 319.421 Mass found: 320, 202, 243.

EXAMPLE 198

(1R)-1-phenyl-N-((3-(5-pyrimidinyl)phenyl)methyl) ethanamine

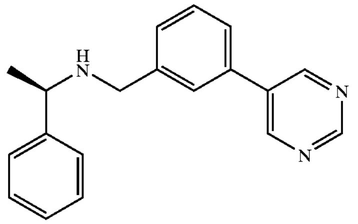

MW 289.38 Mass found: 290, 693, 331

EXAMPLE 199

(1R)-N-((4'-fluoro-1,1'-biphenyl-3-yl)methyl)-1-(3-(methyloxy)phenyl)ethanamine

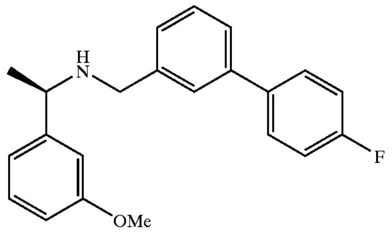

MW 335.42 Mass found: 336, 202, 243.

EXAMPLE 200

(1R)-1-(4-methylphenyl)-N-((3-(5-pyrimidinyl)phenyl)methyl)ethanamine

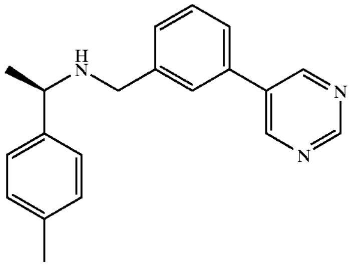

MW 303.407 Mass found: 304, 721, 345.

EXAMPLE 201

(1R)-1-(4-(methyloxy)phenyl)-N-((3-(5-pyrimidinyl)phenyl)methyl)ethanamine

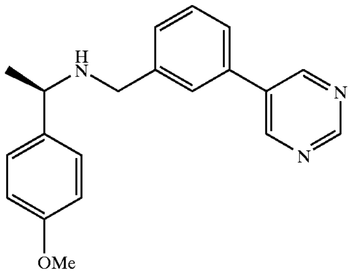

MW 319.406 Mass found: 320, 753.

EXAMPLE 202

(1R)-1-(3-(methyloxy)phenyl)-N-((3-(5-pyrimidinyl)phenyl)methyl)ethanamine

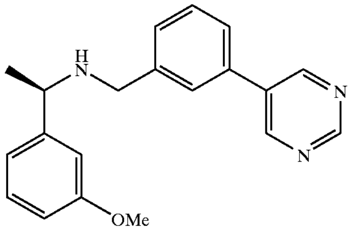

MW 319.406 Mass found: 320, 753, 361.

EXAMPLE 203

(1R)-N-((4-(methyloxy)-3-(1,3-thiazol-2-yl)phenyl)methyl)-1-(2-naphthalenyl)ethanamine

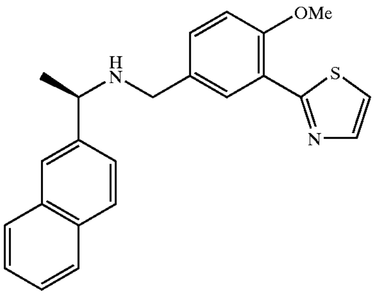

MW 374.506 Mass found: 375, 749.

EXAMPLE 204

(1R)-N-((4-(methyloxy)-3-(1,3-thiazol-2-yl)phenyl)methyl)-1-phenylethanamine

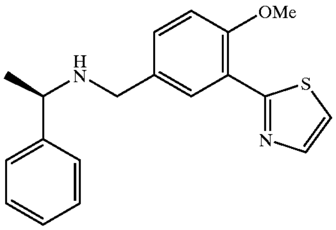

MW 324.446 Mass found: 325, 649.

EXAMPLE 205

(1R)-N-((4-(methyloxy)-3-(1,3-thiazol-2-yl)phenyl)methyl)-1-(1-naphthalenyl)ethanamine

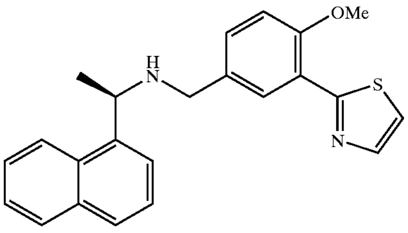

MW 374.506 Mass found: 375, 749.

EXAMPLE 206

(1R)-N-((4-(methyloxy)-3-(1,3-thiazol-2-yl)phenyl)methyl)-1-(4-methylphenyl)ethanamine

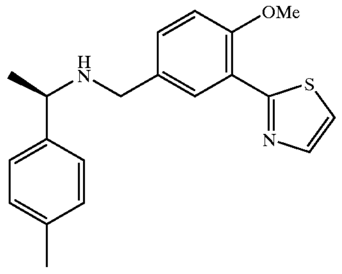

MW 338.473 Mass found: 339, 677.

EXAMPLE 207

(1R)-1-(4-(methyloxy)phenyl)-N-((4-(methyloxy)-3-(1,3-thiazol-2-yl)phenyl)methyl)ethanamine

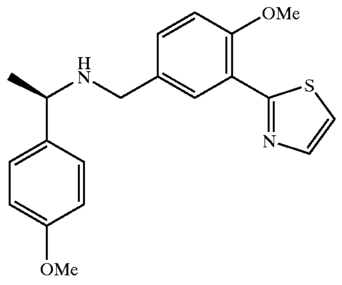

MW 354.472 Mass found: 355, 709.

EXAMPLE 208

(1R)-1-(3-(methyloxy)phenyl)-N-((4-(methyloxy)-3-(1,3-thiazol-2-yl)phenyl)methyl)ethanamine

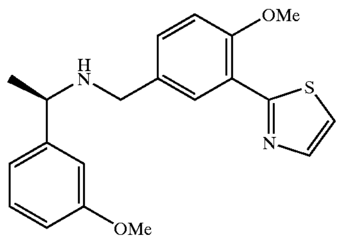

MW 354.472 Mass found: 355, 709.

EXAMPLE 209

(1R)-N-((3',4'-dimethyl-1,1'-biphenyl-3-yl)methyl)-1-(4-methylphenyl)ethanamine

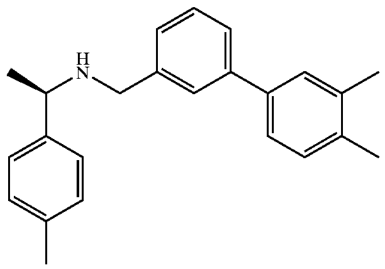

MW 329.484 Mass found: 330, 195, 212.

EXAMPLE 210

(1R)-N-((6-(methyloxy)-1,1'-biphenyl-3-yl)methyl)-1-(4-methylphenyl)ethanamine

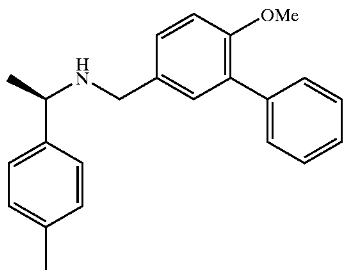

MW 331.457 Mass found: 197, 332.

EXAMPLE 211

(1R)-N-((6-(methyloxy)-1,1'-biphenyl-3-yl)methyl)-1-(4-(methyloxy)phenyl)ethanamine

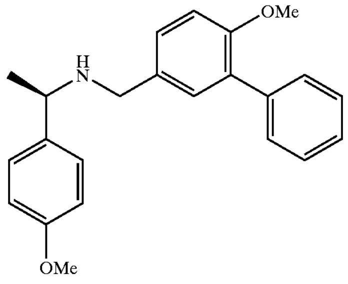

MW 347.456 Mass found: 197, 348.

EXAMPLE 212

(1R)-N-((6-(methyloxy)-1,1'-biphenyl-3-yl)methyl)-1-(3-(methyloxy)phenyl)ethanamine

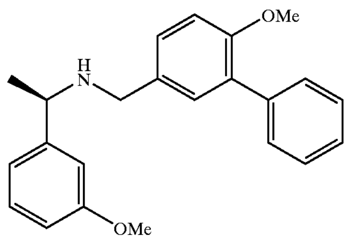

MW 347.456 Mass found: 197, 348.

EXAMPLE 213

(1R)-1-phenyl-N-((4-(1-pyrrolidinyl)phenyl)methyl) ethanamine

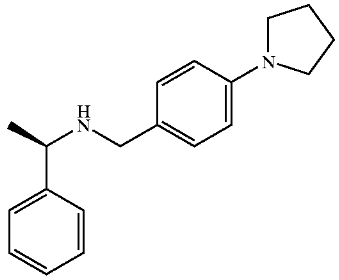

MW 280.413 Mass found: 160, 561, 281.

EXAMPLE 214

(1R)-N-((4-(3,5-dimethyl-4-isoxazolyl)phenyl) methyl)-1-(1-naphthalenyl)ethanamine

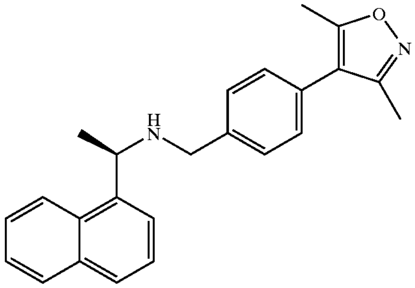

MW 356.467 Mass found: 155, 357, 203.

EXAMPLE 215

(1R)-N-((4'-fluoro-6-(methyloxy)-1,1'-biphenyl-3-yl) methyl)-1-(4-methylphenyl)ethanamine

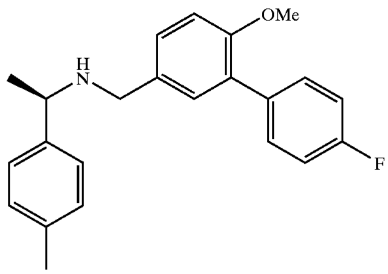

MW 349.447 Mass found: 350.

EXAMPLE 216

(1R)-N-((4'-fluoro-6-(methyloxy)-1,1'-biphenyl-3-yl) methyl)-1-(4(methyloxy)phenyl)ethanamine

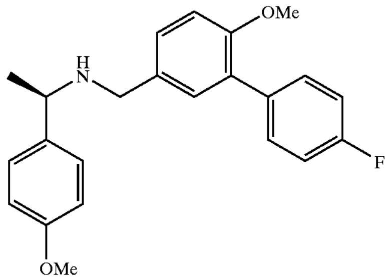

MW 365.446 Mass found: 366.

EXAMPLE 217

(1R)-1-(1-naphthalenyl)-N-((3-(1,3-thiazol-2-yl) phenyl)methyl)ethanamine

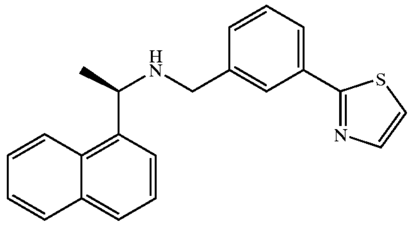

MW 344.48 Mass found: 345, 689.

EXAMPLE 218

(1R)-1-phenyl-N-((3-(1,3-thiazol-2-yl)phenyl)methyl)ethanamine

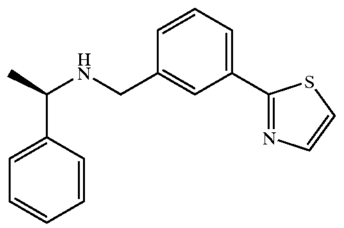

MW 294.42 Mass found: 295, 589.

EXAMPLE 219

(1R)-1-(4-methylphenyl)-N-((3-(1,3-thiazol-2-yl)phenyl)methyl)ethanamine

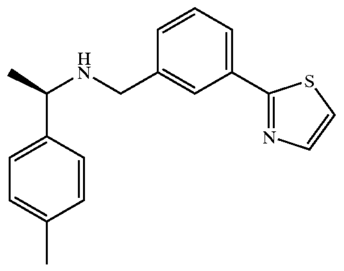

MW 303.407 Mass found: 304, 607.

EXAMPLE 220

(1R)-1-(4-(methyloxy)phenyl)-N-((3-(1,3-thiazol-2-yl)phenyl)methyl)ethanamine

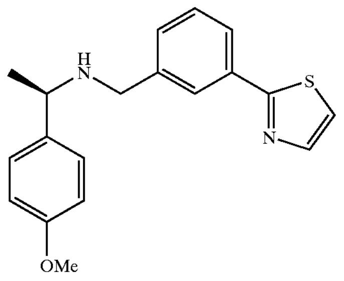

MW 324.446 Mass found: 325, 649.

EXAMPLE 221

5-(2-(methyloxy)-5-((((1R)-1-(4-methylphenyl)ethyl)amino)methyl)phenyl)-3-pyridinecarboxamide

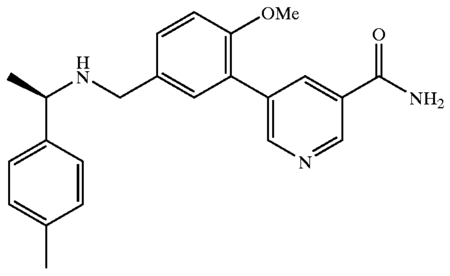

MW 375.47 Mass found: 376, 417, 751, 865.

EXAMPLE 222

(1R)-N-((3-(3-furanyl)phenyl)methyl)-1-(3-(methyloxy)phenyl)ethanamine

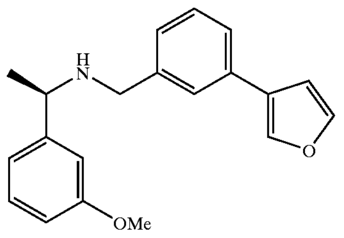

MW 307.391 Mass found: 308, 615.

EXAMPLE 223

(1R)-N-((3-(3-furanyl)phenyl)methyl)-1-(4-(methyloxy)phenyl)ethanamine

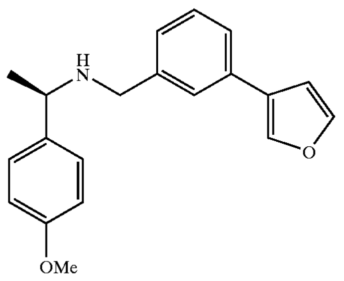

MW 307.391 Mass found: 308, 615.

EXAMPLE 224

(1R)-N-((3-(3-furanyl)phenyl)methyl)-1-(4-methylphenyl)ethanamine

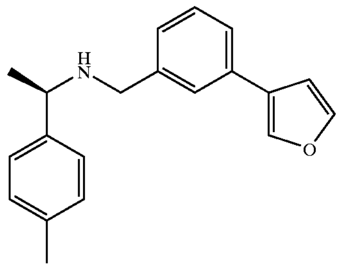

MW 291.392 Mass found: 292, 583.

EXAMPLE 225

(1R)-N-((3-(3-furanyl)phenyl)methyl)-1-(1-naphthalenyl)ethanamine

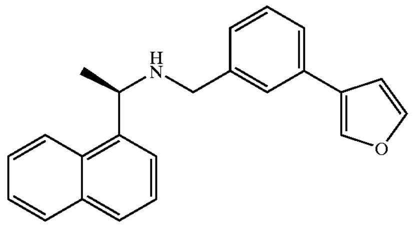

MW 327.425 Mass found: 328, 655.

EXAMPLE 226

(1R)-N-((3-(3-furanyl)phenyl)methyl)-1-phenylethanamine

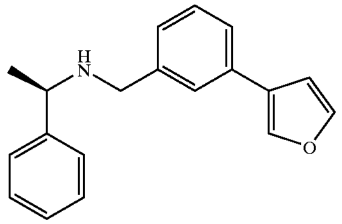

MW 277.365 Mass found: 278, 555.

EXAMPLE 227

5-(2-(methyloxy)-5-((((1R)-1-(1-naphthalenyl)ethyl)amino)methyl)phenyl)-3pyridinecarboxamide

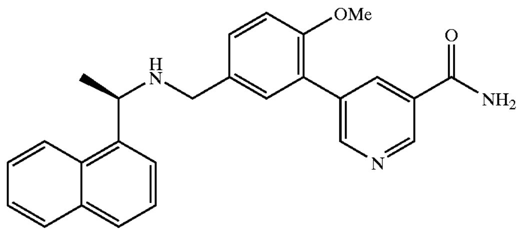

MW 411.503 Mass found: 412, 823.

EXAMPLE 228

(1R)-N-((4-(methyloxy)-3-(6-(methyloxy)-3-pyridazinyl)phenyl)methyl)-1-(3-(methyloxy)phenyl)ethanamine

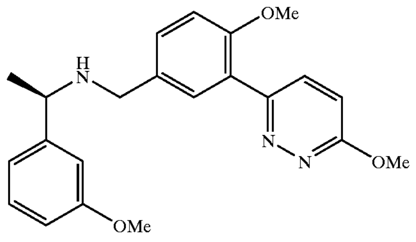

MW 379.457 Mass found: 380, 759.

EXAMPLE 229

(1R)-N-((4-(methyloxy)-3-(6-(methyloxy)-3-pyridazinyl)phenyl)methyl)-1-(4-(methyloxy)phenyl)ethanamine

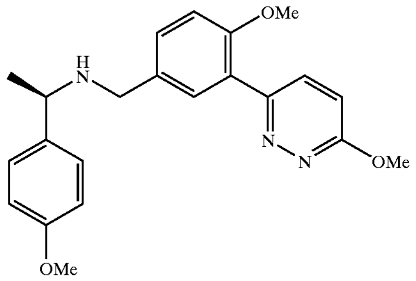

MW 379.457 Mass found: 380, 759.

EXAMPLE 230

(1R)-N-((4-(methyloxy)-3-(6-(methyloxy)-3-pyridazinyl)phenyl)methyl)-1-(4-methylphenyl)ethanamine

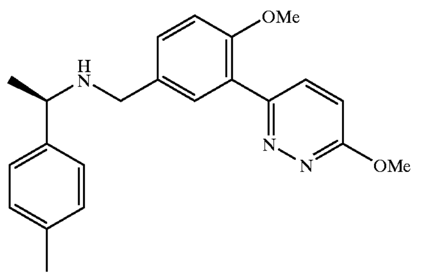

MW 363.458 Mass found: 364, 727.

EXAMPLE 231

(1R)-N-((4-(methyloxy)-3-(6-(methyloxy)-3-pyridazinyl)phenyl)methyl)-1-phenylethanamine

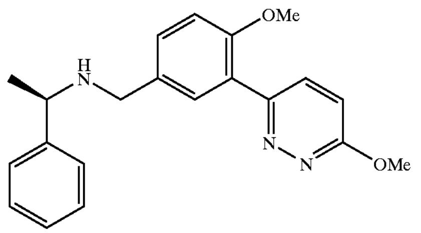

MW 349.432 Mass found: 350, 699.

EXAMPLE 232

(1R)-N-((4-(methyloxy)-3-(6-(methyloxy)-3-pyridazinyl)phenyl)methyl)-1-(2-naphthalenyl)ethanamine

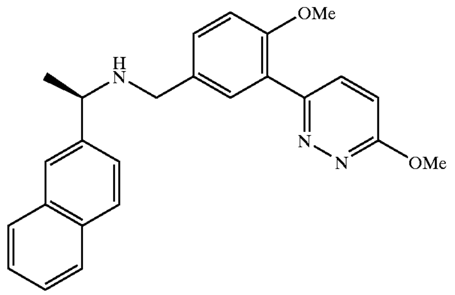

MW 399.491 Mass found: 400, 799.

EXAMPLE 233

5-(2-(methyloxy)-5-((((1R)-1-phenylethyl)amino)methyl)phenyl)-3-pyridinecarboxamide

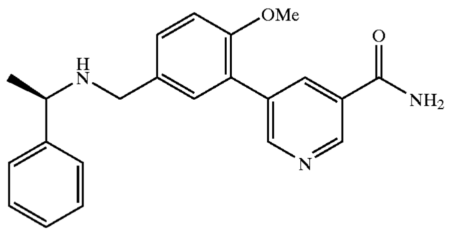

MW 361.443 Mass found: 362, 403, 723, 837.

EXAMPLE 234

(1R)-1-(3-(methyloxy)phenyl)-N-((4-(methyloxy)-3-(2-pyrazinyl)phenyl)methyl)ethanamine

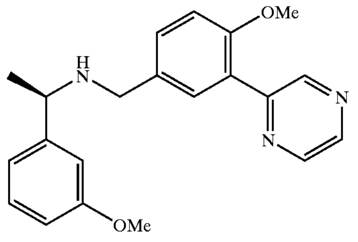

MW 349.432 Mass found: 350, 699.

EXAMPLE 235

(1R)-1-(4-(methyloxy)phenyl)-N-((4-(methyloxy)-3-(2-pyrazinyl)phenyl)methyl)ethanamine

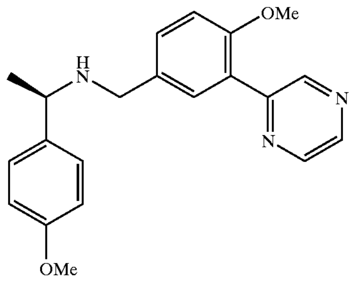

MW 349.432 Mass found: 350, 699.

EXAMPLE 236

(1R)-N-((4-(methyloxy)-3-(2-pyrazinyl)phenyl) methyl)-1-(4-methylphenyl)ethanamine

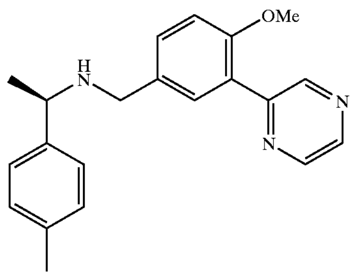

MW 333.433 Mass found: 334, 667.

EXAMPLE 237

(1R)-N-((4-(methyloxy)-3-(2-pyrazinyl)phenyl) methyl)-1-(1-naphthalenyl)ethanamine

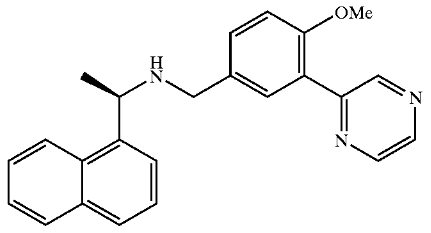

MW 369.466 Mass found: 370, 739.

EXAMPLE 238

(1R)-N-((4-(methyloxy)-3-(2-pyrazinyl)phenyl) methyl)-1-phenylethanamine

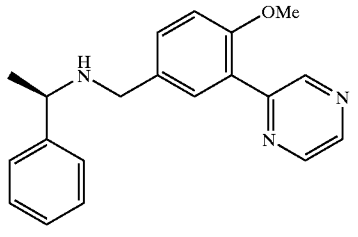

MW 319.406 Mass found: 320, 639.

EXAMPLE 239

5-(2-(methyloxy)-5-((((1R)-1-(2-naphthalenyl)ethyl) amino)methyl)phenyl)-3-pyridinecarboxamide

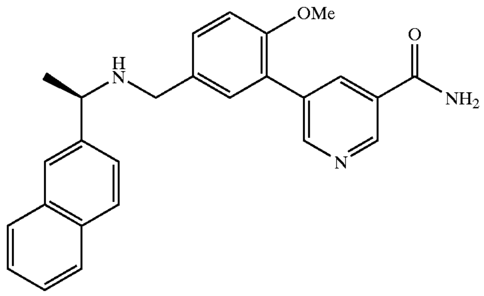

MW 411.503 Mass found: 412, 453, 823, 937.

EXAMPLE 240

(1R)-N-((4-(methyloxy)-3-(2-pyrazinyl)phenyl) methyl)-1-(2-naphthalenyl)ethanamine

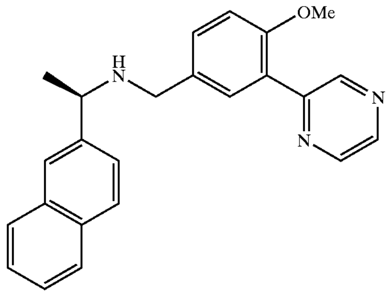

MW 369.466 Mass found: 370, 739.

EXAMPLE 241

(1R)-1-(4-methylphenyl)-N-((3-(9-methyl-9H-purin-6-yl)phenyl)methyl)ethanamine

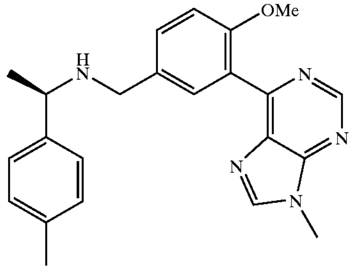

MW 357.459 Mass found: 358, 715.

EXAMPLE 242

(1R)-N-((6-(methyloxy)-4'-(methylsulfonyl)-1,1'-biphenyl-3-yl)methyl)-1-(3-(methyloxy)phenyl)ethanamine

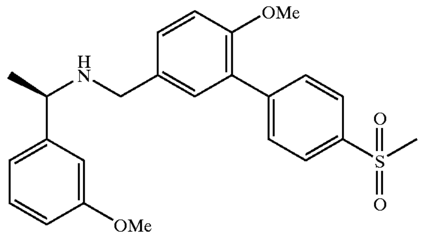

MW 425.546 Mass found: 426, 851.

EXAMPLE 243

(1R)-N-((6-(methyloxy)-4'-(methylsulfonyl)-1,1'-biphenyl-3-yl)methyl)-1-phenylethanamine

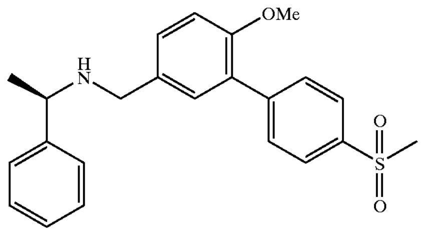

MW 395.521 Mass found: 396, 437.

EXAMPLE 244

(1R)-N-((4-(methyloxy)-3-(6-methyl-3-pyridinyl)phenyl)methyl)-1-(4-methylphenyl)ethanamine

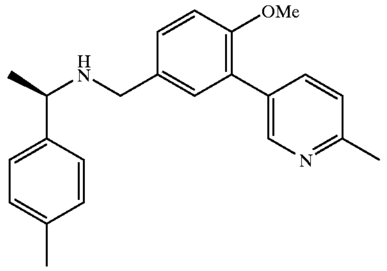

MW 346.471 Mass found: 347, 807, 693.

EXAMPLE 245

(1R)-N-((4-(methyloxy)-3-(6-methyl-3-pyridinyl)phenyl)methyl)-1-(2-naphthalenyl)ethanamine

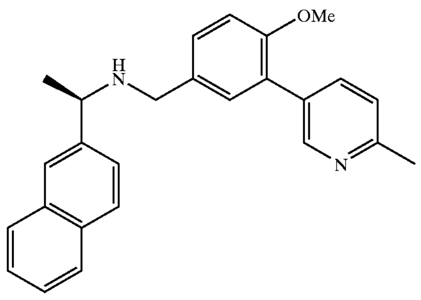

MW 382.504 Mass found: 383, 879, 765.

EXAMPLE 246

N-(5-(3-((((1R)-1-(3-(methyloxy)phenyl)ethyl)amino)methyl)phenyl)-2-pyridinyl)acetamide

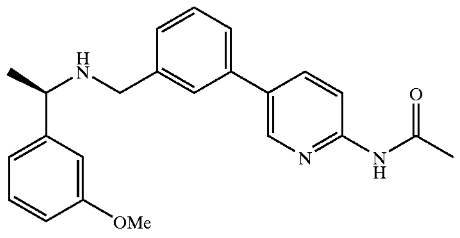

MW 375.47 Mass found: 242, 376.

EXAMPLE 247

N-(5-(3-((((1R)-1-(4-(methyloxy)phenyl)ethyl)amino)methyl)phenyl)-2-pyridinyl)acetamide

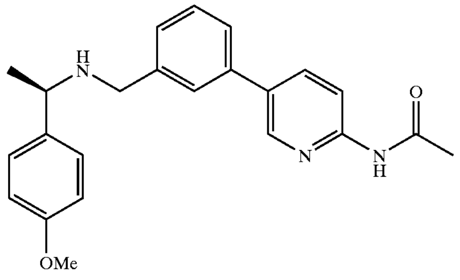

MW 375.47 Mass found: 375, 242, 751.

EXAMPLE 248

N-(5-(3-((((1R)-1-(4-methylphenyl)ethyl)amino)methyl)phenyl)-2-pyridinyl)acetamide

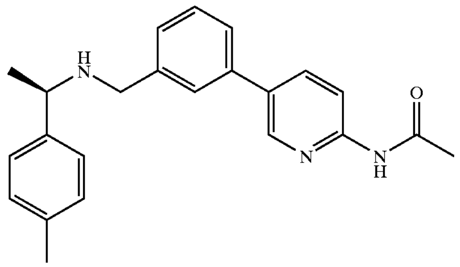

MW 359.47 Mass found: 242, 360.

EXAMPLE 249

N-(5-(3-((((1R)-1-(1-naphthalenyl)ethyl)amino)methyl)phenyl)-2-pyridinyl)acetamide

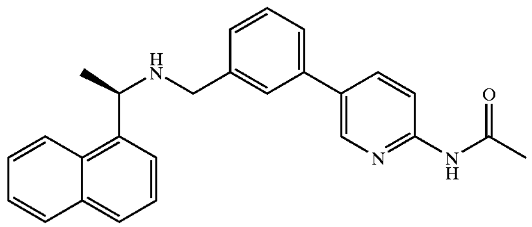

MW 395.504 Mass found: 155, 242, 396.

EXAMPLE 250

N-(5-(3-((((1R)-1-phenylethyl)amino)methyl)phenyl)-2-pyridinyl)acetamide

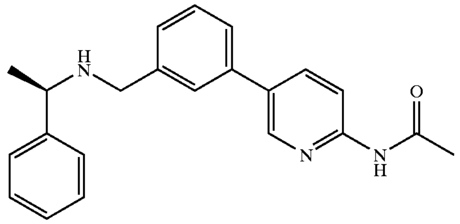

MW 345.444 Mass found: 242, 346.

EXAMPLE 251

(1R)-N-((4',6-difluoro-1,1'-biphenyl-3-yl)methyl)-1-phenylethanamine

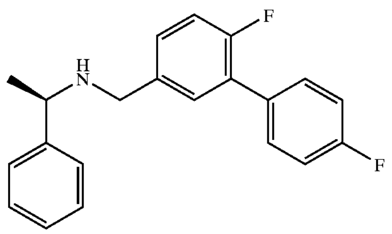

MW 323.384 Mass found: 324, 647, 761.

EXAMPLE 252

(1R)-N-((4',6-difluoro-1,1'-biphenyl-3-yl)methyl)-1-(4-(methyloxy)phenyl)ethanamine

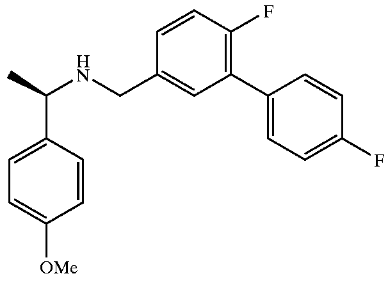

MW 353.41 Mass found: 354, 707, 821.

Examples 253–451 Were Prepared using Method C:

EXAMPLE 253

(1R)-N-((2',6-bis(methyloxy)-1,1'-biphenyl-3-yl)methyl)-1-phenylethanamine

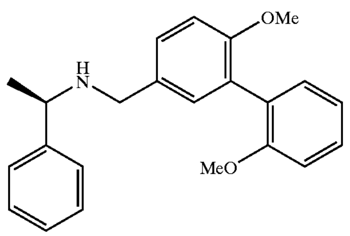

MW 347.456 Mass found: 227, 348.

EXAMPLE 254

(1R)-N-((3-(2-methyl-1,3-benzoxazol-5-yl)-4-(methyloxy)phenyl)methyl)-1-(3-(methyloxy)phenyl)ethanamine

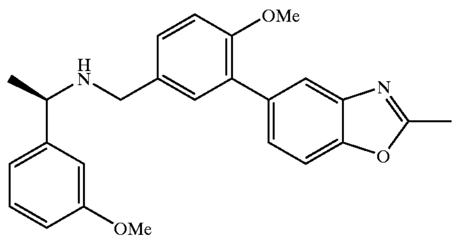

MW 402.491 Mass found: 403.

EXAMPLE 255

(1R)-N-((3-(2-methyl-1,3-benzoxazol-5-yl)-4-(methyloxy)phenyl)methyl)-1-(1-naphthalenyl)ethanamine

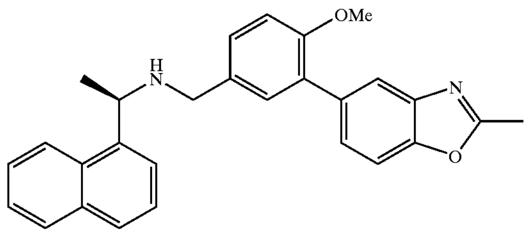

MW 422.525 Mass found: 423.

EXAMPLE 256

(1R)-N-((3-(2-methyl-1,3-benzoxazol-5-yl)-4-(methyloxy)phenyl)methyl)-1-phenylethanamine

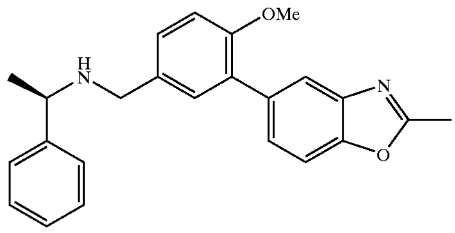

MW 372.466 Mass found: 373.

EXAMPLE 257

N-(4'-(methyloxy)-5-((((1R)-1-(1-naphthalenyl)ethyl)amino)methyl)-1,1'-biphenyl-2-yl)methanesulfonamide

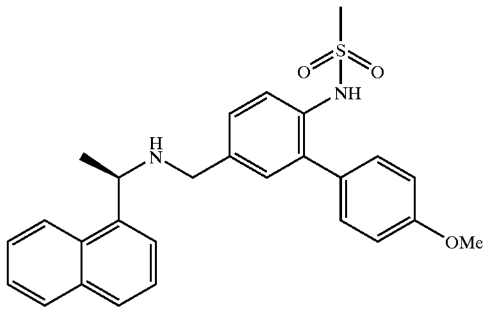

MW 460.595 Mass found: 155, 290, 461.

EXAMPLE 258

N-ethyl-N'-(4'-(methyloxy)-5-((((1R)-1-(1-naphthalenyl)ethyl)amino)methyl)-1,1'-biphenyl-2-yl)urea

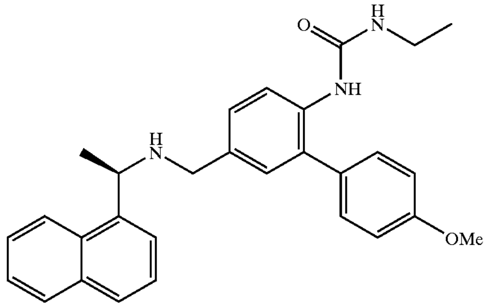

MW 453.583 Mass found: 283, 454.

EXAMPLE 259

N-(4'-(methyloxy)-5-((((1R)-1-phenylethyl)amino)methyl)-1,1'-biphenyl-2-yl)methanesulfonamide

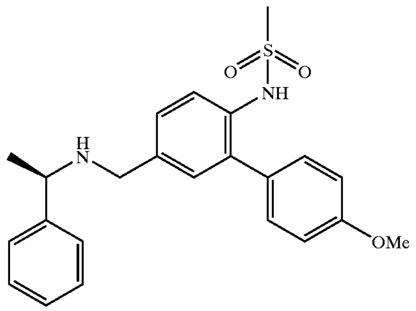

MW 410.535 Mass found: 411.

EXAMPLE 260

(1R)-N-((3-(1,3-benzoxazol-5-yl)-4-(methyloxy) phenyl)methyl)-1-(1-naphthalenyl)ethanamine

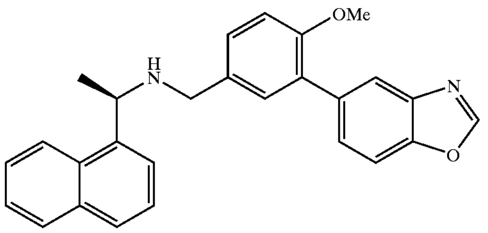

MW 408.499 Mass found: 409.

EXAMPLE 261

N-ethyl-N'-(4'-(methyloxy)-5-((((1R)-1-phenylethyl) amino)methyl)-1,1'-biphenyl-2-yl)urea

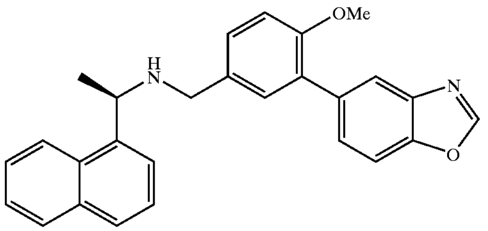

MW 403.523 Mass found: 404, 283.

EXAMPLE 262

(1R)-N-((4-(methyloxy)-3-(2-pyridinyl)phenyl) methyl)-1-(1-naphthalenyl)ethanamine

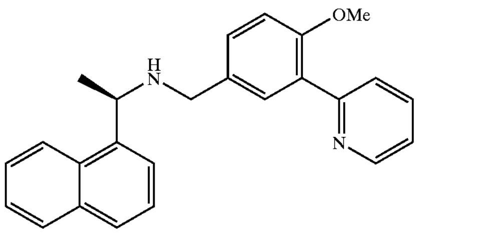

MW 368.478 Mass found: 369, 737.

EXAMPLE 263

N-ethyl-N'-(4'-(methyloxy)-5-((((1R)-1-(3-(methyloxy)phenyl)ethyl)amino)methyl)-1,1'-biphenyl-2-yl)urea

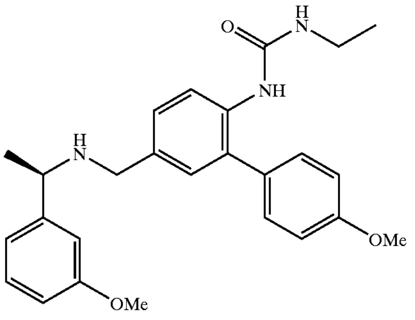

MW 433.549 Mass found: 434.

EXAMPLE 264

(1R)-N-((3-(1,3-benzoxazol-5-yl)-4-(methyloxy) phenyl)methyl)-1phenylethanamine

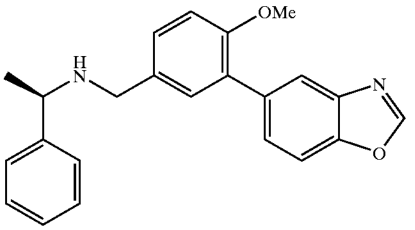

MW 358.439 Mass found: 359.

EXAMPLE 265

N-(4'-(methyloxy)-5-((((1R)-1-(3-(methyloxy) phenyl)ethyl)amino)methyl)-1,1'-biphenyl-2-yl) methanesulfonamide

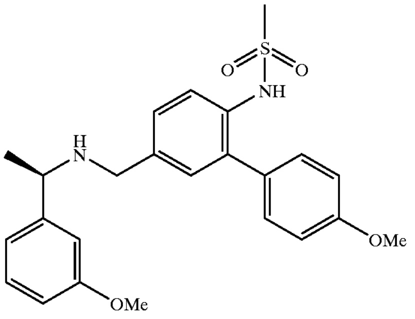

MW 440.561 Mass found: 290, 441.

EXAMPLE 266

(1R)-N-((3-(1,3-benzoxazol-5-yl)-4-(methyloxy)phenyl)methyl)-1-(3-(methyloxy)phenyl)ethanamine

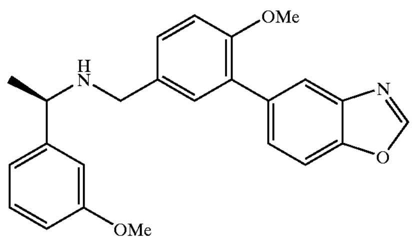

MW 388.465 Mass found: 389, 891.

EXAMPLE 267

(1R)-N-((4-(methyloxy)-3-(6-methyl-3-pyridinyl)phenyl)methyl)-1-(1-naphthalenyl)ethanamine

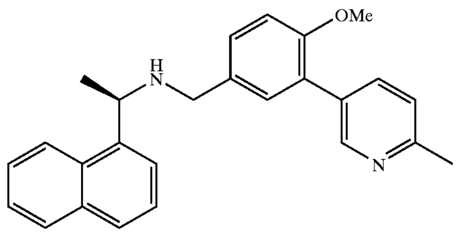

MW 382.504 Mass found: 383, 229, 155.

EXAMPLE 268

(1R)-1-(3-(methyloxy)phenyl)-N-((4-(methyloxy)-3-(2-thienyl)phenyl)methyl)ethanamine

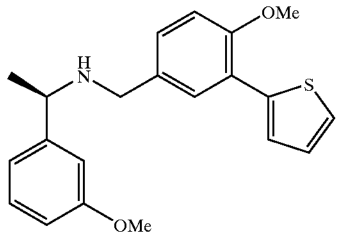

MW 353.484 Mass found: 354.

EXAMPLE 269

(1R)-N-((4-(methyloxy)-3-(2-thienyl)phenyl)methyl)-1-(1-naphthalenyl)ethanamine

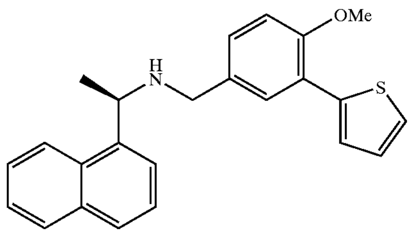

MW 373.518 Mass found: 374.

EXAMPLE 270

(1R)-N-((4-(methyloxy)-3-(2-thienyl)phenyl)methyl)-1-phenylethanamine

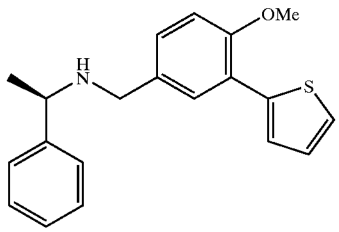

MW 323.458 Mass found: 324, 203, 647.

EXAMPLE 271

(1R)-N-((4-(methyloxy)-3-(1-methyl-2-(trifluoromethyl)-1H-benzimidazol-5-yl)phenyl)methyl)-1-phenylethanamine

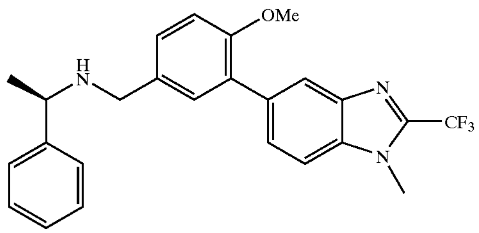

MW 439.479 Mass found: 440,481.

EXAMPLE 272

(1R)-N-((4-(methyloxy)-3-(1-methyl-2-(trifluoromethyl)-1H-benzimidazol-5-yl)phenyl)methyl)-1-(1-naphthalenyl)ethanamine

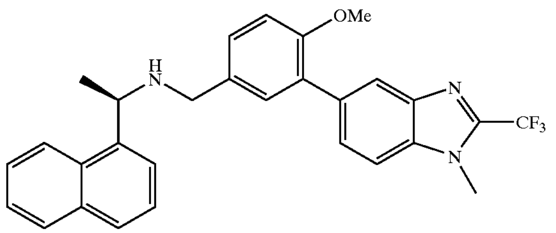

MW 489

Mass found: 490, 155.

EXAMPLE 273

(1R)-1-(3-(methyloxy)phenyl)-N-((6-(methyloxy)-4'-((trifluoromethyl)oxy)-1,1'-biphenyl-3-yl)methyl)ethanamine

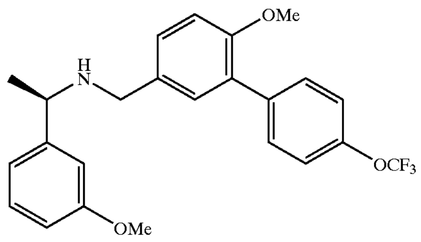

MW 431. 452 Mass found: 432.

EXAMPLE 274

(1R)-N-((4-(methyloxy)-3-(4-piperidinyl)phenyl)methyl)-1-(1-naphthalenyl)ethanamine

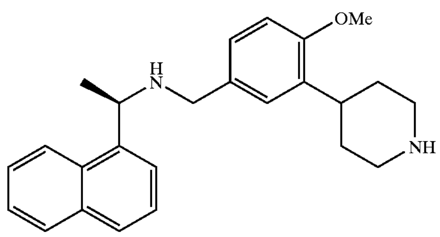

MW 374.525 Mass found: 375, 489, 155.

EXAMPLE 275

(1R)-N-((4-(methyloxy)-3-(4-piperidinyl)phenyl)methyl)-1-phenylethanamine

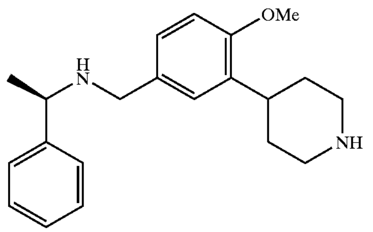

MW 324.465 Mass found: 325, 439.

EXAMPLE 276

2-(5-(2-(methyloxy)-5-((((1R)-1-(1-naphthalenyl)ethyl)amino)methyl)phenyl)-1H-indol-1-yl)acetamide

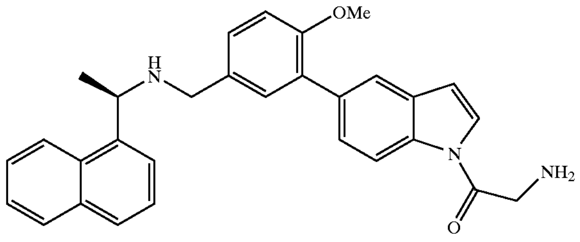

MW 463.578 Mass found: 464.

EXAMPLE 277

2-(5-(2-(methyloxy)-5-((((1R)-1-(3-(methyloxy)phenyl)ethyl)amino)methyl)phenyl)-1H-indol-1-yl)acetamide

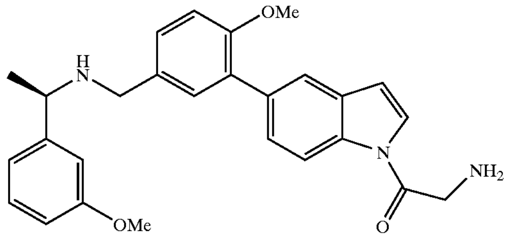

MW 443.544 Mass found: 444.

EXAMPLE 278

2-(5-(2-(methyloxy)-5-((((1R)-1-phenylethyl)amino) methyl)phenyl)-1H-indol-1-yl)acetamide

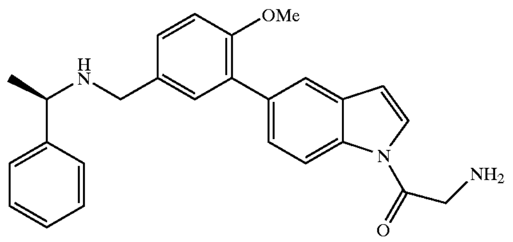

MW 413.518 Mass found: 414.

EXAMPLE 279

(1R)-N-((3-(1-(cyclopropylmethyl)-1H-indol-5-yl)-4-(methyloxy)phenyl)methyl)-1-(1-naphthalenyl) ethanamine

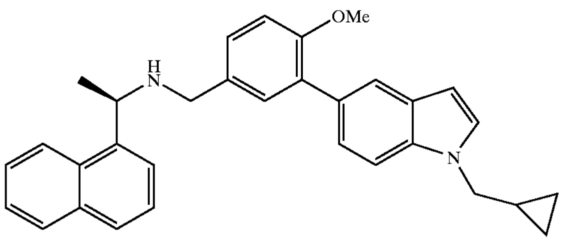

MW 460.618 Mass found: 491.

EXAMPLE 280

(1R)-N-((3-(1-(cyclopropylmethyl)-1H-indol-5-yl)-4-(methyloxy)phenyl)methyl)-1-(3-(methyloxy) phenyl)ethanamine

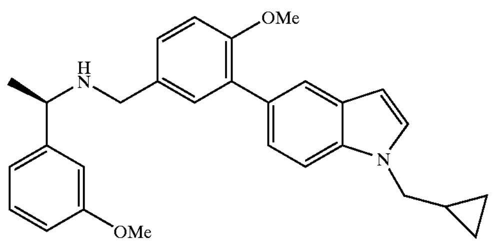

MW 440.584 Mass found: 441.

EXAMPLE 281

(1R)-N-((3-(1-(cyclopropylmethyl)-1H-indol-5-yl)-4-(methyloxy)phenyl)methyl)-1-phenylethanamine

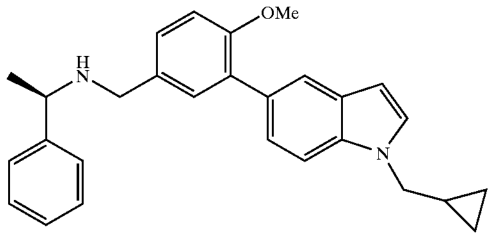

MW 410.558 Mass found: 411.

EXAMPLE 282

4-(2-(methyloxy)-5-((((1R)-1-phenylethyl)amino) methyl)phenyl)-1,3-thiazol-2-amine

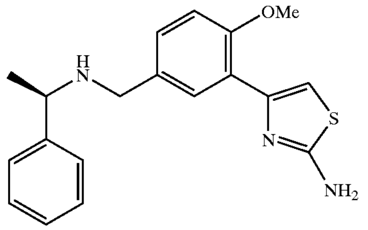

MW 339.461 Mass found: 340, 679.

EXAMPLE 283

(1R)-N-((3-(1-methyl-1H-imidazol-4-yl)-4-(methyloxy)phenyl)methyl)-1-(1-naphthalenyl) ethanamine

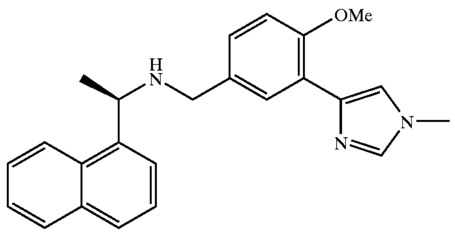

MW 371.482 Mass found: 372, 155, 743.

EXAMPLE 284

(1R)-N-((3-(1-methyl-1H-imidazol-4-yl)-4-(methyloxy)phenyl)methyl)-1-phenylethanamine

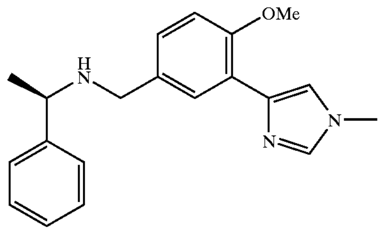

MW 321.422 Mass found: 322, 643.

EXAMPLE 285

N-((3-(6-((3-(diethylamino)propyl)oxy)-3-pyridinyl)-4-(methyloxy)phenyl)methyl)-N-((1R)-1-(3-(methyloxy)phenyl)ethyl)amine

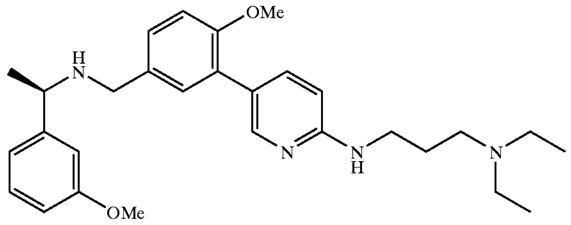

MW 477.645 Mass found: 478, 344.

EXAMPLE 286

N-((3-(6-((3-(diethylamino)propyl)oxy)-3-pyridinyl)-4-(methyloxy)phenyl)methyl)-N-((1R)-1-(1-naphthalenyl)ethyl)amine

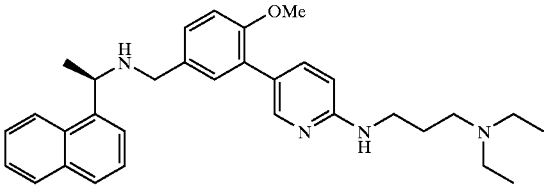

MW 497.679 Mass found: 498, 155, 344.

EXAMPLE 287

N-((3-(6-((3-(diethylamino)propyl)oxy)-3-pyridinyl)-4-(methyloxy)phenyl)methyl)-N-((1R)-1-phenylethyl)amine

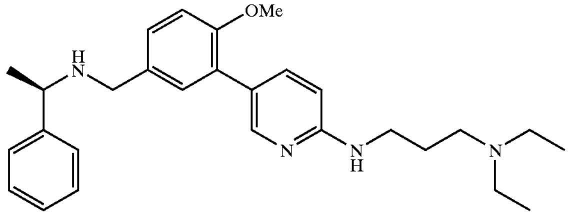

MW 447.619 Mass found: 448, 344.

EXAMPLE 288

(1R)-1-(3-(methyloxy)phenyl)-N-((4-(methyloxy)-3-(6-((2-(1-pyrrolidinyl)ethyl)oxy)-3-pyridinyl)phenyl)methyl)ethanamine

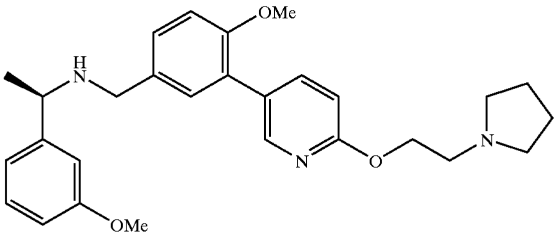

MW 461.603 Mass found: 462, 328.

EXAMPLE 289

(1R)-N-((4-(methyloxy)-3-(6-((2-(1-pyrrolidinyl)ethyl)oxy)-3-pyridinyl)phenyl)methyl)-1-(1-naphthalenyl)ethanamine

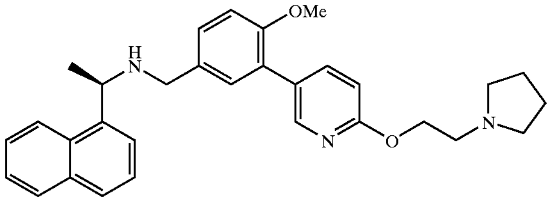

MW 481.637 Mass found: 155, 482, 328.

EXAMPLE 290

(1R)-N-((4-(methyloxy)-3-(1-pyrrolidinyl)phenyl) methyl)-1-(1-naphthalenyl)ethanamine

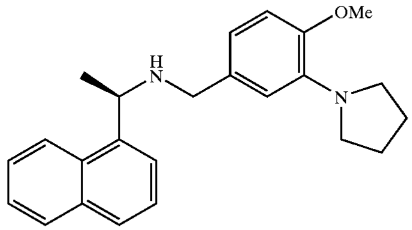

MW 360.498 Mass found: 361, 721.

EXAMPLE 291

(1R)-N-((4-(methyloxy)-3-(1-pyrrolidinyl)phenyl) methyl)-1-phenylethanamine

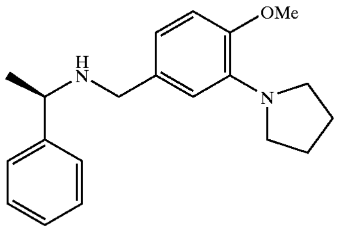

MW 310.438 Mass found: 311, 621.

EXAMPLE 292

(1R)-N-((4-(methyloxy)-3-(6-((2-(1-pyrrolidinyl) ethyl)oxy)-3-pyridinyl)phenyl)methyl)-1-phenylethanamine

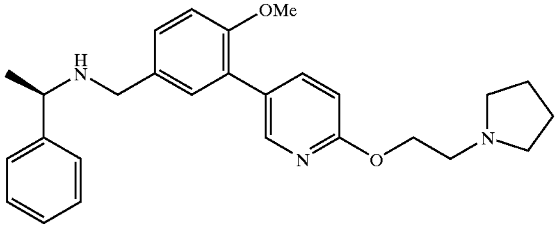

MW 431.577 Mass found: 432, 328.

EXAMPLE 293

(1R)-N-((3-(2-methyl-2H-indazol-5-yl)-4-(methyloxy)phenyl)methyl)-1-phenylethanamine

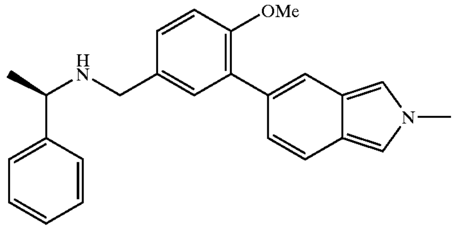

MW 371.482 Mass found: 372, 744, 858.

EXAMPLE 294

2'-(methyloxy)-5'-((((1R)-1-(3-(methyloxy)phenyl) ethyl)amino)methyl)-1,1'-biphenyl-4-carboxamide

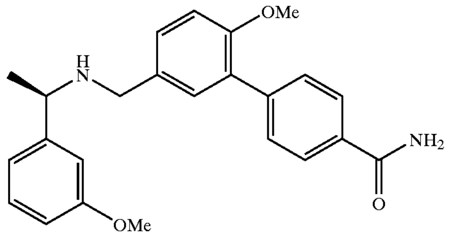

MW 390.48 Mass found: 240, 391, 781.

EXAMPLE 295

(1R)-N-((4-(methyloxy)-3-(1-methyl-4-piperidinyl) phenyl)methyl)-1-(3-(methyloxy)phenyl)ethanamine

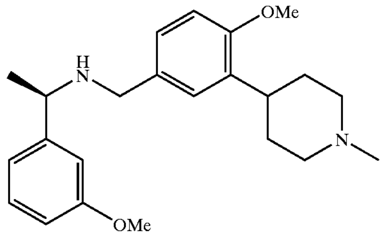

MW 368.518 Mass found: 369, 483.

EXAMPLE 296

(1R)-N-((4-(methyloxy)-3-(1-methyl-4-piperidinyl)phenyl)methyl)-1-phenylethanamine

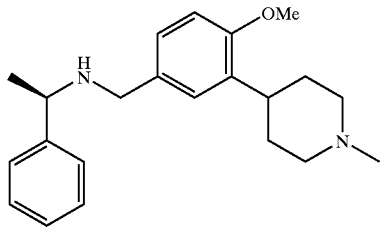

MW 338.492 Mass found: 339, 453.

EXAMPLE 297

2'-(methyloxy)-5'-((((1R)-1-(1-naphthalenyl)ethyl)amino)methyl)-1,1'-biphenyl-4-carboxamide

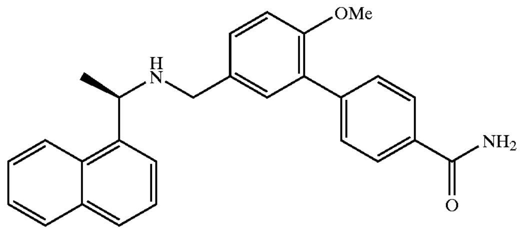

MW 410.514 Mass found: 155, 411, 240, 257.

EXAMPLE 298

(1R)-N-((4-(methyloxy)-3-(1-methyl-4-piperidinyl)phenyl)methyl)-1-(1-naphthalenyl)ethanamine

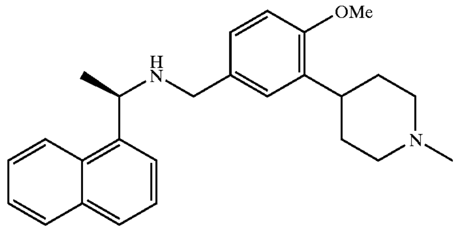

MW 388.552 Mass found: 389, 503.

EXAMPLE 299 ethyl 2'-(methyloxy)-5'-((((1R)-1-(3-(methyloxy)phenyl)ethyl)amino)methyl)-1,1'-biphenyl-4-carboxylate

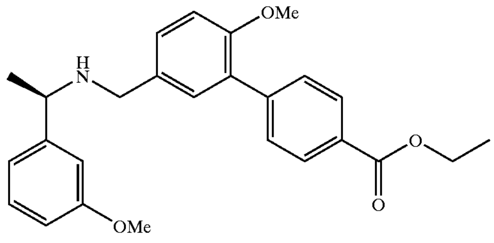

MW 419.518 Mass found: 953, 420.

EXAMPLE 300 ethyl 2'-(methyloxy)-5'-((((1R)-1-(1-naphthalenyl)ethyl)amino)methyl)-1,1'-biphenyl-4-carboxylate

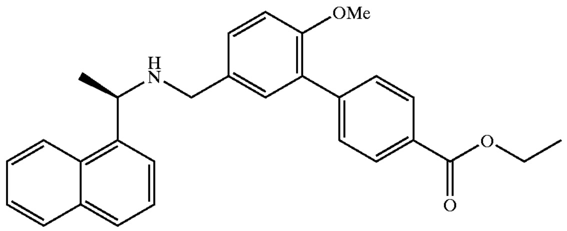

MW 439.552 Mass found: 440, 993.

EXAMPLE 301 ethyl 2'-(methyloxy)-5'-((((1R)-1-phenylethyl)amino)methyl)-1,1'-biphenyl-4-carboxylate

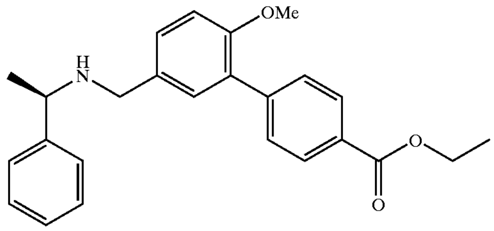

MW 389.492 Mass found: 390, 893.

EXAMPLE 302 ethyl 4-(2-(methyloxy)-5-((((1R)-1-(1-naphthalenyl) ethyl)amino)methyl)phenyl)-1-piperidinecarboxylate

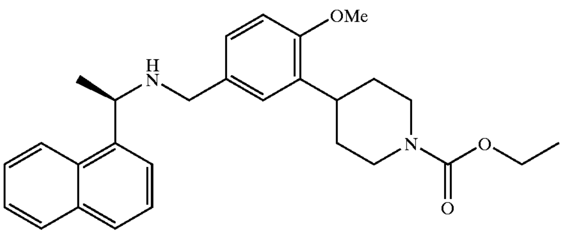

MW 446.588 Mass found: 447.

EXAMPLE 303 ethyl 4-(2-(methyloxy)-5-((((1R)-1-(3-(methyloxy) phenyl)ethyl)amino)methyl)phenyl)-1-piperidinecarboxylate

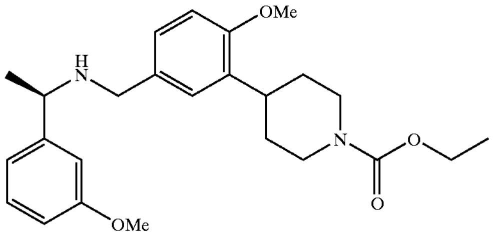

MW 426.554 Mass found: 427, 967.

EXAMPLE 304 ethyl 4-(2-(methyloxy)-5-((((1R)-1-phenylethyl) amino)methyl)phenyl)-1-piperidinecarboxylate

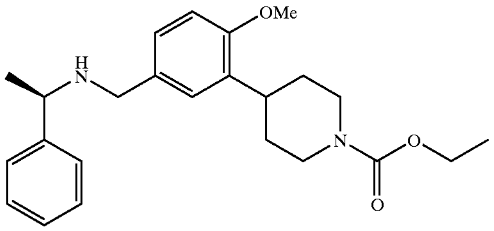

MW 396.528 Mass found: 397, 907.

EXAMPLE 305

(1R)-N-((3-(2-methyl-1,3-oxazol-4-yl)-4-(methyloxy)phenyl)methyl)-1-(3-(methyloxy) phenyl)ethanamine

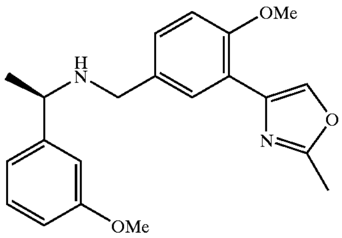

MW 352.432 Mass found: 353, 705.

EXAMPLE 306

(1R)-N-((3-(2-methyl-1,3-oxazol-4-yl)-4-(methyloxy)phenyl)methyl)-1-(1-naphthalenyl) ethanamine

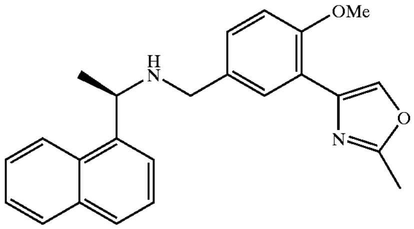

MW 372.466 Mass found: 373, 745.

EXAMPLE 307

(1R)-N-((3-(2-methyl-1,3-oxazol-4-yl)-4-(methyloxy)phenyl)methyl)-1-phenylethanamine

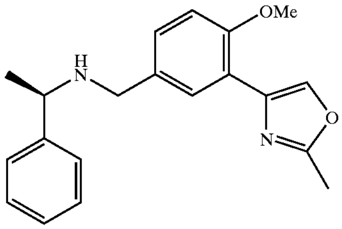

MW 322.406 Mass found: 323, 645.

EXAMPLE 308

2'-(methyloxy)-5'-((((1R)-1-phenylethyl)amino) methyl)-1,1'-biphenyl-4-carboxamide

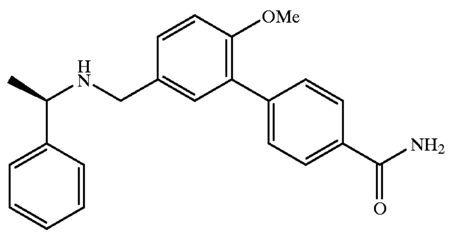

MW 360.455 Mass found: 835, 361.

EXAMPLE 309

5-(2-(methyloxy)-5-((((1R)-1-(1-naphthalenyl)ethyl) amino)methyl)phenyl)-1-(1-(2,2,2-trifluoroethyl)-2 (1H)-pyridinone

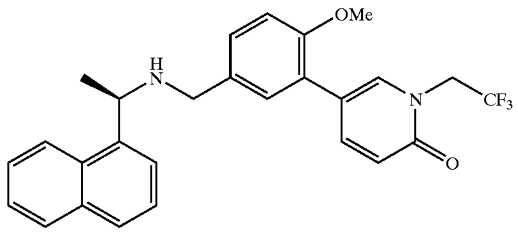

MW 466.5 Mass found: 155, 296, 467.

EXAMPLE 310

1-(2-(methyloxy)ethyl)-5-(2-(methyloxy)-5-((((1R)-1-(3-(methyloxy)phenyl)ethyl)amino)methyl) phenyl)-2(1H)-pyridinone

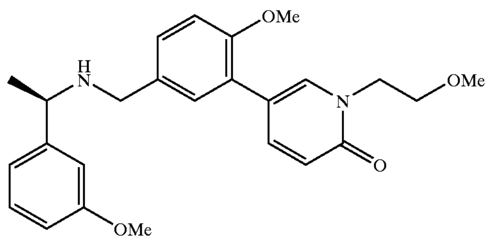

MW 422.522 Mass found: 272, 423, 290.

EXAMPLE 311

1-(2-(methyloxy)ethyl)-5-(2-(methyloxy)-5-((((1R)-1-phenylethyl)amino)methyl)phenyl)-2(1H)-pyridinone

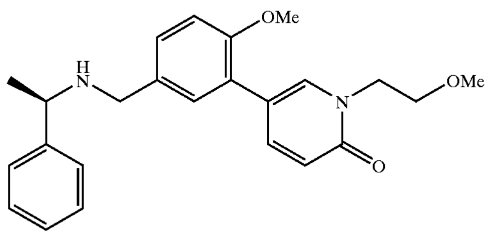

MW 392.496 Mass found: 272, 393.

EXAMPLE 312

1-(2-(methyloxy)ethyl)-5-(2-(methyloxy)-5-((((1R)-1-(1-naphthalenyl)ethyl)amino)methyl)phenyl)-2 (1H)-pyridinone

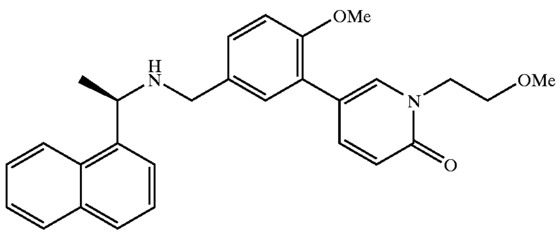

MW 442.556 Mass found: 289, 272, 443.

EXAMPLE 313

(1R)-N-((6-(methyloxy)-4'-(methylsulfonyl)-1,1'-biphenyl-3-yl)methyl)-1-(1-naphthalenyl)ethanamine

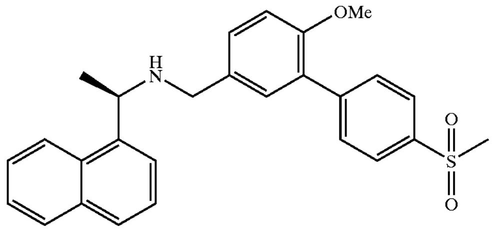

MW 445.58 Mass found: 155, 446, 275.

EXAMPLE 314

(1R)-N-((4',6-bis(trifluoromethyl)-1,1'-biphenyl-3-yl)methyl)-1-phenylethanamine

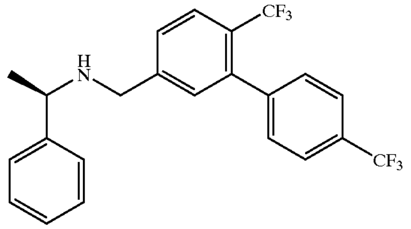

MW 423.398 Mass found: 424, 361.

EXAMPLE 315

(1R)-N-((4'-chloro-6-(methyloxy)-1,1'-biphenyl-3-yl)methyl)-1-(1-naphthalenyl)ethanamine

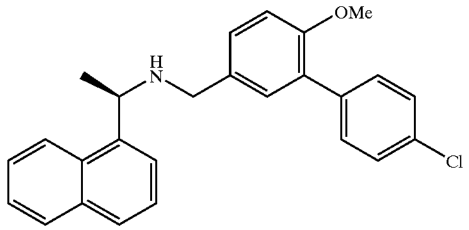

MW 401.935 Mass found: 155, 231, 402.

EXAMPLE 316

N,N-dimethyl-2'-(methyloxy)-5'-((((1R)-1-(3-(methyloxy)phenyl)ethyl)amino)methyl)-1,1'-biphenyl-4-carboxamide

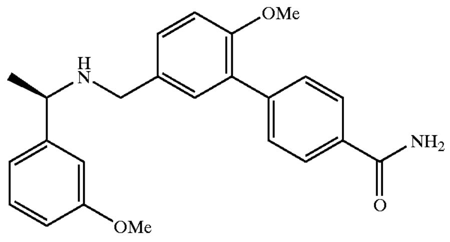

MW 418.534 Mass found: 286, 268, 441, 419.

EXAMPLE 317

N,N-dimethyl-2'-(methyloxy)-5'-((((1R)-1-(1-naphthalenyl)ethyl)amino)methyl)-1,1'-biphenyl-4-carboxamide

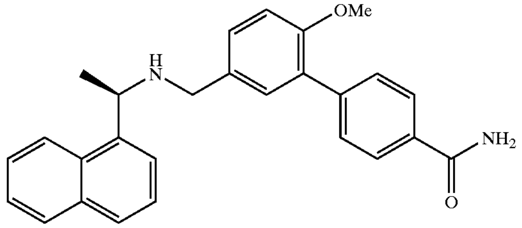

MW 438.568 Mass found: 268, 155, 461, 439.

EXAMPLE 318

N,N-dimethyl-2'-(methyloxy)-5'-((((1R)-1-phenylethyl)amino)methyl)-1,1'-biphenyl-4-carboxamide.

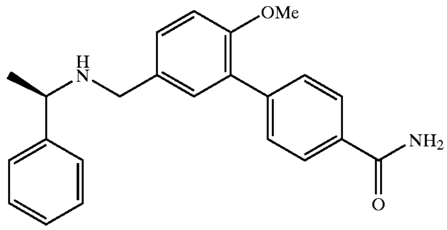

MW 388.508 Mass found: 286, 268, 389, 411.

EXAMPLE 319

(1R)-N-((6-iodo-4'-(trifluoromethyl)-1,1'-biphenyl-3-yl)methyl)-1-(3-(methyloxy)phenyl)ethanamine

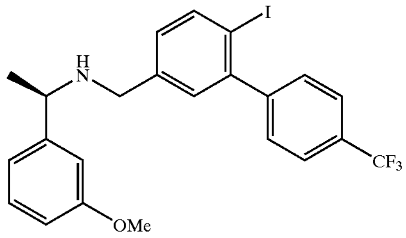

MW 511.319 Mass found: 512, 402, 361.

EXAMPLE 320

(1R)-N-((6-iodo-4'-(trifluoromethyl)-1,1'-biphenyl-3-yl)methyl)-1-phenylethanamine

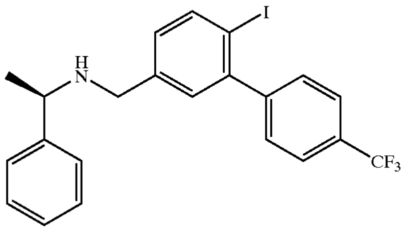

MW 481.293 Mass found: 482, 523.

EXAMPLE 321

(1R)-N-((6-iodo-4'-(trifluoromethyl)-1,1'-biphenyl-3-yl)methyl)-1-(1-naphthalenyl)ethanamine

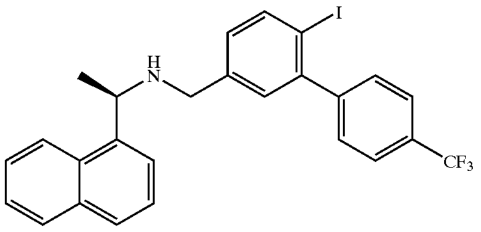

MW 531.353 Mass found: 155, 532.

EXAMPLE 322

(1R)-N-((6-(methyloxy)-3'-((trifluoromethyl)oxy)-1,1'-biphenyl-3-yl)methyl)-1-(1-naphthalenyl)ethanamine

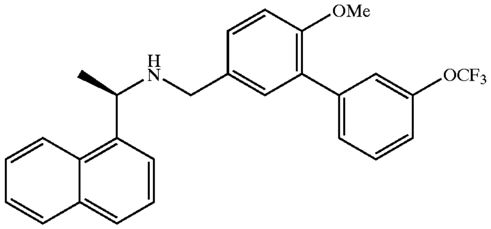

MW 451.486 Mass found: 155, 452, 281.

EXAMPLE 323

(1R)-1-(3-(methyloxy)phenyl)-N-((6-(methyloxy)-3'-((trifluoromethyl)oxy)-1,1'-biphenyl-3-yl)methyl)ethanamine

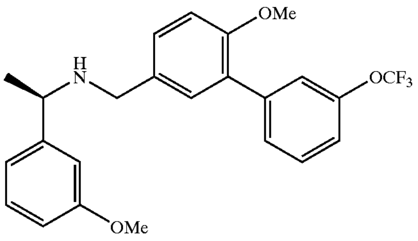

MW 431.452 Mass found: 432, 281.

EXAMPLE 324

(1R)-N-((6-(methyloxy)-3'-((trifluoromethyl)oxy)-1,1'-biphenyl-3-yl)methyl)-1-phenylethanamine

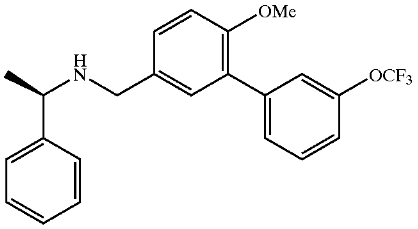

MW 401.426 Mass found: 281, 402.

EXAMPLE 325

(1R)-N-((4'-chloro-6-(methyloxy)-1,1'-biphenyl-3-yl)methyl)-1-(3-(methyloxy)phenyl)ethanamine

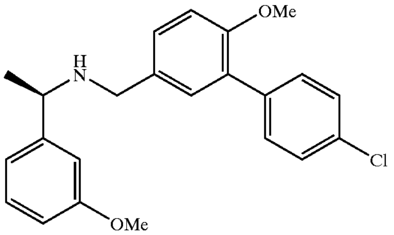

MW 381.901 Mass found: 231, 382.

EXAMPLE 326

(1R)-1-(3-(methyloxy)phenyl)-N-((4-(methyloxy)-3-(2-((2,2,2-trifluoroethyl)oxy)-5-pyrimidinyl)phenyl)methyl)ethanamine

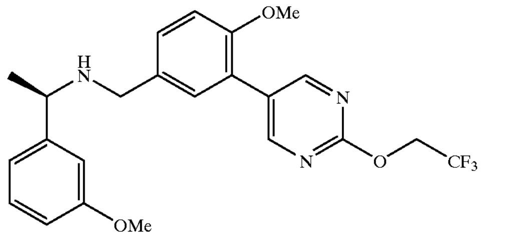

MW 447.455 Mass found: 448.

EXAMPLE 327

(1R)-N-((4-(methyloxy)-3-(2-((2,2,2-trifluoroethyl)oxy)-5-pyrimidinyl)phenyl)methyl)-1-(1-naphthalenyl)ethanamine

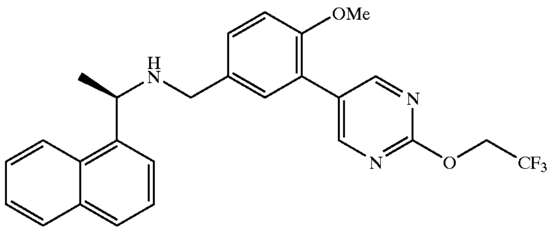

MW 467.489 Mass found: 155, 468.

EXAMPLE 328

(1R)-N-((4-(methyloxy)-3-(2-((2,2,2-trifluoroethyl)oxy)-5-pyrimidinyl)phenyl)methyl)-1-phenylethanamine

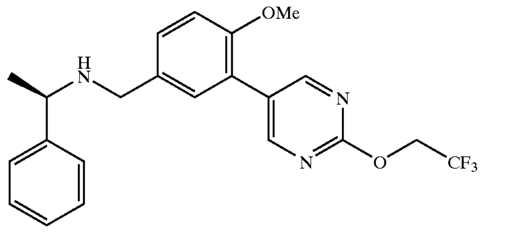

MW 417.429 Mass found: 418, 297.

EXAMPLE 329

(1R)-1-(3-(methyloxy)phenyl)-N-((4-(methyloxy)-3-(6-quinoxalinyl)phenyl)methyl)ethanamine

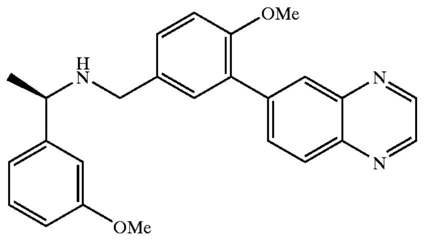

MW 399.491 Mass found: 249, 400.

EXAMPLE 330

(1R)-N-((4-(methyloxy)-3-(6-quinoxalinyl)phenyl)methyl)-1-(1-naphthalenyl)ethanamine

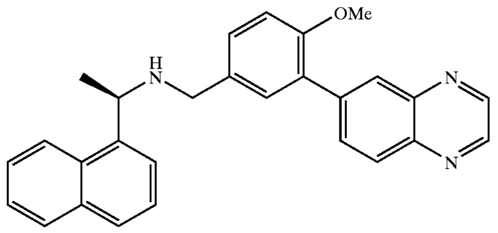

MW 419.526 Mass found: 420, 249, 155.

EXAMPLE 331

(1R)-N-((4-(methyloxy)-3-(6-quinoxalinyl)phenyl)methyl)-1-phenylethanamine

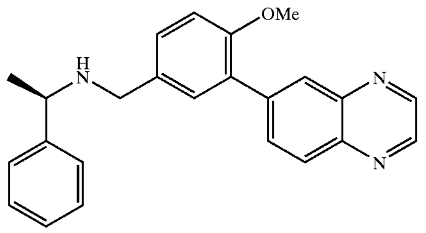

MW 369.466 Mass found: 370, 249.

EXAMPLE 332

(1R)-N-((4'-chloro-6-(methyloxy)-1,1'-biphenyl-3-yl)methyl)-1-phenylethanamine

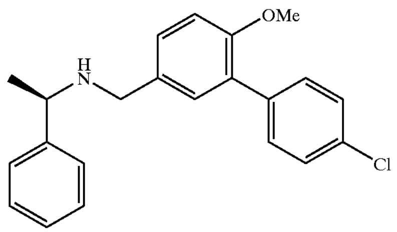

MW 351.875 Mass found: 231, 352.

EXAMPLE 333

(1R)-N-((3-(1,3-benzothiazol-2-yl)-4-(methyloxy)phenyl)methyl)-1-phenylethanamine

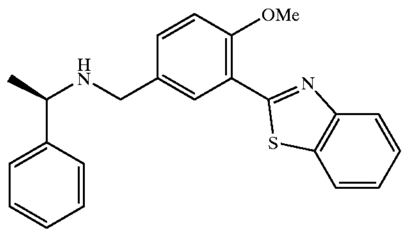

MW 374.506 Mass found: 375, 749.

EXAMPLE 334

(1R)-N-((4-(methyloxy)-3-(2-(1-piperidinyl)-1,3-thiazol-4-yl)phenyl)methyl)-1-(1-naphthalenyl)ethanamine

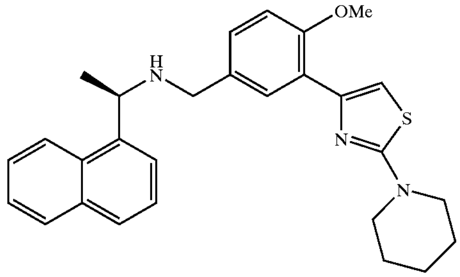

MW 457.639 Mass found: 458, 155.

EXAMPLE 335

(1R)-N-((4-(methyloxy)-3-(2-(1-piperidinyl)-1,3-thiazol-4-yl)phenyl)methyl)-1-phenylethanamine

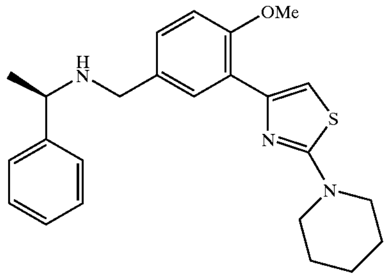

MW 407.579 Mass found: 408, 304.

EXAMPLE 336

(1R)-1-phenyl-N-((6-((2,2,2-trifluoroethyl)oxy)-4'-(trifluoromethyl)-1,1'-biphenyl-3-yl)methyl)ethananamine

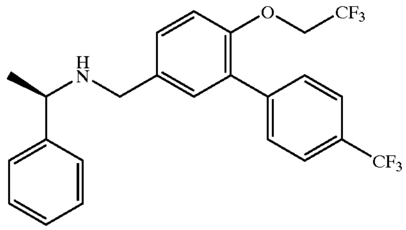

MW 453.424 Mass found: 454, 333.

EXAMPLE 337

(1R)-N-((6-((2-(methyloxy)ethyl)oxy)-4'-(trifluoromethyl)-1,1'-biphenyl-3-yl)methyl)-1-(3-(methyloxy)phenyl)ethanamine

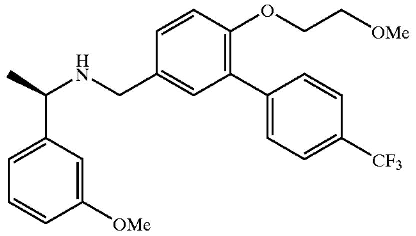

MW 459.505 Mass found: 460, 309.

EXAMPLE 338

N,N-dimethyl-2-((5-((((1R)-1-(3-(methyloxy) phenyl)ethyl)amino)methyl)-4'-(trifluoromethyl)-1, 1'-biphenyl-2-yl)oxy)acetamide

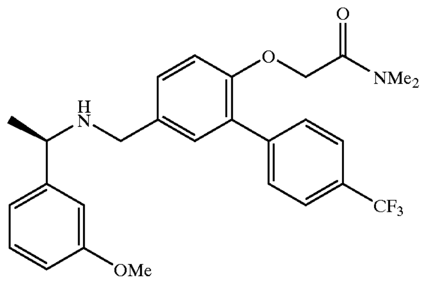

MW 486.531 Mass found: 487, 336, 509.

EXAMPLE 339

N,N-dimethyl-2-((5-((((1R)-1-(1-naphthalenyl)ethyl) amino)methyl)-4'-(trifluoromethyl)-1,1'-biphenyl-2-yl)oxy)acetamide

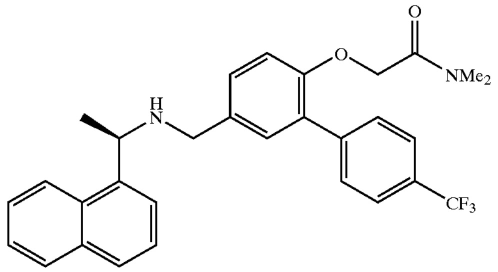

MW 506.565 Mass found: 507, 336, 529.

EXAMPLE 340

(1R)-N-((3-(4-morpholinylsulfonyl)phenyl)methyl)-1-phenylethanamine

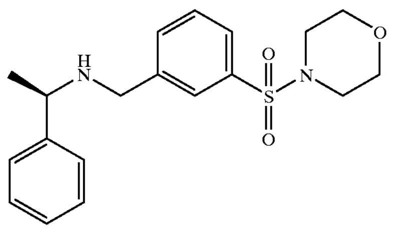

MW 360.476 Mass found: 298, 361, 402.

EXAMPLE 341

(1R)-N-((6-chloro-4'-((trifluoromethyl)oxy)-1,1'-biphenyl-3-yl)methyl)-1-(1-naphthalenyl)ethanamine

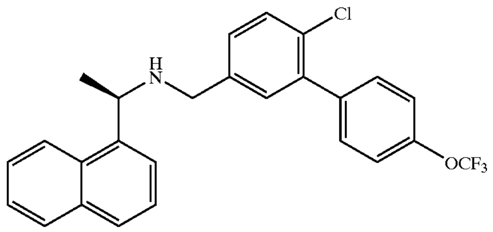

MW 455.905 Mass found: 456, 911.

EXAMPLE 342

(1R)-N-((3-(1,3-benzothiazol-2-yl)-4-(methyloxy) phenyl)methyl)-1-(3-(methyloxy)phenyl)ethanamine

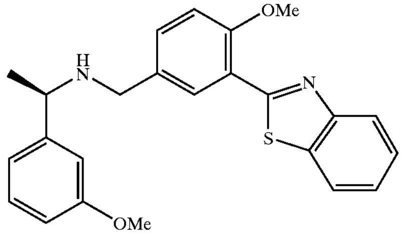

MW 404.532 Mass found: 405, 809.

EXAMPLE 343

(1R)-N-((3-(1,3-benzothiazol-2-yl)-4-(methyloxy) phenyl)methyl)-1-(1-naphthalenyl)ethanamine

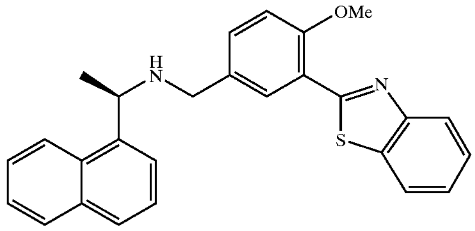

MW 424.566 Mass found: 425, 849.

EXAMPLE 344

N,N-dimethyl-2-((5-((((1R)-1-phenylethyl)amino)methyl)-4'-(trifluoromethyl)-1,1'-biphenyl-2-yl)oxy)acetamide

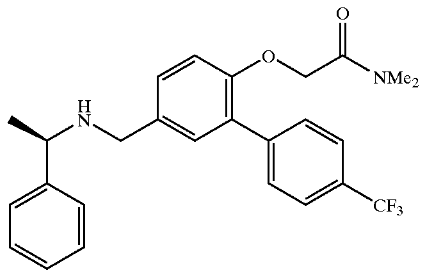

MW 456.505 Mass found: 336, 457, 354.

EXAMPLE 345

(1R)-N-((4-(methyloxy)-3-(2-naphthalenyl)phenyl)methyl)-1-(3-(methyloxy)phenyl)ethanamine

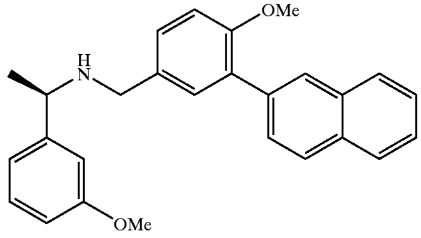

MW 433.98 Mass found: 247, 398.

EXAMPLE 346

(1R)-N-((4-(methyloxy)-3-(2-naphthalenyl)phenyl)methyl)-1-(1-naphthalenyl)ethanamine

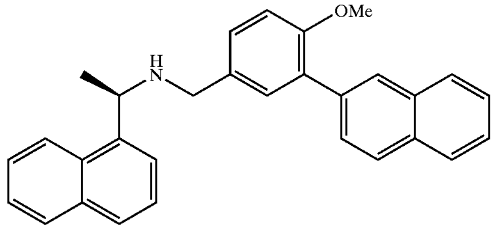

MW 454.02 Mass found: 247, 155, 418.

EXAMPLE 347

(1R)-N-((4-(methyloxy)-3-(2-naphthalenyl)phenyl)methyl)-1-phenylethanamine

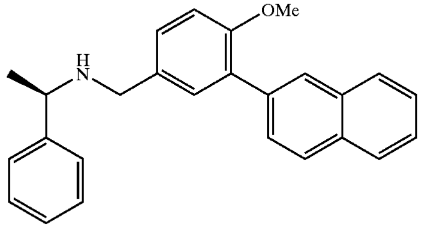

MW 403.96 Mass found: 247, 368.

EXAMPLE 348

(1R)-N-((3-(1-benzothien-3-yl)-4-(methyloxy)phenyl)methyl)-1-(1-naphthalenyl)ethanamine

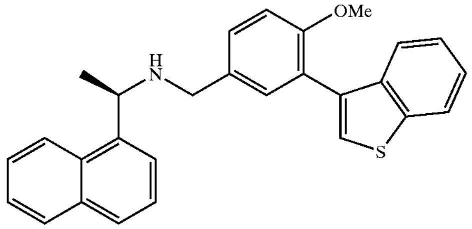

MW 460.04 Mass found: 253, 155, 424.

EXAMPLE 349

(1R)-N-((3-(1-benzothien-3-yl)-4-(methyloxy)phenyl)methyl)-1-phenylethanamine

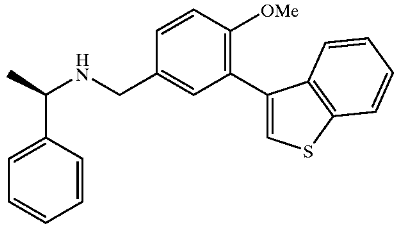

MW 409.98 Mass found: 253, 374.

EXAMPLE 350

(1R)-N-((3-(2,1,3-benzothiadiazol-5-yl)-4-(methyloxy)phenyl)methyl)-1-(3-(methyloxy)phenyl)ethanamine

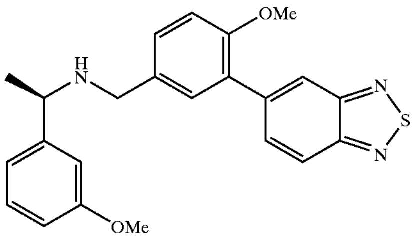

MW 441.98 Mass found: 273, 255, 406.

EXAMPLE 351

(1R)-N-((3-(2,1,3-benzothiadiazol-5-yl)-4-(methyloxy)phenyl)methyl)-1-phenylethanamine

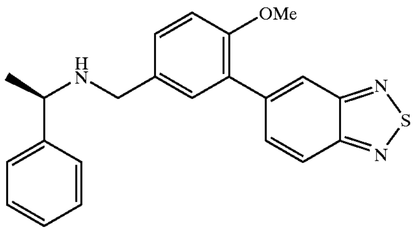

MW411.96 Mass found: 273, 255, 376.

EXAMPLE 352

(1R)-N-((4',6-bis(trifluoromethyl)-1,1'-biphenyl-3-yl)methyl)-1-(3-(methyloxy)phenyl)ethanamine

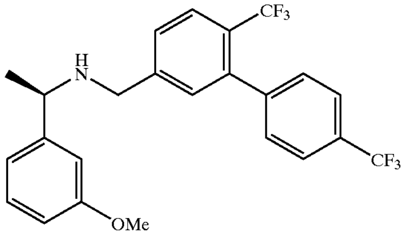

MW 489.89 Mass found: 454, 361, 344.

EXAMPLE 353

(1R)-N-((4',6-bis(trifluoromethyl)-1,1'-biphenyl-3-yl)methyl)-1-(1-naphthalenyl)ethanamine

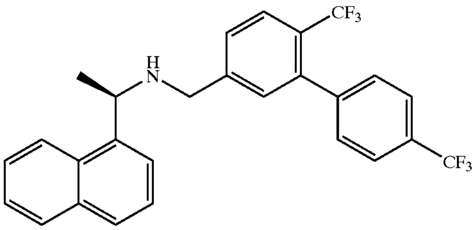

MW 509.93 Mass found: 155.

EXAMPLE 354

(1R)-N-((6-chloro-4'-(trifluoromethyl)-1,1'-biphenyl-3-yl)methyl)-1-(1-naphthalenyl)ethanamine

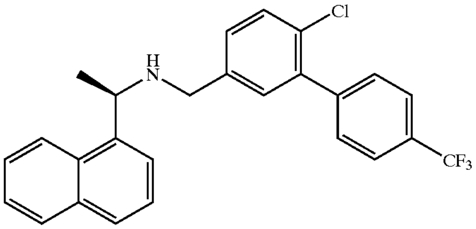

MW 439.91 Mass found: 155.

EXAMPLE 355

(1R)-N-((6-chloro-4'-(trifluoromethyl)-1,1'-biphenyl-3-yl)methyl)-1-phenylethanamine

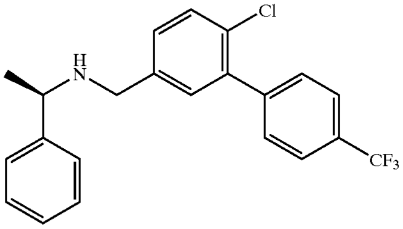

MW 389.95 Mass found: 390, 269, 310.

EXAMPLE 356

1-(2-(methyloxy)-5-((((1R)-1-phenylethyl)amino) methyl)phenyl)-2-pyrrolidinone

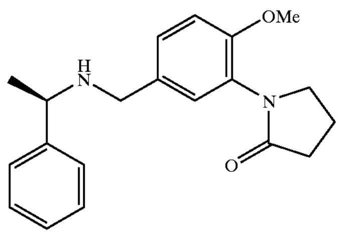

MW 324.43 Mass found: 204, 347, 325.

EXAMPLE 357

(1R)-N-((3-(2,3-dihydro-1-benzofuran-5-yl)-4-(methyloxy)phenyl)methyl)-1-(1-naphthalenyl) ethamine

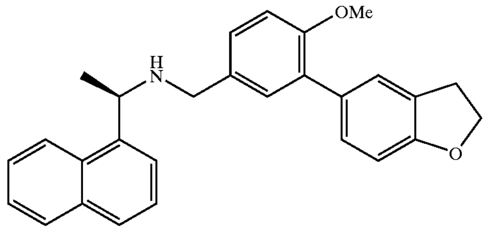

MW 409.53 Mass found: 239, 410.

EXAMPLE 358

(1R)-N-((3-(2,3-dihydro-1-benzofuran-5-yl)-4-(methyloxy)phenyl)methyl)-1-(3-(methyloxy) phenyl)ethanamine

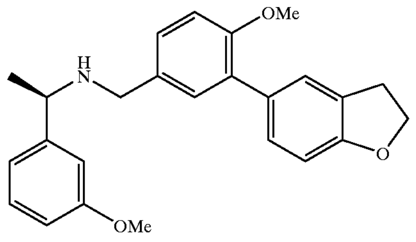

MW 389.50 Mass found: 239, 390.

EXAMPLE 359

(1R)-N-((3-(2,3-dihydro-1-benzofuran-5-yl)-4-(methyloxy)phenyl)methyl)-1-phenylethanamine

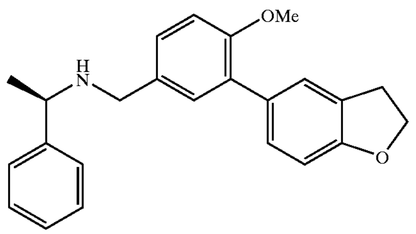

MW 359.47 Mass found: 239, 360.

EXAMPLE 360

(1R)-N-((3-(2,1,3-benzoxadiazol-5-yl)-4-(methyloxy)phenyl)methyl)-1-phenylethanamine

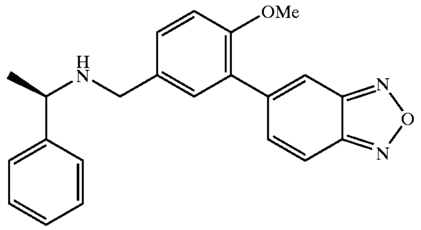

MW 359.43 Mass found: 239, 360, 401.

EXAMPLE 361

(1R)–N-((3-(2,1,3-benzoxadiazol-5-yl)-4-(methyloxy)phenyl)methyl)-1-(3-(methyloxy) phenyl)ethanamine

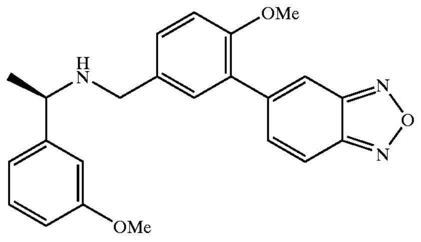

MW 389.46 Mass found: 390, 431, 779.

EXAMPLE 362

(1R)-N-((4-chloro-3-(6-((2,2,2-tifluoroethyl)oxy)-3-pyridinyl)phenyl)methyl)-1-(1-naphthalenyl) ethanamine

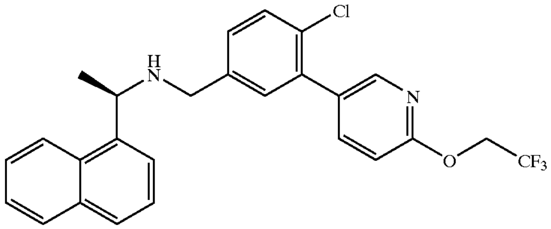

MW 470.93 Mass found: 155, 472.

EXAMPLE 363

(1R)-N-((4-(methyloxy)-3-(1-(2,2,2-trifluoroethyl)-1H-indol-5-yl)phenyl)methyl)-1-(1-napthalenyl) ethanamine

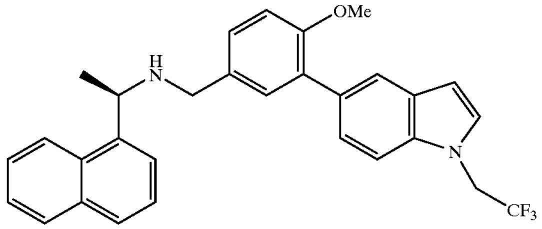

MW 488.55 Mass found: 318, 489.

EXAMPLE 364

(1R)-N-((4-(methyloxy)-3-(1-(2,2,2-trifluoroethyl)-1H-indol-5-yl)phenyl)methyl)-1-phenylethanamine

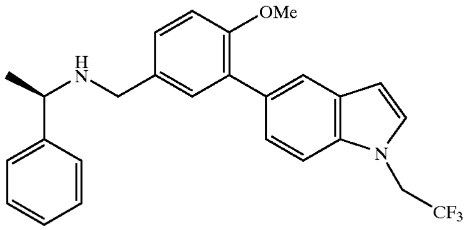

MW 438.491 Mass found: 318, 439.

EXAMPLE 365

1-(2-(methyloxy)-5-((((1R)-1-(1-naphthalenyl)ethyl) amino)methyl)phenyl)-2-pyrrolidinone

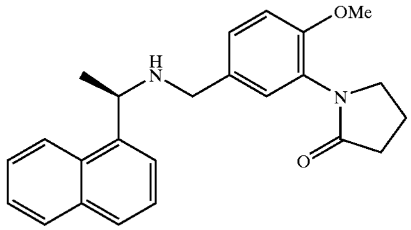

MW 374.49 Mass found: 240, 375, 397, 749.

EXAMPLE 366

(1R)-N-((3-(2,1,3-benzoxadiazol-5-yl)-4-(methyloxy)phenyl)methyl)-1-(1-naphthalenyl) ethanamine

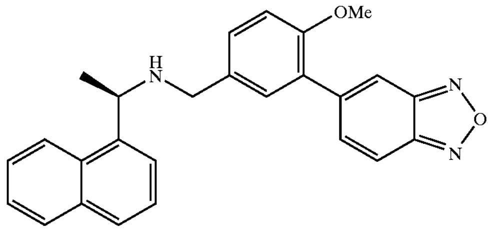

MW 409.49 Mass found: 155, 410, 239.

EXAMPLE 367

5-(2-(methyloxy)-5-((((1R)-1-(3-(methyloxy)phenyl) ethyl)amino)methyl)phenyl)-1-(2,2,2-trifluoroethyl)-2(1H)-pyridinone

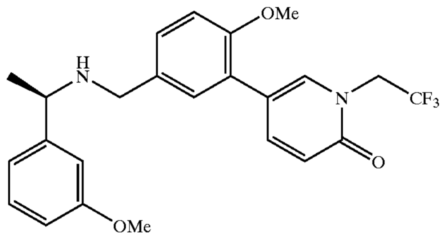

MW 446.466 Mass found: 296, 447, 314.

EXAMPLE 368

5-(2-(methyloxy)-5-((((1R)-1-phenylethyl)amino)methyl)phenyl)-1-(2,2,2-trifluoroethyl)-2(1H)-pyridinone

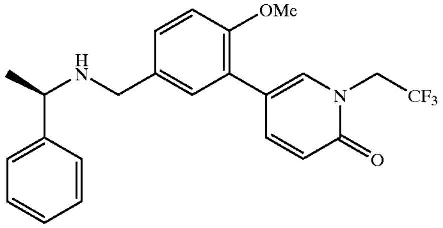

MW 416.441 Mass found: 296, 314, 417.

EXAMPLE 369

1-methyl-5-(2-(methyloxy)-5-((((1R)-1-(1-naphthalenyl)ethyl)amino)methyl)phenyl)-2(1H)-pyridinone

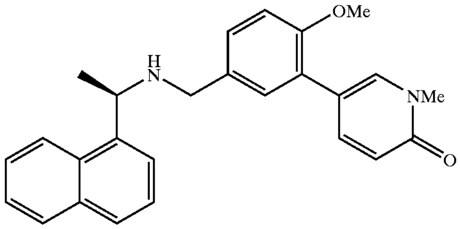

MW 398.503 Mass found: 245, 399, 228, 155.

EXAMPLE 370

1-methyl-5-(2-(methyloxy)-5-((((1R)-1-phenylethyl)amino)methyl)phenyl)-2(1H)-pyridinone

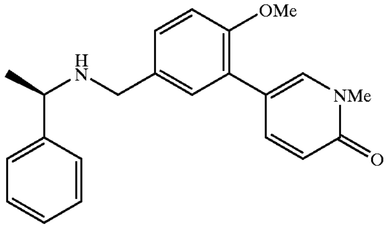

MW 348.444 Mass found: 228, 349.

EXAMPLE 371

(1R)-N-((6-((2-(methyloxy)ethyl)oxy)-4'-(trifluoromethyl)-1,1'-biphenyl-3-yl)methyl)-1-(1-naphthalenyl)ethanamine

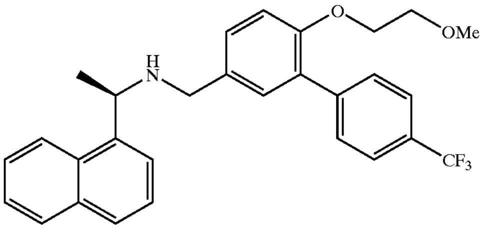

MW 479.539 Mass found: 480, 959.

EXAMPLE 372

(1R)-N-((6-((2-(methyloxy)ethyl)oxy)-4'-(trifluoromethyl)-1,1'-biphenyl-3-yl)methyl)-1-phenylethanamine

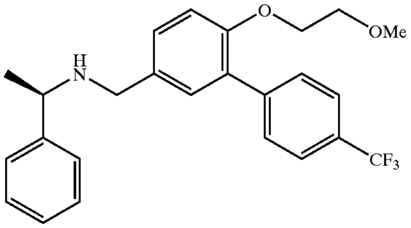

MW 429.479 Mass found: 309, 430.

EXAMPLE 373

(1R)-N-((3-imidazo[1,2-a]pyridin-6-yl-4-(methyloxy)phenyl)methyl)-1-(1-naphthalenyl)ethanamine

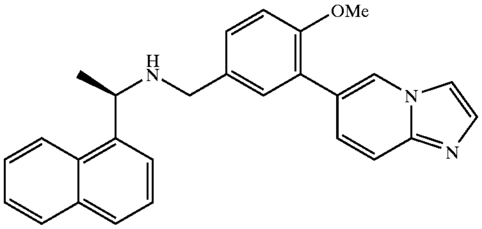

MW 407.514 Mass found: 408, 254, 155.

EXAMPLE 374

(1R)-1-(3-(methyloxy)phenyl)-N-((4-(methyloxy)-3-(6-quinolinyl)phenyl)methyl)ethanamine

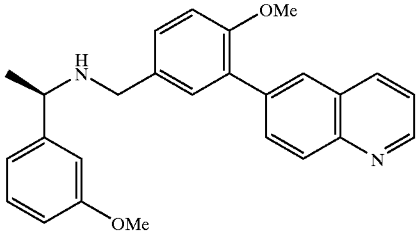

MW 398.503 Mass found: 399, 248, 265.

EXAMPLE 375

(1R)-N-((4-(methyloxy)-3-(6-quinolinyl)phenyl)methyl)-1-phenylethanamine

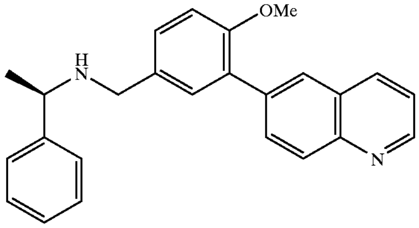

MW 368.478 Mass found: 248, 369, 265.

EXAMPLE 376

(1R)-N-((4-(methyloxy)-3-(6-quinolinyl)phenyl)methyl)-1-(1-naphthalenyl)ethanamine

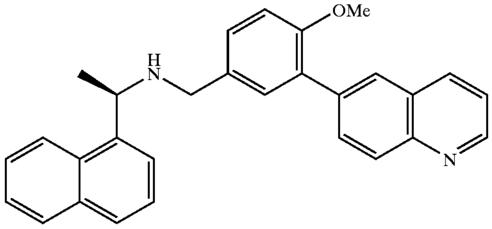

MW 418.537 Mass found: 419, 248, 265.

EXAMPLE 377

2'-(methyloxy)-5'-((((1R)-1-(1-naphthalenyl)ethyl)amino)methyl)-1,1'-biphenyl-3-carboxamide

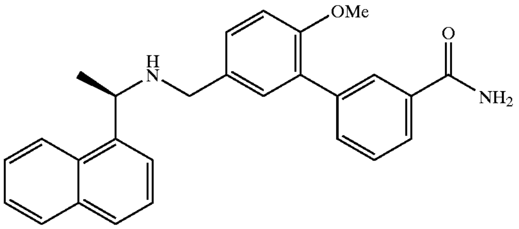

MW 410.514 Mass found: 411, 821.

EXAMPLE 378

(1R)-1-(1-naphthalenyl)-N-((6-((2,2,2-trifluoroethyl)oxy)-4'-(trifluoromethyl)-1,1'-biphenyl-3-yl)methyl)ethanamine

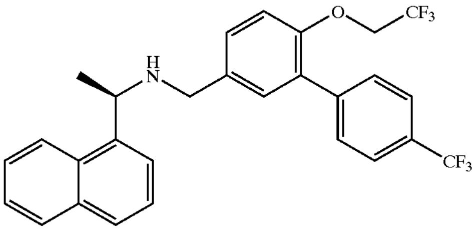

MW 503.484 Mass found: 155, 504.

EXAMPLE 379

1-methyl-5-(2-(methyloxy)-5-((((1R)-1-(3-(methyloxy)phenyl)ethyl)amino)methyl)phenyl)-2(1H)-pyridinone

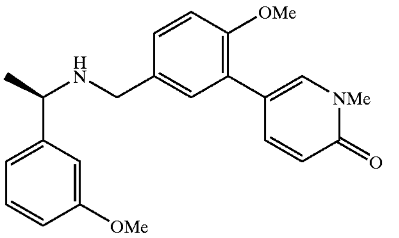

MW 378.469 Mass found: 228, 379.

EXAMPLE 380

(1R)-1-(3-(methyloxy)phenyl)-N-((4-(methyloxy)-3-(2-(1-piperidinyl)-1,3-thiazol-4-yl)phenyl)methyl) ethanamine

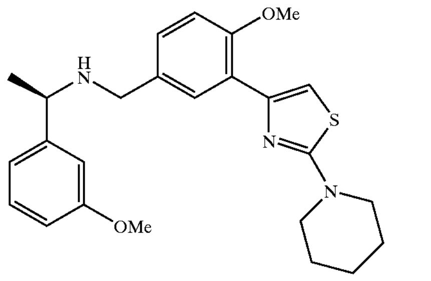

MW 437.605 Mass found: 438, 875.

EXAMPLE 381

(1R)-N-((6-chloro-4'-((trifluoromethyl)oxy)-1,1'-biphenyl-3-yl)methyl)-1-(3-(methyloxy)phenyl) ethanamine

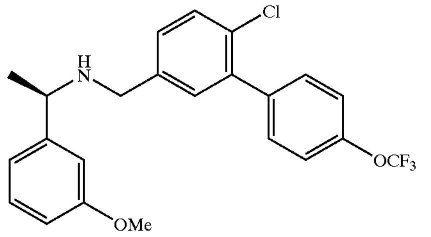

MW 435.871 Mass found: 436, 477.

EXAMPLE 382

(1R)-N-((6-chloro-4'-((trifluoromethyl)oxy)-1,1'-biphenyl-3-yl)methyl)-1-phenylethanamine

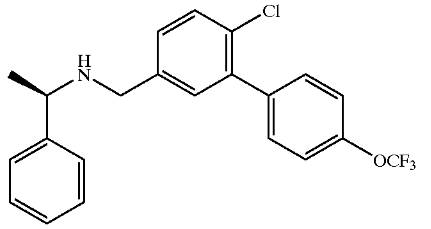

MW 405.845 Mass found: 406.

EXAMPLE 383

2'-(methyloxy)-5'-((((1R)-1-(3-(methyloxy)phenyl) ethyl)amino)methyl)-1,1'-biphenyl-3-carboxamide

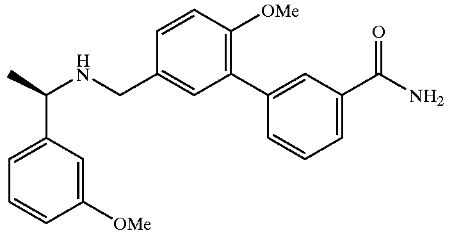

MW 390.48 Mass found: 391, 432, 781, 895.

EXAMPLE 384

2'-(methyloxy)-5'-((((1R)-1-phenylethyl)amino) methyl)-1,1'-biphenyl-3-carboxamide

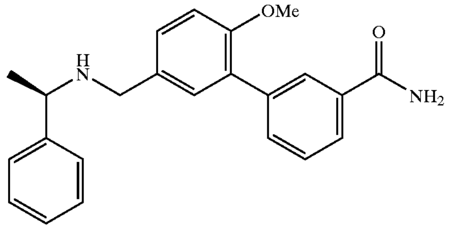

MW 360.455 Mass found: 361, 721, 402.

EXAMPLE 385

(1R)-N-((3-(3-furanyl)-4-(methyloxy)phenyl) methyl)-1-(3-(methyloxy)phenyl)ethanamine

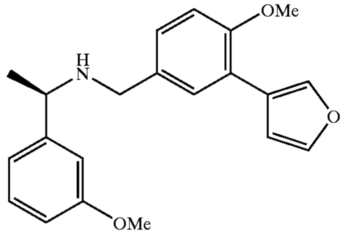

MW 337.417 Mass found: 187, 338.

EXAMPLE 386

(1R)-1-(1-naphthalenyl)-N-((3-(6-(trifluoromethyl)-3-pyridinyl)phenyl)methyl)ethanamine

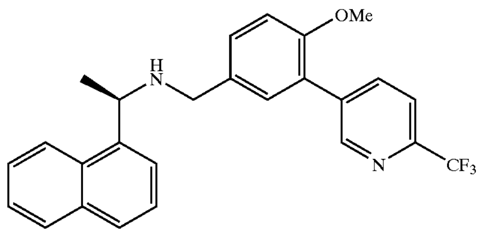

MW 406.449 Mass found: 155, 407.

EXAMPLE 387

(1R)-N-((3-(2,2-difluoro-1,3-benzodioxol-5-yl)-4-(methyloxy)phenyl)methyl)1-(3-(methyloxy)phenyl) ethanamine

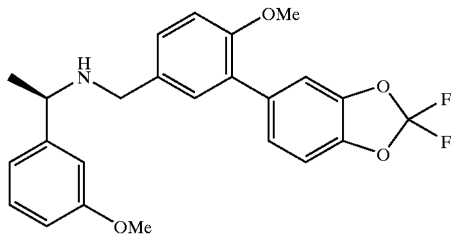

MW 427.445 Mass found: 428, 855, 969.

EXAMPLE 388

(1R)-N-((3-(2,2-difluoro-1,3-benzodioxol-5-yl)-4-(methyloxy)phenyl)methyl)-1-phenylethanamine

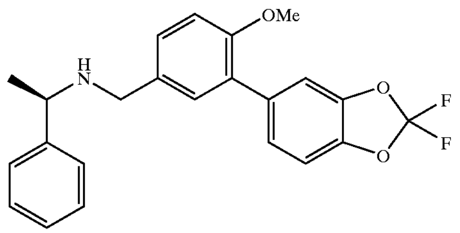

MW 397.419 Mass found: 398, 277.

EXAMPLE 389

(1R)-N-((3-(2,2-difluoro-1,3-benzodioxol-5-yl)-4-(methyloxy)phenyl)methyl)-1-(1-naphthalenyl) ethanamine

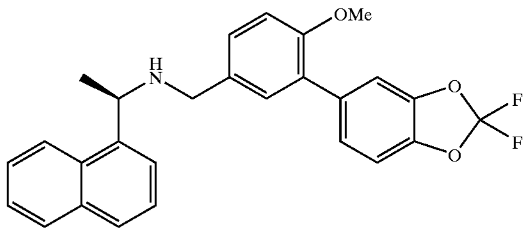

MW 447.479 Mass found: 448, 895.

EXAMPLE 390

(1R)-N-((3-(3-furanyl)-4-(methyloxy)phenyl) methyl)-1-(1-naphthalenyl)ethanamine

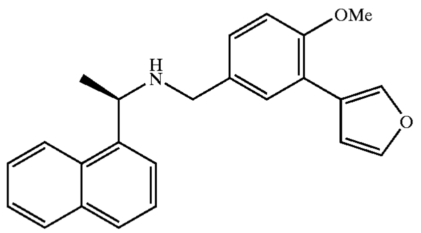

MW 357.451 Mass found: 358.

EXAMPLE 391

4'-(methyloxy)-5-((((1R)-1-phenylethyl)amino) methyl)-1,1'-biphenyl-2-ol

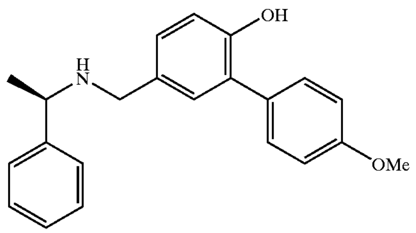

MW 333.429 Mass found: 334, 213.

EXAMPLE 392

(1R)-N-((3-imidazo[1,2-a]pyridin-6-yl-4-(methyloxy)phenyl)methyl)-1-phenylethanamine

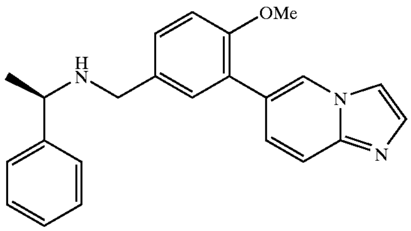

MW 357.455 Mass found: 358.

EXAMPLE 393

(1R)-N-((3-(3-furanyl)-4-(methyloxy)phenyl)methyl)-1-phenylethanamine

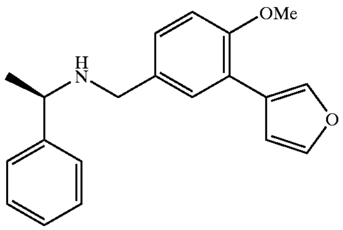

MW 307.391 Mass found: 308, 187.

EXAMPLE 394

(1R)-N-((3-(1-acetyl-4-piperidinyl)-4-(methyloxy)phenyl)methyl)-1-(1-naphthalenyl)ethanamine

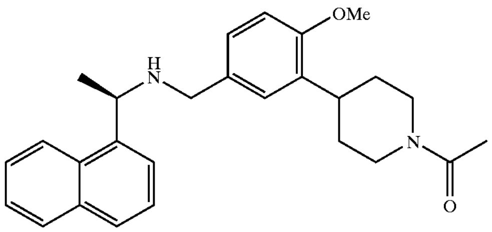

MW 416.562 Mass found: 417.

EXAMPLE 395

(1R)-N-((4-(methyloxy)-3-(1-((methyloxy)acetyl)-4-piperidinyl)phenyl)methyl)-1-(1-naphthalenyl)ethanamine

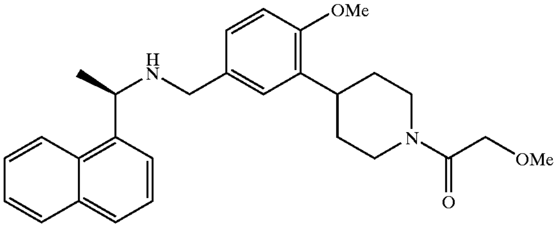

MW 446.588 Mass found: 447.

EXAMPLE 396

(1R)-N-((4-(methyloxy)-3-(1-((methyloxy)acetyl)-4-piperidinyl)phenyl)methyl)-1-phenylethanamine

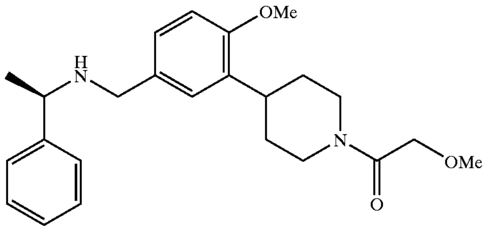

MW 396.528 Mass found: 397.

EXAMPLE 397

(1R)-N-((6-(methyloxy)-3'-(trifluoromethyl)-1,1'-biphenyl-3-yl)methyl)-1-(1-naphthalenyl)ethanamine

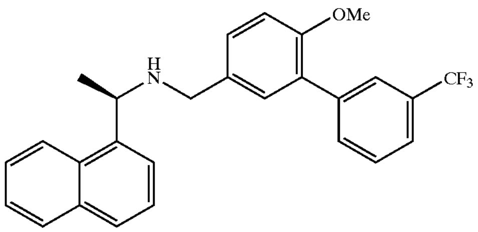

MW 435.487 Mass found: 155, 436.

EXAMPLE 398

(1R)-N-((6-(methyloxy)-3'-(trifluoromethyl)-1,1'-biphenyl-3-yl)methyl)-1-phenylethanamine

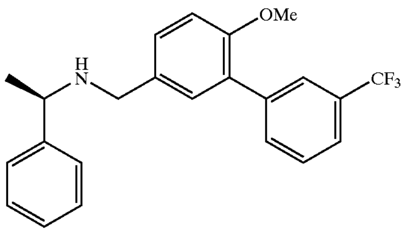

MW 385.427 Mass found: 386, 265.

EXAMPLE 399

(1R)-N-((4-(methyloxy)-3-(2-methyl-1,3-thiazol-4-yl)phenyl)methyl)-1-(3-(methyloxy)phenyl) ethanamine

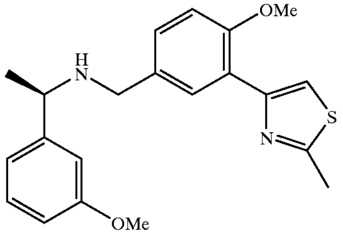

MW 368.499 Mass found: 369, 218.

EXAMPLE 400

(1R)-N-((4-(methyloxy)-3-(2-methyl-1,3-thiazol-4-yl)phenyl)methyl)-1-(1-naphthalenyl)ethanamine

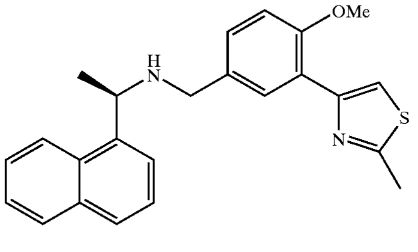

MW 388.533 Mass found: 389, 218.

EXAMPLE 401

(1R)-N-((4-(methyloxy)-3-(2-methyl-1,3-thiazol-4-yl)phenyl)methyl)-1-phenylethanamine

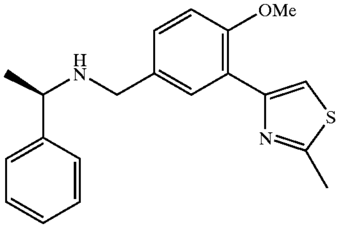

MW 338.473

Mass found: 218, 339.

EXAMPLE 402

(1R)-1-(3-(methyloxy)phenyl)-N-((4-(methyloxy)-3-(5-(trifluoromethyl)-1,3,4-oxadiazol-2-yl)phenyl) methyl)ethanamine

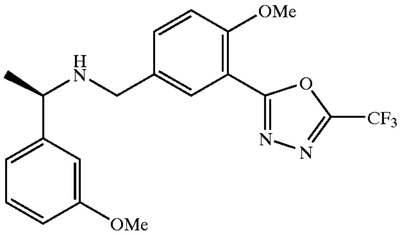

MW 407.39 Mass found: 408, 274.

EXAMPLE 403 ethyl 4-(2-(methyloxy)-5-((((1R)-1-(1-naphthalenyl) ethyl)amino)methyl)phenyl)-3,6-dihydro-1(2H)-pyridinecarboxylate

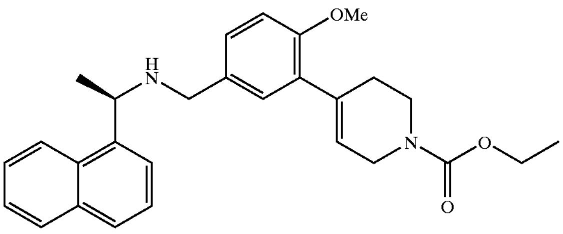

MW 444.572 Mass found: 445, 274, 155.

EXAMPLE 404

(1R)-N-((4-(methyloxy)-3-(4-(methyloxy)-2-pyridinyl)phenyl)methyl)-1-(3-(methyloxy)phenyl) ethanamine

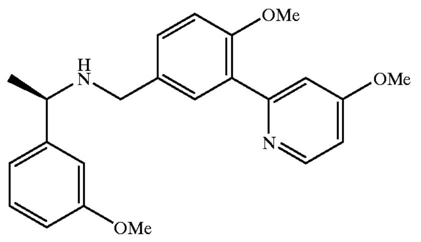

MW 378.469 Mass found: 379.

EXAMPLE 405

(1R)-N-((4-(methyloxy)-3-(4-(methyloxy)-2-pyridinyl)phenyl)methyl)-1-phenylethanamine

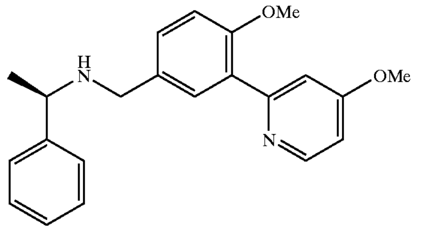

MW 348.444 Mass found: 349.

EXAMPLE 406

(1R)-N-((4-((difluoromethyl)oxy)-3-(3-pyridinyl) phenyl)methyl)-1-(3-(methyloxy)phenyl)ethanamine

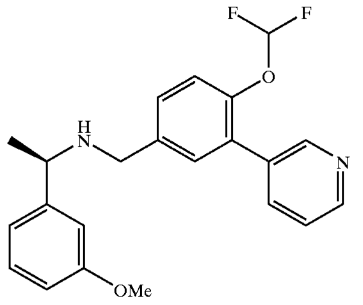

MW 384.424 Mass found: 385, 251.

EXAMPLE 407

(1R)-N-((4-((difluoromethyl)oxy)-3-(3-pyridinyl) phenyl)methyl)-1-(1-naphthalenyl)ethanamine

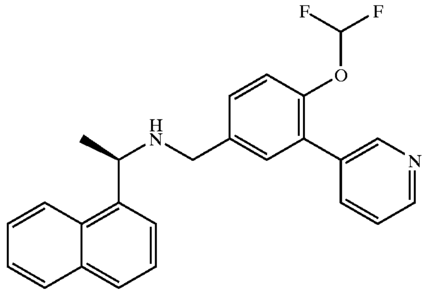

MW 404.458 Mass found: 405, 155.

EXAMPLE 408

(1R)-N-((4-((difluoromethyl)oxy)-3-(3-pyridinyl) phenyl)methyl)-1-phenylethanamine

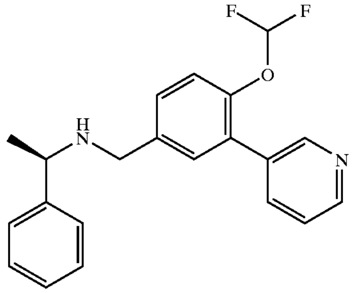

MW 354.398 Mass found: 355, 251.

EXAMPLE 409

2'-(methyloxy)-5'-((((1R)-1-(3-(methyloxy)phenyl) ethyl)amino)methyl)-1,1'-biphenyl-3-carboxylic acid

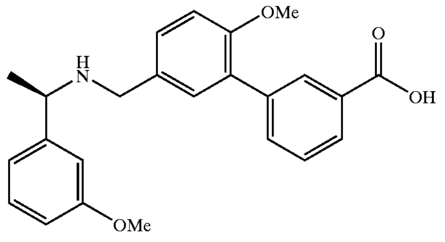

MW 391.465 Mass found: 241, 392.

EXAMPLE 410

2'-(methyloxy)-5'-((((1R)-1-(1-naphthalenyl)ethyl) amino)methyl)-1,1'-biphenyl-3-carboxylic acid

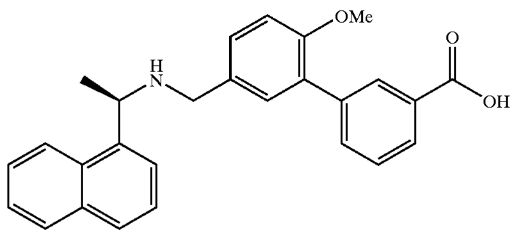

MW 411.499 Mass found: 155, 412, 241.

EXAMPLE 411

2'-(methyloxy)-5'-((((1R)-1-phenylethyl)amino) methyl)-1,1'-biphenyl-3-carboxylic acid

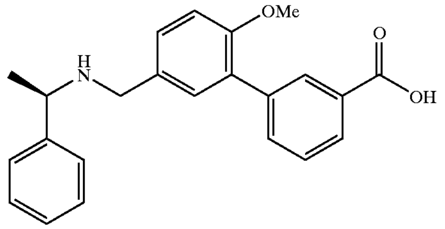

MW 361.439 Mass found: 241, 362.

EXAMPLE 412

(1R)-N-((4-(methyloxy)-3-(5-(trifluoromethyl)-1,3,4-oxadiazol-2-yl)phenyl)methyl)-1-phenylethanamine

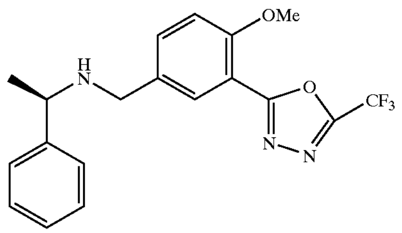

MW 377.364 Mass found: 274, 378.

EXAMPLE 413

(1R)-N-((4-(methyloxy)-3-(1H-pyrrol-1-yl)phenyl) methyl)-1-phenylethanamine

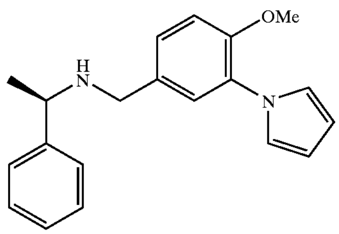

MW 306.407 Mass found: 186, 307.

EXAMPLE 414

(1R)-1-(3-(methyloxy)phenyl)-N-((6-(methyloxy)-4'-(trifluoromethyl)-1,1'-biphenyl-3-yl)methyl) ethanamine

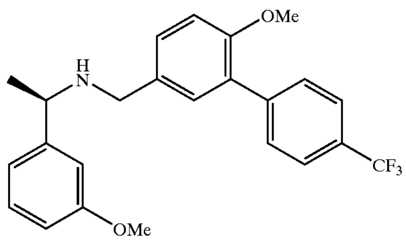

MW 415.453 Mass found: 265, 416.

EXAMPLE 415

(1R)-N-((6-(methyloxy)-4'-(trifluoromethyl)-1,1'-biphenyl-3-yl)methyl)-1-(1-naphthalenyl)ethanamine

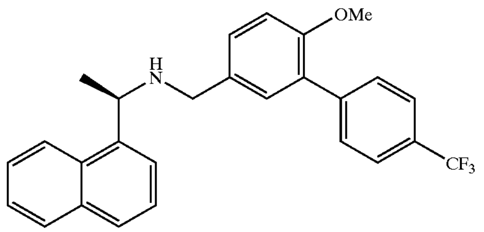

MW 435.487 Mass found: 155, 436.

EXAMPLE 416

(1R)-N-((3-(1-methyl-1H-indazol-5-yl)-4-(methyloxy)phenyl)methyl)-1-phenylethanamine

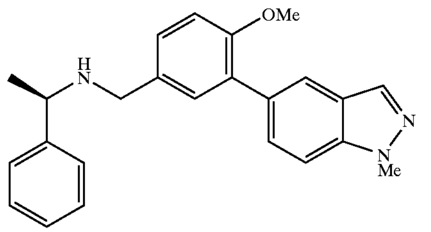

MW 371.482 Mass found: 251, 372.

EXAMPLE 417

(1R)-N-((3-(1-methyl-1H-indazol-5-yl)-4-(methyloxy)phenyl)methyl)-1-(1-naphthalenyl)ethanamine

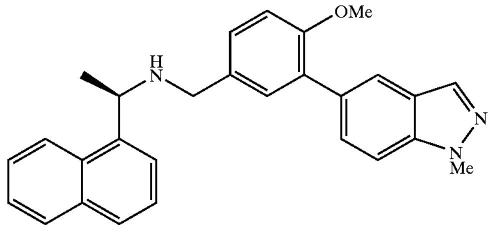

MW 421.541 Mass found: 251, 422.

EXAMPLE 418

(1R)-N-((3-(2-methyl-2H-indazol-5-yl)-4-(methyloxy)phenyl)methyl)-1-(1-naphthalenyl)ethanamine

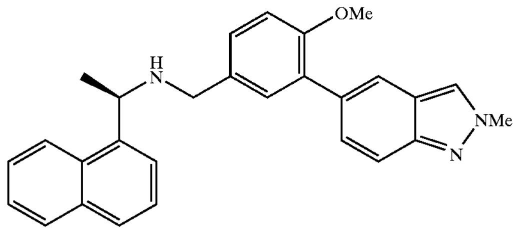

MW 421.541 Mass found: 422, 251, 155.

EXAMPLE 419

(1R)-1-(3-(methyloxy)phenyl)-N-((6-(methyloxy)-3'-(trifluoromethyl)-1,1'-biphenyl-3-yl)methyl)ethanamine

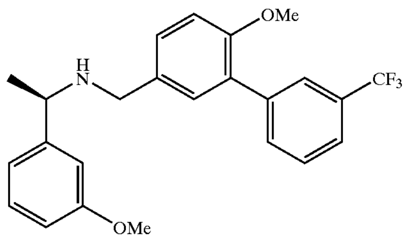

MW 415.453 Mass found: 416, 265.

EXAMPLE 420

(1R)-N-((4-(methyloxy)-3-(5-(trifluoromethyl)-1,3,4-oxadiazol-2-yl)phenyl)methyl)-1-(1-naphthalenyl)ethanamine

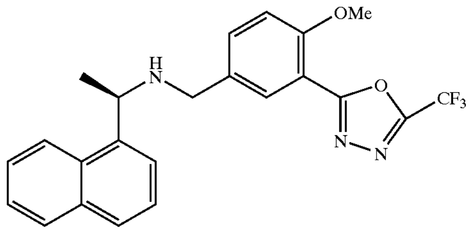

MW 427.424 Mass found: 155, 428.

EXAMPLE 421

(1R)-N-((4-(methyloxy)-3-(1-methyl-1H-pyrrolo[2,3-b]pyridin-5-yl)phenyl)methyl)-1-(3-(methyloxy)phenyl)ethanamine

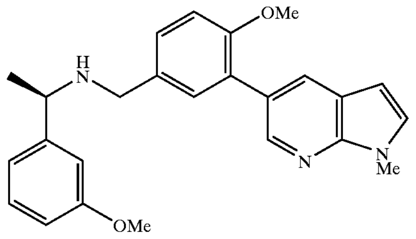

MW 401.507 Mass found: 251, 402, 268.

EXAMPLE 422

(1R)-N-((4-(methyloxy)-3-(1-methyl-1H-pyrrolo[2,3-b]pyridin-5-yl)phenyl)methyl)-1-(1-naphthalenyl)ethanamine

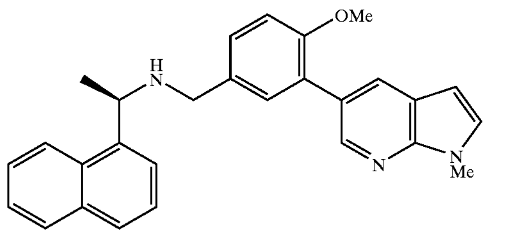

MW 421.541 Mass found: 422, 251, 155, 268.

EXAMPLE 423

(1R)-N-((4-(methyloxy)-3-(1H-pyrrol-1-yl)phenyl)methyl)-1-(1-naphthalenyl)ethanamine

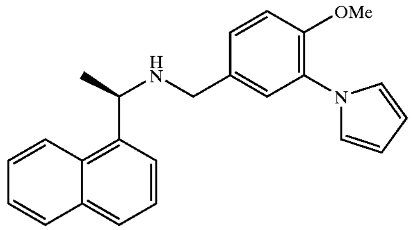

MW 356.467 Mass found: 155, 357.

EXAMPLE 424

(1R)-N-((4-(methyloxy)-3-(5-(methyloxy)-2-pyridinyl)phenyl)methyl)-1-(3-(methyloxy)phenyl)ethanamine

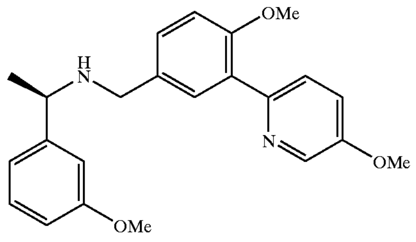

MW 378.469 Mass found: 379, 757.

EXAMPLE 425

(1R)-N-((4-(methyloxy)-3-(5-(methyloxy)-2-pyridinyl)phenyl)methyl)-1-(1-naphthalenyl)ethanamine

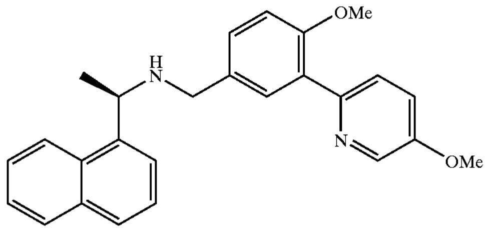

MW 398.503 Mass found: 399, 797.

EXAMPLE 426

(1R)-N-((4-(methyloxy)-3-(5-(methyloxy)-2-pyridinyl)phenyl)methyl)-1-phenylethanamine

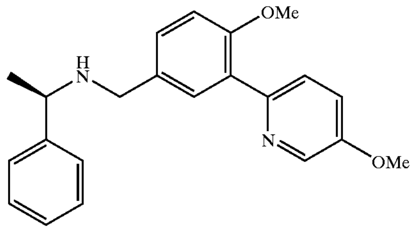

MW 348.444 Mass found: 349, 697.

EXAMPLE 427

(1R)-N-((3-(6-(ethyloxy)-3-pyridinyl)-4-(methyloxy)phenyl)methyl)-1-(1-naphthalenyl)ethanamine

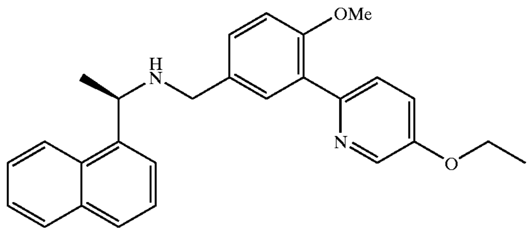

MW 412.53 Mass found: 413, 155, 242, 259.

EXAMPLE 428

(1R)-N-((3-(6-(ethyloxy)-3-pyridinyl)-4-(methyloxy)phenyl)methyl)-1-phenylethanamine

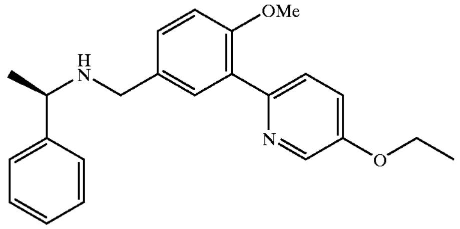

MW 362.47 Mass found: 242, 363, 725.

EXAMPLE 429

(1R)-N-((3-(1-methyl-1H-benzimidazol-2-yl)-4-(methyloxy)phenyl)methyl)-1-(1-naphthalenyl)ethanamine

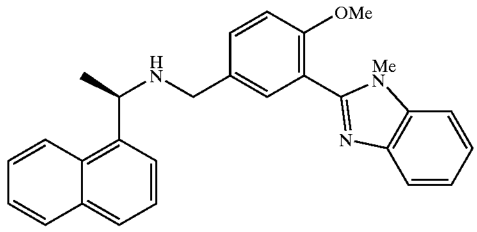

MW 421.541 Mass found: 422, 155.

EXAMPLE 430

(1R)-N-((3-(1-methyl-1H-benzimidazol-5-yl)-4-(methyloxy)phenyl)methyl)-1-phenylethanamine

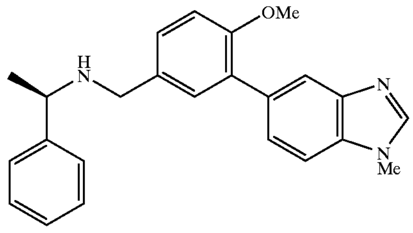

MW 371.482 Mass found: 251, 268, 372, 743.

EXAMPLE 431

(1R)-N-((4-(methyloxy)-3-(1-methyl-1H-pyrrolo[2,3-b]pyridin-5-yl)phenyl)methyl)-1-phenylethanamine

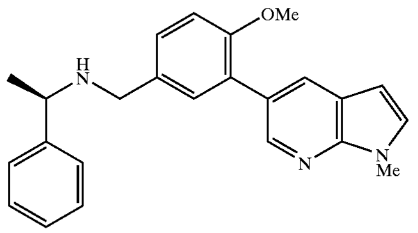

MW 371.482 Mass found: 251, 372, 268.

EXAMPLE 432

(1R)-1-(3-(methyloxy)phenyl)-N-((4-(methyloxy)-3-(6-((2,2,2-trifluoroethyl)oxy)-3-pyridinyl)phenyl)methyl)ethanamine

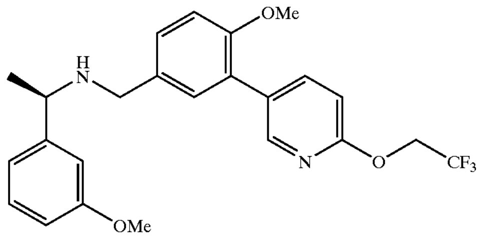

MW 446.466 Mass found: 447, 296.

EXAMPLE 433

(1R)-N-((4-(methyloxy)-3-(6-((2,2,2-trifluoroethyl)oxy)-3-pyridinyl)phenyl)methyl)-1-phenylethanamine

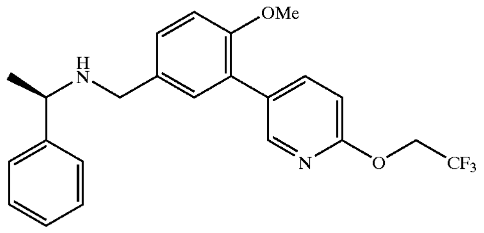

MW 416.441 Mass found: 417, 296.

EXAMPLE 434

(1R)-N-((4-chloro-3-(3-pyridinyl)phenyl)methyl)-1-phenylethanamine

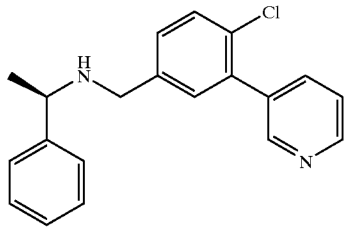

MW 322.837 Mass found: 323, 219, 645.

EXAMPLE 435

(1R)-N-((4-chloro-3-(3-pyridinyl)phenyl)methyl)-1-(1-naphthalenyl)ethanamine

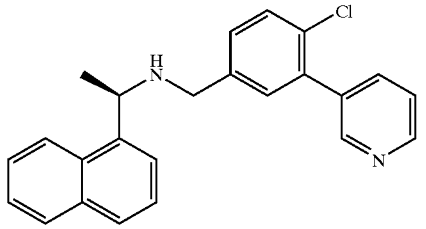

MW 372.897 Mass found: 155, 373, 219.

EXAMPLE 436

(1R)-N-((4-chloro-3-(3-pyridinyl)phenyl)methyl)-1-(3-(methyloxy)phenyl)ethanamine

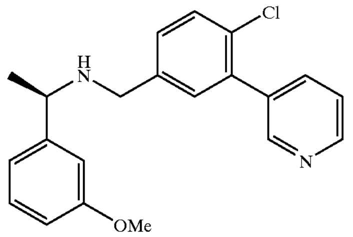

MW 352.863 Mass found: 353, 219.

EXAMPLE 437

(1R)-N-((3-(1-methyl-1H-benzimidazol-5-yl)-4-(methyloxy)phenyl)methyl)-1-(3-(methyloxy)phenyl)ethanamine

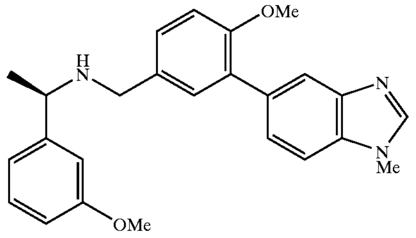

MW 401.507 Mass found: 402, 251, 268.

EXAMPLE 438

(1R)-N-((3-(1-methyl-1H-benzimidazol-5-yl)-4-(methyloxy)phenyl)methyl)-1-(1-naphthalenyl)ethanamine

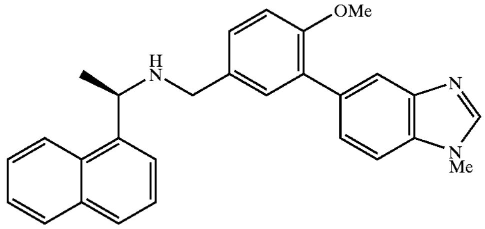

MW 421.541 Mass found: 155, 422, 251, 268.

EXAMPLE 439

(1R)-N-((3-(1-methyl-1H-indol-6-yl)-4-(methyloxy)phenyl)methyl)-1-phenylethanamine

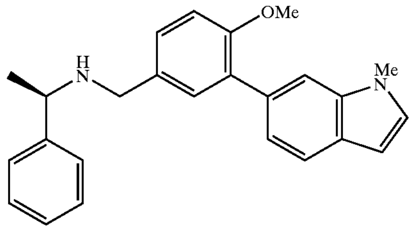

MW 370.493 Mass found: 250, 371.

EXAMPLE 440

(1R)-N-((3-(1-methyl-1H-indol-6-yl)-4-(methyloxy)phenyl)methyl)-1-(3-(methyloxy)phenyl)ethanamine

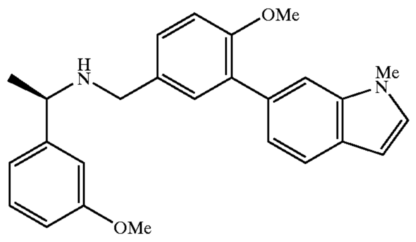

MW 400.519 Mass found: 401, 250.

EXAMPLE 441

(1R)-N-((3-(1-methyl-1H-indol-6-yl)-4-(methyloxy)phenyl)methyl)-1-(1-naphthalenyl)ethanamine

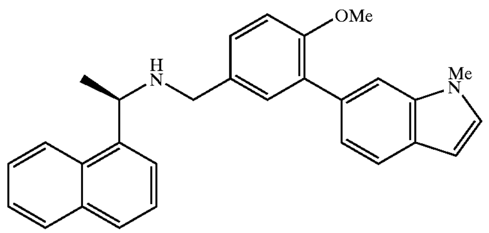

MW 420.553 Mass found: 421, 250.

EXAMPLE 442

(1R)-1-(3-(methyloxy)phenyl)-N-((4-(methyloxy)-3-(6-(trifluoromethyl)-3-pyridinyl)phenyl)methyl)ethanamine

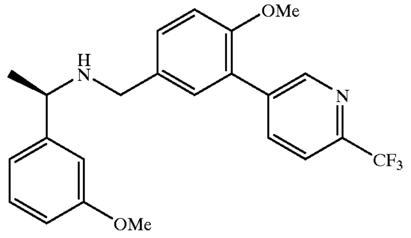

MW 416.441 Mass found: 417, 947.

EXAMPLE 443

(1R)-N-((4-(methyloxy)-3-(6-(trifluoromethyl)-3-pyridinyl)phenyl)methyl)-1-phenylethanamine

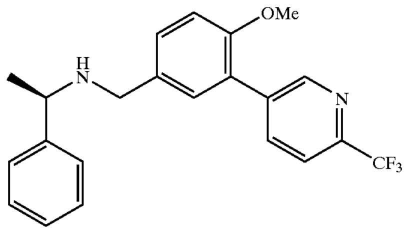

MW 386.415 Mass found: 887, 387, 428.

EXAMPLE 444

(1R)-N-((3-(2-ethyl-2H-1,2,3-benzotriazol-5-yl)-4-(methyloxy)phenyl)methyl)-1-phenylethanamine

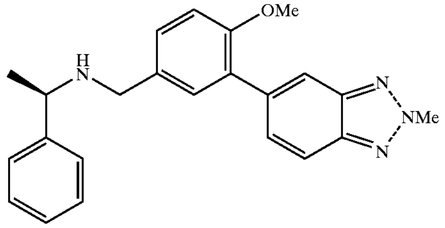

MW 386.496 Mass found: 887, 387.

EXAMPLE 445

N-1,N-1-dimethyl-N-2-(4-((((1R)-1-(3-(methyloxy)phenyl)ethyl)amino)methyl)phenyl)-N-2-phenyl-1,2-ethanediamine

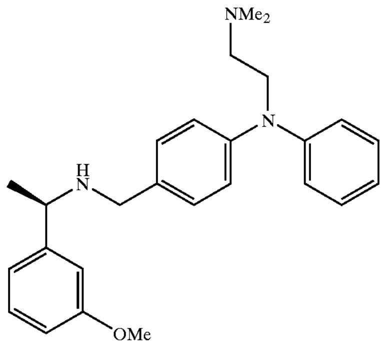

MW 403.567 Mass found: 253, 404.

EXAMPLE 446

N-1,N-1-dimethyl-N-2-(4-((((1R)-1-(1-naphthalenyl)ethyl)amino)methyl)phenyl)-N-2-phenyl-1,2-ethanediamine

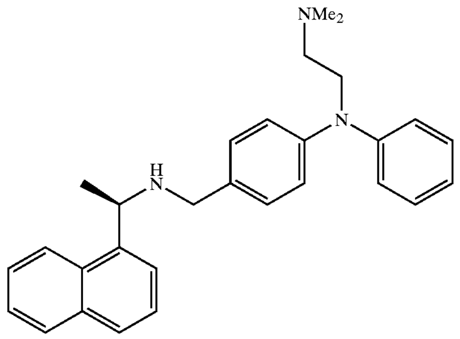

MW 423.601 Mass found: 253, 424.

EXAMPLE 447

(1R)-N-((3',6-bis(methyloxy)-1,1'-biphenyl-3-yl)methyl)-1-(1-naphthalenyl)ethanamine

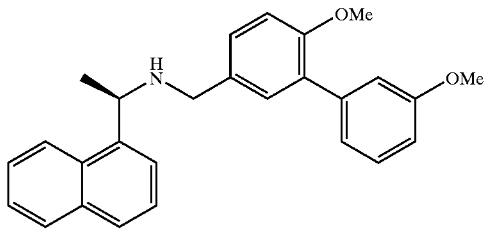

MW 397.515 Mass found: 398.

EXAMPLE 448

(1R)-N-((3',6-bis(methyloxy)-1,1'-biphenyl-3-yl)methyl)-1-(3-(methyloxy)phenyl)ethanamine

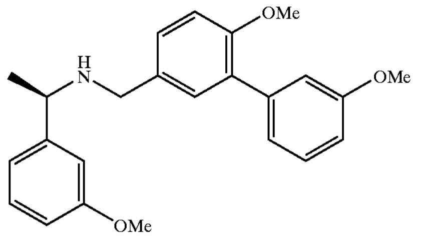

MW 377.481 Mass found: 378.

EXAMPLE 449

(1R)-N-((3',6-bis(methyloxy)-1,1'-biphenyl-3-yl)methyl)-1-phenylethanamine

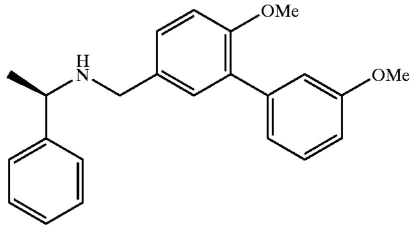

MW 347.456 Mass found: 348.

EXAMPLE 450

(1R)-N-((4',6-bis(methyloxy)-1,1'-biphenyl-3-yl)methyl)-1-phenyl-1-propanamine

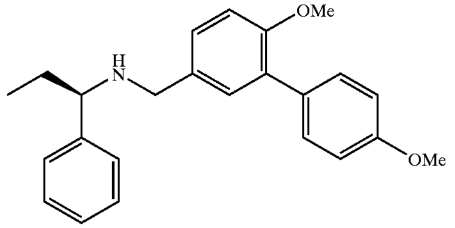

MW 361.482 Mass found: MS(EI) calcd for $C_{24}H_{27}NO_2$ 362 (MH+), Found: 362, 227, 212.

EXAMPLE 451

(1R)-N-((4-methyl-3-(3-pyridinyl)phenyl)methyl)-1-phenylethanamine

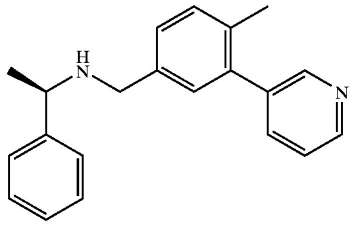

MW 302.419 Mass found: MS(EI) calcd for $C_{21}H_{22}N_2$ 303 (MH+) Found: 303, 199,183.

Examples 452–465 were prepared using Method A:

EXAMPLE 452

(1R)-N-((3-(3-methyl-1,2,4-oxadiazol-5-yl)phenyl)methyl)-1-(3-(methyloxy)phenyl)ethanamine

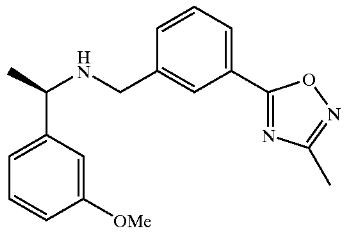

MW 323.394 Mass found: 324, 231, 190.

EXAMPLE 453

(1R)-N-((3-(3-methyl-1,2,4-oxadiazol-5-yl)phenyl)methyl)-1-phenylethanamine

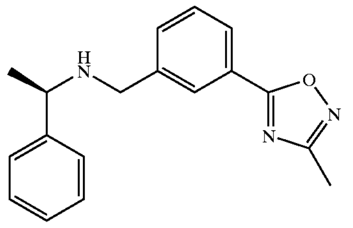

MW 293.368 Mass found: 294, 231, 190.

EXAMPLE 454

(1R)-N-((4-(methyloxy)-3-(6-(methyloxy)-3-pyridinyl)phenyl)methyl)-1-(1-naphthalenyl)ethanamine

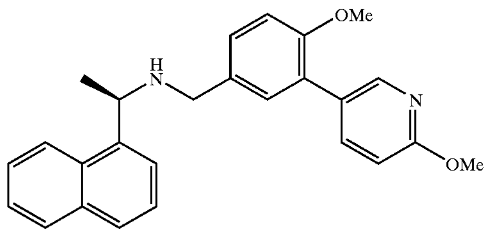

MW 398.503 Mass found: 399, 155, 245, 228.

EXAMPLE 455

(1R)-N-((4-(methyloxy)-3-(6-(methyloxy)-3-pyridinyl)phenyl)methyl)-1-(3-(methyloxy)phenyl)ethanamine

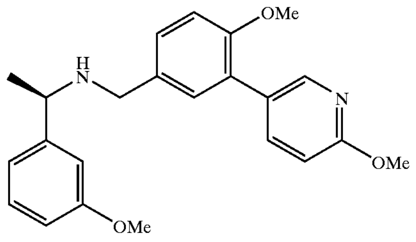

MW 378.469 Mass found: 379.

EXAMPLE 456

(1R)-N-((4',6-difluoro-1,1'-biphenyl-3-yl)methyl)-1-(3-(methyloxy)phenyl)ethanamine

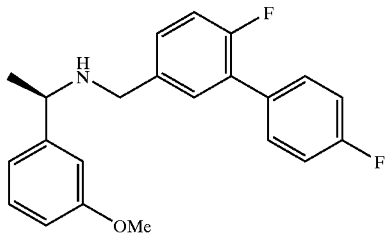

MW 353.41 Mass found: 354.

EXAMPLE 457

5-(2-(methyloxy)-5-((((1R)-1-(4-methylphenyl)ethyl)amino)methyl)phenyl)-2-pyrimidinamine

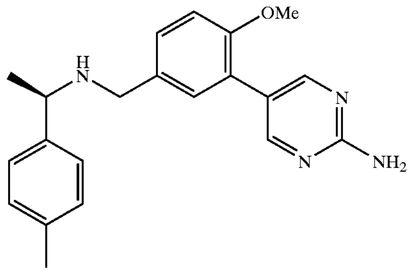

MW 348.448 Mass found: 214, 349, 231.

EXAMPLE 458

5-(2-(methyloxy)-5-((((1R)-1-(2-naphthalenyl)ethyl) amino)methyl)phenyl)-2-pyrimidinamine

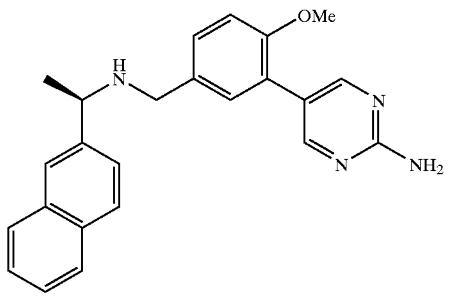

MW 384.481 Mass found: 155, 385, 231.

EXAMPLE 459

5-(3-((((1R)-1-(3-(methyloxy)phenyl)ethyl)amino) methyl)phenyl)-3-pyridinecarboxamide

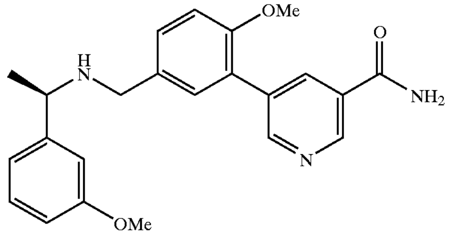

MW 361.443 Mass found: 362, 228.

EXAMPLE 460

5-(3-((((1R)-1-(1-naphthalenyl)ethyl)amino)methyl) phenyl)-3-pyridinecarboxamide

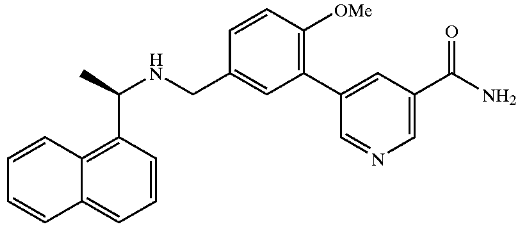

MW 381.477 Mass found: 155, 382, 228.

EXAMPLE 461

5-(3-((((1R)-1-(2-naphthalenyl)ethyl)amino)methyl) phenyl)-3-pyridinecarboxamide

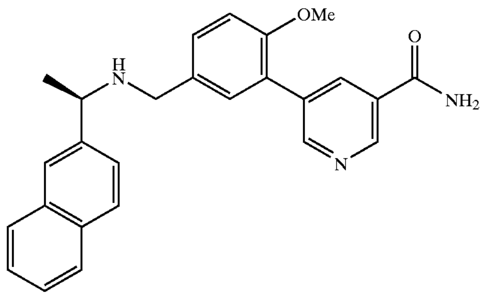

MW 381.477 Mass found: 155, 382, 228.

EXAMPLE 462

(1R)-N-((6-fluoro-4'-(methyloxy)-1,1'-biphenyl-3-yl) methyl)-1-(3-(methyloxy)phenyl)ethanamine

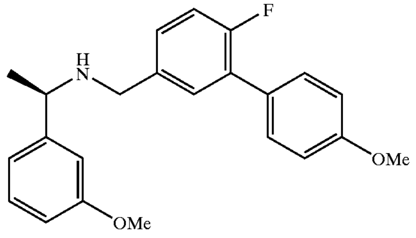

MW 365.446 Mass found: 366, 215.

EXAMPLE 463

(1R)-N-((6-fluoro-4'-(methyloxy)-1,1'-biphenyl-3-yl) methyl)-1-(4-(methyloxy)phenyl)ethanamine

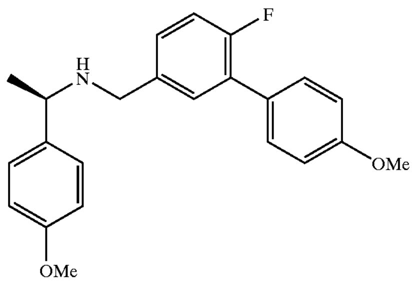

MW 365.446 Mass found: 366, 215.

EXAMPLE 464
(1R)-N-((6-fluoro-4'-(methyloxy)-1,1'-biphenyl-3-yl) methyl)-1-(4-methylphenyl)ethanamine
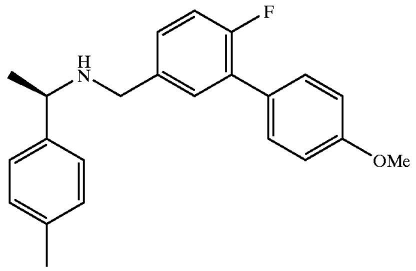
MW 349.447 Mass found: 350, 215.
EXAMPLE 465
(1R)-N-((6-fluoro-4'-(methyloxy)-1,1'-biphenyl-3-yl) methyl)-1-phenylethanamine
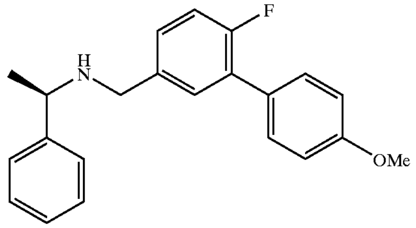
MW 335.42 Mass found: 336, 215.
The following compounds were prepared using Synthetic Method C:
| Example No: | Structure |
|---|---|
| 466 | 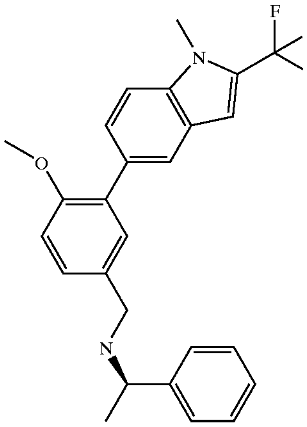 |
-continued
| Example No: | Structure |
|---|---|
| 467 | 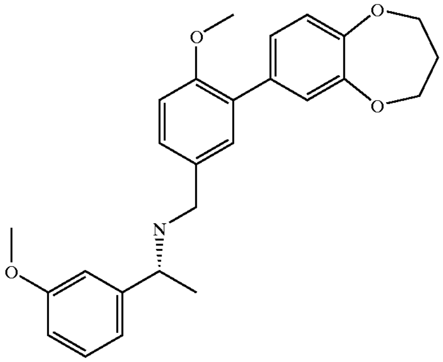 |
| 468 | 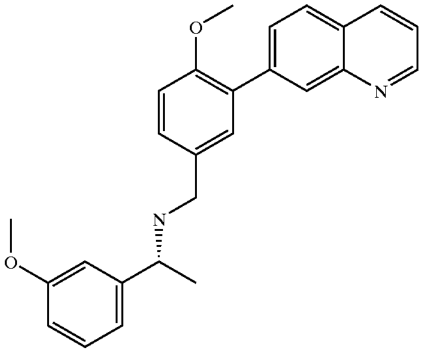 |
| 469 | 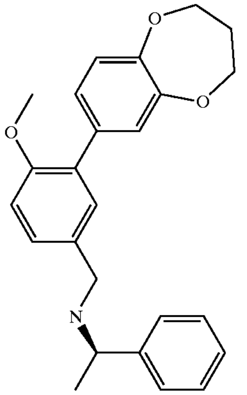 |
| 470 | 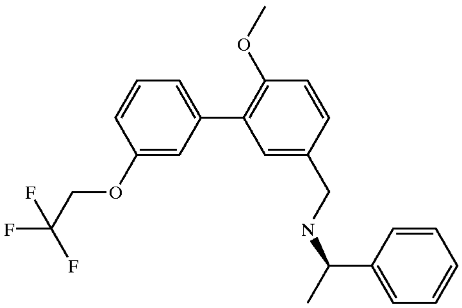 |

-continued
| Example No: | Structure |
| --- | --- |
| 471 | 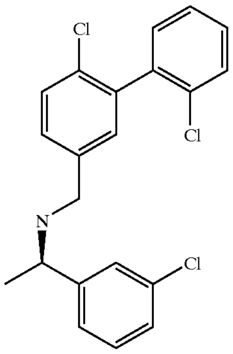 |
| 472 | 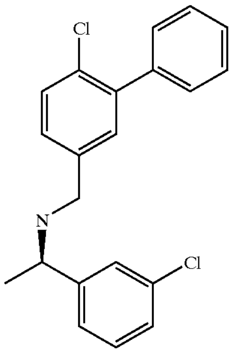 |
| 473 | 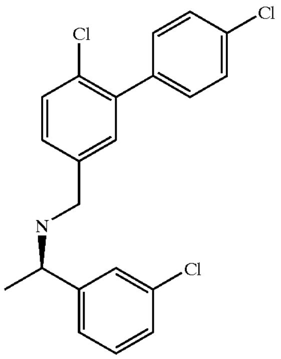 |
| 474 | 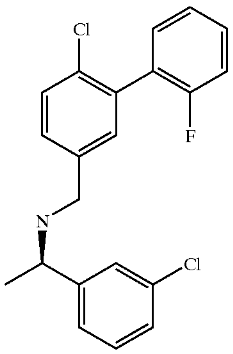 |
-continued
| Example No: | Structure |
| --- | --- |
| 475 | 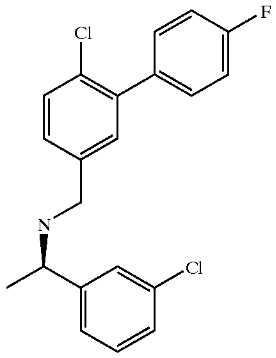 |
| 476 | 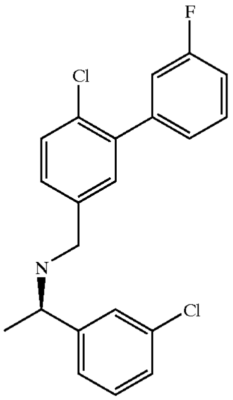 |
| 477 | 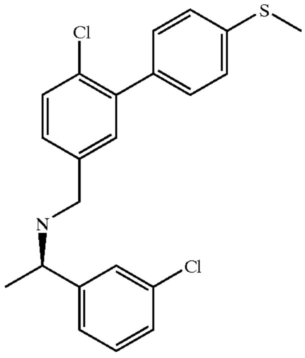 |
| 478 | 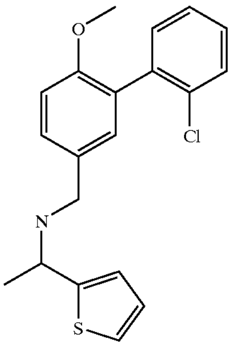 |

-continued

| Example No: | Structure |
| --- | --- |
| 479 | 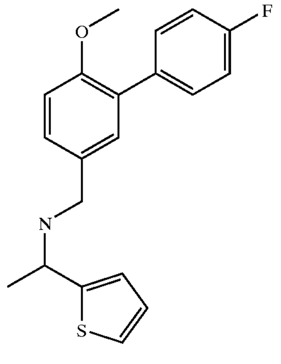 |
| 480 | 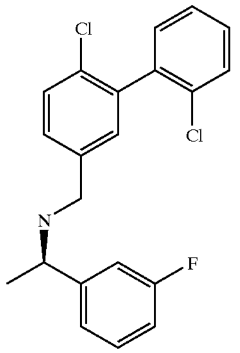 |
| 481 | 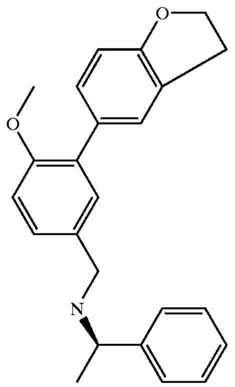 |
| 482 | 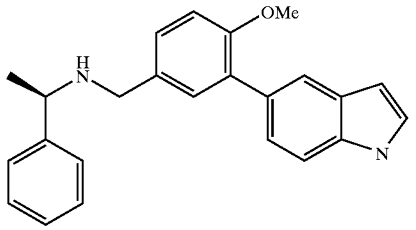 |

Biological Activity

The activities of the compounds of the present invention on calcium receptors were measured. In one embodiment, the measurement was performed in accordance with the method described in Example 4 of Nemeth et al., PCT/US95/13704 (International Publication No. WO96/12697) herein incorporated by reference.

A 4.0-kb NotI-HindIII fragment of the human parathyroid cell $Ca^{2+}$ receptor (hPCaR) cDNA was subcloned into the mammalian expression vector pCEP4 (Invitrogen) containing the hygromycin-resistant gene as a selectable marker. This plasmid was transfected into HEK 293 cells by calcium phosphate precipitation. Transfected cells were grown in Dulbecco's modified Eagle's medium containing 10% fetal bovine serum and hygromycin (200 $\mu$g/mL). Hygromycin-resistant colonies were subcloned and assayed for hPCaR mRNA by solution hybridization using a $^{32}$P-labeled RNA probe complementary to the (4.0 kb) hPCaR sequence (Garrett, et al., J. Biol. Chem. 270, 12919–12925 (1995)). Clone 7 was used to assess the effects of compounds on $[Ca^{2+}]_i$. This stably transfected cell line is termed HEK 293 4.0–7. For measurements of $[Ca^{2+}]_i$, the cells were recovered from tissue culture flasks by brief treatment with 0.02% EDTA and then washed and resuspended in PCB containing 1 mM $CaCl_2$ and 0.1% Bovine Serum Albumin ("BSA"). The cells were loaded with fluo-3 by incubation for 30 min at 37° C., with parathyroid cell buffer (126 mM NaCl, 4 mM KCl, 1 mM $MgSO_4$, 0.7 mM $K_2HPO/KH_2PO_4$, 20 mM HEPES.NaOH (pH 7.45)) containing 0.5% BSA in lmM $CaCl_2$ and 2 $\mu$M fluo-3 acetoxymethyl ester. The cells were subsequently washed, each test compound was added to the cells and the fluorescence was recorded by using excitation and emission wavelengths of 485 and 530 nm, respectively.

The following compounds of the invention were tested according to the procedure described above and found to have an EC50 of 10 $\mu$M or less:

(1R)-N-((6-(methyloxy)-4'-(trifluoromethyl)-1,1'-biphenyl-3-yl)methyl)-1-phenylethanamine;

(1R)-N-((4-(methyloxy)-3-(6-((2,2,2-trifluoroethyl)oxy)-3-pyridinyl)phenyl)methyl)-1-(1-naphthalenyl)ethanamine;

(1R)-N-((6-(methyloxy)-4'-((trifluoromethyl)oxy)-1,1'-biphenyl-3-yl)methyl)-1-phenylethanamine;

(1R)-N-((4-(methyloxy)-3-(6-(trifluoromethyl)-3-pyridinyl)phenyl)methyl)-1-(1-1-naphthalenyl)ethanamine;

(1R)-N-((4-(methyloxy)-3-(3-pyridinyl)phenyl)methyl)-1-(1-naphthalenyl)ethanamine;

(1R)-N-((6-(ethyloxy)-4'-(methyloxy)-1,1'-biphenyl-3-yl)methyl)-1-phenylethanamine;

(1R)-1-(3-chlorophenyl)-N-((6-(methyloxy)-4'-(trifluoromethyl)-1,1'-biphenyl-3-yl)methyl)ethanamine;

(1R)-1-(3-fluorophenyl)-N-((6-(methyloxy)-4'-(trifluoromethyl)-1,1'-biphenyl-3-yl)methyl)ethanamine (1R)-N-((6-(methyloxy)-4'-((trifluoromethyl)oxy)-1,1'-biphenyl-3-yl)methyl)-1-(1-naphthalenyl)ethanamine;

(1R)-1-(3-(methyloxy)phenyl)-N-((4-(methyloxy)-3-(3-pyridinyl)phenyl)methyl)ethanamine;

(1R)-1-(3-(methyloxy)phenyl)-N-((3-(1,3-thiazol-2-yl)phenyl)methyl)ethanamine;

(1R)-N-((4-(methyloxy)-3-(3-pyridinyl)phenyl)methyl)-1-(4-methylphenyl)ethanamine;

(1R)-1-(4-(methyloxy)phenyl)-N-((4-(methyloxy)-3-(3-pyridinyl)phenyl)methyl)ethanamine;

(1R)-N-((3-(1,3-benzodioxol-5-yl)phenyl)methyl)-1-phenylethanamine;

(1R)-N-((3-(1,3-benzodioxol-5-yl)phenyl)methyl)-1-(4-methylphenyl)ethanamine;

(1R)-N-((3-(1,3-benzodioxol-5-yl)phenyl)methyl)-1-(4-(methyloxy)phenyl)ethanamine;

(1R)-N-((3-(1,3-benzodioxol-5-yl)phenyl)methyl)-1-(4-(methyloxy)phenyl)ethanamine;

2'-(methyloxy)-5'-((((1R)-1-(1-naphthalenyl)ethyl)amino)methyl)-1,1'-biphenyl-3-carbonitrile;

2'-(methyloxy)-5'-((((1R)-1-phenylethyl)amino)methyl)-1,1'-biphenyl-3-carbonitrile;

2'-(methyloxy)-5'-((((1R)-1-(4-methylphenyl)ethyl)amino)methyl)-1,1'-biphenyl-3-carbonitrile;

2'-(methyloxy)-5'-((((1R)-1-(4-(methyloxy)phenyl)ethyl)amino)methyl)-1,1'-biphenyl-3-carbonitrile;

2'-(methyloxy)-5'-((((1R)-1-(3-(methyloxy)phenyl)ethyl)amino)methyl)-1,1'-biphenyl-3-carbonitrile;

(1R)-N-((4-(methyloxy)-3-(2-pyrimidinyl)phenyl)methyl)-1-(1-naphthalenyl)ethanamine;

(1R)-N-((4-(methyloxy)-3-(2-pyrimidinyl)phenyl)methyl)-1-phenylethanamine;

(1R)-1-(3-(methyloxy)phenyl)-N-((4-(methyloxy)-3-(2-pyrimidinyl)phenyl)methyl)ethanamine;

(1R)-N-((3'-(methyloxy)-1,1'-biphenyl-3-yl)methyl)-1-phenylethanamine;

(1R)-N-((3'-(methyloxy)-1,1'-biphenyl-3-yl)methyl)-1-(4-methylphenyl)ethanamine;

(1R)-N-((3'-(methyloxy)-1,1'-biphenyl-3-yl)methyl)-1-(4-(methyloxy)phenyl)ethanamine;

(1R)-N-((3'-(methyloxy)-1,1'-biphenyl-3-yl)methyl)-1-(3-(methyloxy)phenyl)ethanamine;

(1R)-N-((2'-methyl-1,1'-biphenyl-3-yl)methyl)-1-(4-methylphenyl)ethanamine;

(1R)-N-((2'-methyl-1,1'-biphenyl-3-yl)methyl)-1-(4-(methyloxy)phenyl)ethanamine;

(1R)-N-((2'-fluoro-1,1'-biphenyl-3-yl)methyl)-1-(4-methylphenyl)ethanamine;

(1R)-N-((2'-fluoro-1,1'-biphenyl-3-yl)methyl)-1-(4-(methyloxy)phenyl)ethanamine;

(1R)-N-((2'-fluoro-1,1'-biphenyl-3-yl)methyl)-1-(3-(methyloxy)phenyl)ethanamine;

5-(2-(methyloxy)-5-((((1R)-1-(3-(methyloxy)phenyl)ethyl)amino)methyl)phenyl)-2-furancarboxylic acid;

4-oxo-4-((5-(3-((((1R)-1-phenylethyl)amino)methyl)phenyl)-2-pyridinyl)amino)butanoic acid;

4-((5-(3-((((1R)-1-(4-(methyloxy)phenyl)ethyl)amino)methyl)phenyl)-2-pyridinyl)amino)-4-oxobutanoic acid;

(1R)-N-((3-(6-(methyloxy)-3-pyridazinyl)phenyl)methyl)-1-(1-naphthalenyl)ethanamine;

(1R)-N-((3-(1H-indol-5-yl)-4-(methyloxy)phenyl)methyl)-1-(4-(methyloxy)phenyl)ethanamine;

(1R)-N-((3-(1H-indol-5-yl)-4-(methyloxy)phenyl)methyl)-1-(3-(methyloxy)phenyl)ethanamine;

(1R)-N-((3-(1H-indol-5-yl)-4-(methyloxy)phenyl)methyl)-1-(2-naphthalenyl)ethanamine;

(1R)-N-((3-(6-(methyloxy)-3-pyridazinyl)phenyl)methyl)-1-phenylethanamine;

(1R)-1-(4-(methyloxy)phenyl)-N-((3-(6-(methyloxy)-3-pyridazinyl)phenyl)methyl)ethanamine;

(1R)-1-(3-(methyloxy)phenyl)-N-((3-(6-(methyloxy)-3-pyridazinyl)phenyl)methyl)ethanamine;

(1R)-N-((4'-(methyloxy)-1,1'-biphenyl-3-yl)methyl)-1-(2-naphthalenyl)ethanamine;

(1R)-N-((4'-(methyloxy)-1,1'-biphenyl-3-yl)methyl)-1-(1-naphthalenyl)ethanamine;

(1R)-N-((4'-(methyloxy)-1,1'-biphenyl-3-yl)methyl)-1-(4-(methyloxy)phenyl)ethanamine;

(1R)-N-((4'-(methyloxy)-1,1'-biphenyl-3-yl)methyl)-1-(3-(methyloxy)phenyl)ethanamine;

(1R)-1-phenyl-N-((3-(2-pyrazinyl)phenyl)methyl)ethanamine;

(1R)-1-(4-(methyloxy)phenyl)-N-((3-(2-pyrazinyl)phenyl)methyl)ethanamine;

(1R)-1-(3-(methyloxy)phenyl)-N-((3-(2-pyrazinyl)phenyl)methyl)ethanamine;

(1R)-1-(2-naphthalenyl)-N-((3-(2-pyridinyl)phenyl)methyl)ethanamine;

(1R)-1-phenyl-N-((3-(2-pyridinyl)phenyl)methyl)ethanamine;

(1R)-1-(1-naphthalenyl)-N-((3-(2-pyridinyl)phenyl)methyl)ethanamine;

(1R)-1-(4-methylphenyl)-N-((3-(2-pyridinyl)phenyl)methyl)ethanamine;

(1R)-1-(4-(methyloxy)phenyl)-N-((3-(2-pyridinyl)phenyl)methyl)ethanamine;

(1R)-1-(3-(methyloxy)phenyl)-N-((3-(2-pyridinyl)phenyl)methyl)ethanamine;

(1R)-N-((3-(6-methyl-3-pyridinyl)phenyl)methyl)-1-(2-naphthalenyl)ethanamine;

(1R)-N-((3-(6-methyl-3-pyridinyl)phenyl)methyl)-1-phenylethanamine;

(1R)-N-((3-(6-methyl-3-pyridinyl)phenyl)methyl)-1-(1-naphthalenyl)ethanamine;

(1R)-1-(4-methylphenyl)-N-((3-(6-methyl-3-pyridinyl)phenyl)methyl)ethanamine;

(1R)-1-(4-(methyloxy)phenyl)-N-((3-(6-methyl-3-yridinyl)phenyl)methyl)ethanamine;

(1R)-1-(3-(methyloxy)phenyl)-N-((3-(6-methyl-3yridinyl)phenyl)methyl)ethanamine;

(1R)-N-((4-(methyloxy)-3-(3-thienyl)phenyl)methyl)-1-(2-naphthalenyl)ethanamine;

(1R)-N-((4-(methyloxy)-3-(3-thienyl)phenyl)methyl)-1-phenylethanamine;

(1R)-N-((4-(methyloxy)-3-(3-thienyl)phenyl)methyl)-1-(1-naphthalenyl)ethanamine;

(1R)-N-((4-(methyloxy)-3-(3-thienyl)phenyl)methyl)-1-(4-methylphenyl)ethanamine;

(1R)-1-(4-(methyloxy)phenyl)-N-((4-(methyloxy)-3-(3-thienyl)phenyl)methyl)ethanamine;

(1R)-1-(3-(methyloxy)phenyl)-N-((4-(methyloxy)-3-(3-thienyl)phenyl)methyl)ethanamine;

(1R)-N-((4-(methyloxy)-3-(5-pyrimidinyl)phenyl)methyl)-1-phenylethanamine;

(1R)-N-((4-(methyloxy)-3-(5-pyrimidinyl)phenyl)methyl)-1-(4-methylphenyl)ethanamine;

(1R)-1-(4-(methyloxy)phenyl)-N-((4-(methyloxy)-3-(5-pyrimidinyl)phenyl)methyl)ethanamine;

(1R)-1-(3-(methyloxy)phenyl)-N-((4-(methyloxy)-3-(5-pyrimidinyl)phenyl)methyl)ethanamine;

(1R)-N-((4'-fluoro-1,1'-biphenyl-3-yl)methyl)-1-phenylethanamine;

N-(3'-((((1R)-1-phenylethyl)amino)methyl)-1,1'-biphenyl-3-yl)acetamide;

N-(3'-((((1R)-1-(1-naphthalenyl)ethyl)amino)methyl)-1,1'-biphenyl-3-yl)acetamide;

N-(3'-((((1R)-1-(3-(methyloxy)phenyl)ethyl)amino)methyl)-1,1'-biphenyl-3-yl)acetamide;

(1R)-N-((4'-fluoro-1,1'-biphenyl-3-yl)methyl)-1-(4-methylphenyl)ethanamine;

(1R)-N-((4'-fluoro-1,1'-biphenyl-3-yl)methyl)-1-(3-(methyloxy)phenyl)ethanamine;

(1R)-1-(3-(methyloxy)phenyl)-N-((3-(5-pyrimidinyl)phenyl)methyl)ethanamine;

(1R)-N-((4-(methyloxy)-3-(1,3-thiazol-2-yl)phenyl)methyl)-1-(2-naphthalenyl)ethanamine;

(1R)-N-((4-(methyloxy)-3-(1,3-thiazol-2-yl)phenyl)methyl)-1-phenylethanamine;

(1R)-N-((4-(methyloxy)-3-(1,3-thiazol-2-yl)phenyl)methyl)-1-(1-naphthalenyl)ethanamine;

(1R)-N-((4-(methyloxy)-3-(1,3-thiazol-2-yl)phenyl)methyl)-1-(4-methylphenyl)ethanamine;

(1R)-1-(4-(methyloxy)phenyl)-N-((4-(methyloxy)-3-(1,3-thiazol-2-yl)phenyl)methyl)ethanamine;

(1R)-1-(3-(methyloxy)phenyl)-N-((4-(methyloxy)-3-(1,3-thiazol-2-yl)phenyl)methyl)ethanamine;

(1R)-N-((3',4'-dimethyl-1,1'-biphenyl-3-yl)methyl)-1-(4-methylphenyl)ethanamine;

(1R)-N-((6-(methyloxy)-1,1'-biphenyl-3-yl)methyl)-1-(4-methylphenyl)ethanamine;

(1R)-N-((6-(methyloxy)-1,1'-biphenyl-3-yl)methyl)-1-(4-(methyloxy)phenyl)ethanamine;
(1R)-N-((6-(methyloxy)-1,1'-biphenyl-3-yl)methyl)-1-(3-(methyloxy)phenyl)ethanamine;
(1R)-N-((4'-fluoro-6-(methyloxy)-1,1'-biphenyl-3-yl)methyl)-1-(4-methylphenyl)ethanamine;
(1R)-N-((4'-fluoro-6-(methyloxy)-1,1'-biphenyl-3-yl)methyl)-1-(4-(methyloxy)phenyl)ethanamine;
(1R)-1-(1-naphthalenyl)-N-((3-(1,3-thiazol-2-yl)phenyl)methyl)ethanamine;
(1R)-1-phenyl-N-((3-(1,3-thiazol-2-yl)phenyl)methyl)ethanamine;
(1R)-1-phenyl-N-((4-(1-pyrrolidinyl)phenyl)methyl)ethanamine;
(1R)-N-((4-(3,5-dimethyl-4-isoxazolyl)phenyl)methyl)-1-(1-naphthalenyl)ethanamine;
5-(2-(methyloxy)-5-((((1R)-1-(4-methylphenyl)ethyl)amino)methyl)phenyl)-3-pyridinecarboxamide;
(1R)-N-((3-(3-furanyl)phenyl)methyl)-1-(3-(methyloxy)phenyl)ethanamine;
(1R)-N-((3-(3-furanyl)phenyl)methyl)-1-(4-(methyloxy)phenyl)ethanamine;
(1R)-N-((3-(3-furanyl)phenyl)methyl)-1-(4-methylphenyl)ethanamine;
(1R)-N-((3-(3-furanyl)phenyl)methyl)-1-(1-naphthalenyl)ethanamine;
(1R)-N-((3-(3-furanyl)phenyl)methyl)-1-phenylethanamine;
5-(2-(methyloxy)-5-((((1R)-1-(1-naphthalenyl)ethyl)amino)methyl)phenyl)-3-pyridinecarboxamide;
(1R)-N-((4-(methyloxy)-3-(6-(methyloxy)-3-pyridazinyl)phenyl)methyl)-1-(3-(methyloxy)phenyl)ethanamine;
(1R)-N-((4-(methyloxy)-3-(6-(methyloxy)-3-pyridazinyl)phenyl)methyl)-1-(4-(methyloxy)phenyl)ethanamine;
(1R)-N-((4-(methyloxy)-3-(6-(methyloxy)-3-pyridazinyl)phenyl)methyl)-1-phenylethanamine;
(1R)-N-((4-(methyloxy)-3-(6-(methyloxy)-3-pyridazinyl)phenyl)methyl)-1-(2-naphthalenyl)ethanamine;
5-(2-(methyloxy)-5-((((1R)-1-phenylethyl)amino)methyl)phenyl)-3-pyridinecarboxamide;
(1R)-1-(3-(methyloxy)phenyl)-N-((4-(methyloxy)-3-(2-pyrazinyl)phenyl)methyl)ethanamine;
(1R)-1-(4-(methyloxy)phenyl)-N-((4-(methyloxy)-3-(2-pyrazinyl)phenyl)methyl)ethanamine;
(1R)-N-((4-(methyloxy)-3-(2-pyrazinyl)phenyl)methyl)-1-(4-methylphenyl)ethanamine;
(1R)-N-((4-(methyloxy)-3-(2-pyrazinyl)phenyl)methyl)-1-(1-naphthalenyl)ethanamine;
(1R)-N-((4-(methyloxy)-3-(2-pyrazinyl)phenyl)methyl)-1-phenylethanamine;
5-(2-(methyloxy)-5-((((1R)-1-(2-naphthalenyl)ethyl)amino)methyl)phenyl)-3-pyridinecarboxamide;
(1R)-N-((4-(methyloxy)-3-(2-pyrazinyl)phenyl)methyl)-1-(2-naphthalenyl)ethanamine;
(1R)-1-(4-methylphenyl)-N-((3-(9-methyl-9H-purin-6-yl)phenyl)methyl)ethanamine;
(1R)-N-((6-(methyloxy)-4'-(methylsulfonyl)-1,1'-biphenyl-3-yl)methyl)-1-(3-(methyloxy)phenyl)ethanamine;
(1R)-N-((6-(methyloxy)-4'-(methylsulfonyl)-1,1'-biphenyl-3-yl)methyl)-1-phenylethanamine;
N-(5-(3-((((1R)-1-(3-(methyloxy)phenyl)ethyl)amino)methyl)phenyl)-2-pyridinyl)acetamide;
N-(5-(3-((((1R)-1-(1-naphthalenyl)ethyl)amino)methyl)phenyl)-2-pyridinyl)acetamide;
N-(5-(3-((((1R)-1-phenylethyl)amino)methyl)phenyl)-2-pyridinyl)acetamide;
(1R)-N-((4',6-difluoro-1,1'-biphenyl-3-yl)methyl)-1-phenylethanamine;

(1R)-N-((4',6-difluoro-1,1'-biphenyl-3-yl)methyl)-1-(4-(methyloxy)phenyl)ethanamine;
(1R)-N-((2',6-bis(methyloxy)-1,1'-biphenyl-3-yl)methyl)-1-phenylethanamine;
(1R)-N-((3-(2-methyl-1,3-benzoxazol-5-yl)-4-(methyloxy)phenyl)methyl)-1-(3-(methyloxy)phenylethanamine;
(1R)-N-((3-(2-methyl-1,3-benzoxazol-5-yl)-4-(methyloxy)phenyl)methyl)-1-(1-naphthalenyl)ethanamine;
(1R)-N-((3-(2-methyl-1,3-benzoxazol-5-yl)-4-(methyloxy)phenyl)methyl)-1-phenylethanamine;
N-(4'-(methyloxy)-5-((((1R)-1-(1-naphthalenyl)ethyl)amino)methyl)-1,1'-biphenyl-2-yl)methanesulfonamide;
N-ethyl-N'-(4'-(methyloxy)-5-((((1R)-1-(1-naphthalenyl)ethyl)amino)methyl)-1,1'-biphenyl-2-yl)urea;
N-(4'-(methyloxy)-5-((((1R)-1-phenylethyl)amino)methyl)-1,1'-biphenyl-2-yl)methanesulfonamide;
(1R)-N-((3-(1,3-benzoxazol-5-yl)-4-(methyloxy)phenyl)methyl)-1-(1-naphthalenyl)ethanamine;
N-ethyl-N'-(4'-(methyloxy)-5-((((1R)-1-phenylethyl)amino)methyl)-1,1'-biphenyl-2-yl)urea;
(1R)-N-((4-(methyloxy)-3-(2-pyridinyl)phenyl)methyl)-1-(1-naphthalenyl)ethanamine;
N-ethyl-N'-(4'-(methyloxy)-5-((((1R)-1-(3-(methyloxy)phenyl)ethyl)amino)methyl)-1,1'-biphenyl-2-yl)urea;
(1R)-N-((3-(1,3-benzoxazol-5-yl)-4-(methyloxy)phenyl)methyl)-1-phenylethanamine;
N-(4'-(methyloxy)-5-((((1R)-1-(3-(methyloxy)phenyl)ethyl)amino)methyl)-1,1'-biphenyl-2-yl)methanesulfonamide;
(1R)-N-((4-(methyloxy)-3-(6-methyl-3-pyridinyl)phenyl)methyl)-1-(1-naphthalenyl)ethanamine;
(1R)-1-(3-(methyloxy)phenyl)-N-((4-(methyloxy)-3-(2-thienyl)phenyl)methyl)ethanamine;
(1R)-N-((4-(methyloxy)-3-(2-thienyl)phenyl)methyl)-1-(1-naphthalenyl)ethanamine;
(1R)-N-((4-(methyloxy)-3-(2-thienyl)phenyl)methyl)-1-phenylethanamine;
(1R)-N-((4-(methyloxy)-3-(1-methyl-2-(trifluoromethyl)-1H-benzimidazol-5-yl)phenyl)methyl)-1-phenylethanamine;
(1R)-N-((4-(methyloxy)-3-(1-methyl-2-(trifluoromethyl)-1H-benzimidazol-5-yl)phenyl)methyl)-1-(1-naphthalenyl)ethanamine;
(1R)-1-(3-(methyloxy)phenyl)-N-((6-(methyloxy)-4'-((trifluoromethyl)oxy)-1,1'-biphenyl-3-yl)methyl)ethanamine;
3-(2-(methyloxy)-5-((((1R)-1-phenylethyl)amino)methyl)phenyl)-N-(3-(4-morpholinyl)propyl)-2-pyridinamine;
(1R)-N-((4-(methyloxy)-3-(6-((tetrahydro-2-furanylmethyl)oxy)-3-pyridinyl)phenyl)methyl)-1-phenylethanamine;
3-(2-(methyloxy)-5-((((1R)-1-phenylethyl)amino)methyl)phenyl)-N-(tetrahydro-2-furanylmethyl)-2-pyridinamine;
5-(2-(methyloxy)-5-((((1R)-1-phenylethyl)amino)methyl)phenyl)-2-pyridinamine;
N,N-dimethyl-5-(2-(methyloxy)-5-((((1R)-1-phenylethyl)amino)methyl)phenyl)-2-pyridinamine;
(1R)-N-((4-(methyloxy)-3-(4-piperidinyl)phenyl)methyl)-1-(1-naphthalenyl)ethanamine;
2-(5-(2-(methyloxy)-5-((((1R)-1-(1-naphthalenyl)ethyl)amino)methyl)phenyl)-1H-indol-1-yl)acetamide;
2-(5-(2-(methyloxy)-5-((((1R)-1-(3-(methyloxy)phenyl)ethyl)amino)methyl)phenyl)-1H-indol-1-yl)acetamide;
2-(5-(2-(methyloxy)-5-((((1R)-1-phenylethyl)amino)methyl)phenyl)-1H-indol-1-yl)acetamide;
(1R)-N-((4-(methyloxy)-3-(2-(4-morpholinyl)-3-pyridinyl)phenyl)methyl)-1-phenylethanamine;
(1R)-N-((3-(2-fluoro-3-pyridinyl)-4-(methyloxy)phenyl)methyl)-1-phenylethanamine;

(1R)-N-((4-(methyloxy)-3-(2-((2,2,2-trifluoroethyl)oxy)-3-pyridinyl)phenyl)methyl)-1-phenylethanamine;
(1R)-N-((4-(methyloxy)-3-(2-((tetrahydro-2-furanylmethyl)oxy)-3-pyridinyl)phenyl)methyl)-1-phenylethanamine;
(1R)-N-((3-(1-(cyclopropylmethyl)-1H-indol-5-yl)-4-(methyloxy)phenyl)methyl)-1-(1-naphthalenyl)ethanamine;
(1R)-N-((3-(1-(cyclopropylmethyl)-1H-indol-5-yl)-4-(methyloxy)phenyl)methyl)-1-(3-(methyloxy)phenyl)ethanamine;
(1R)-N-((3-(1-(cyclopropylmethyl)-1H-indol-5-yl)-4-(methyloxy)phenyl)methyl)-1-phenylethanamine;
4-(2-(methyloxy)-5-((((1R)-1-phenylethyl)amino)methyl)phenyl)-1,3-thiazol-2-amine;
(1R)-N-((3-(1-methyl-1H-imidazol-4-yl)-4-(methyloxy)phenyl)methyl)-1-(1-naphthalenyl)ethanamine;
(1R)-N-((3-(1-methyl-1H-imidazol-4-yl)-4-(methyloxy)phenyl)methyl)-1-phenylethanamine;
N-((3-(6-((3-(diethylamino)propyl)oxy)-3-pyridinyl)-4-(methyloxy)phenyl)methyl)-N-((1R)-1-(3-(methyloxy)phenyl)ethyl)amine;
N-((3-(6-((3-(diethylamino)propyl)oxy)-3-pyridinyl)-4-(methyloxy)phenyl)methyl)-N-((1R)-1-(1-naphthalenyl)ethyl)amine;
(1R)-N-((4-(methyloxy)-3-(6-((2-(1-pyrrolidinyl)ethyl)oxy)-3-pyridinyl)phenyl)methyl)-1-(1-naphthalenyl)ethanamine;
(1R)-N-((4-(methyloxy)-3-(1-pyrrolidinyl)phenyl)methyl)-1-(1-naphthalenyl)ethanamine;
(1R)-N-((4-(methyloxy)-3-(1-pyrrolidinyl)phenyl)methyl)-1-phenylethanamine;
(1R)-N-((4-(methyloxy)-3-(6-((2-(1-pyrrolidinyl)ethyl)oxy)-3-pyridinyl)phenyl)methyl)-1-phenylethanamine;
(1R)-N-((3-(2-methyl-2H-imidazol-5-yl)-4-(methyloxy)phenyl)methyl)-1-phenylethanamine;
2'-(methyloxy)-5'-((((1R)-1-(3-(methyloxy)phenyl)ethyl)amino)methyl)-1,1'-biphenyl-4-carboxamide;
(1R)-N-((4-(methyloxy)-3-(1-methyl-4-piperidinyl)phenyl)methyl)-1-(3-(methyloxy)phenyl)ethanamine;
2'-(methyloxy)-5'-((((1R)-1-(1-naphthalenyl)ethyl)amino)methyl)-1,1'-biphenyl-4-carboxamide;
(1R)-N-((4-(methyloxy)-3-(1-methyl-4-piperidinyl)phenyl)methyl)-1-(1-naphthalenyl)ethanamine;
ethyl 2'-(methyloxy)-5'-((((1R)-1-(3-(methyloxy)phenyl)ethyl)amino)methyl)-1,1'-biphenyl-4-carboxylate;
ethyl 2'-(methyloxy)-5'-((((1R)-1-(1-naphthalenyl)ethyl)amino)methyl)-1,1'-biphenyl-4-carboxylate;
ethyl 2'-(methyloxy)-5'-((((1R)-1-phenylethyl)amino)methyl)-1,1'-biphenyl-4-carboxylate;
ethyl 4-(2-(methyloxy)-5-((((1R)-1-(1-naphthalenyl)ethyl)amino)methyl)phenyl)-1-piperidinecarboxylate;
ethyl 4-(2-(methyloxy)-5-((((1R)-1-(3-(methyloxy)phenyl)ethyl)amino)methyl)phenyl)-1-piperidinecarboxylate;
ethyl 4-(2-(methyloxy)-5-((((1R)-1-phenylethyl)amino)methyl)phenyl)-1-piperidinecarboxylate;
(1R)-N-((3-(2-methyl-1,3-oxazol-4-yl)-4-(methyloxy)phenyl)methyl)-1-(1-naphthalenyl)ethanamine;
(1R)-N-((3-(2-methyl-1,3-oxazol-4-yl)-4-(methyloxy)phenyl)methyl)-1-phenylethanamine;
2'-(methyloxy)-5'-((((1R)-1-phenylethyl)amino)methyl)-1,1'-biphenyl-4-carboxamide;
1-(2-(methyloxy)ethyl)-5-(2-(methyloxy)-5-((((1R)-1-(3-(methyloxy)phenyl)ethyl)amino)methyl)phenyl)-2-(1H)-pyridinone;
1-(2-(methyloxy)ethyl)-5-(2-(methyloxy)-5-((((1R)-1-(1-naphthalenyl)ethyl)amino)methyl)phenyl)-2(1H)-pyridinone;
(1R)-N-((6-(methyloxy)-4'-(methylsulfonyl)-1,1'-biphenyl-3-yl)methyl)-1-(1-naphthalenyl)ethanamine;
(1R)-N-((4',6-bis(trifluoromethyl)-1,1'-biphenyl-3-yl)methyl)-1-phenylethanamine;
N-((6-(methyloxy)-4'-(trifluoromethyl)-1,1'-biphenyl-3-yl)methyl)-1-(3-methylphenyl)ethanamine;
3-(1-(((6-(methyloxy)-4'-(trifluoromethyl)-1,1'-biphenyl-3-yl)methyl)amino)ethyl)benzonitrile;
(1R)-1-(3-((2-(methyloxy)ethyl)oxy)phenyl)-N-((6-(methyloxy)-4'-(trifluoromethyl)-1,1'-biphenyl-3-yl)methyl)ethanamine;
(1R)-N-((6-fluoro-4'-(trifluoromethyl)-1,1'-biphenyl-3-yl)methyl)-1-phenylethanamine;
(1R)-N-((4'-chloro-6-(methyloxy)-1,1'-biphenyl-3-yl)methyl)-1-(1-naphthalenyl)ethanamine;
N,N-dimethyl-2'-(methyloxy)-5'-((((1R)-1-(3-(methyloxy)phenyl)ethyl)amino)methyl)-1,1'-biphenyl-4-carboxamide;
N,N-dimethyl-2'-(methyloxy)-5'-((((1R)-1-(1-naphthalenyl)ethyl)amino)methyl)-1,1'-biphenyl-4-carboxamide;
N,N-dimethyl-2'-(methyloxy)-5'-((((1R)-1-phenylethyl)amino)methyl)-1,1'-biphenyl-4-carboxamide;
(1R)-N-((6-iodo-4'-(trifluoromethyl)-1,1'-biphenyl-3-yl)methyl)-1-(3-(methyloxy)phenyl)ethanamine;
(1R)-N-((6-iodo-4'-(trifluoromethyl)-1,1'-biphenyl-3-yl)methyl)-1-phenylethanamine;
(1R)-N-((6-iodo-4'-(trifluoromethyl)-1,1'-biphenyl-3-yl)methyl)-1-(1-naphthalenyl)ethanamine;
(1R)-N-((6-(methyloxy)-3'-((trifluoromethyl)oxy)-1,1'-biphenyl-3-yl)methyl)-1-(1-naphthalenyl)ethanamine;
(1R)-1-(3-(methyloxy)phenyl)-N-((6-(methyloxy)-3'-((trifluoromethyl)oxy)-1,1'-biphenyl-3-yl)methyl)ethanamine;
(1R)-N-((6-(methyloxy)-3'-((trifluoromethyl)oxy)-1,1'-biphenyl-3-yl)methyl)-1-phenylethanamine;
(1R)-N-((4'-chloro-6-(methyloxy)-1,1'-biphenyl-3-yl)methyl)-1-(3-(methyloxy)phenyl)ethanamine;
(1R)-1-(3-(methyloxy)phenyl)-N-((4-(methyloxy)-3-(2-((2,2,2-trifluoroethyl)oxy)-5-pyrimidinyl)phenyl)methyl)ethanamine;
(1R)-N-((4-(methyloxy)-3-(2-((2,2,2-trifluoroethyl)oxy)-5-pyrimidinyl)phenyl)methyl)-1-(1-naphthalenyl)ethanamine;
(1R)-N-((4-(methyloxy)-3-(2-((2,2,2-trifluoroethyl)oxy)-5-pyrimidinyl)phenyl)methyl)-1-phenylethanamine;
(1R)-1-(3-(methyloxy)phenyl)-N-((4-(methyloxy)-3-(6-quinoxalinyl)phenyl)methyl)ethanamine;
(1R)-N-((4-(methyloxy)-3-(6-quinoxalinyl)phenyl)methyl)-1-(1-naphthalenyl)ethanamine;
(1R)-N-((4-(methyloxy)-3-(6-quinoxalinyl)phenyl)methyl)-1-phenylethanamine;
(1R)-N-((4'-chloro-6-(methyloxy)-1,1'-biphenyl-3-yl)methyl)-1-phenylethanamine;
(1R)-N-((3-(1,3-benzothiazol-2-yl)-4-(methyloxy)phenyl)methyl)-1-phenylethanamine;
(1R)-N-((4-(methyloxy)-3-(2-(1-piperidinyl)-1,3-thiazol-4-yl)phenyl)methyl)-1-(1-naphthalenyl)ethanamine;
(1R)-N-((4-(methyloxy)-3-(2-(1-piperidinyl)-1,3-thiazol-4-yl)phenyl)methyl)-1-phenylethanamine;
(1R)-1-phenyl-N-((6-((2,2,2-trifluoroethyl)oxy)-4'-(trifluoromethyl)-1,1'-biphenyl-3-yl)methyl)ethanamine;
(1R)-N-((6-((2-(methyloxy)ethyl)oxy)-4'-(trifluoromethyl)-1,1'-biphenyl-3-yl)methyl)-1-(3-(methyloxy)phenyl)ethanamine;
(1R)-N-((6-chloro-4'-((trifluoromethyl)oxy)-1,1'-biphenyl-3-yl)methyl)-1-(1-naphthalenyl)ethanamine;
(1R)-N-((3-(1,3-benzothiazol-2-yl)-4-(methyloxy)phenyl)methyl)-1-(3-(methyloxy)phenyl)ethanamine;

(1R)-N-((3-(1,3-benzothiazol-2-yl)-4-(methyloxy)phenyl)methyl)-1-(1-naphthalenyl)ethanamine;

1-(3,5-difluorophenyl)-N-((6-(methyloxy)-4'-(trifluoromethyl)-1,1'-biphenyl-3-yl)methyl)ethanamine;

1-(3-bromophenyl)-N-((6-(methyloxy)-4'-(trifluoromethyl)-1,1'-biphenyl-3-yl)methyl)ethanamine;

1-(3-fluorophenyl)-N-((6-(methyloxy)-4'-(trifluoromethyl)-1,1'-biphenyl-3-yl)methyl)ethanamine;

(1S)-N-((6-(methyloxy)-4'-(trifluoromethyl)-1,1'-biphenyl-3-yl)methyl)-1-phenylethanamine;

(1R)-N-(3-(2-chloropyrid-4-yl)-4-methoxyphenyl)methyl-N-1-phenylethylamine;

(1R)-1-(3-fluorophenyl)-N-((6-(methyloxy)-4'-(methylsulfonyl)-1,1'-biphenyl-3-yl)methyl)ethanamine;

(1R)-1-(3-fluorophenyl)-N-((6-(methyloxy)-1,1'-biphenyl-3-yl)methyl)ethanamine;

(1R)-1-(3-chlorophenyl)-N-((6-(methyloxy)-1,1'-biphenyl-3-yl)methyl)ethanamine;

(1R)-N-((4-(methyloxy)-3-(2-naphthalenyl)phenyl)methyl)-1-(3-(methyloxy)phenyl)ethanamine;

(1R)-N-((4-(methyloxy)-3-(2-naphthalenyl)phenyl)methyl)-1-(1-naphthalenyl)ethanamine;

(1R)-N-((4-(methyloxy)-3-(2-naphthalenyl)phenyl)methyl)-1-phenylethanamine;

(1R)-N-((3-(1-benzothien-3-yl)-4-(methyloxy)phenyl)methyl)-1-(1-naphthalenyl)ethanamine;

(1R)-N-((3-(1-benzothien-3-yl)-4-(methyloxy)phenyl)methyl)-1-phenylethanamine;

(1R)-N-((3-(2,1,3-benzothiadiazol-5-yl)-4-(methyloxy)phenyl)methyl)-1-(3-(methyloxy)phenyl)ethanamine;

(1R)-N-((3-(2,1,3-benzothiadiazol-5-yl)-4-(methyloxy)phenyl)methyl)-1-phenylethanamine;

(1R)-N-((4',6-bis(trifluoromethyl)-1,1'-biphenyl-3-yl)methyl)-1-(3-(methyloxy)phenyl)ethanamine;

(1R)-N-((4',6-bis(trifluoromethyl)-1,1'-biphenyl-3-yl)methyl)-1-(1-naphthalenyl)ethanamine;

(1R)-N-((4'-fluoro-6-(methyloxy)-1,1'-biphenyl-3-yl)methyl)-1-(3-fluorophenyl)ethanamine;

(1R)-N-((6-chloro-4'-(trifluoromethyl)-1,1'-biphenyl-3-yl)methyl)-1-(1-naphthalenyl)ethanamine;

(1R)-N-((6-chloro-4'-(trifluoromethyl)-1,1'-biphenyl-3-yl)methyl)-1-phenylethanamine;

(1R)-N-((3-(2,3-dihydro-1-benzofuran-5-yl)-4-(methyloxy)phenyl)methyl)-1-(1-naphthalenyl)ethanamine;

(1R)-N-((3-(2,3-dihydro-1-benzofuran-5-yl)-4-(methyloxy)phenyl)methyl)-1-(3-(methyloxy)phenyl)ethanamine;

(1R)-N-((3-(2,3-dihydro-1-benzofuran-5-yl)-4-(methyloxy)phenyl)methyl)-1-phenylethanamine;

(1R)-N-((3-(2,1,3-benzoxadiazol-5-yl)-4-(methyloxy)phenyl)methyl)-1-phenylethanamine;

(1R)-N-((3-(2,1,3-benzoxadiazol-5-yl)-4-(methyloxy)phenyl)methyl)-1-(3-(methyloxy)phenyl)ethanamine;

(1R)-N-((4-chloro-3-(6-((2,2,2-trifluoroethyl)oxy)-3-pyridinyl)phenyl)methyl)-1-(1-naphthalenyl)ethanamine;

(1R)-N-((4-(methyloxy)-3-(1-(2,2,2-trifluoroethyl)-1H-indol-5-yl)phenyl)methyl)-1-(1-naphthalenyl)ethanamine;

(1R)-N-((4-(methyloxy)-3-(1-(2,2,2-trifluoroethyl)-1H-indol-5-yl)phenyl)methyl)-1-phenylethanamine;

(1R)-N-((3-(2,1,3-benzoxadiazol-5-yl)-4-(methyloxy)phenyl)methyl)-1-(1-naphthalenyl)ethanamine;

N-1-(3-(dimethylamino)phenyl)ethyl)-N-((6-(methyloxy)-4'-(trifluoromethyl)-1,1'-biphenyl-3-yl)methyl)amine;

N-((6-(methyloxy)-4'-(trifluoromethyl)-1,1'-biphenyl-3-yl)methyl)-1-(3-((trifluoromethyl)oxy)phenyl)ethanamine;

5-(2-(methyloxy)-5-((((1R)-1-(3-(methyloxy)phenyl)ethyl)amino)methyl)phenyl)-1-(2,2,2-trifluoromethyl)-2(1H)-pyridinone;

5-(2-(methyloxy)-5-((((1R)-1-phenylethyl)amino)methyl)phenyl)-1-(2,2,2-trifluoroethyl)-2(1H)-pyridinone;

1-(4-fluorophenyl)-N-((6-(methyloxy)-4'-(trifluoromethyl)-1,1'-biphenyl-3-yl)methyl)ethanamine;

1-(2,3-dichlorophenyl)-N-((6-(methyloxy)-4'-(trifluoromethyl)-1,1'-biphenyl-3-yl)methyl)ethanamine;

1-methyl-5-(2-(methyloxy)-5-((((1R)-1-(1-naphthalenyl)ethyl)amino)methyl)phenyl)-2-(1H)-pyridinone;

1-methyl-5-(2-(methyloxy)-5-((((1R)-1-phenylethyl)amino)methyl)phenyl)-2(1H)-pyridinone;

(1R)-N-((6-((2-(methyloxy)ethyl)oxy)-4'-(trifluoromethyl)-1,1'-biphenyl-3-yl)methyl)-1-(1-naphthalenyl)ethanamine;

(1R)-N-((6-((2-(methyloxy)ethyl)oxy)-4'-(trifluoromethyl)-1,1'-biphenyl-3-yl)methyl)-1-phenylethanamine;

(1R)-N-((3-imidazo[1,2-a]pyridin-6-yl-4-(methyloxy)phenyl)methyl)-1-(1-naphthalenyl)ethanamine;

(1R)-1-(3-(methyloxy)phenyl)-N-((4-(methyloxy)-3-(6-quinolinyl)phenyl)methyl)ethanamine;

(1R)-N-((4-(methyloxy)-3-(6-quinolinyl)phenyl)methyl)-1-phenylethanamine;

(1R)-N-((4-(methyloxy)-3-(6-quinolinyl)phenyl)methyl)-1-(1-naphthalenyl)ethanamine;

2'-(methyloxy)-5'-((((1R)-1-(1-naphthalenyl)ethyl)amino)methyl)-1,1'-biphenyl-3-carboxamide;

(1R)-1-(1-naphthalenyl)-N-((6-((2,2,2-trifluoroethyl)oxy)-4'-(trifluoromethyl)-1,1'-biphenyl-3-yl)methyl)ethanamine;

1-methyl-5-(2-(methyloxy)-5-((((1R)-1-(3-(methyloxy)phenyl)ethyl)amino)methyl)phenyl)-2(1H)-pyridinone;

(1R)-1-(3-(methyloxy)phenyl)-N((4-(methyloxy)-3-(2-(1-piperidinyl)-1,3-thiazol-4-yl)phenyl)methyl)ethanamine;

(1R)-N-((6-chloro-4'-((trifluoromethyl)oxy)-1,1'-biphenyl-3-yl)methyl)-1-(3-(methyloxy)phenyl)ethanamine;

(1R)-N-((6-chloro-4'-((trifluoromethyl)oxy)-1,1'-biphenyl-3-yl)methyl)-1-phenylethanamine;

2'-(methyloxy)-5'-((((1R)-1-(3-(methyloxy)phenyl)ethyl)amino)methyl)-1,1'-biphenyl-3-carboxamide;

2'-(methyloxy)-5'-((((1R)-1-phenylethyl)amino)methyl)-1,1'-biphenyl-3-carboxamide;

(1R)-N-((3-(3-furanyl)-4-(methyloxy)phenyl)methyl)-1-(3-(methyloxy)phenyl)ethanamine;

(1R)-1-(1-naphthalenyl)-N-((3-(6-(trifluoromethyl)-3-pyridinyl)phenyl)methyl)ethanamine;

(1R)-N-((3-(2,2-difluoro-1,3-benzodioxol-5-yl)-4-(methyloxy)phenyl)methyl)-1-(3-(methyloxy)phenyl)ethanamine;

(1R)-N-((3-(2,2-difluoro-1,3-benzodioxol-5-yl)-4-(methyloxy)phenyl)methyl)-1-phenylethanamine;

(1R)-N-((3-(2,2-difluoro-1,3-benzodioxol-5-yl)-4-(methyloxy)phenyl)methyl)-1-(1-naphthalenyl)ethanamine;

(1R)-N-((3-(3-furanyl)-4-(methyloxy)phenyl)methyl)-1-(1-naphthalenyl)ethanamine;

4'-(methyloxy)-5-((((1R)-1-phenylethyl)amino)methyl)-1,1'-biphenyl-2-ol;

(1R)-N-((3-imidazo[1,2-a]pyridin-6-yl-4-(methyloxy)phenyl)methyl)-1-phenylethanamine;

(1R)-N-((3-(3-furanyl)-4-(methyloxy)phenyl)methyl)-1-phenylethanamine;

(1R)-N-((3-(1-acetyl-4-piperidinyl)-4-(methyloxy)phenyl)methyl)-1-(1-naphthalenyl)ethanamine;

(1R)-N-((4-(methyloxy)-3-(1-((methyloxy)acetyl)-4-piperidinyl)phenyl)methyl)-1-(1-naphthalenyl)ethanamine;

(1R)-N-((4-(methyloxy)-3-(6-((2-(methyloxy)ethyl)oxy)-3-pyridinyl)phenyl)methyl)-1-phenylethanamine;

(1R)-N-((6-(methyloxy)-3'-(trifluoromethyl)-1,1'-biphenyl-3-yl)methyl)-1-(1-naphthalenyl)ethanamine;

(1R)-N-((6-(methyloxy)-3'-(trifluoromethyl)-1,1'-biphenyl-3-yl)methyl)-1-phenylethanamine;

(1R)-N-((4-(methyloxy)-3-(2-methyl-1,3-thiazol-4-yl)phenyl)methyl)-1-(3-(methyloxy)phenyl)ethanamine;

(1R)-N-((4-(methyloxy)-3-(2-methyl-1,3-thiazol-4-yl)phenyl)methyl)-1-(1-naphthalenyl)ethanamine;

(1R)-N-((4-(methyloxy)-3-(2-methyl-1,3-thiazol-4-yl)phenyl)methyl)-1-phenylethanamine;

(1R)-1-(3-(methyloxy)phenyl)-N-((4-(methyloxy)-3-(5-(trifluoromethyl)-1,3,4oxadiazol-2-yl)phenyl)methyl)ethanamine;

ethyl 4-(2-(methyloxy)-5-((((1R)-1-(1-naphthalenyl)ethyl)amino)methyl)phenyl)-3,6-dihydro-1(2H)-pyridinecarboxylate;

(1R)-N-((4-(methyloxy)-3-(4-(methyloxy)-2-pyridinyl)phenyl)methyl)-1-(3-(methyloxy)phenyl)ethanamine;

(1R)-N-((4-(methyloxy)-3-(4-(methyloxy)-2-pyridinyl)phenyl)methyl)-1-phenylethanamine;

(1R)-N-((4-((difluoromethyl)oxy)-3-(3-pyridinyl)phenyl)methyl)-1-(3-(methyloxy)phenyl)ethanamine;

(1R)-N-((4-((difluoromethyl)oxy)-3-(3-pyridinyl)phenyl)methyl)-1-(1-naphthalenyl)ethanamine;

(1R)-N-((4-((difluoromethyl)oxy)-3-(3-pyridinyl)phenyl)methyl)-1-phenylethanamine;

2'-(methyloxy)-5'-((((1R)-1-(3-(methyloxy)phenyl)ethyl)amino)methyl)-1,1'-biphenyl-3-carboxylic acid;

2'-(methyloxy)-5'-((((1R)-1-(1-naphthalenyl)ethyl)amino)methyl)-1,1'-biphenyl-3-carboxylic acid;

2'-(methyloxy)-5'-((((1R)-1-phenylethyl)amino)methyl)-1,1'-biphenyl-3-carboxylic acid;

(1R)-N-((4-(methyloxy)-3-(5-(trifluoromethyl)-1,3,4-oxadiazol-2-yl)phenyl)methyl)-1-phenylethanamine;

(1R)-N-((4-(methyloxy)-3-(1H-pyrrol-1-yl)phenyl)methyl)-1-phenylethanamine;

(1R)-1-(3-(methyloxy)phenyl)-N-((6-(methyloxy)-4'-(trifluoromethyl)-1,1'-biphenyl-3-yl)methyl)ethanamine;

(1R)-N-((6-(methyloxy)-4'-(trifluoromethyl)-1,1'-biphenyl-3-yl)methyl)-1-(1-naphthalenyl)ethanamine;

(1R)-N-((3-(1-methyl-1H-indazol-5-yl)-4-(methyloxy)phenyl)methyl)-1-phenylethanamine;

(1R)-N-((3-(1-methyl-1H-indazol-5-yl)-4-(methyloxy)phenyl)methyl)-1-(1-naphthalenyl)ethanamine;

(1R)-N-((3-(2-methyl-2H-indazol-5-yl)-4-(methyloxy)phenyl)methyl)-1-(1-naphthalenyl)ethanamine;

(1R)-1-(3-(methyloxy)phenyl)-N-((6-(methyloxy)-3'-(trifluoromethyl)-1,1'-biphenyl-3-yl)methyl)ethanamine;

(1R)-N-((4-(methyloxy)-3-(5-(trifluoromethyl)-1,3,4-oxadiazol-2-yl)phenyl)methyl)-1-(1-naphthalenyl)ethanamine;

(1R)-N-((4-(methyloxy)-3-(1-methyl-1H-pyrrolo[2,3-b]pyridin-5-yl)phenyl)methyl)-1-(3-(methyloxy)phenyl)ethanamine;

(1R)-N-((4-(methyloxy)-3-(1-methyl-1H-pyrrolo[2,3-b]pyridin-5-yl)phenyl)methyl)-1-(1-naphthalenyl)ethanamine;

(1R)-N-((4-(methyloxy)-3-(1H-pyrrol-1-yl)phenyl)methyl)-1-(1-naphthalenyl)ethanamine;

(1R)-N-((4-(methyloxy)-3-(5-(methyloxy)-2-pyridinyl)phenyl)methyl)-1-(3-(methyloxy)phenyl)ethanamine;

(1R)-N-((4-(methyloxy)-3-(5-(methyloxy)-2-pyridinyl)phenyl)methyl)-1-(1-naphthalenyl)ethanamine;

(1R)-N-((4-(methyloxy)-3-(5-(methyloxy)-2-pyridinyl)phenyl)methyl)-1-phenylethanamine;

(1R)-N-((3-(6-(ethyloxy)-3-pyridinyl)-4-(methyloxy)phenyl)methyl)-1-(1-naphthalenyl)ethanamine;

(1R)-N-((3-(6-(ethyloxy)-3-pyridinyl)-4-(methyloxy)phenyl)methyl)-1-phenylethanamine;

(1R)-N-((3-(1-methyl-1H-benzimidazol-2-yl)-4-(methyloxy)phenyl)methyl)-1-(1-naphthalenyl)ethanamine;

(1R)-N-((3-(1-methyl-1H-benzimidazol-5-yl)-4-(methyloxy)phenyl)methyl)-1-phenylethanamine;

(1R)-N-((4-(methyloxy)-3-(1-methyl-1H-pyrrolo[2,3-b]pyridin-5-yl)phenyl)methyl)-1-phenylethanamine;

(1R)-1-(3-(methyloxy)phenyl)-N-((4-(methyloxy)-3-(6-((2,2,2-trifluoroethyl)oxy)-3-pyridinyl)phenyl)methyl)ethanamine;

(1R)-N-((4-(methyloxy)-3-(6-((2,2,2-trifluoroethyl)oxy)-3-pyridinyl)phenyl)methyl)-1-phenylethanamine;

(1R)-N-((4-chloro-3-(3-pyridinyl)phenyl)methyl)-1-phenylethanamine;

(1R)-N-((4-chloro-3-(3-pyridinyl)phenyl)methyl)-1-(1-naphthalenyl)ethanamine;

(1R)-N-((4-chloro-3-(3-pyridinyl)phenyl)methyl)-1-(3-(methyloxy)phenyl)ethanamine;

(1R)-N-((3-(1-methyl-1H-benzimidazol-5-yl)-4-(methyloxy)phenyl)methyl)-1-(3-(methyloxy)phenyl)ethanamine;

(1R)-N-((3-(1-methyl-1H-benzimidazol-5-yl)-4-(methyloxy)phenyl)methyl)-1-(1-naphthalenyl)ethanamine;

(1R)-N-((3-(1-methyl-1H-indol-6-yl)-4-(methyloxy)phenyl)methyl)-1-phenylethanamine;

(1R)-N-((3-(1-methyl-1H-indol-6-yl)-4-(methyloxy)phenyl)methyl)-1-(3-(methyloxy)phenyl)ethanamine;

(1R)-N-((3-(1-methyl-1H-indol-6-yl)-4-(methyloxy)phenyl)methyl)-1-(1-naphthalenyl)ethanamine;

(1R)-1-(3-(methyloxy)phenyl)-N-((4-(methyloxy)-3-(6-(trifluoromethyl)-3-pyridinyl)phenyl)methyl)ethanamine;

(1R)-N-((4-(methyloxy)-3-(6-(trifluoromethyl)-3-pyridinyl)phenyl)methyl)-1-phenylethanamine;

(1R)-N-((3-(2-ethyl-2H-1,2,3-benzotriazol-5-yl)-4-(methyloxy)phenyl)methyl)-1-phenylethanamine;

(1R)-N-((3',6-bis(methyloxy)-1,1'-biphenyl-3-yl)methyl)-1-(1-naphthalenyl)ethanamine;

(1R)-N-((3',6-bis(methyloxy)-1,1'-biphenyl-3-yl)methyl)-1-(3-(methyloxy)phenyl)ethanamine;

(1R)-N-((3',6-bis(methyloxy)-1,1'-biphenyl-3-yl)methyl)-1-phenylethanamine;

(1R)-N-((4',6-bis(methyloxy)-1,1'-biphenyl-3-yl)methyl)-1-phenyl-1-propanamine;

(1R)-N-((4-methyl-3-(3-pyridinyl)phenyl)methyl)-1-phenylethanamine;

(1R)-N-((3-(3-methyl-1,2,4-oxadiazol-5-yl)phenyl)methyl)-1-(3-(methyloxy)phenyl)ethanamine;

(1R)-N-((3-(3-methyl-1,2,4-oxadiazol-5-yl)phenyl)methyl)-1-phenylethanamine;

(1R)-N-((4-(methyloxy)-3-(6-(methyloxy)-3-pyridinyl)phenyl)methyl)-1-(1-naphthalenyl)ethanamine;

(1R)-N-((4-(methyloxy)-3-(6-(methyloxy)-3-pyridinyl)phenyl)methyl)-1-(3-(methyloxy)phenyl)ethanamine;

(1R)-N-((4',6-difluoro-1,1'-biphenyl-3-yl)methyl)-1-(3-(methyloxy)phenyl)ethanamine;

5-(2-(methyloxy)-5-((((1R)-1-(4-methylphenyl)ethyl)amino)methyl)phenyl)-2-pyrimidinamine;

5-(2-(methyloxy)-5-((((1R)-1-(2-naphthalenyl)ethyl)amino)methyl)phenyl)-2-pyrimidinamine;

5-(3-((((1R)-1-(3-(methyloxy)phenyl)ethyl)amino)methyl)phenyl)-3-pyridinecarboxamide;

5-(3-((((1R)-1-(1-naphthalenyl)ethyl)amino)methyl)phenyl)-3-pyridinecarboxamide;

5-(3-((((1R)-1-(2-naphthalenyl)ethyl)amino)methyl)phenyl)-3-pyridinecarboxamide;

(1R)-N-((6-fluoro-4'-(methyloxy)-1,1'-biphenyl-3-yl)methyl)-1-(3-(methyloxy)phenyl)ethanamine;

(1R)-N-((6-fluoro-4'-(methyloxy)-1,1'-biphenyl-3-yl)methyl)-1-(4-(methyloxy)phenyl)ethanamine;

(1R)-N-((6-fluoro-4'-(methyloxy)-1,1'-biphenyl-3-yl)methyl)-1-(4-methylphenyl)ethanamine; and (1R)-N-((6-fluoro-4'-(methyloxy)-1,1'-biphenyl-3-yl)methyl)-1-phenylethanamine;

For the treatment of bone disorders, such as osteoporosis, excessive secretion of PTH, such as hyperparathyroidism, and the like, the compounds of the present invention may be administered orally, parentally, by inhalation spray, rectally, or topically in dosage unit formulations containing conventional pharmaceutically acceptable carriers, adjuvants, and vehicles. The term "parenteral" as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating the disclosed diseases with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% w/w of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of formula (I):

(I)

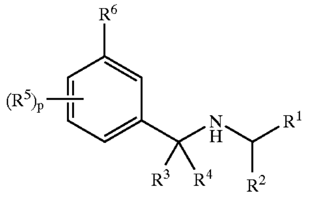

or a pharmaceutically acceptable salt thereof, wherein:

$R^1$ is aryl, substituted aryl, heterocyclyl, substituted heterocyclyl, cycloalkyl, or substituted cycloalkyl;

$R^2$ is alkyl or haloalkyl;

$R^3$ is H, alkyl, or haloalkyl;

$R^4$ is H, alkyl, or haloalkyl;

each $R^5$ present is independently alkyl, substituted alkyl, alkoxy, substituted alkoxy, halogen, —C(═O)OH, —CN, $—NR^dS(═O)_mR^d$, $—NR^dC(═O)NR^dR^d$, $—NR^dS(═O)_mNR^dR^d$, or $—NR^dC(═O)R^d$;

$R^6$ is aryl, substituted aryl, heterocyclyl, substituted heterocyclyl, cycloalkyl, or substituted cycloalkyl;

each $R^a$ is, independently, H, alkyl or haloalkyl;

each $R^b$ is, independently, aryl, aralkyl, heterocyclyl, or heterocyclylalkyl, each of which may be unsubstituted or substituted by up to 3 substituents selected from the group consisting of alkyl, halogen, haloalkyl, alkoxy, cyano, and nitro;

each $R^c$ is, independently, alkyl, haloalkyl, phenyl or benzyl, each of which may be substituted or unsubstituted;

each $R^d$ is, independently, H, alkyl, aryl, aralkyl, heterocyclyl, or heterocyclylalkyl wherein the alkyl, aryl, aralkyl, heterocyclyl, and heterocyclylalkyl are substituted by 0, 1, 2, 3 or 4 substituents selected from alkyl, halogen, haloalkyl, alkoxy, cyano, nitro, $R^b$, $—C(═O)R^c$, $—OR^b$, $—NR^aR^a$, $—NR^aR^b$, $—C(═O)OR^c$, $—C(═O)NR^aR^a$, $—OC(═O)R^c$, $—NR^aC(═O)R^c$, $—NR^aS(═O)_nR^c$ and $—S(═O)_nNR^aR^a$;

m is 1 or 2;

n is 0, 1 or 2; and p is 0, 1, 2, 3, or 4, provided that if $R^2$ is methyl, p is 0, and $R^6$ is unsubstituted phenyl, then $R^1$ is not 2,4-dihalophenyl, 2,4-dimethylphenyl, 2,4-diethylphenyl, 2,4,6-trihalophenyl, or 2,3,4-trihalophenyl.

2. A compound or salt of claim 1 wherein $R^1$ is aryl or substituted aryl.

3. A compound or salt of claim 1 wherein $R^1$ is phenyl, substituted phenyl, naphthyl, or substituted naphthyl.

4. A compound or salt of claim 1 wherein $R^1$ is phenyl or substituted phenyl.

5. A compound or salt of claim 1 wherein $R^1$ is phenyl that is unsubstituted or substituted by a substituent selected from the group consisting of halogen, $C_{1-4}$alkyl, $C_{1-4}$alkoxy, and cyano.

6. A compound or salt of claim 1 wherein $R^1$ is phenyl substituted by a halogen, methyl, or methoxy group.

7. A compound or salt of claim 6 wherein the substituent is in the 3-position.

8. A compound or salt of claim 1 wherein $R^1$ is heteroaryl or substituted heteroaryl.

9. A compound or salt of claim 1 wherein $R^6$ is heterocyclyl or substituted heterocyclyl.

10. A compound or salt of claim 1 wherein $R^6$ is a 2-pyridyl or 3-pyridyl group that is substituted or unsubstituted.

11. A compound or salt of claim 1 wherein $R^6$ is phenyl, substituted phenyl, naphthyl, or substituted naphthyl.

12. A compound or salt of claim 1 wherein $R^6$ is phenyl or substituted phenyl.

13. A compound or salt of claim 1 wherein $R^6$ is phenyl that is unsubstituted or substituted by 1 or 2 substituents selected from the group consisting of $C_{1-4}$haloalkyl, $C_{1-4}$haloalkoxy, $C_{1-4}$ alkoxy, methylenedioxy, cyano, $C_{1-4}$ alkyl, —NH—C(═O)—$C_{1-4}$ alkyl, $—(CH_2)_{0-3}—C(═O)—NH_2$, $—S(═O)_2—C_{1-4}$ alkyl, $—(CH_2)_{0-3}—C(═O)O—C_{1-4}$ alkyl, and $—(CH_2)_{0-3}—C(═O)—OH$.

14. A compound or salt of claim 1 wherein $R^6$ is phenyl that is unsubstituted or substituted by a halogen, methoxy, trifluoromethyl, or trifluoromethoxy group.

15. A compound or salt of claim 1 wherein $R^6$ is a phenyl group that is substituted at the 4-position and may be further substituted.

16. A compound or salt of claim 1 wherein each $R^5$ present is independently selected from the group consisting of halogen, $C_{1-4}$ alkyl, $C_{1-4}$ alkoxy, $C_{1-4}$ haloalkoxy, $—NR^a—S(═O)_2—C_{1-4}$ alkyl, $—NR^a—C(═O)—NR^a—C_{1-4}$ alkyl, $—O—C_{1-4}$ alkylene-$C(═O)—NR^aR^a$, and $—O—C_{1-4}$ alkylene-O—$C_{1-4}$ alkyl.

17. A compound or salt of claim 1 wherein p is 0.

18. A compound or salt of claim 1 wherein p is 1 and $R^5$ is methoxy.

19. A compound or salt of claim 18 wherein $R^5$ is in the 4-position.

20. A compound or salt of claim 19 wherein $R^1$ is phenyl, substituted phenyl, or naphthyl.

21. A compound or salt of claim 19 wherein $R^6$ is phenyl or substituted phenyl.

22. A compound or salt of claim 19 wherein $R^6$ is phenyl that is unsubstituted or substituted by a halogen, methoxy, trifluoromethyl, or trifluoromethoxy group.

23. A compound or salt of claim 22 wherein $R^1$ is phenyl, 1-naphthyl, or 2-naphthyl that is unsubstituted or substituted by 1 or 2 substituents selected from the group consisting of halogen, $C_{1-4}$alkyl, $C_{1-4}$alkoxy, and cyano.

24. A compound or salt of claim 22 wherein $R^1$ is phenyl substituted by 1 or 2 substituents selected from the group consisting of halogen, methyl, methoxy, and cyano.

25. A compound or salt of claim 1 wherein $R^2$ is methyl.

26. A compound or salt of claim 23 wherein $R^2$ is methyl.

27. A compound or salt of claim 1 wherein $R^3$ and $R^4$ are both hydrogen.

28. A compound or salt of claim 26 wherein $R^3$ and $R^4$ are both hydrogen.

29. A compound selected from the group consisting of:

(1R)-N-((6-fluoro-4'-(methyloxy)-1,1'-biphenyl-3-yl)methyl)-1-(4-(methyloxy)phenyl)ethanamine;

(1R)-N-((4-(methyloxy)-3-(6-(methyloxy)-3-pyridinyl)phenyl)methyl)-1-(1-naphthalenyl)ethanamine;

(1R)-N-((3',6-bis(methyloxy)-1,1'-biphenyl-3-yl)methyl)-1-(3-(methyloxy)phenyl)ethanamine;

(1R)-N-((3',6-bis(methyloxy)-1,1'-biphenyl-3-yl)methyl)-1-(1-naphthalenyl)ethanamine;

(1R)-N-((4-(methyloxy)-3-(6-(trifluoromethyl)-3-pyridinyl)phenyl)methyl)-1-phenylethanamine;

(1R)-1-(3-(methyloxy)phenyl)-N-((4-(methyloxy)-3-(6-(trifluoromethyl)-3-pyridinyl)phenyl)methyl)ethanamine;

(1R)-N-((3-(1-methyl-1H-indol-6-yl)-4-(methyloxy)phenyl)methyl)-1-(1-naphthalenyl)ethanamine;

(1R)-N-((3-(1-methyl-1H-indol-6-yl)-4-(methyloxy)phenyl)methyl)-1-phenylethanamine;

(1R)-N-((4-(methyloxy)-3-(6-((2,2,2-trifluoroethyl)oxy)-3-pyridinyl)phenyl)methyl)-1-phenylethanamine;

(1R)-1-(3-(methyloxy)phenyl)-N-((4-(methyloxy)-3-(6-((2,2,2-trifluoroethyl)oxy)-3-pyridinyl)phenyl)methyl-1-phenylethanamine;

(1R)-N-((3-(1-methyl-1H-benzimidazol-2-yl)-4-(methyloxy)phenyl)methyl)-1-(1-naphthalenyl)ethanamine;

(1R)-N-((3-(6-(ethyloxy)-3-pyridinyl)-4-(methyloxy)phenyl)methyl)-1-phenylethanamine;

(1R)-N-((3-(6-(ethyloxy)-3-pyridinyl)-4-(methyloxy)phenyl)methyl)-1-(1-naphthalenyl)ethanamine;

(1R)-N-((4-(methyloxy)-3-(1H-pyrrol-1-yl)phenyl)methyl)-1-(1-naphthalenyl)ethanamine;

(1R)-N-((4-(methyloxy)-3-(1-methyl-1H-pyrrolo[2,3-b]pyridin-5-yl)phenyl)methyl)-1-(3-(methyloxy)phenyl)ethanamine;

(1R)-N-((3-(1-methyl-1H-imidazol-5-yl)-4-(methyloxy)phenyl)methyl)-1-(1-naphthalenyl)ethanamine;

(1R)-N-((3-(1-methyl-1H-imidazol-5-yl)-4-(methyloxy)phenyl)methyl)-1-phenylethanamine;

(1R)-1-(3-(methyloxy)phenyl)-N-((6-(methyloxy)-4'-(trifluoromethyl)-1,1'-biphenyl-3-yl)methyl)ethanamine;

(1R)-N-((4-(methyloxy)-3-(1H-pyrrol-1-yl)phenyl)methyl)-1-phenylethanamine;

(1R)-N-((4-(methyloxy)-3-(4-(methyloxy)-2-pyridinyl)phenyl)methyl)-1-phenylethanamine;

ethyl 4-(2-(methyloxy)-5-((((1R)-1-(1-naphthalenyl)ethyl)amino)methyl)phenyl)-3,6-dihydro-1(2H)-pyridinecarboxylate;

(1R)-N-((6-(methyloxy)-3'-(trifluoromethyl)-1,1'-biphenyl-3-yl)methyl)-1-phenylethanamine;

(1R)-N-((3-(3-furanyl)-4-(methyloxy)phenyl)methyl)-1-(1-naphthalenyl)ethanamine;

(1R)-N-((3-(2,2-difluoro-1,3-benzodioxol-5-yl)-4-(methyloxy)phenyl)methyl)-1-(1-naphthalenyl)ethanamine;

(1R)-N-((3-(2,2-difluoro-1,3-benzodioxol-5-yl)-4-(methyloxy)phenyl)methyl)-1-phenylethanamine;

(1R)-N-((3-(2,2-difluoro-1,3-benzodioxol-5-yl)-4-(methyloxy)phenyl)methyl)-1-(3-(methyloxy)phenyl)ethanamine;

(1R)-N-((3-(3-furanyl)-4-(methyloxy)phenyl)methyl)-1-(3-(methyloxy)phenyl)ethanamine;

(1R)-N-((6-chloro-4'-((trifluoromethyl)oxy)-1,1'-biphenyl-3-yl)methyl)-1-phenylethanamine;

(1R)-N-((6-chloro-4'-((trifluoromethyl)oxy)-1,1'-biphenyl-3-yl)methyl)-1-(3-(methyloxy)phenyl)ethanamine;

(1R)-N-((4-(methyloxy)-3-(6-quinolinyl)phenyl)methyl)-1-(1-naphthalenyl)ethanamine;

(1R)-N-((4-(methyloxy)-3-(6-quinolinyl)phenyl)methyl)-1-phenylethanamine;

(1R)-N-((3-(2,1,3-benzoxadiazol-5-yl)-4-(methyloxy)phenyl)methyl)-1-(1-naphthalenyl)ethanamine;

(1R)-N-((4-(methyloxy)-3-(1-(2,2,2-trifluoroethyl)-1H-indol-5-yl)phenyl)methyl)-1-(1-naphthalenyl)ethanamine;

(1R)-N-((4-chloro-3-(6-((2,2,2-trifluoroethyl)oxy)-3-pyridinyl)phenyl)methyl)-1-(1-naphthalenyl)ethanamine;

(1R)-N-((3-(2,1,3-benzoxadiazol-5-yl)-4-(methyloxy)phenyl)methyl)-1-(3-(methyloxy)phenyl)ethanamine;

(1R)-N-((3-(2,1,3-benzoxadiazol-5-yl)-4-(methyloxy)phenyl)methyl)-1-phenylethanamine;

(1R)-N-((3-(2,3-dihydro-1-benzofuran-5-yl)-4-(methyloxy)phenyl)methyl)-1-phenylethanamine;

(1R)-N-((3-(2,3-dihydro-1-benzofuran-5-yl)-4-(methyloxy)phenyl)methyl)-1-(3-(methyloxy)phenyl)ethanamine;

(1R)-N-((3-(2,3-dihydro-1-benzofuran-5-yl)-4-(methyloxy)phenyl)methyl)-1-(1-naphthalenyl)ethanamine;

(1R)-N-((4'-fluoro-6-(methyloxy)-1,1'-biphenyl-3-yl)methyl)-1-(3-fluorophenyl)ethanamine;

(1R)-N-((4',6-bis(trifluoromethyl)-1,1'-biphenyl-3-yl)methyl)-1-(3-(methyloxy)phenyl)ethanamine;

(1R)-N-((3-(2,1,3-benzothiadiazol-5-yl)-4-(methyloxy)phenyl)methyl)-1-phenylethanamine;

(1R)-N-((3-(2,1,3-benzothiadiazol-5-yl)-4-(methyloxy)phenyl)methyl)-1-(3-(methyloxy)phenyl)ethanamine;

(1R)-N-((3-(1-benzothien-3-yl)-4-(methyloxy)phenyl)methyl)-1-phenylethanamine;

1-(3-fluorophenyl)-N-((6-(methyloxy)-4'-(trifluoromethyl)-1,1'-biphenyl-3-yl)methyl)ethanamine;

1-(3-bromophenyl)-N-((6-(methyloxy)-4'-(trifluoromethyl)-1,1'-biphenyl-3-yl)methyl)ethanamine;

1-(3,5-difluorophenyl)-N-((6-(methyloxy)-4'-(trifluoromethyl)-1,1'-biphenyl-3-yl)methyl)ethanamine;

(1R)-N-((3-(1,3-benzothiazol-2-yl)-4-(methyloxy)phenyl)methyl)-1-(3-(methyloxy)phenyl)ethanamine;

(1R)-N-((6-chloro-4'-((trifluoromethyl)oxy)-1,1'-biphenyl-3-yl)methyl)-1-(1-naphthalenyl)ethanamine;

(1R)-N-((4'-chloro-6-(methyloxy)-1,1'-biphenyl-3-yl)methyl)-1-phenylethanamine;

(1R)-N-((4-(methyloxy)-3-(6-quinoxalinyl)phenyl)methyl)-1-(1-naphthalenyl)ethanamine;

(1R)-N-((6-(methyloxy)-3'-((trifluoromethyl)oxy)-1,1'-biphenyl-3-yl)methyl)-1-phenylethanamine;

(1R)-N-((6-iodo-4'-(trifluoromethyl)-1,1'-biphenyl-3-yl)methyl)-1-(1-naphthalenyl)ethanamine;

(1R)-N-((6-iodo-4'-(trifluoromethyl)-1,1'-biphenyl-3-yl)methyl)-1-(3-(methyloxy)phenyl)ethanamine;

(1R)-N-((4'-chloro-6-(methyloxy)-1,1'-biphenyl-3-yl)methyl)-1-(1-naphthalenyl)ethanamine;

(1R)-N-((3-(2-methyl-1,3-oxazol-4-yl)-4-(methyloxy)phenyl)methyl)-1-phenylethanamine;

(1R)-N-((3-(2-methyl-1,3-oxazol-4-yl)-4-(methyloxy)phenyl)methyl)-1-(1-naphthalenyl)ethanamine;

ethyl 2'-(methyloxy)-5'-((((1R)-1-phenylethyl)amino)methyl)-1,1'-biphenyl-4-carboxylate;

ethyl 2'-(methyloxy)-5'-((((1R)-1-(1-naphthalenyl)ethyl)amino)methyl)-1,1'-biphenyl-4-carboxylate;

4-(2-(methyloxy)-5-((((1R)-1-phenylethyl)amino)methyl)phenyl)-1,3-thiazol-2-amine;

(1R)-N-((3-(1-(cyclopropylmethyl)-1H-indol-5-yl)-4-(methyloxy)phenyl)methyl)-1-phenylethanamine;

(1R)-N-((6-(methyloxy)-4'-(trifluoromethyl)-1,1'-biphenyl-3-yl)methyl)-1-phenylethanamine;

(1R)-N-((3-(1-(cyclopropylmethyl)-1H-indol-5-yl)-4-(methyloxy)phenyl)methyl)-1-(1-naphthalenyl)ethanamine;

(1R)-N-((4-(methyloxy)-3-(2-((tetrahydro-2-furanylmethyl)oxy)-3-pyridinyl)phenyl)methyl)-1-phenylethanamine;

(1R)-N-((3-(2-fluoro-3-pyridinyl)-4-(methyloxy)phenyl)methyl)-1-phenylethanamine;

N,N-dimethyl-5-(2-(methyloxy)-5-((((1R)-1-phenylethyl)amino)methyl)phenyl)-2-pyridinamine;

(1R)-N-((4-(methyloxy)-3-(1-methyl-2-(trifluoromethyl)-1H-benzimidazol-5-yl)phenyl)methyl)-1-(1-naphthalenyl)ethanamine;

(1R)-N-((4-(methyloxy)-3-(1-methyl-2-(trifluoromethyl)-1H-benzimidazol-5-yl)phenyl)methyl)-1-phenylethanamine;

(1R)-N-((4-(methyloxy)-3-(2-thienyl)phenyl)methyl)-1-phenylethanamine;

(1R)-N-((4-(methyloxy)-3-(2-thienyl)phenyl)methyl)-1-(1-naphthalenyl)ethanamine;

(1R)-1-(3-(methyloxy)phenyl)-N-((4-(methyloxy)-3-(2-thienyl)phenyl)methyl)ethanamine;

(1R)-N-((4-(methyloxy)-3-(6-methyl-3-pyridinyl)phenyl)methyl)-1-(1-naphthalenyl)ethanamine;

(1R)-N-((4-(methyloxy)-3-(2-pyridinyl)phenyl)methyl)-1-(1-naphthalenyl)ethanamine;

(1R)-N-((3-(1,3-benzoxazol-5-yl)-4-(methyloxy)phenyl)methyl)-1-(1-naphthalenyl)ethanamine;

(1R)-N-((3-(2-methyl-1,3-benzoxazol-5-yl)-4-(methyloxy)phenyl)methyl)-1-phenylethanamine;

2'-(methyloxy)-5'-((((1R)-1-phenylethyl)amino)methyl)-1,1'-biphenyl-3-carbonitrile;

(1R)-N-((6-(methyloxy)-4'-((trifluoromethyl)oxy)-1,1'-biphenyl-3-yl)methyl)-1-(1-naphthalenyl)ethanamine;

(1R)-1-(3-fluorophenyl)-N-((6-(methyloxy)-4'-(trifluoromethyl)-1,1'-biphenyl-3-yl)methyl)ethanamine;

(1R)-N-((6-(ethyloxy)-4'-(methyloxy)-1,1'-biphenyl-3-yl)methyl)-1-phenylethanamine;

(1R)-N-((4-(methyloxy)-3-(3-pyridinyl)phenyl)methyl)-1-(1-naphthalenyl)ethanamine;

(1R)-N-((4-(methyloxy)-3-(6-(trifluoromethyl)-3-pyridinyl)phenyl)methyl)-1-(1-naphthalenyl)ethanamine;

(1R)-N-((4-(methyloxy)-3-(6-((2,2,2-trifluoroethyl)oxy)-3-pyridinyl)phenyl)methyl)-1-(1-naphthalenyl)ethanamine; and (1R)-1-(3-chlorophenyl)-N-((6-(methyloxy)-4'-(trifluoromethyl)-1,1'-biphenyl-3-yl)methyl)ethanamine;

or a pharmaceutically acceptable salt thereof.

30. A compound selected from the group consisting of:

(1R)-1-(3-(methyloxy)phenyl)-N-((4-(methyloxy)-3-(3-pyridinyl)phenyl)methyl)ethanamine;

2'-(methyloxy)-5'-((((1R)-1-(1-naphthalenyl)ethyl)amino)methyl)-1,1'-biphenyl-3-carbonitrile;

(1R)-N-((2'-fluoro-1,1'-biphenyl-3-yl)methyl)-1-(4-methylphenyl)ethanamine;

(1R)-N-((6-(methyloxy)-1,1'-biphenyl-3-yl)methyl)-1-(4-methylphenyl)ethanamine;

(1R)-N-((4-(methyloxy)-3-(6-(methyloxy)-3-pyridazinyl)phenyl)methyl)-1-(3-(methyloxy)phenyl)ethanamine;

(1R)-N-((4-(methyloxy)-3-(2-pyrazinyl)phenyl)methyl)-1-(1-naphthalenyl)ethanamine;

(1R)-N-((4-(methyloxy)-3-(6-((tetrahydro-2-furanylmethyl)oxy)-3-pyridinyl)phenyl)methyl)-1-phenylethanamine;

(1R)-N-((4-(methyloxy)-3-(2-(4-morpholinyl)-3-pyridinyl)phenyl)methyl)-1-phenylethanamine;

(1R)-N-((3-(1-methyl-1H-imidazol-4-yl)-4-(methyloxy)phenyl)methyl)-1-(1-naphthalenyl)ethanamine;

(1R)-N-((4-(methyloxy)-3-(1-pyrrolidinyl)phenyl)methyl)-1-phenylethanamine;

ethyl 2'-(methyloxy)-5'-((((1R)-1-(3-(methyloxy)phenyl)ethyl)amino)methyl)-1,1'-biphenyl-4-carboxylate;

N-((6-(methyloxy)-4'-(trifluoromethyl)-1,1'-biphenyl-3-yl)methyl)-1-(3-methylphenyl)ethanamine;

(1R)-N-((6-fluoro-4'-(trifluoromethyl)-1,1'-biphenyl-3-yl)methyl)-1-phenylethanamine;

N,N-dimethyl-2'-(methyloxy)-5'-((((1R)-1-(3-(methyloxy)phenyl)ethyl)amino)methyl)-1,1'-biphenyl-4-carboxamide;

N,N-dimethyl-2'-(methyloxy)-5'-((((1R)-1-(1-naphthalenyl)ethyl)amino)methyl)-1,1'-biphenyl-4-carboxamide;

N,N-dimethyl-2'-(methyloxy)-5'-((((1R)-1-phenylethyl)amino)methyl)-1,1'-biphenyl-4-carboxamide;

(1R)-N-((6-iodo-4'-(trifluoromethyl)-1,1'-biphenyl-3-yl)methyl)-1-phenylethanamine;

(1R)-N-((6-(methyloxy)-3'-((trifluoromethyl)oxy)-1,1'-biphenyl-3-yl)methyl)-1-(1-naphthalenyl)ethanamine;

(1R)-1-(3-(methyloxy)phenyl)-N-((6-(methyloxy)-3'-((trifluoromethyl)oxy)-1,1'-biphenyl-3-yl)methyl)ethanamine;

(1R)-N-((4'-chloro-6-(methyloxy)-1,1'-biphenyl-3-yl)methyl)-1-(3-(methyloxy)phenyl)ethanamine;

(1R)-1-(3-(methyloxy)phenyl)-N-((4-(methyloxy)-3-(2-((2,2,2-trifluoroethyl)oxy)-5-pyrimidinyl)phenyl)methyl)ethanamine;

(1R)-N-((4-(methyloxy)-3-(6-quinoxalinyl)phenyl)methyl)-1-phenylethanamine;

(1R)-N-((3-(1,3-benzothiazol-2-yl)-4-(methyloxy)phenyl)methyl)-1-phenylethanamine;

(1R)-N-((6-((2-(methyloxy)ethyl)oxy)-4'-(trifluoromethyl)-1,1'-biphenyl-3-yl)methyl)-1-(3-(methyloxy)phenyl)ethanamine;

(1R)-N-((4-(methyloxy)-3-(2-naphthalenyl)phenyl)methyl)-1-(3-(methyloxy)phenyl)ethanamine;

(1R)-N-((4-(methyloxy)-3-(2-naphthalenyl)phenyl)methyl)-1-(1-naphthalenyl)ethanamine;

(1R)-N-((4-(methyloxy)-3-(2-naphthalenyl)phenyl)methyl)-1-phenylethanamine;

(1R)-N-((6-chloro-4'-(trifluoromethyl)-1,1'-biphenyl-3-yl)methyl)-1-phenylethanamine;

(1R)-N-((4-(methyloxy)-3-(1-(2,2,2-trifluoroethyl)-1H-indol-5-yl)phenyl)methyl)-1-phenylethanamine;

(1R)-N-((6-((2-(methyloxy)ethyl)oxy)-4'-(trifluoromethyl)-1,1'-biphenyl-3-yl)methyl)-1-(1-naphthalenyl)ethanamine;

(1R)-N-((6-((2-(methyloxy)ethyl)oxy)-4'-(trifluoromethyl)-1,1'-biphenyl-3-yl)methyl)-1-phenylethanamine;

(1R)-1-(3-(methyloxy)phenyl)-N-((4-(methyloxy)-3-(6-quinolinyl)phenyl)methyl)ethanamine;

2'-(methyloxy)-5'-((((1R)-1-(1-naphthalenyl)ethyl)amino)methyl)-1,1'-biphenyl-3-carboxamide;

(1R)-1-(1-naphthalenyl)-N-((3-(6-(trifluoromethyl)-3-pyridinyl)phenyl)methyl)ethanamine;

(1R)-N-((3-(3-furanyl)-4-(methyloxy)phenyl)methyl)-1-phenylethanamine;

(1R)-N-((6-(methyloxy)-3'-(trifluoromethyl)-1,1'-biphenyl-3-yl)methyl)-1-(1-naphthalenyl)ethanamine;

(1R)-N-((4-(methyloxy)-3-(2-methyl-1,3-thiazol-4-yl)phenyl)methyl)-1-(3-(methyloxy)phenyl)ethanamine;

(1R)-N-((4-((difluoromethyl)oxy)-3-(3-pyridinyl)phenyl)methyl)-1-(1-naphthalenyl)ethanamine;

(1R)-N-((3-(2-methyl-2H-indazol-5-yl)-4-(methyloxy)phenyl)methyl)-1-(1-naphthalenyl)ethanamine;

(1R)-N-((4-(methyloxy)-3-(5-(trifluoromethyl)-1,3,4-oxadiazol-2-yl)phenyl)methyl)-1-(1-naphthalenyl)ethanamine;

(1R)-N-((4-chloro-3-(3-pyridinyl)phenyl)methyl)-1-(3-(methyloxy)phenyl)ethanamine;

(1R)-N-((3-(2-ethyl-2H-1,2,3-benzotriazol-5-yl)-4-(methyloxy)phenyl)methyl)-1-phenylethanamine; and (1R)-N-((4',6-difluoro-1,1'-biphenyl-3-yl)methyl)-1-(3-(methyloxy)phenyl)ethanamine or a pharmaceutically acceptable salt thereof.

31. A composition comprising a pharmaceutically acceptable amount of a compound of the formula Ia:

(Ia)

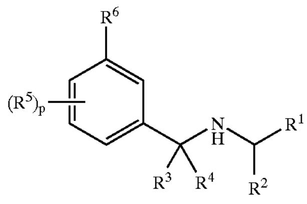

or a pharmaceutically acceptable salt thereof, wherein:

$R^1$ is aryl, substituted aryl, heteroaryl, substituted heteroaryl, heterocyclyl, or substituted heterocyclyl;

$R^2$ is alkyl or haloalkyl;

$R^3$ is H, alkyl, or haloalkyl;

$R^4$ is H, alkyl, or haloalkyl;

each $R^5$ present is independently alkyl, substituted alkyl, haloalkyl, alkoxy, substituted alkoxy, halogen, —C(═O)OH, —CN, $—NR^aR^d$, $—NR^dS(═O)_mR^d$, $—NR^dC(═O)NR^dR^d$, $—NR^dS(═O)_mNR^dR^d$, or $—NR^dC(═O)R^d$;

$R^6$ is aryl, substituted aryl, heteroaryl, substituted heteroaryl, heterocyclyl, or substituted heterocyclyl;

each $R^a$ is, independently, H, alkyl or haloalkyl;

each $R^b$ is, independently aryl, aralkyl, heterocyclyl, or heteroaryl, each of which may be unsubstituted or substituted by up to 3 substituents selected from the group consisting of alkyl, halogen, haloalkyl, alkoxy, cyano, and nitro;

each $R^c$ is, independently, alkyl, haloalkyl, phenyl or benzyl;

each $R^d$ is, independently, H, alkyl, aryl, aralkyl, or heterocyclyl, wherein the alkyl , aryl, aralkyl, and heterocycle are substituted by 0, 1, 2, 3 or 4 substituents selected from alkyl, halogen, haloalkyl, alkoxy, cyano, nitro, $R^b$, $—C(═O)R^c$, $—OR^b$, $—NR^aR^a$, $—NR^aR^b$, $—C(═O)OR^c$, $—C(═O)NR^aR^a$, $—OC(═O)R^c$, $—NR^aC(═O)R^c$, $—NR^aS(═O)_nR^c$ and $—S(═O)_nNR^aR^a$;

m is 1 or 2;

n is 0, 1 or 2; and p is 0, 1, 2, 3, or 4, in combination with a pharmaceutically acceptable carrier.

32. A method of treating osteoperosis or hyperparathyroidism comprising administering a therapeutically effective amount of a composition of claim 31 to a patient in need thereof.

33. A compound having the formula

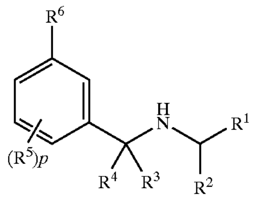

or a pharmaceutically acceptable salt thereof, wherein:

$R^1$ is phenyl, benzyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl, naphthyl or heterocycle are substituted by 0, 1, 2 or 3 substituents selected from $C_{1-6}$alkyl, halogen, $C_{1-4}$haloalkyl, $—OC_{1-6}$alkyl, cyano and nitro;

$R^2$ is $C_{1-8}$alkyl or $C_{1-4}$haloalkyl;

$R^3$ is H, $C_{1-4}$haloalkyl or $C_{1-8}$alkyl;

$R^4$ is H, $C_{1-4}$haloalkyl or $C_{1-8}$alkyl;

$R^5$ is, independently, in each instance, H, $C_{1-8}$alkyl, $C_{1-4}$haloalkyl, halogen, cyano, $—NR^aR^d$, $—NS(═O)_2R^c$, $—NR^aC(═)NR^aR^d$, $—NR^dC(═O)R^d$ or $—OC_{1-6}$alkyl substituted by 0, 1, 2 or 3 substituents selected from halogen, $—OC_{1-6}$alkyl, $—NR^aR^d$, $—NS(═O)_2R^c$, $—NR^aC(═O)NR^aR^d$, $—NR^dC(═O)R^d$ or cyano;

$R^6$ is phenyl, benzyl, naphthyl, a saturated or unsaturated 5- or 6-membered ring heterocycle containing 1, 2 or 3 atoms selected from N, O and S, with no more than 2 of the atoms selected from O and S, or a saturated or unsaturated 8-, 9-, 10- or 11-membered heterobicycle containing 1, 2, 3, 4 or 5 atoms selected from N, O and S, with no more than 2 of the atoms selected from O and S, wherein the phenyl, benzyl, naphthyl, heterocycle and heterobicycle are substituted by 0, 1, 2 or 3 substituents selected from $C_{1-6}$alkyl, halogen, $C_{1-4}$haloalkyl, $—OC_{1-6}$alkyl, $—OC_{1-4}$haloalkyl, $—NR^aR^a$, $—NR^aC(═O)C_{1-6}$alkyl, $—S(═O)_nC_{1-6}$ alkyl, cyano and nitro;

$R^a$ is, independently, at each instance, H, $C_{1-4}$haloalkyl or $C_{1-6}$alkyl;

$R^b$ is, independently, aryl, aralkyl, heterocyclyl, or heterocyclylalkyl, each of which may be unsubstituted or substituted by up to 3 substituents selected from the group consisting of alkyl, halogen, haloalkyl, alkoxy, cyano, and nitro;

$R^c$ is, independently, at each instance, $C_{1-6}$alkyl, $C_{1-4}$haloalkyl, phenyl or benzyl, each of which may be unsubstituted or substituted;

$R^d$ is, independently, at each instance, H, $C_{1-6}$alkyl, phenyl, benzyl or a saturated or unsaturated 5- or 6-membered ring heterocycle containing 1, 2 or 3 atoms selected from N, O and S, with no more than 2 of the atoms selected from O and S, wherein the $C_{1-6}$alkyl , phenyl, benzyl, naphthyl and heterocycle are substituted by 0, 1, 2, 3 or 4 substituents selected from $C_{1-6}$alkyl, halogen, $C_{1-4}$haloalkyl, —$OC_{1-6}$alkyl, cyano and nitro, $R^b$, —C(=O)$R^c$, —$OR^b$, —$NR^aR^a$, —$NR^aR^b$, —C(=O)$OR^c$, —C(=)$NR^aR^a$, —OC(=) $R^c$, —$NR^a$C(=O)$R^c$, —$NR^a$S(=O)$_m R^c$, and —S(=O)$_m NR^aR^a$;

m is 1 or 2; and n is 0, 1 or 2.

34. A compound according to claim 33 wherein $R^1$ is phenyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl, naphthyl or heterocycle are substituted by 0, 1, 2 or 3 substituents selected from $C_{1-6}$alkyl, halogen, $C_{1-4}$haloalkyl, —$OC_{1-6}$alkyl, cyano and nitro and $R^6$ is phenyl, naphthyl, a saturated or unsaturated 5- or 6-membered ring heterocycle containing 1, 2 or 3 atoms selected from N, O and S, with no more than 2 of the atoms selected from O and S, or a saturated or unsaturated 8-, 9-, 10- or 11-membered heterobicycle containing 1, 2, 3, 4 or 5 atoms selected from N, O and S, with no more than 2 of the atoms selected from O and S, wherein the phenyl, benzyl, naphthyl, heterocycle and heterobicycle are substituted by 0, 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^a$C(=O)$C_{1-6}$alkyl, —S(=O)$_n C_{1-6}$alkyl, cyano and nitro.

35. A compound according to claim 33, wherein $R^1$ is phenyl substituted by 0, 1, 2 or 3 substituents selected from $C_{1-6}$alkyl, halogen, $C_{1-4}$haloalkyl, —$OC_{1-6}$alkyl, cyano and nitro.

36. A compound according to claim 33, wherein $R^1$ is benzyl substituted by 0, 1, 2 or 3 substituents selected from $C_{1-6}$alkyl, halogen, $C_{1-4}$haloalkyl, —$OC_{1-6}$alkyl, cyano and nitro.

37. A compound according to claim 33, wherein $R^1$ is naphthyl substituted by 0, 1, 2 or 3 substituents selected from $C_{1-6}$alkyl, halogen, $C_{1-4}$haloalkyl, —$OC_{1-6}$alkyl, cyano and nitro.

38. A compound according to claim 33, wherein $R^1$ a saturated or unsaturated 5- or 6-membered ring heterocycle containing 1, 2 or 3 atoms selected from N, O and S, with no more than 2 of the atoms selected from O and S, wherein the heterocycle is substituted by 0, 1, 2 or 3 substituents selected from $C_{1-6}$alkyl, halogen, $C_{1-4}$haloalkyl, —$OC_{1-6}$alkyl, cyano and nitro.

39. A compound according to claim 33, wherein $R^6$ is phenyl, wherein the phenyl is substituted by 0, 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^a$C(=O)$C_{1-6}$alkyl, —S(=O)$_n C_{1-6}$alkyl, cyano and nitro.

40. A compound according to claim 33, wherein $R^6$ is benzyl, wherein the benzyl is substituted by 0, 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^a$C(=O)$C_{1-6}$alkyl, —S(=O)$_n C_{1-6}$alkyl, cyano and nitro.

41. A compound according to claim 33, wherein $R^6$ is naphthyl, wherein the naphthyl is substituted by 0, 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^a$C(=O)$C_{1-6}$alkyl, —S(=O)$_n C_{1-6}$alkyl, cyano and nitro.

42. A compound according to claim 33, wherein $R^6$ is a saturated or unsaturated 5- or 6-membered ring heterocycle containing 1, 2 or 3 atoms selected from N, O and S, with no more than 2 of the atoms selected from O and S, wherein the heterocycle is substituted by 0, 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^a$C(=O)$C_{1-6}$alkyl, —S(=O)$_n C_{1-6}$alkyl, cyano and nitro.

43. A compound according to claim 33, wherein $R^6$ is a saturated or unsaturated 8-, 9-, 10- or 11-membered heterobicycle containing 1, 2, 3, 4 or 5 atoms selected from N, O and S, with no more than 2 of the atoms selected from O and S, wherein the heterobicycle is substituted by 0, 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, $NR^a$C(=)$C_{1-6}$alkyl, —S(=O)$_n C_{1-6}$alkyl, cyano and nitro.

44. A compound according to claim 33, wherein $R^1$ is phenyl, naphthyl or ($OC_{1-4}$alkyl)phenyl.

45. A compound according to claim 33, wherein $R^1$ is phenyl substituted by 2 or 3 substituents selected from $C_{1-6}$alkyl, halogen, $C_{1-4}$haloalkyl, —$OC_{1-6}$alkyl, cyano and nitro.

46. A compound according to claim 33, wherein $R^1$ is benzyl substituted by 1, 2 or 3 substituents selected from $C_{1-6}$alkyl, halogen, $C_{1-4}$haloalkyl, —$OC_{1-6}$alkyl, cyano and nitro.

47. A compound according to claim 33, wherein $R^1$ is naphthyl substituted by 1, 2 or 3 substituents selected from $C_{1-6}$alkyl, halogen, $C_{1-4}$haloalkyl, —$OC_{1-6}$alkyl, cyano and nitro.

48. A compound according to claim 33, wherein $R^1$ a saturated or unsaturated 5- or 6-membered ring heterocycle containing 1, 2 or 3 atoms selected from N, O and S, with no more than 2 of the atoms selected from O and S, wherein the heterocycle is substituted by 1, 2 or 3 substituents selected from $C_{1-6}$alkyl, halogen, $C_{1-4}$haloalkyl, —$OC_{1-6}$alkyl, cyano and nitro.

49. A compound according to claim 33, wherein one of $R^3$ or $R^4$ is $C_{1-4}$haloalkyl or $C_{1-8}$alkyl.

50. A compound according to claim 33, wherein $R^5$ is $C_{1-8}$alkyl, $C_{1-4}$haloalkyl, halogen or —$OC_{1-6}$alkyl.

51. A compound according to claim 33, wherein $R^6$ is phenyl, wherein the phenyl is substituted by 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^a$C(=O)$C_{1-6}$alkyl, —S(=O)$_n C_{1-6}$alkyl, cyano and nitro.

52. A compound according to claim 33, wherein $R^6$ is benzyl, wherein the benzyl is substituted by 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^a$C(=O)$C_{1-6}$alkyl, —S(=O)$_n C_{1-6}$alkyl, cyano and nitro.

53. A compound according to claim 33, wherein $R^6$ is naphthyl, wherein the naphthyl is substituted by 0, 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^a$C(=O)$C_{1-6}$alkyl, —S(=O)$_n C_{1-6}$alkyl, cyano and nitro.

54. A compound according to claim 33, wherein $R^6$ is a saturated or unsaturated 5- or 6-membered ring heterocycle containing 1, 2 or 3 atoms selected from N, O and S, with no more than 2 of the atoms selected from O and S, wherein the heterocycle is substituted by 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^aC(=O)C_{1-6}$alkyl, —$S(=O)_nC_{1-6}$alkyl, cyano and nitro.

55. A compound according to claim 33, wherein $R^6$ is a saturated or unsaturated 8-, 9-, 10- or 11-membered heterobicycle containing 1, 2, 3, 4 or 5 atoms selected from N, O and S, with no more than 2 of the atoms selected from O and S, wherein the heterobicycle is substituted by 1, 2 or 3 substituents selected from $C_{1-6}$alkyl, halogen, $C_{1-4}$haloalkyl, —$OC_{1-6}$alkyl, —$OC_{1-4}$haloalkyl, —$NR^aR^a$, —$NR^aC(=O)C_{1-6}$alkyl, —$S(=O)_nC_{1-6}$alkyl, cyano and nitro.

56. A pharmaceutical composition comprising a compound according to claim 33 and a pharmaceutically acceptable diluent or carrier.

57. A process for making a compound according to claim 1, wherein $R^3$ and $R^4$ are both H comprising the steps of:

placing a compound having the structure

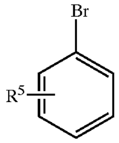

in the presence of acid followed by treatment with a hydride and methanol to form

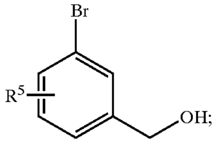

reacting the resulting alcohol with $R^6$—$B(OH)_2$ to form

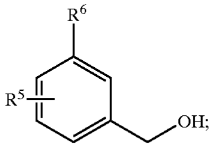

oxidizing the alcohol to form

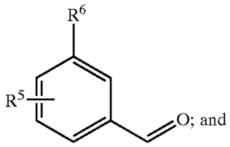

reacting the aldehyde with an amine having the structure

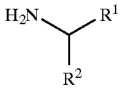

to obtain a compound of claim 1.

* * * * *